US010759998B2

(12) United States Patent
Tanaka

(10) Patent No.: US 10,759,998 B2
(45) Date of Patent: Sep. 1, 2020

(54) POLYMERIZABLE POLAR COMPOUND, LIQUID CRYSTAL COMPOSITION AND LIQUID CRYSTAL DISPLAY ELEMENT

(71) Applicants: JNC CORPORATION, Tokyo (JP); JNC PETROCHEMICAL CORPORATION, Tokyo (JP)

(72) Inventor: Hiroyuki Tanaka, Chiba (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 49 days.

(21) Appl. No.: 16/215,655

(22) Filed: Dec. 11, 2018

(65) Prior Publication Data

US 2019/0390115 A1    Dec. 26, 2019

(30) Foreign Application Priority Data

Jun. 26, 2018    (JP) .................................. 2018-120934

(51) Int. Cl.
| | | |
|---|---|---|
| *G02F 1/1333* | (2006.01) | |
| *C09K 19/56* | (2006.01) | |
| *C09K 19/30* | (2006.01) | |
| *C09K 19/34* | (2006.01) | |
| *C07C 59/56* | (2006.01) | |
| *C07C 59/58* | (2006.01) | |
| *G02F 1/137* | (2006.01) | |

(52) U.S. Cl.
CPC .............. *C09K 19/56* (2013.01); *C07C 59/56* (2013.01); *C07C 59/58* (2013.01); *C09K 19/3001* (2013.01); *C09K 19/3003* (2013.01); *C09K 19/3068* (2013.01); *C09K 19/3402* (2013.01); *G02F 1/137* (2013.01); *C09K 2019/301* (2013.01); *C09K 2019/3004* (2013.01); *C09K 2019/3009* (2013.01); *C09K 2019/3016* (2013.01); *C09K 2019/3025* (2013.01); *C09K 2019/3077* (2013.01); *C09K 2019/3083* (2013.01); *C09K 2019/3422* (2013.01); *G02F 2001/13706* (2013.01); *G02F 2001/13712* (2013.01); *G02F 2001/13775* (2013.01)

(58) Field of Classification Search
CPC ........................... C09K 19/56; C09K 19/3001; C09K 19/3003; C09K 19/3068; C09K 19/3402; C09K 2019/3004; C09K 2019/3009; C09K 2019/301; C09K 2019/3016; C09K 2019/3025; C09K 2019/3077; C09K 2019/3083; C09K 2019/3422; G02F 1/1333; G02F 1/137; G02F 2001/13706; G02F 2001/13712; G02F 2001/13775; C07C 59/56; C07C 59/58

USPC ...................................................... 252/299.4
See application file for complete search history.

(56) References Cited

U.S. PATENT DOCUMENTS

2016/0168466 A1    6/2016   Tanaka et al.
2019/0390115 A1*   12/2019   Tanaka ............... C09K 19/3402

FOREIGN PATENT DOCUMENTS

JP           2016108310        6/2016

OTHER PUBLICATIONS

"Certificate of submission for exception of loss of novelty," with English translation thereof, filed on Jul. 25, 2018, p. 1-p. 26.

* cited by examiner

*Primary Examiner* — Geraldina Visconti
(74) *Attorney, Agent, or Firm* — JCIPRNET

(57) ABSTRACT

To provide a polar compound having high chemical stability, a high ability to align liquid crystal molecules, and high solubility in a liquid crystal composition, and a high voltage holding ratio of a liquid crystal display element.
A compound represented by Formula (1):

$$R^1\text{-}(CF_2)_a\text{-}Sp^1\text{-}O\text{-}C(=O)\text{-}C(R^2)=C(M^1)(M^2) \quad (1)$$

$R^1$ is a hydrogen atom or an alkyl group that may be substituted; $a$ is 2 to 12; and $R^2$ is Formula (1-a), Formula (1-b), and Formula (1-c);

$$-Sp^2-X^1 \quad (1\text{-a})$$

$$-Sp^2-C(R^3)(Sp^3-X^1)(Sp^3-X^1) \quad (1\text{-b})$$

$$-Sp^2-C(Sp^3-X^1)(Sp^3-X^1)(Sp^3-X^1) \quad (1\text{-c})$$

$Sp^1$ to $Sp^3$ are a single bond or an alkylene group that may be substituted; $M^1$ and $M^2$ are H, F, Cl, or an alkyl group that may be substituted; and $X^1$ is —OH, —$NH_2$, —$OR^3$, —$N(R^3)_2$, —COOH, —SH or —$Si(R^3)_3$.

20 Claims, No Drawings

POLYMERIZABLE POLAR COMPOUND, LIQUID CRYSTAL COMPOSITION AND LIQUID CRYSTAL DISPLAY ELEMENT

CROSS-REFERENCE TO RELATED APPLICATION

This application claims the priority of Japan patent application serial no. 2018-120934, filed on Jun. 26, 2018. The entirety of the above-mentioned patent application is hereby incorporated by reference herein and made a part of this specification.

BACKGROUND

Technical Field

The disclosure relates to a polymerizable polar compound, a liquid crystal composition, and a liquid crystal display element, and more specifically, to a polymerizable polar compound having both a perfluoroalkyl chain and an acryloyloxy group substituted with a polar group such as a hydroxyalkyl group, a liquid crystal composition containing the compound and having positive or negative dielectric anisotropy, and a liquid crystal display element including the composition or a cured material of a part thereof.

Description of Related Art

Liquid crystal display elements can be classified into modes such as phase change (PC), twisted nematic (TN), super twisted nematic (STN), electrically controlled birefringence (ECB), optically compensated bend (OCB), in-plane switching (IPS), vertical alignment (VA), fringe field switching (FFS), and field-induced photo-reactive alignment (FPA) based on an operation mode of liquid crystal molecules. In addition, liquid crystal display elements can be classified as passive matrix (PM) and active matrix (AM) based on an element driving method. PMs are classified into static and multiplex matrixes and AMs are classified as thin film transistor (TFT) and metal insulator metal (MIM). In addition, TFTs can be classified as amorphous silicon and polycrystal silicon. The latter is classified into a high temperature type and a low temperature type according to a production process. Liquid crystal display elements can be classified into a reflective type that uses natural light, a transmissive type that uses a backlight, and a semi-transmissive type that uses both natural light and a backlight based on a light source.

A liquid crystal composition having a nematic phase has appropriate characteristics. It is possible to obtain an AM element having favorable characteristics by improving characteristics of this composition. The relationship between characteristics of the composition and characteristics of the AM element is summarized in the following Table 1.

TABLE 1

Characteristics of compositions and AM elements

| Number | Characteristics of composition | Characteristics of AM element |
|---|---|---|
| 1 | Wide temperature range of a nematic phase | Wide temperature range in which the element can be used |
| 2 | Low viscosity[1] | Short response time |
| 3 | Appropriate optical anisotropy | Large contrast ratio |
| 4 | Large positive or negative dielectric anisotropy | Low threshold voltage, low power consumption, and large contrast ratio |
| 5 | Large specific resistance | High voltage holding ratio and large contrast ratio |
| 6 | Stable with respect to ultraviolet radiation and heat | Long lifespan |
| 7 | Large elastic constant | Large contrast ratio and short response time |

[1]The time taken for a composition to be inserted into a liquid crystal display element can be shortened Characteristics of the composition will be further described based on commercially available AM elements. A temperature range of a nematic phase (a temperature range in which a nematic phase is exhibited) is related to a temperature range in which an element can be used. A preferable upper limit temperature of a nematic phase is about 70° C. or higher and a preferable lower limit temperature of a nematic phase is about −10° C. or lower.

The viscosity of the composition is related to a response time of the element. A short response time is preferable in order to display a moving image with elements. A shorter response time is desirable even if it is only 1 millisecond. Therefore, a lower viscosity of the composition is preferable and a lower viscosity at low temperatures is more preferable.

The optical anisotropy of the composition is related to a contrast ratio of the element. According to a mode of the element, large optical anisotropy or small optical anisotropy, that is, appropriate optical anisotropy is necessary. A product (Δn×d) of the optical anisotropy (Δn) of the composition and the cell gap (d) of the element is designed to maximize the contrast ratio. An appropriate product value depends on the type of operation mode. This value is about 0.45 μm in an element in a mode such as TN. This value is a range of about 0.30 μm to about 0.40 μm in an element in a VA mode and is a range of about 0.20 μm to about 0.30 μm in an element in an IPS mode or an FFS mode. In these cases, in an element having a small cell gap, a composition having large optical anisotropy is preferable.

Large dielectric anisotropy of the composition contributes to a low threshold voltage, low power consumption, and a large contrast ratio in the element. Therefore, large positive or negative dielectric anisotropy is preferable. A large specific resistance of the composition contributes to a high voltage holding ratio and a large contrast ratio in the element. Therefore, a composition having a large specific resistance not only at room temperature in an initial stage of use but also at a temperature close to an upper limit temperature of a nematic phase is preferable. A composition having a large specific resistance not only at room temperature but also at a temperature close to an upper limit temperature of a nematic phase after long term use is preferable.

The stability of the composition with respect to ultraviolet radiation and heat is related to a lifespan of the element. When this stability is higher, the lifespan of the element is longer. Such a characteristic is preferable for an AM element used in a liquid crystal projector and a liquid crystal television.

In a polymer sustained alignment (PSA) type liquid crystal display element, a liquid crystal composition containing a polymer is used. First, a composition to which a small amount of a polymerizable compound is added is inserted into the element. Here, a polymerizable compound having a plurality of polymerizable groups is generally used. Next, ultraviolet rays are emitted to the composition while a voltage is applied between substrates of the element. The polymerizable compound is polymerized and forms a polymer network structure in the composition. When this composition is used, since it is possible to control the alignment of liquid crystal molecules according to the polymer, a response time of the element is shortened and image burn is lessened. Such effects of the polymer can be expected for elements having modes such as TN, ECB, OCB, IPS, VA, FFS, and FPA.

In general purpose liquid crystal display elements, vertical alignment of liquid crystal molecules is achieved using a polyimide alignment film. On the other hand, for liquid crystal display elements having no alignment film, a mode in which a polar compound is added to a liquid crystal composition and liquid crystal molecules are aligned has been proposed. First, a composition in which a small amount of a polar compound and a small amount of a polymerizable compound are added is inserted into the element. As the polymerizable compound, a polymerizable compound having a plurality of polymerizable groups is generally used. Here, liquid crystal molecules are aligned according to an action of the polar compound. Next, ultraviolet rays are emitted to the composition while a voltage is applied between substrates of the element. Here, the polymerizable compound is polymerized and stabilizes the alignment of liquid crystal molecules. When this composition is used, since it is possible to control the alignment of liquid crystal molecules according to the polar compound and the polymer, a response time of the element is shortened and image burn is lessened. In addition, in elements having no alignment film, a process of forming an alignment film is unnecessary. Since there is no alignment film, a reduction in electrical resistance of the element due to an interaction between the alignment film and the composition does not occur. Such an effect caused by a combination of the polar compound and the polymer can be expected for elements having modes such as TN, ECB, OCB, IPS, VA, FFS, and FPA.

In liquid crystal display elements having no alignment film, as compounds to be added to a liquid crystal composition in order to align liquid crystal molecules, polar compounds having a perfluoroalkyl chain have been synthesized so far (Patent Document 1). For example, in Patent Document 1, a polar compound (S-1) having a perfluoroalkyl chain and a hydroxyl group is described.

(S-1)

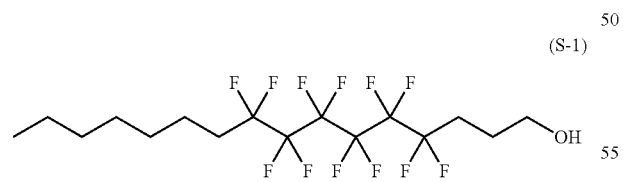

[Patent Document 1] Japanese Unexamined Patent Application Publication No. 2016-108310

SUMMARY

One aspect of the disclosure is to provide a compound having at least one of high chemical stability, a high ability to align liquid crystal molecules, and high solubility in a liquid crystal composition, and a high voltage holding ratio when used for a liquid crystal display element. Another aspect is to provide a liquid crystal composition which contains the compound and has at least one of characteristics such as a high upper limit temperature of a nematic phase, a low lower limit temperature of a nematic phase, a low viscosity, appropriate optical anisotropy, large positive or negative dielectric anisotropy, a large specific resistance, high stability with respect to ultraviolet rays, high stability with respect to heat, and a large elastic constant. Still another aspect is to provide a liquid crystal display element having at least one of characteristics such as a wide temperature range in which an element can be used, a short response time, a high transmittance, a high voltage holding ratio, a low threshold voltage, a large contrast ratio, a prolonged lifespan, and a favorable vertical alignment property.

The disclosure relates to a compound represented by Formula (1), a liquid crystal composition containing the compound, and a liquid crystal display element including the composition and/or a polymerization product obtained by polymerizing at least some of the composition.

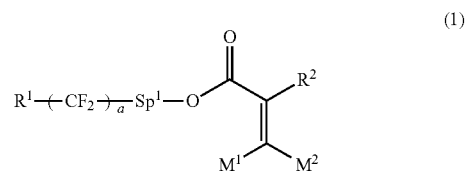

In Formula (1), $R^1$ is an alkyl group having 1 to 15 carbon atoms, and in this alkyl group, at least one —$CH_2$— is optionally substituted with —O— or —S—, and at least one —$(CH_2)_2$— is optionally substituted with —CH=CH— or —C≡C—, and in these groups, at least one hydrogen atom is optionally substituted with a fluorine or chlorine atom;

a is an integer of 2 to 12;

$M^1$ and $M^2$ are independently a hydrogen atom, a fluorine atom, a chlorine atom, an alkyl group having 1 to 5 carbon atoms, or an alkyl group having 1 to 5 carbon atoms in which at least one hydrogen atom is substituted with a fluorine atom or a chlorine atom; and $R^2$ is a group selected from among groups represented by Formula (1-a), Formula (1-b), and Formula (1-c);

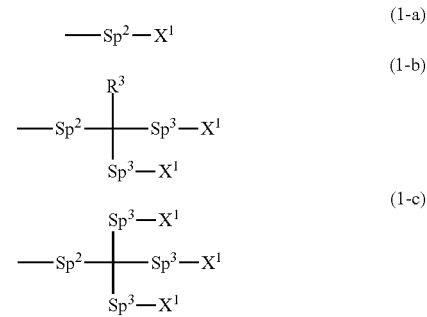

in Formula (1-a), Formula (1-b), and Formula (1-c), $Sp^2$ and $Sp^3$ are independently a single bond or an alkylene group having 1 to 10 carbon atoms, and in this alkylene group, at least one —$CH_2$— is optionally substituted with —O—, —CO—, —COO—, —OCO—, or —OCOO—, and at least one —$(CH_2)_2$— is optionally substituted with —CH═CH— or —C≡C—, and in these groups, at least one hydrogen atom is optionally substituted with a fluorine or chlorine atom;

$R^3$ is a hydrogen atom, an alkyl group having 1 to 10 carbon atoms, an alkoxy group having 1 to 9 carbon atoms, or an alkoxyalkyl group having 1 to 9 carbon atoms;

$X^1$ is independently —OH, —NH$_2$, —N(R$^4$)$_2$, —COOH, —SH, or —Si(R$^4$)$_3$;

in —N(R$^4$)$_2$, and —Si(R$^4$)$_3$, $R^4$ is a hydrogen atom or an alkyl group having 1 to 10 carbon atoms, and in this alkyl group, at least one —CH$_2$— is optionally substituted with —O—, and at least one —(CH$_2$)$_2$— is optionally substituted with —CH═CH—, and in these groups, at least one hydrogen atom is optionally substituted with a fluorine or chlorine atom;

in Formula (1), $Sp^1$ is a single bond or an alkylene group having 1 to 15 carbon atoms, and in this alkylene group, at least one —CH$_2$— is optionally substituted with —O—, —CO—, —COO—, —OCO—, or —OCOO—, and at least one —(CH$_2$)$_2$— is optionally substituted with —CH═CH— or —C≡C—, and in these groups, at least one hydrogen atom is optionally substituted with a fluorine atom, a chlorine atom, or a group represented by Formula (1-d);

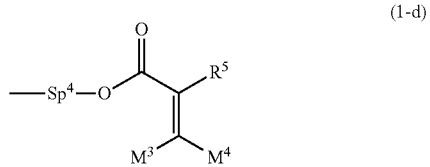

(1-d)

in Formula (1-d), $Sp^4$ is a single bond or an alkylene group having 1 to 10 carbon atoms, and in this alkylene group, at least one —CH$_2$— is optionally substituted with —O—, —CO—, —COO—, —OCO—, or —OCOO—, and at least one —(CH$_2$)$_2$— is optionally substituted with —CH═CH— or —C≡C—, and in these groups, at least one hydrogen atom is optionally substituted with a fluorine or chlorine atom;

$M^3$ and $M^4$ are independently a hydrogen atom, a fluorine atom, a chlorine atom, an alkyl group having 1 to 5 carbon atoms, or an alkyl group having 1 to 5 carbon atoms in which at least one hydrogen atom is substituted with a fluorine atom or a chlorine atom; and $R^5$ is a hydrogen atom or an alkyl group having 1 to 10 carbon atoms, and in this alkyl group, at least one —CH$_2$— is optionally substituted with —O—, at least one —(CH$_2$)$_2$— is optionally substituted with —CH═CH— or —C≡C—, and at least one hydrogen atom is optionally substituted with a fluorine atom or a chlorine atom.

DESCRIPTION OF THE EMBODIMENTS

The disclosure provides a compound having at least one of high chemical stability, a high ability to align liquid crystal molecules, high polymerization reactivity according to ultraviolet radiation, and high solubility in a liquid crystal composition, and a high voltage holding ratio when used for a liquid crystal display element. The disclosure further provides a liquid crystal composition which contains the compound and has at least one of characteristics such as a high upper limit temperature of a nematic phase, a low lower limit temperature of a nematic phase, a low viscosity, appropriate optical anisotropy, large positive or negative dielectric anisotropy, a large specific resistance, high stability with respect to ultraviolet rays, high stability with respect to heat, and a large elastic constant. The disclosure further provides a liquid crystal display element having at least one of characteristics such as a wide temperature range in which an element can be used, a short response time, a high transmittance, a high voltage holding ratio, a low threshold voltage, a large contrast ratio, a prolonged lifespan, and a favorable vertical alignment property.

The terms used herein are used as follows. The terms "liquid crystalline compound," "liquid crystal composition," and "liquid crystal display element" may be abbreviated as a "compound," a "composition," and an "element."

A "liquid crystalline compound" generally refers to a compound having a liquid crystal phase such as a nematic phase or a smectic phase and a compound which does not have a liquid crystal phase and is added in order to adjust physical properties of a composition such as an upper limit temperature, a lower limit temperature, a viscosity, and dielectric anisotropy. Generally, this compound has a six-membered ring such as 1,4-cyclohexylene or 1,4-phenylene, and has a rod-like molecular structure.

A "polymerizable compound" is a compound that is added to form a polymer in the composition. A liquid crystalline compound having an alkenyl group is not a polymerizable compound in that sense.

A "polar compound" assists the alignment of liquid crystal molecules due to a polar group that interacts with a surface of a substrate or the like.

A "liquid crystal display element" generally refers to a liquid crystal display panel, a liquid crystal display module, and the like.

A liquid crystal composition is generally prepared by mixing a plurality of liquid crystalline compounds together. Additives such as a polymerizable compound, a polymerization initiator, a polymerization inhibitor, an optically active compound, an antioxidant, a UV absorber, a light stabilizer, a heat stabilizer, a dye, and an antifoaming agent are added to this composition as necessary in order to further adjust physical properties. Also when additives are added, a proportion (content) of a liquid crystalline compound in the liquid crystal composition is expressed as a weight percentage (weight %) based on a weight of a liquid crystal composition containing no additives. A proportion (amount added) of additives in the liquid crystal composition is expressed as a weight percentage (weight %) based on a weight of a liquid crystal composition containing no additives. That is, a proportion of a liquid crystalline compound or an additive is computed based on a total weight of a liquid crystalline compound. Parts per million (ppm) by weight may be used. Proportions of a polymerization initiator and a polymerization inhibitor in the liquid crystal composition are otherwise expressed based on a weight of a polymerizable compound.

The "clearing point" is a transition temperature of a liquid crystal phase-isotropic phase in a liquid crystalline compound. A "lower limit temperature of a liquid crystal phase" is a transition temperature of a solid-liquid crystal phase (such as a smectic phase and a nematic phase) in a liquid crystalline compound. An "upper limit temperature of a nematic phase" is a transition temperature of a nematic phase-isotropic phase in a mixture of a liquid crystalline compound and a mother liquid crystal, or a liquid crystal composition, and may be abbreviated as an "upper limit temperature." A "lower limit temperature of a nematic phase" may be abbreviated as a "lower limit temperature." The expression "increasing dielectric anisotropy" or "large dielectric anisotropy" means that an absolute value of a value thereof increases or is large. The expression "a voltage holding ratio is high" means that a voltage holding ratio is high not only at room temperature when an element is in an initial stage of use but also at a temperature close to the upper limit temperature, and thus, even after the element is used for a long time, it has a high voltage holding ratio not only at room temperature but also at a temperature close to the upper limit temperature. Characteristics of compositions and elements may be examined before and after an aging test (including an accelerated deterioration test). The expression "solubility in a liquid crystal composition is high" means that solubility is high in any composition containing a liquid crystalline compound at room temperature, but a composition used for evaluating solubility in the following examples can be used as a reference for the composition.

A compound represented by Formula (1) may be abbreviated as "Compound (1)." Compound (1) refers to one compound represented by Formula (1), a mixture of two compounds, or a mixture of three or more compounds. These rules apply to at least one compound selected from the group of compounds represented by Formula (2).

Symbols such as $A^1$, $B^1$, and $C^1$ surrounded by a hexagon correspond to a ring $A^1$, a ring $B^1$, and a ring $C^1$, respectively. A hexagon refers to a six-membered ring such as a cyclohexane ring or a benzene ring or a condensed ring such as a naphthalene ring. A straight line crossing one side of this hexagon indicates that any hydrogen atom on the ring is optionally substituted with a group such as $-Sp^1-P^1$.

A suffix such as f, g, or h indicates the number of groups substituted. When the suffix is 0, there is no such substitution.

In the expression "a ring A and a ring C are independently, X, Y, or Z," since the subject is plural, "independently" is used. When the subject is a "ring A," since the subject is singular, "independently" is not used.

In a chemical formula, the symbol of a terminal group $R^{11}$ is used for a plurality of compounds. In these compounds, groups represented by $R^{11}$ may be the same as or different from each other. For example, when $R^{11}$ of Compound (2) is an ethyl group, $R^{11}$ of Compound (3) may be an ethyl group or another group such as a propyl group. These rules also apply to other symbols. In Compound (8), when i is 2, there are two rings $D^1$. In this compound, two groups represented by two rings $D^1$ may be the same as or different from each other. When i is greater than 2, this rule also applies to any two rings $D^1$. These rules also apply to other symbols.

The expression "at least one 'A'" means that the number of 'A' is arbitrary. The expression "at least one 'A' is optionally substituted with 'B'" includes a case in which 'A' itself is not substituted with 'B,' a case in which one 'A' is substituted with 'B,' and a case in which two or more 'A' are substituted with 'B,' and in these cases, a position of 'A' that is substituted with 'B' is arbitrary. A rule in which a substitution position is arbitrary also applies to the expression "at least one 'A' is substituted with 'B'". The expression "at least one A is optionally substituted with B, C, or D" means a case in which A is not substituted, a case in which at least one A is substituted with B, a case in which at least one A is substituted with C, a case in which at least one A is substituted with D, and also a case in which a plurality of A' are substituted with at least two of B, C, and D. An alkyl group in which at least one $-CH_2-$ (or $-CH_2CH_2-$) is optionally substituted with $-O-$ (or $-CH=CH-$) includes, for example, an alkyl group, an alkenyl group, an alkoxy group, an alkoxyalkyl group, an alkoxyalkenyl group, and an alkenyloxyalkyl group. Here, it is not preferable for two consecutive $-CH_2-$ to be substituted with $-O-$ and $-O-O-$ be formed. In an alkyl group and the like, it is not preferable for $-CH_2-$ in a methyl moiety ($-CH_2-H$) to be substituted with $-O-$ and $-O-H$ be formed.

The expression "$R^{11}$ and $R^{12}$ are independently an alkyl group having 1 to 10 carbon atoms or an alkenyl group having 2 to 10 carbon atoms, and in the alkyl and alkenyl groups, at least one $-CH_2-$ is optionally substituted with $-O-$, and in these groups, at least one hydrogen atom is optionally substituted with a fluorine atom" may be used. In this expression, "in these groups" may be interpreted literally. In this expression, "these groups" refer to an alkyl group, an alkenyl group, an alkoxy group, and an alkenyloxy group. That is, "these groups" indicate all of groups shown before the expression "in these groups." This common interpretation also applies to other terms.

A halogen includes fluorine, chlorine, bromine, and iodine. A preferable halogen is fluorine or chlorine. A more preferable halogen is fluorine. In a liquid crystalline compound, an alkyl group is linear or branched, and does not contain a cyclic alkyl group. Generally, a linear alkyl group is more preferable than a branched alkyl group. This also applies to a terminal group such as an alkoxy group and an alkenyl group. Regarding the configuration, the trans configuration of 1,4-cyclohexylene is more preferable than the cis configuration in order to increase an upper limit temperature of a nematic phase. 2-Fluoro-1,4-phenylene refers to the following two divalent groups. In the chemical formulae, fluorine may be leftward (L) or rightward (R). These rules also apply to a bilaterally asymmetric divalent group that is formed by removing two hydrogen atoms from a ring such as tetrahydropyran-2,5-diyl.

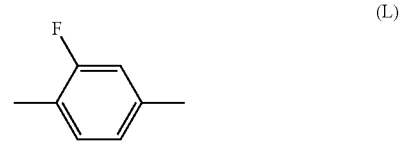

(L)

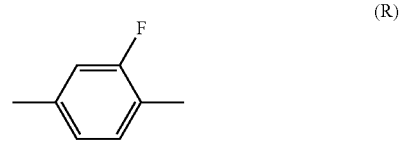

(R)

The disclosure includes the following items and the like.

Item 1.

A compound represented by Formula (1):

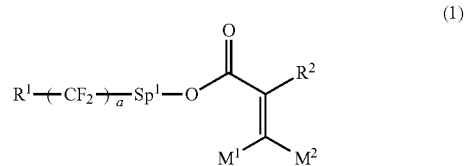

(1)

In Formula (1), $R^1$ is an alkyl group having 1 to 15 carbon atoms, and in this alkyl group, at least one $-CH_2-$ is optionally substituted with $-O-$ or $-S-$, and at least one $-(CH_2)_2-$ is optionally substituted with $-CH=CH-$ or $-C\equiv C-$, and in these groups, at least one hydrogen atom is optionally substituted with a fluorine or chlorine atom;

a is an integer of 2 to 12;

$M^1$ and $M^2$ are independently a hydrogen atom, a fluorine atom, a chlorine atom, an alkyl group having 1 to 5 carbon atoms, or an alkyl group having 1 to 5 carbon atoms in which at least one hydrogen atom is substituted with a fluorine atom or a chlorine atom; and $R^2$ is a group selected from among groups represented by Formula (1-a), Formula (1-b), and Formula (1-c);

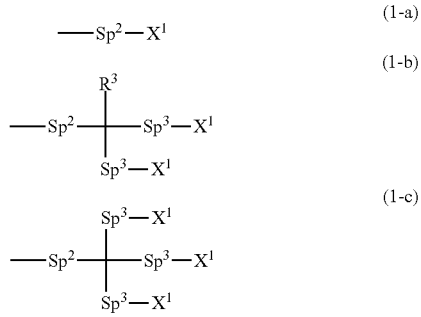

(1-a)
(1-b)
(1-c)

in Formula (1-a), Formula (1-b), and Formula (1-c), $Sp^2$ and $Sp^3$ are independently a single bond or an alkylene group having 1 to 10 carbon atoms, and in this alkylene group, at least one —$CH_2$— is optionally substituted with —O—, —CO—, —COO—, —OCO—, or —OCOO—, and at least one —$(CH_2)_2$— is optionally substituted with —CH=CH— or —C≡C—, and in these groups, at least one hydrogen atom is optionally substituted with a fluorine or chlorine atom;

$R^3$ is a hydrogen atom, an alkyl group having 1 to 10 carbon atoms, an alkoxy group having 1 to 9 carbon atoms, or an alkoxyalkyl group having 1 to 9 carbon atoms;

$X^1$ is independently —OH, —$NH_2$, —$N(R^4)_2$, —COOH, —SH, or —$Si(R^4)_3$;

in —$N(R^4)_2$, and —$Si(R^4)_3$, $R^4$ is a hydrogen atom or an alkyl group having 1 to 10 carbon atoms, and in this alkyl group, at least one —$CH_2$— is optionally substituted with —O—, and at least one —$(CH_2)_2$— is optionally substituted with —CH=CH—, and in these groups, at least one hydrogen atom is optionally substituted with a fluorine or chlorine atom, in Formula (1), $Sp^1$ is a single bond or an alkylene group having 1 to 15 carbon atoms, and in this alkylene group, at least one —$CH_2$— is optionally substituted with —O—, —CO—, —COO—, —OCO—, or —OCOO—, and at least one —$(CH_2)_2$— is optionally substituted with —CH=CH— or —C≡C—, and in these groups, at least one hydrogen atom is optionally substituted with a fluorine atom, a chlorine atom, or a group represented by Formula (1-d);

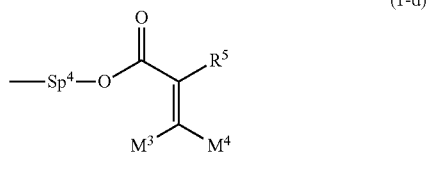

(1-d)

in Formula (1-d), $Sp^4$ is a single bond or an alkylene group having 1 to 10 carbon atoms, and in this alkylene group, at least one —$CH_2$— is optionally substituted with —O—, —CO—, —COO—, —OCO—, or —OCOO—, and at least one —$(CH_2)_2$— is optionally substituted with —CH=CH— or —C≡C—, and in these groups, at least one hydrogen atom is optionally substituted with a fluorine or chlorine atom;

$M^3$ and $M^4$ are independently a hydrogen atom, a fluorine atom, a chlorine atom, an alkyl group having 1 to 5 carbon atoms, or an alkyl group having 1 to 5 carbon atoms in which at least one hydrogen atom is substituted with a fluorine atom or a chlorine atom; and $R^5$ is a hydrogen atom or an alkyl group having 1 to 10 carbon atoms, and in this alkyl group, at least one —$CH_2$— is optionally substituted with —O—, at least one —$(CH_2)_2$— is optionally substituted with —CH=CH— or —C≡C—, and at least one hydrogen atom is optionally substituted with a fluorine atom or a chlorine atom.

Item 2.

The compound according to Item 1, wherein, in Formula (1), $R^2$ is a group represented by Formula (1-a) or Formula (1-b).

Item 3.

The compound according to Item 1, wherein, in Formula (1), $R^2$ is a group represented by Formula (1-a) or Formula (1-b), and in Formula (1-a) and Formula (1-b), $X^1$ is independently —OH, —$NH_2$, —COOH, or —SH.

Item 4.

The compound according to any one of Items 1 to 3, which is represented by any one of Formula (1-1) to Formula (1-6):

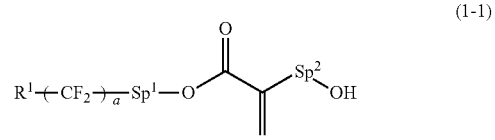

(1-1)

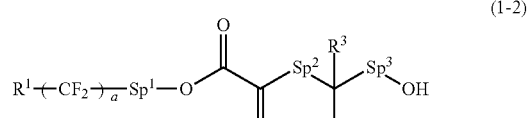

(1-2)

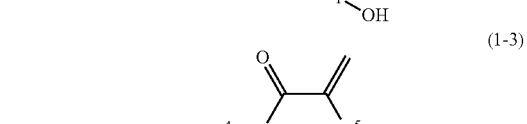

(1-3)

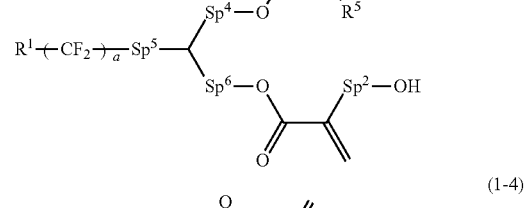

(1-4)

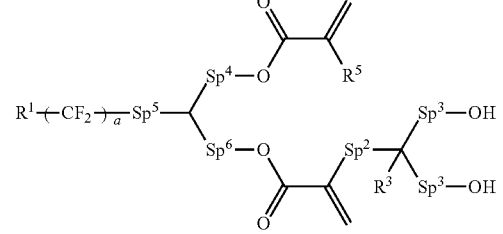

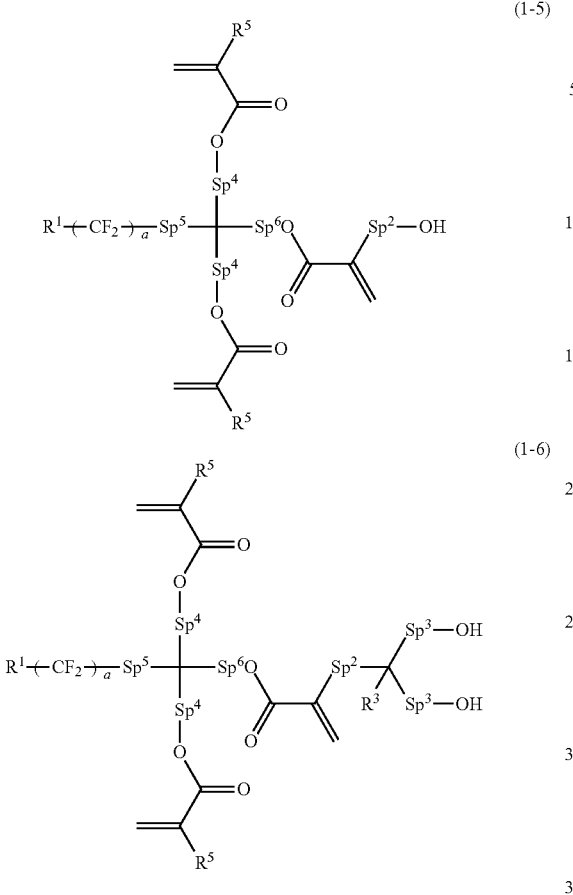
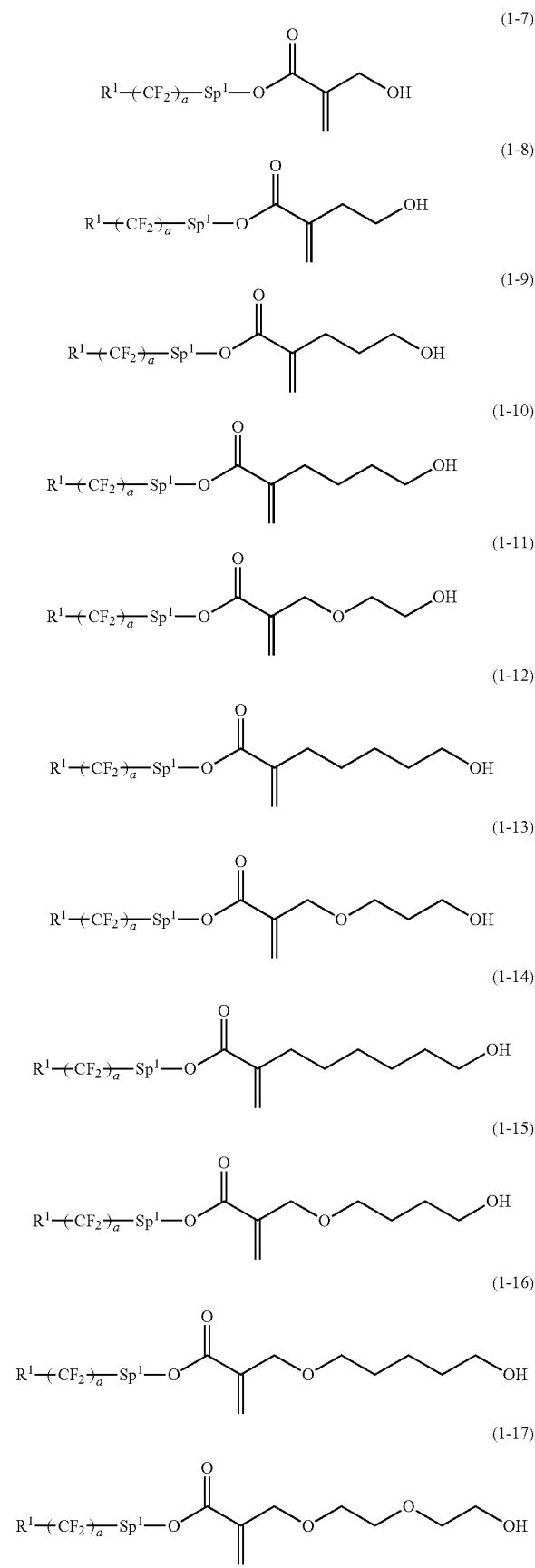

In Formula (1-1) to Formula (1-6), $R^1$ is an alkyl group having 1 to 15 carbon atoms, and in this alkyl group, at least one —CH$_2$— is optionally substituted with —O—, and at least one —(CH$_2$)$_2$— is optionally substituted with —CH=CH—, and in these groups, at least one hydrogen atom is optionally substituted with a fluorine atom;

a is an integer of 2 to 8;

$Sp^1$, $Sp^2$, $Sp^3$, and $Sp^4$ are independently a single bond or an alkylene group having 1 to 10 carbon atoms, and in this alkylene group, at least one —CH$_2$— is optionally substituted with —O—;

$Sp^5$ and $Sp^6$ are independently a single bond or an alkylene group having 1 to 7 carbon atoms, and in this alkylene group, at least one —CH$_2$— is optionally substituted with —O—;

$R^3$ is a hydrogen atom, an alkyl group having 1 to 7 carbon atoms, an alkoxy group having 1 to 6 carbon atoms, or an alkoxyalkyl group having 1 to 6 carbon atoms;

$R^5$ is a hydrogen atom or an alkyl group having 1 to 5 carbon atoms.

Item 5.

The compound according to any one of Items 1 to 4, which is represented by any one of Formula (1-7) to Formula (1-24):

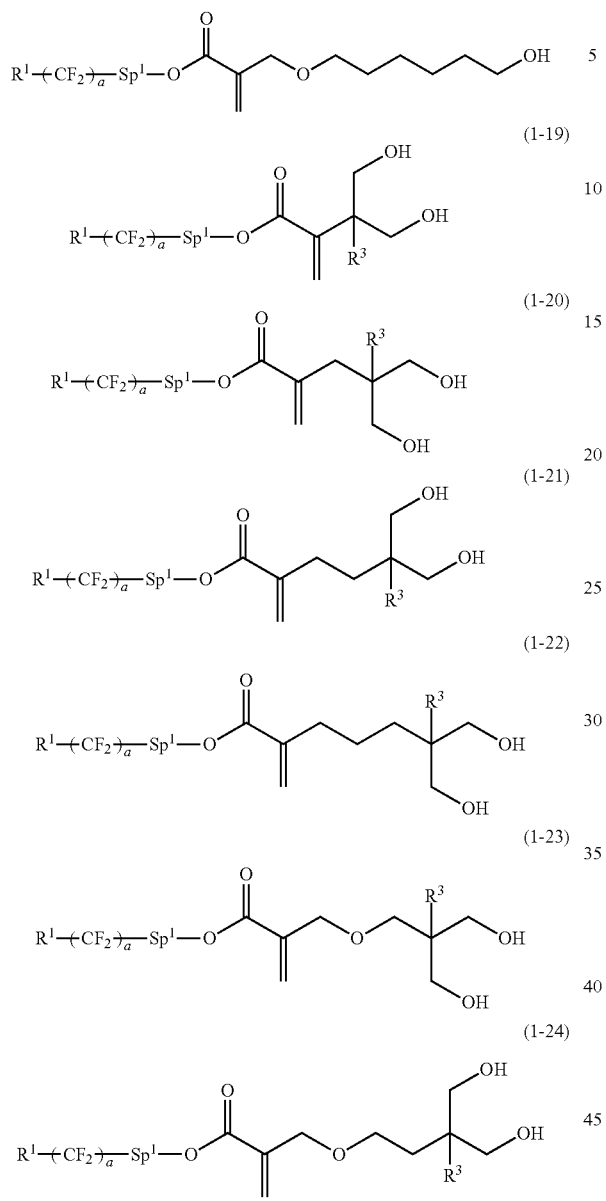
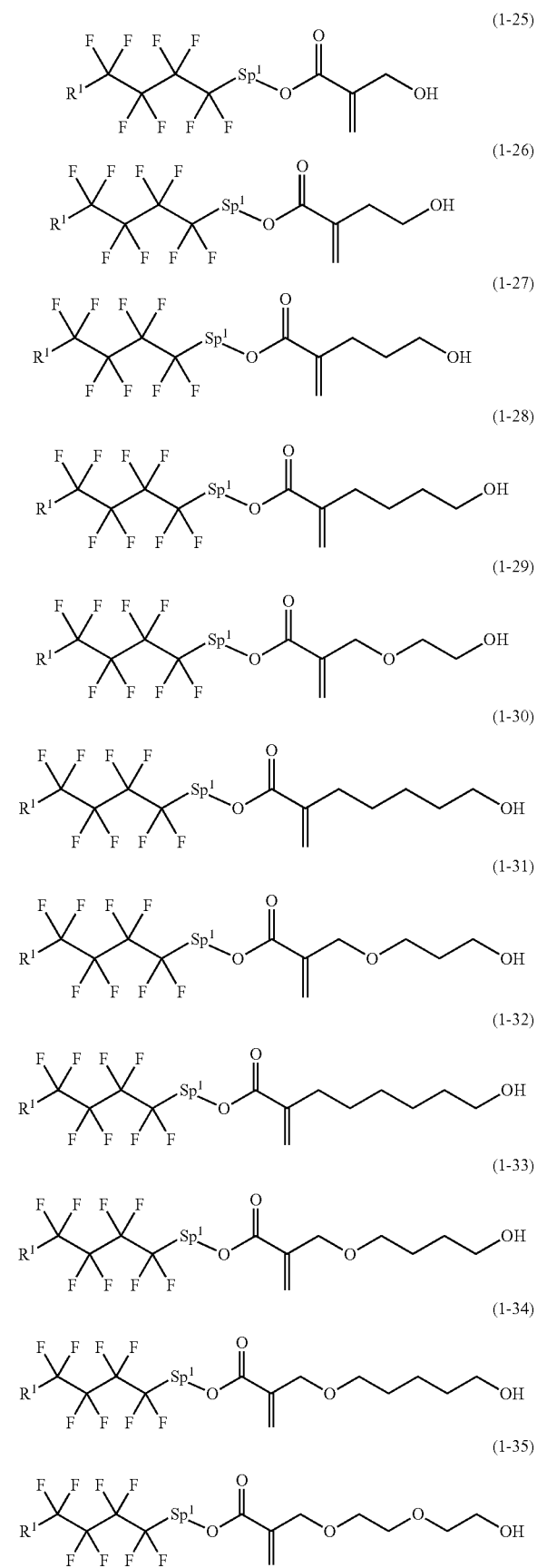

in Formula (1-7) to Formula (1-24), $R^1$ is an alkyl group having 1 to 15 carbon atoms, and in this alkyl group, at least one —$CH_2$— is optionally substituted with —O—, and at least one —$(CH_2)_2$— is optionally substituted with —CH=CH—;

a is an integer of 2 to 8;

$Sp^1$ is a single bond or an alkylene group having 1 to 7 carbon atoms, and in this alkylene group, at least one —$CH_2$— is optionally substituted with —O—; and $R^3$ is a hydrogen atom or an alkyl group having 1 to 5 carbon atoms.

Item 6.

The compound according to any one of Items 1 to 5, which is represented by any one of Formula (1-25) to Formula (1-48):

(1-36)
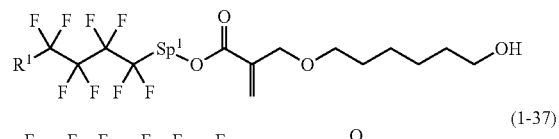

(1-37)
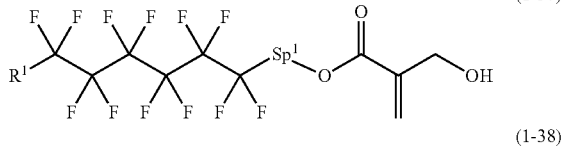

(1-38)
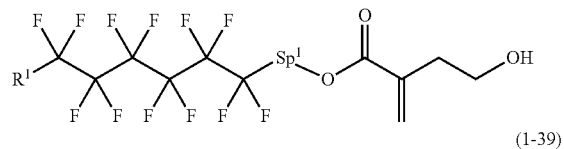

(1-39)
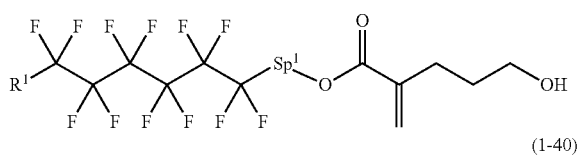

(1-40)
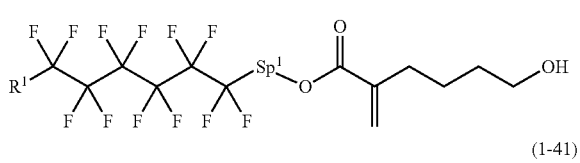

(1-41)
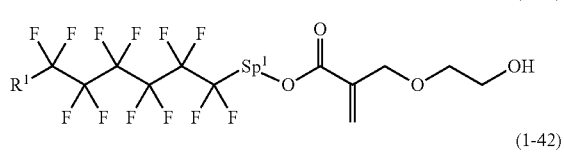

(1-42)
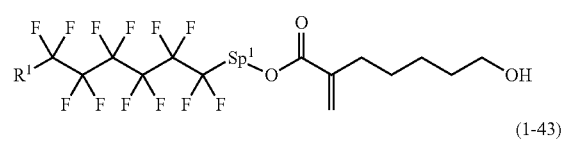

(1-43)
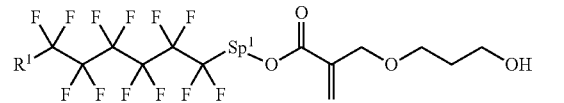

(1-44)
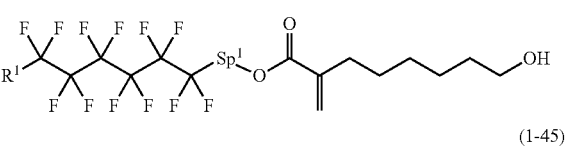

(1-45)
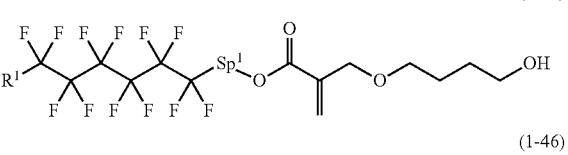

(1-46)
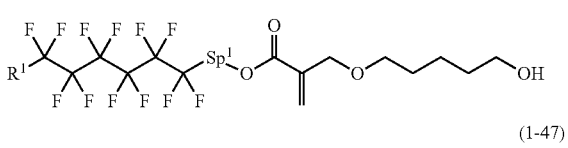

(1-47)
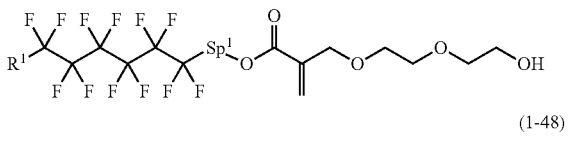

(1-48)
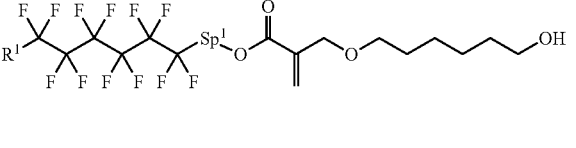

In Formula (1-25) to Formula (1-48), $R^1$ is an alkyl group having 1 to 15 carbon atoms, and in this alkyl group, at least one —$CH_2$— is optionally substituted with —O—;

$Sp^1$ is an alkylene group having 1 to 7 carbon atoms, and in this alkylene group, at least one —$CH_2$— is optionally substituted with —O—.

Item 7.

The compound according to any one of Items 1 to 6, which is represented by any one of Formula (1-49) to Formula (1-56):

(1-49)
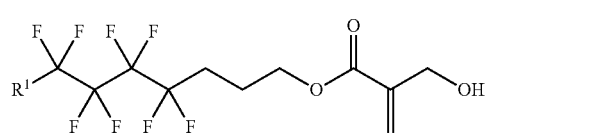

(1-50)
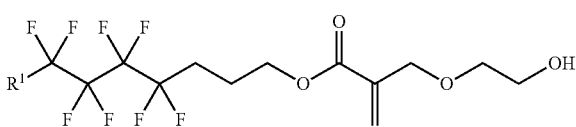

(1-51)
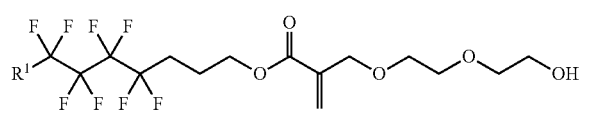

(1-52)
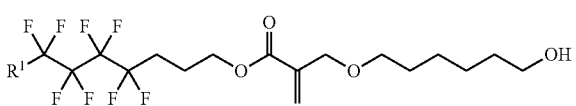

-continued

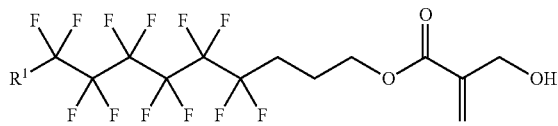
(1-53)

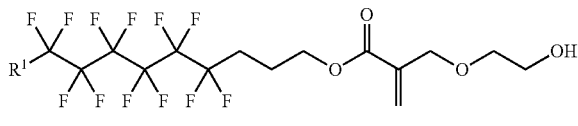
(1-54)

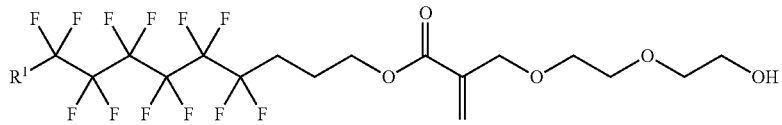
(1-55)

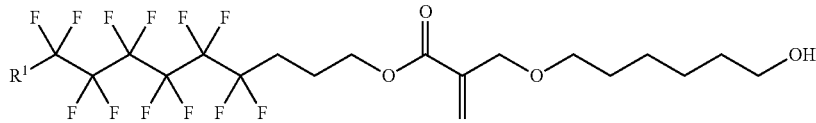
(1-56)

In Formula (1-49) to Formula (1-56), $R^1$ is an alkyl group having 1 to 10 carbon atoms.

Item 8.

A liquid crystal composition containing at least one compound according to any one of Items 1 to 7.

Item 9.

The liquid crystal composition according to Item 8, which contains at least one compound selected from the group of compounds represented by Formulae (2) to (4):

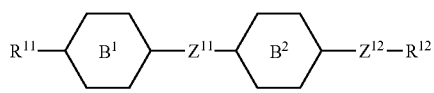
(2)

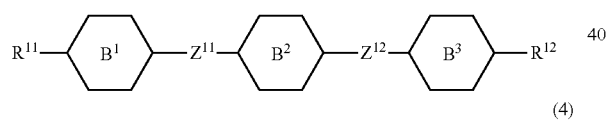
(3)

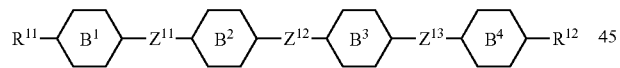
(4)

In Formulae (2) to (4), $R^{11}$ and $R^{12}$ are independently an alkyl group having 1 to 10 carbon atoms or an alkenyl group having 2 to 10 carbon atoms, and in these alkyl and alkenyl groups, at least one —CH$_2$— is optionally substituted with —O—, and in these groups, at least one hydrogen atom is optionally substituted with a fluorine atom;

the ring $B^1$, the ring $B^2$, the ring $B^3$, and the ring $B^4$ are independently 1,4-cyclohexylene, 1,4-phenylene, 2-fluoro-1,4-phenylene, 2,5-difluoro-1,4-phenylene, or pyrimidine-2,5-diyl; and $Z^{11}$, $Z^{12}$, and $Z^{13}$ are independently a single bond, —COO—, —CH$_2$CH$_2$—, —CH=CH—, or —C≡C—.

Item 10.

The liquid crystal composition according to Item 8 or 9, which contains at least one compound selected from the group of compounds represented by Formulae (5) to (7):

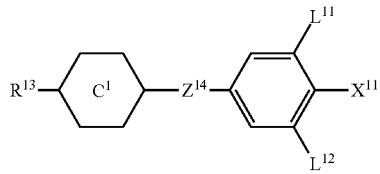
(5)

(6)

(7)

In Formulae (5) to (7), $R^{13}$ is an alkyl group having 1 to 10 carbon atoms or an alkenyl group having 2 to 10 carbon atoms, and in these alkyl and alkenyl groups, at least one —CH$_2$— is optionally substituted with —O—, and in these groups, at least one hydrogen atom is optionally substituted with a fluorine atom;

$X^{11}$ is a fluorine atom, a chlorine atom, —OCF$_3$, —OCHF$_2$, —CF$_3$, —CHF$_2$, —CH$_2$F, —OCF$_2$CHF$_2$, or —OCF$_2$CHFCF$_3$;

the ring $C^1$, the ring $C^2$, and the ring $C^3$ are independently 1,4-cyclohexylene, 1,4-phenylene, tetrahydropyran-2,5-diyl, 1,3-dioxane-2,5-diyl, pyrimidine-2,5-diyl, or 1,4-phenylene in which at least one hydrogen atom is substituted with a fluorine atom;

$Z^{14}$, $Z^{15}$, and $Z^{16}$ are independently a single bond, —COO—, —OCO—, —CH$_2$O—, —OCH$_2$—, —CF$_2$O—, —OCF$_2$—, —CH$_2$CH$_2$—, —CH=CH—, —C≡C—, or —(CH$_2$)$_4$—; and $L^{11}$ and $L^{12}$ are independently a hydrogen atom or a fluorine atom.

Item 11.

The liquid crystal composition according to any one of Items 8 to 10, which contains at least one compound selected from the group of compounds represented by Formula (8):

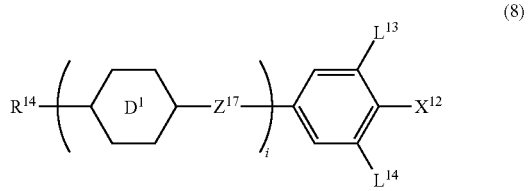
(8)

In Formula (8), $R^{14}$ is an alkyl group having 1 to 10 carbon atoms or an alkenyl group having 2 to 10 carbon atoms, and in these alkyl and alkenyl groups, at least one —CH$_2$— is optionally substituted with —O—, and in these groups, at least one hydrogen atom is optionally substituted with a fluorine atom;

$X^{12}$ is —C≡N or —C≡C—C≡N;

the ring $D^1$ is 1,4-cyclohexylene, 1,4-phenylene, tetrahydropyran-2,5-diyl, 1,3-dioxane-2,5-diyl, pyrimidine-2,5-diyl, or 1,4-phenylene in which at least one hydrogen atom is substituted with a fluorine atom;

$Z^{17}$ is a single bond, —COO—, —OCO—, —CH$_2$O—, —OCH$_2$—, —CF$_2$O—, —OCF$_2$—, —CH$_2$CH$_2$—, or —C≡C—;

$L^{13}$ and $L^{14}$ are independently a hydrogen atom or a fluorine atom; and i is 1, 2, 3, or 4.

Item 12.

The liquid crystal composition according to any one of Items 8 to 11, which contains at least one compound selected from the group of compounds represented by Formulae (11) to (19):

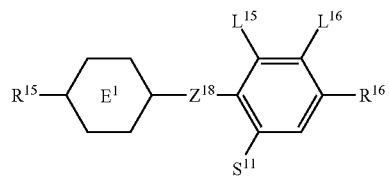
(11)

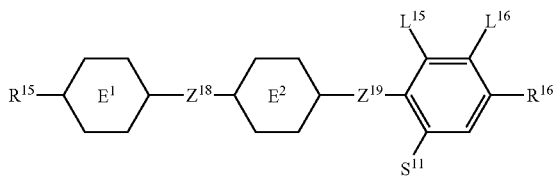
(12)

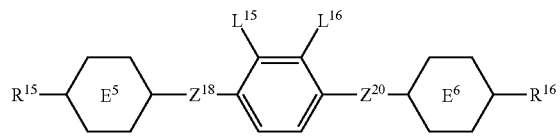
(13)

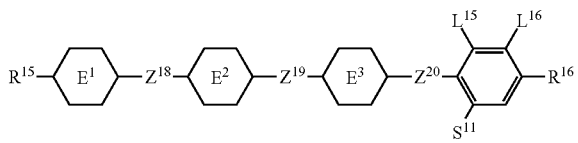
(14)

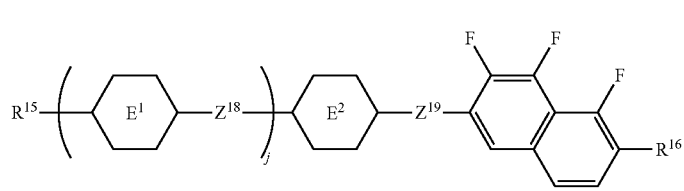
(15)

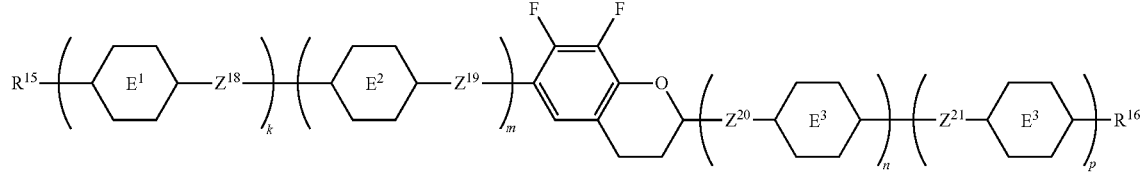
(16)

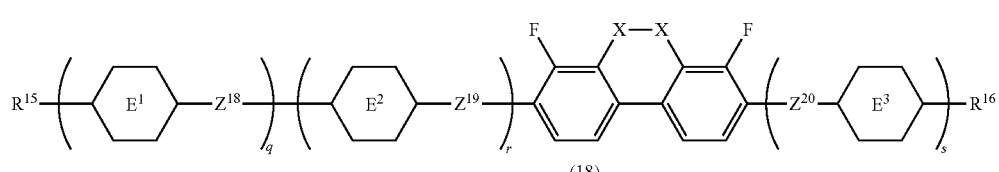
(17)

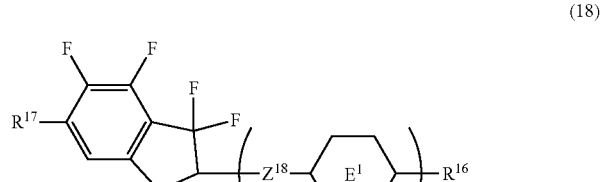
(18)

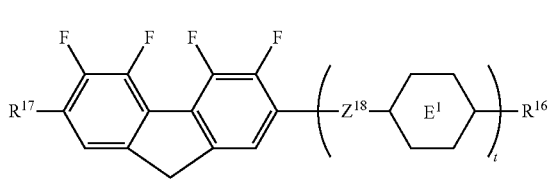
(19)

In Formulae (11) to (19), $R^{15}$, $R^{16}$, and $R^{17}$ are independently an alkyl group having 1 to 10 carbon atoms or an alkenyl group having 2 to 10 carbon atoms, and in these alkyl and alkenyl groups, at least one —CH$_2$— is optionally substituted with —O—, and in these groups, at least one hydrogen atom is optionally substituted with a fluorine atom, and $R^{17}$ may be a hydrogen atom or a fluorine atom;

the ring $E^1$, the ring $E^2$, the ring $E^3$, and the ring $E^4$ are independently 1,4-cyclohexylene, 1,4-cyclohexenylene, 1,4-phenylene, tetrahydropyran-2,5-diyl, decahydronaphthalene-2,6-diyl, or 1,4-phenylene in which at least one hydrogen atom is substituted with a fluorine atom;

the ring $E^5$ and the ring $E^6$ are independently 1,4-cyclohexylene, 1,4-cyclohexenylene, 1,4-phenylene, tetrahydropyran-2,5-diyl, or decahydronaphthalene-2,6-diyl;

$Z^{18}$, $Z^{19}$, $Z^{20}$, and $Z^{21}$ are independently a single bond, —COO—, —OCO—, —CH$_2$O—, —OCH$_2$—, —CF$_2$O—, —OCF$_2$—, —CH$_2$CH$_2$—, —CF$_2$OCH$_2$CH$_2$—, or —OCF$_2$CH$_2$CH$_2$—;

$L^{15}$ and $L^{16}$ are independently a fluorine atom or a chlorine atom;

$S^{11}$ is a hydrogen atom or a methyl group;

X is —CHF— or —CF$_2$—;

j, k, m, n, p, q, r, and s are independently 0 or 1, a sum of k, m, n, and p is 1 or 2, and a sum of q, r, and s is 0, 1, 2, or 3, and t is 1, 2, or 3.

Item 13.

The liquid crystal composition according to any one of Items 8 to 12, which contains at least one polymerizable compound represented by Formula (20) other than the compound represented by Formula (1):

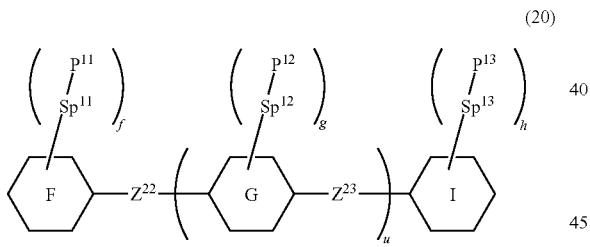

(20)

In Formula (20), the ring F and the ring I are independently cyclohexyl, cyclohexenyl, phenyl, 1-naphthyl, 2-naphthyl, tetrahydropyran-2-yl, 1,3-dioxan-2-yl, pyrimidin-2-yl, or pyridin-2-yl, and in these rings, at least one hydrogen atom is optionally substituted with a halogen atom, an alkyl group having 1 to 12 carbon atoms, an alkoxy group having 1 to 12 carbon atoms, or an alkyl group having 1 to 12 carbon atoms in which at least one hydrogen atom is substituted with a halogen atom;

the ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, phenanthrene-2,7-diyl, tetrahydropyran-2,5-diyl, 1,3-dioxane-2,5-diyl, pyrimidine-2,5-diyl, or pyridine-2,5-diyl, and in these rings, at least one hydrogen atom is optionally substituted with a halogen atom, an alkyl group having 1 to 12 carbon atoms, an alkoxy group having 1 to 12 carbon atoms, or an alkyl group having 1 to 12 carbon atoms in which at least one hydrogen atom is substituted with a halogen atom;

$Z^{22}$ and $Z^{23}$ are independently a single bond or an alkylene group having 1 to 10 carbon atoms, and in this alkylene group, at least one —CH$_2$— is optionally substituted with —O—, —CO—, —COO—, or —OCO—, and at least one —CH$_2$CH$_2$— is optionally substituted with —CH=CH—, —C(CH$_3$)=CH—, —CH=C(CH$_3$)—, or —C(CH$_3$)=C(CH$_3$)—, and in these groups, at least one hydrogen atom is optionally substituted with a fluorine or chlorine atom;

$P^{11}$, $P^{12}$, and $P^{13}$ are independently a polymerizable group;

$Sp^{11}$, $Sp^{12}$, and $Sp^{13}$ are independently a single bond or an alkylene group having 1 to 10 carbon atoms, and in this alkylene group, at least one —CH$_2$— is optionally substituted with —O—, —COO—, —OCO—, or —OCOO—, and at least one —CH$_2$CH$_2$— is optionally substituted with —CH=CH— or —C≡C—, and in these groups, at least one hydrogen atom is optionally substituted with a fluorine or chlorine atom;

u is 0, 1, or 2; and f, g, and h are independently 0, 1, 2, 3, or 4, and a sum of f, g, and h is 1 or more.

Item 14.

The liquid crystal composition according to Item 13, wherein, in Formula (20), $P^{11}$, $P^{12}$, and $P^{13}$ are independently a group selected from the group of polymerizable groups represented by Formula (P-1) to Formula (P-5):

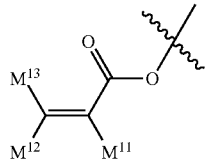

(P-1)

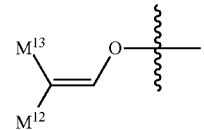

(P-2)

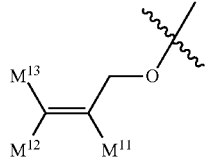

(P-3)

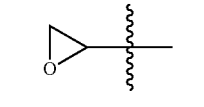

(P-4)

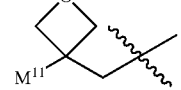

(P-5)

In Formula (P-1) to Formula (P-5), $M^{11}$, $M^{12}$, and $M^{13}$ are independently a hydrogen atom, a fluorine atom, an alkyl group having 1 to 5 carbon atoms, or an alkyl group having 1 to 5 carbon atoms in which at least one hydrogen atom is substituted with a halogen atom.

Item 15.

The liquid crystal composition according to Item 13 or 14, wherein the polymerizable compound represented by Formula (20) is at least one compound selected from the group of polymerizable compounds represented by Formula (20-1) to Formula (20-7):

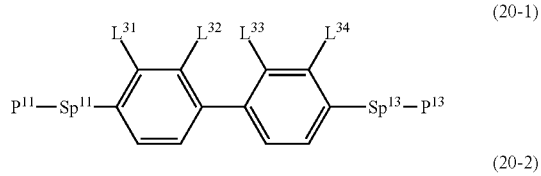
(20-1)

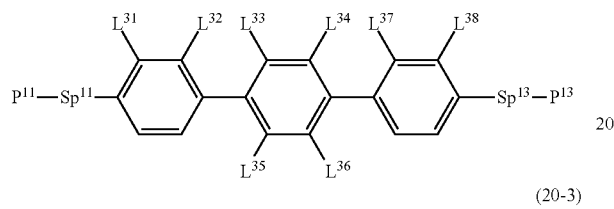
(20-2)

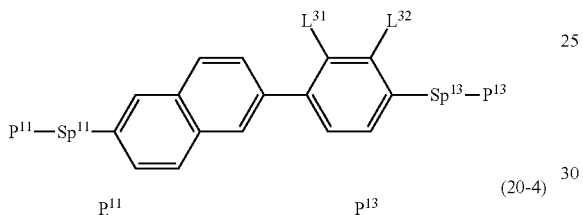
(20-3)

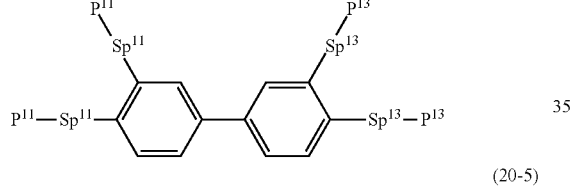
(20-4)

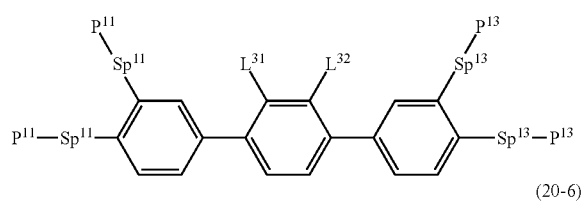
(20-5)

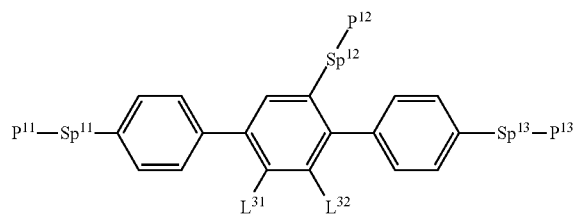
(20-6)

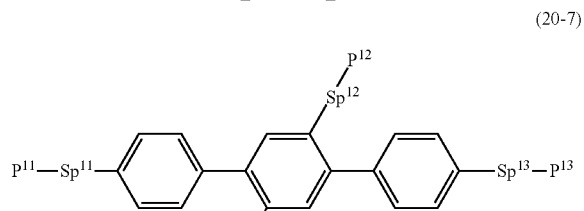
(20-7)

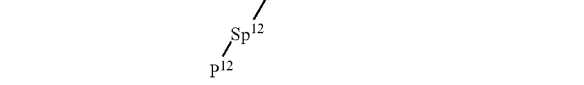

In Formula (20-1) to Formula (20-7), $L^{31}$, $L^{32}$, $L^{33}$, $L^{34}$, $L^{35}$, $L^{36}$, $L^{37}$, and $L^{38}$ are independently a hydrogen atom, a fluorine atom, or a methyl group;

$Sp^{11}$, $Sp^{12}$, and $Sp^{13}$ are independently a single bond or an alkylene group having 1 to 10 carbon atoms, and in this alkylene group, at least one —CH$_2$— is optionally substituted with —O—, —COO—, —OCO—, or —OCOO—, and at least one —CH$_2$CH$_2$— is optionally substituted with —CH=CH— or —C≡C—, and in these groups, at least one hydrogen atom is optionally substituted with a fluorine atom or a chlorine atom $P^{11}$, $P^{12}$, and $P^{13}$ are independently a group selected from the group of polymerizable groups represented by Formula (P-1) to Formula (P-3),

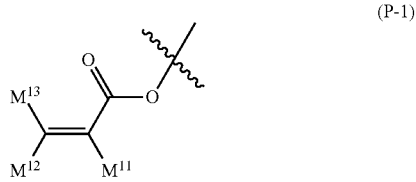
(P-1)

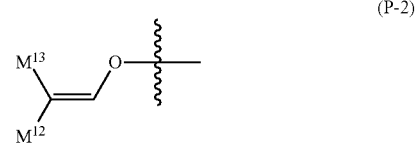
(P-2)

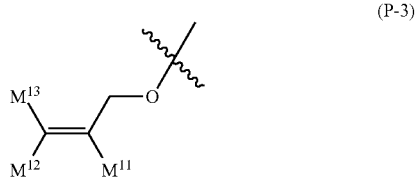
(P-3)

In Formula (P-1) to Formula (P-3), $M^{11}$, $M^{12}$, and $M^{13}$ are independently a hydrogen atom, a fluorine atom, an alkyl group having 1 to 5 carbon atoms, or an alkyl group having 1 to 5 carbon atoms in which at least one hydrogen atom is substituted with a halogen atom.

Item 16.

The liquid crystal composition according to any one of Items 8 to 15, which contains at least one selected from the group consisting of a polymerizable compound different from the compound represented by Formula (1) or Formula (20), a polymerization initiator, a polymerization inhibitor, an optically active compound, an antioxidant, a UV absorber, a light stabilizer, a heat stabilizer, a dye, and an antifoaming agent.

Item 17.

A liquid crystal display element including the liquid crystal composition according to any one of Items 8 to 16 and at least one selected from the group of products obtained by polymerizing at least some of the liquid crystal composition according to any one of Items 8 to 16.

The disclosure also includes the following items.

(a) The liquid crystal composition further containing at least two of additives such as a polymerizable compound, a polymerization initiator, a polymerization inhibitor, an optically active compound, an antioxidant, a UV absorber, a light stabilizer, a heat stabilizer, a dye, and an antifoaming agent.

(b) A polymerizable composition prepared by adding a polymerizable compound different from Compound (1) and Compound (20) to the liquid crystal composition.

(c) A polymerizable composition prepared by adding Compound (1) and Compound (20) to the liquid crystal composition.
(d) A liquid crystal composite prepared by polymerizing the polymerizable composition.
(e) A polymer sustained alignment type element containing the liquid crystal composite.
(f) A polymer sustained alignment type element produced using a polymerizable composition prepared by adding Compound (1) and Compound (20), and a polymerizable compound different from Compound (1) and Compound (20) to the liquid crystal composition.

Embodiments of Compound (1), synthesis of Compound (1), a liquid crystal composition, and a liquid crystal display element will be described below in order.

1. Embodiments of Compound (1)

Compound (1) of the disclosure has a perfluoroalkyl chain, a polar group, and at least one polymerizable moiety. Compound (1) is beneficial because a polar group non-covalently interacts with a surface of a glass (or a metal oxide) substrate. One of applications is an additive for a liquid crystal composition used for a liquid crystal display element. In this application, Compound (1) is added in order to control the alignment of liquid crystal molecules. Such an additive is chemically stable under conditions in which it is sealed in the element, and an additive having a high ability to align liquid crystal molecules, high solubility in a liquid crystal composition, and a high voltage holding ratio when used for a liquid crystal display element is preferable. Compound (1) has such properties to a considerable extent, and has a high voltage holding ratio when it is sued for a liquid crystal display element which was not possible to obtain in compounds of the related art. When Compound (1) is used, it is possible to easily obtain an element having excellent alignment properties and long-term stability compared to a case in which compounds of the related art are used.

Preferable examples of Compound (1) will be described. Preferable examples of symbols such as $R^1$ and $Sp^1$ in Compound (1) also apply to sub-formulas of Compound (1), for example, Formula (1-1). In Compound (1), when types of these groups are appropriately combined, it is possible to arbitrarily adjust properties. Compound (1) may contain a larger amount of isotopes such as $^2H$ (deuterium) and $^{13}C$ than a natural abundance of these isotopes since there are no significant differences in properties of such compounds.

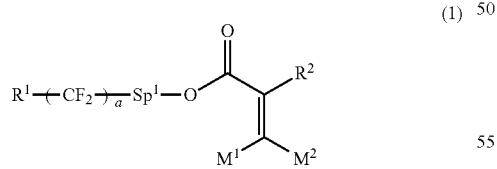

(1)

$R^1$ is an alkyl group having 1 to 15 carbon atoms, and in this alkyl group, at least one $-CH_2-$ is optionally substituted with $-O-$ or $-S-$, and at least one $-(CH_2)_2-$ is optionally substituted with $-CH=CH-$ or $-C\equiv C-$, and in these groups, at least one hydrogen atom is optionally substituted with a fluorine atom or a chlorine atom.

Preferably, $R^1$ is an alkyl group having 1 to 15 carbon atoms, at least one $-CH_2-$ is optionally substituted with $-O-$, and at least one $-(CH_2)_2-$ is optionally substituted with $-CH=CH-$.

More preferably, $R^1$ is an alkyl group having 1 to 15 carbon atoms, and at least one $-CH_2-$ is optionally substituted with $-O-$.

Particularly preferably, $R^1$ is an alkyl group having 1 to 10 carbon atoms.

A compound in which $R^1$ is an alkyl group having 1 to 15 carbon atoms, an alkoxy group having 1 to 14 carbon atoms, or an alkoxyalkyl group having 1 to 14 carbon atoms has high chemical stability. A compound in which $R^1$ is an alkyl group having 1 to 15 carbon atoms, an alkenyl group having 2 to 15 carbon atoms, an alkenyloxy group having 2 to 14 carbon atoms, or an alkenyloxyalkyl group having 2 to 14 carbon atoms has high solubility in a liquid crystal composition. A compound in which $R^1$ is an alkyl group having 1 to 15 carbon atoms has a high ability to align liquid crystal molecules.

a is an integer of 2 to 12. Preferably, a is an integer of 2 to 8. Particularly preferably, a is 4 or 6.

A compound in which a is an integer of 2 to 6 has high solubility in a liquid crystal composition. A compound in which a is an integer of 4 to 12 has a high ability to align liquid crystal molecules. A compound in which a is 4 or 6 has high solubility in a liquid crystal composition, a high ability to align liquid crystal molecules, and a high voltage holding when used for a liquid crystal display element.

$M^1$ and $M^2$ are independently a hydrogen atom, a fluorine atom, a chlorine atom, an alkyl group having 1 to 5 carbon atoms, or an alkyl group having 1 to 5 carbon atoms in which at least one hydrogen atom is substituted with a fluorine or chlorine atom, preferably a hydrogen atom, a fluorine atom, an alkyl group having 1 to 5 carbon atoms, or an alkyl group having 1 to 5 carbon atoms in which at least one hydrogen atom is substituted with a fluorine atom, and more preferably a hydrogen atom in order to obtain a compound having particularly high polymerization reactivity according to ultraviolet radiation.

$R^2$ is a group selected from among groups represented by Formula (1-a), Formula (1-b), and Formula (1-c). Preferably, $R^2$ is a group represented by Formula (1-a) or Formula (1-b). More preferably, $R^2$ is a group represented by Formula (1-a).

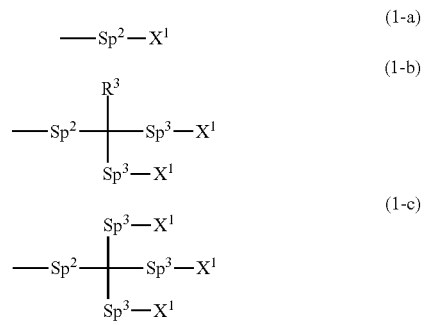

When $R^2$ is a group represented by Formula (1-a), solubility in a liquid crystal composition is high and a voltage holding ratio when used for a liquid crystal display element is high. When $R^2$ is a group represented by Formula (1-b) or Formula (1-c), an ability to align liquid crystal molecules is high. When $R^2$ is a group represented by Formula (1-b), solubility in a liquid crystal composition is high and an ability to align liquid crystal molecules is high.

In Formula (1-a), Formula (1-b), and Formula (1-c), $Sp^2$ and $Sp^3$ are independently a single bond or an alkylene group having 1 to 10 carbon atoms, and in this alkylene group, at least one —CH$_2$— is optionally substituted with —O—, —CO—, —COO—, —OCO—, or —OCOO—, and at least one —(CH$_2$)$_2$— is optionally substituted with —CH=CH— or —C≡C—, and in these groups, at least one hydrogen atom is optionally substituted with a fluorine or chlorine atom.

Preferably, Sp$^2$ and Sp$^3$ are independently a single bond or an alkylene group having 1 to 10 carbon atoms, and in this alkylene group, at least one —CH$_2$— is optionally substituted with —O—, and at least one —(CH$_2$)$_2$— is optionally substituted with —CH=CH—, and in these groups, at least one hydrogen atom is optionally substituted with a fluorine atom. More preferably, Sp$^2$ and Sp$^3$ are an alkylene group having 1 to 8 carbon atoms, and in this alkylene group, at least one —CH$_2$— is optionally substituted with —O—.

A compound in which Sp$^2$ and Sp$^3$ are independently a single bond or an alkylene group having 1 to 8 carbon atoms has high chemical stability. A compound in which Sp$^2$ and Sp$^3$ are independently an alkylene group having 1 to 8 carbon atoms, or a group in which at least one —CH$_2$— of an alkylene group having 1 to 8 carbon atoms is substituted with —O— has high solubility in a liquid crystal composition and a high ability to align liquid crystal molecules.

In Formula (1-b), R$^3$ is a hydrogen atom, an alkyl group having 1 to 10 carbon atoms, an alkoxy group having 1 to 9 carbon atoms, or an alkoxyalkyl group having 1 to 9 carbon atoms. Preferably, R$^3$ is a hydrogen, an alkyl group having 1 to 7 carbon atoms, an alkoxy group having 1 to 6 carbon atoms, or an alkoxyalkyl group having 1 to 6 carbon atoms. More preferably, R$^3$ is a hydrogen atom or an alkyl group having 1 to 5 carbon atoms. Particularly preferably, R$^3$ is a hydrogen atom or an alkyl group having 1 to 5 carbon atoms.

In Formula (1-a), Formula (1-b), and Formula (1-c), X$^1$ is independently —OH, —NH$_2$, —N(R$^4$)$_2$, —COOH, —SH, or —Si(R$^4$)$_3$, and in —N(R$^4$)$_2$, and —Si(R$^4$)$_3$, R$^4$ is a hydrogen atom or an alkyl group having 1 to 10 carbon atoms, and in this alkyl group, at least one —CH$_2$— is optionally substituted with —O—, and at least one —(CH$_2$)$_2$— is optionally substituted with —CH=CH—, and in these groups, at least one hydrogen atom is optionally substituted with a fluorine atom or a chlorine atom.

Preferably, X$^1$ is independently —OH, —NH$_2$, —COOH, or —SH. Particularly preferably, X$^1$ is —OH. When X$^1$ is independently —OH, —NH$_2$, —COOH, or —SH, an ability to align liquid crystal molecules is high. When X$^1$ is —OH, solubility in a liquid crystal composition is high, an ability to align liquid crystal molecules is high, and a voltage holding ratio when used for a liquid crystal display element is high.

In Formula (1), Sp$^1$ is a single bond or an alkylene group having 1 to 15 carbon atoms, and in this alkylene group, at least one —CH$_2$— is optionally substituted with —O—, —CO—, —COO—, —OCO—, or —OCOO— and at least one —(CH$_2$)$_2$— is optionally substituted with —CH=CH— or —C≡C—, and in these groups, at least one hydrogen atom is optionally substituted with a fluorine atom, a chlorine atom, or a group represented by Formula (1-d).

Preferably, Sp$^1$ is a single bond, an alkylene group having 1 to 10 carbon atoms in which at least one —CH$_2$— is optionally substituted with —O—, or an alkylene group having 1 to 10 carbon atoms in which at least one —CH$_2$— is substituted with a group represented by Formula (1-d) and at least one —CH$_2$— is optionally substituted with —O—. More preferably, Sp$^1$ is an alkylene group having 1 to 7 carbon atoms in which at least one —CH$_2$— is optionally substituted with —O—. Particularly preferably, Sp$^1$ is an alkylene group having 3 carbon atoms.

When Sp$^1$ is a single bond or an alkylene group having 1 to 10 carbon atoms in which at least one —CH$_2$— is optionally substituted with —O—, an ability to align liquid crystal molecules is high. When Sp$^1$ is an alkylene group having 1 to 10 carbon atoms in which at least one —CH$_2$— is substituted with a group represented by Formula (1-d) and at least one —CH$_2$— is optionally substituted with —O—, a voltage holding ratio when used for a liquid crystal display element is high. When Sp$^1$ is an alkylene group having 3 carbon atoms, solubility in a liquid crystal composition is high, an ability to align liquid crystal molecules is high, and a voltage holding ratio when used for a liquid crystal display element is high.

In Formula (1-d), Sp$^4$ is a single bond or an alkylene group having 1 to 10 carbon atoms, and in this alkylene group, at least one —CH$_2$— is optionally substituted with —O—, —CO—, —COO—, —OCO—, or —OCOO—, and at least one —(CH$_2$)$_2$— is optionally substituted with —CH=CH— or —C≡C—, and in these groups, at least one hydrogen atom is optionally substituted with a fluorine atom or a chlorine atom.

Preferably, Sp$^4$ is a single bond or an alkylene group having 1 to 10 carbon atoms, and in this alkylene group, at least one —CH$_2$— is optionally substituted with —O—, and at least one —(CH$_2$)$_2$— is optionally substituted with —CH=CH—, and in these groups, at least one hydrogen atom is optionally substituted with a fluorine atom. More preferably, Sp$^4$ is an alkylene group having 1 to 10 carbon atoms, and in this alkylene group, at least one —CH$_2$— is optionally substituted with —O—.

A compound in which Sp$^4$ is a single bond or an alkylene group having 1 to 10 carbon atoms has high chemical stability. A compound in which Sp$^4$ is an alkylene group having 1 to 10 carbon atoms, or a group in which at least one —CH$_2$— of an alkylene group having 1 to 10 carbon atoms is substituted with —O— has high solubility in a liquid crystal composition.

In Formula (1-d), M$^3$ and M$^4$ are independently a hydrogen atom, a fluorine atom, a chlorine atom, an alkyl group having 1 to 5 carbon atoms, or an alkyl group having 1 to 5 carbon atoms in which at least one hydrogen atom is substituted with a fluorine or chlorine atom, preferably a hydrogen atom, a fluorine atom, an alkyl group having 1 to 5 carbon atoms, or an alkyl group having 1 to 5 carbon atoms in which at least one hydrogen atom is substituted with a fluorine atom, and more preferably a hydrogen atom in order to obtain a compound having particularly high polymerization reactivity according to ultraviolet radiation.

In Formula (1-d), R$^5$ is a hydrogen atom or an alkyl group having 1 to 10 carbon atoms, and in this alkyl group, at least one —CH$_2$— is optionally substituted with —O—, at least one —(CH$_2$)$_2$— is optionally substituted with —CH=CH— or —C≡C—, and at least one hydrogen atom is optionally substituted with a fluorine atom or a chlorine atom.

Preferably, R$^5$ is a hydrogen atom or an alkyl group having 1 to 5 carbon atoms. In order to obtain a compound

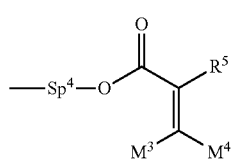

(1-d)

having superior solubility in a liquid crystal composition, high chemical stability, and a high ability to align liquid crystal molecules, particularly preferably, $R^5$ is a methyl group.

Examples of a preferable Compound (1) include Compounds (1-1) to (1-6) described in Item 4. Examples of a more preferable Compound (1) include Compounds (1-7) to (1-24) described in Item 5. Examples of a still more preferable Compound (1) include Compounds (1-25) to (1-48) described in Item 6. Examples a most preferable Compound (1) include Compounds (1-49) to (1-56) described in Item 7.

2. Synthesis of Compound (1)

A synthesis method of Compound (1) will be described. Compound (1) can be synthesized by appropriately combining methods in organic synthetic chemistry. Compounds of which synthesis methods are not described can be synthesized according to methods in books such as "Organic Syntheses" (John Wiley & Sons, Inc), "Organic Reactions" (John Wiley & Sons, Inc), "Comprehensive Organic Synthesis" (Pergamon Press), and "New Course of Experimental Chemistry" (Maruzen)."

2-1. Synthesis Example

Examples of methods of synthesizing Compound (1) are as follows. In these compounds, definitions of $R^1$, $R^2$, $R^3$, $R^4$, $R^5$, a, $Sp^1$, $Sp^2$, $Sp^3$, $Sp^4$, $M^1$, $M^2$, $M^3$, and $M^4$ are the same as those described in Item 1.

Compound (1-61) in which $R^1$ is an alkyl having more than 3 carbon atoms, $Sp^1$ is an alkylene group having more than 2 carbon atoms, $M^1$ and $M^2$ are a hydrogen atom, $R^2$ is a group represented by Formula (1-a), $Sp^2$ is —$CH_2$—, and $X^1$ is —OH in Formula (1) can be synthesized by the following method. Compound (51) and Compound (52) are reacted under radical generation conditions of sodium dithionite and sodium hydrogen carbonate to obtain Compound (53). Compound (53) and Compound (54) are reacted under radical generation conditions to obtain Compound (55). Compound (55) is reduced using lithium aluminum hydride to obtain Compound (56). Compound (56) and Compound (57) synthesized according to the method described in WO2017209161A1 are reacted in the presence of dicyclohexylcarbodiimide (DCC) and 4-dimethylaminophosphine (DMAP) to obtain Compound (58), and then deprotected using pyridinium p-toluenesulfonate (PPTS), and thereby Compound (1-61) can be derived. Here, the two-stage reaction for obtaining Compound (55) from Compound (51) can also be performed in one-pot.

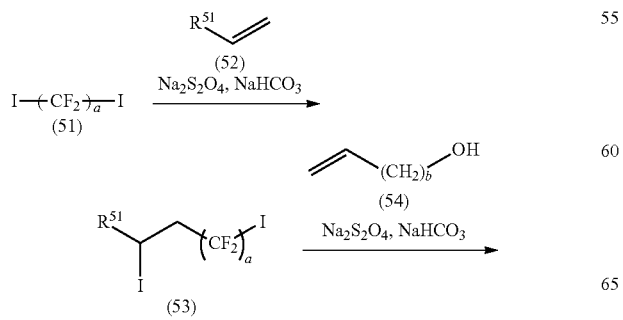

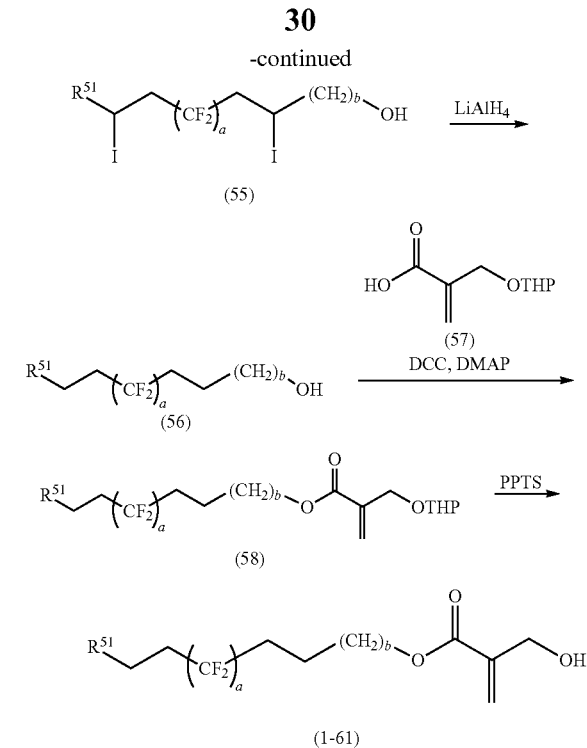

In these formulae, $R^{51}$ is an alkyl group having 1 to 13 carbon atoms, a is an integer of 2 to 12, and b is an integer of 0 to 13.

Compound (1-62) in which $R^1$ is an alkyl having more than 3 carbon atoms, $Sp^1$ is —$CH_2$—, $M^1$ and $M^2$ are a hydrogen atom, $R^2$ is a group represented by Formula (1-a), $Sp^2$ is —$CH_2$—, and $X^1$ is —OH in Formula (1) can be synthesized by the following method. Compound (53) is reacted with formaldehyde and methyl lithium to obtain Compound (59). Compound (59) is reduced using lithium aluminum hydride to obtain Compound (60). Compound (60) and Compound (57) are reacted in the presence of DCC and DMAP to obtain Compound (61) and then deprotected using PPTS, and thereby Compound (1-62) can be derived.

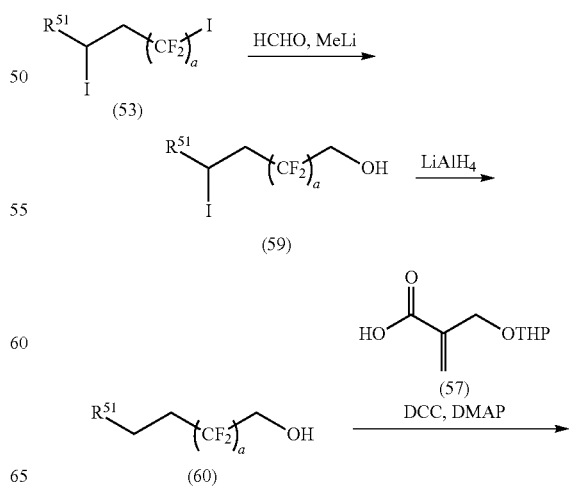

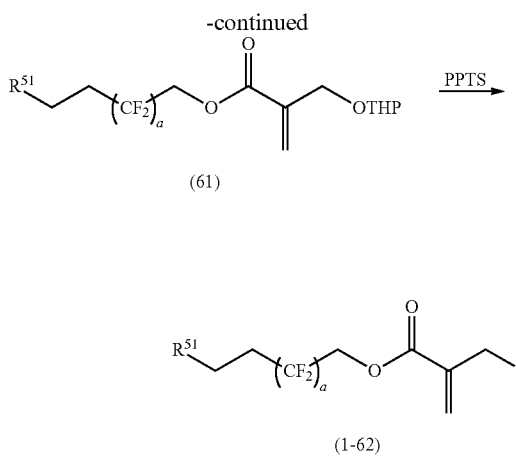

(61)

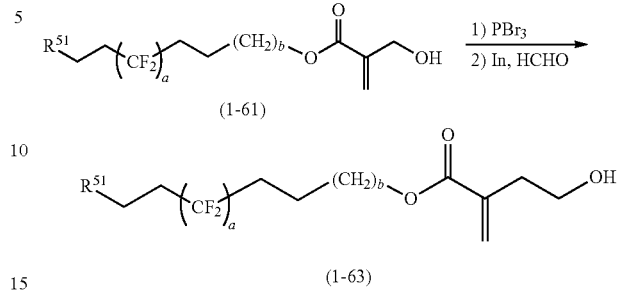

(1-62)

In these formulae, $R^{51}$ is an alkyl group having 1 to 13 carbon atoms, and a is an integer of 2 to 12.

Compound (1-63) in which $R^1$ is an alkyl having more than 3 carbon atoms, $Sp^1$ is an alkylene group having more than 2 carbon atoms, $M^1$ and $M^2$ are a hydrogen atom, $R^2$ is a group represented by Formula (1-a), $Sp^2$ is —CH$_2$CH$_2$—, and $X^1$ is —OH in Formula (1) can be synthesized by the following method. Compound (1-61) is reacted with phosphorus tribromide and brominated, and then reacted with formaldehyde in the presence of an indium catalyst, and thereby Compound (1-63) can be derived.

In these formulae, $R^{51}$ is an alkyl group having 1 to 13 carbon atoms, a is an integer of 2 to 12, and b is an integer of 0 to 13.

Compound (1-64) in which $R^1$ is an alkyl having more than 3 carbon atoms, $Sp^1$ is an alkylene group having more than 2 carbon atoms, $M^1$ and $M^2$ are a hydrogen atom, $R^2$ is a group represented by Formula (1-a), $Sp^2$ is —CH$_2$O(CH$_2$)$_c$—, and $X^1$ is —OH in Formula (1) can be synthesized by the following method. Compound (1-61) is reacted with trifluoromethanesulfonic anhydride (Tf$_2$O) and triethylamine and then reacted with a diol (HO—CH$_2$—OH) corresponding to a carbon number of c, and thereby Compound (1-64) can be derived.

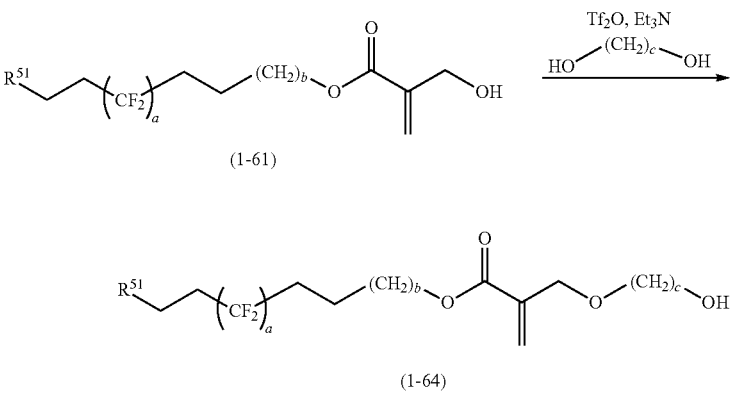

In these formulae, $R^{51}$ is an alkyl group having 1 to 13 carbon atoms, a is an integer of 2 to 12, b is an integer of 0 to 13, and c is an integer of 1 to 8.

Compound (1-65) in which $R^1$ is an alkyl having more than 3 carbon atoms, $Sp^1$ is —CH$_2$CH$_2$(CH$_2$)$_d$CH(CH$_2$OCOC(CH$_3$)=CH$_2$)CH$_2$—, $M^1$, $M^2$, $M^3$, and $M^4$ are a hydrogen atom, $R^2$ is a group represented by Formula (1-a), $Sp^2$ is —CH$_2$—, and $X^1$ is —OH in Formula (1) can be synthesized by the following method.

Compound (56) is brominated with carbon tetrabromide and triphenylphosphine to obtain Compound (62) and is then added to diethyl malonate using sodium hydride to obtain Compound (63). Compound (63) is reduced using lithium aluminum hydride to obtain Compound (64) and then reacted with methacryloyl chloride and triethylamine to obtain Compound (65). Compound (65) and Compound (57) are reacted in the presence of DCC and DMAP to obtain Compound (66) and then deprotected using PPTS, and thereby Compound (1-65) can be derived.

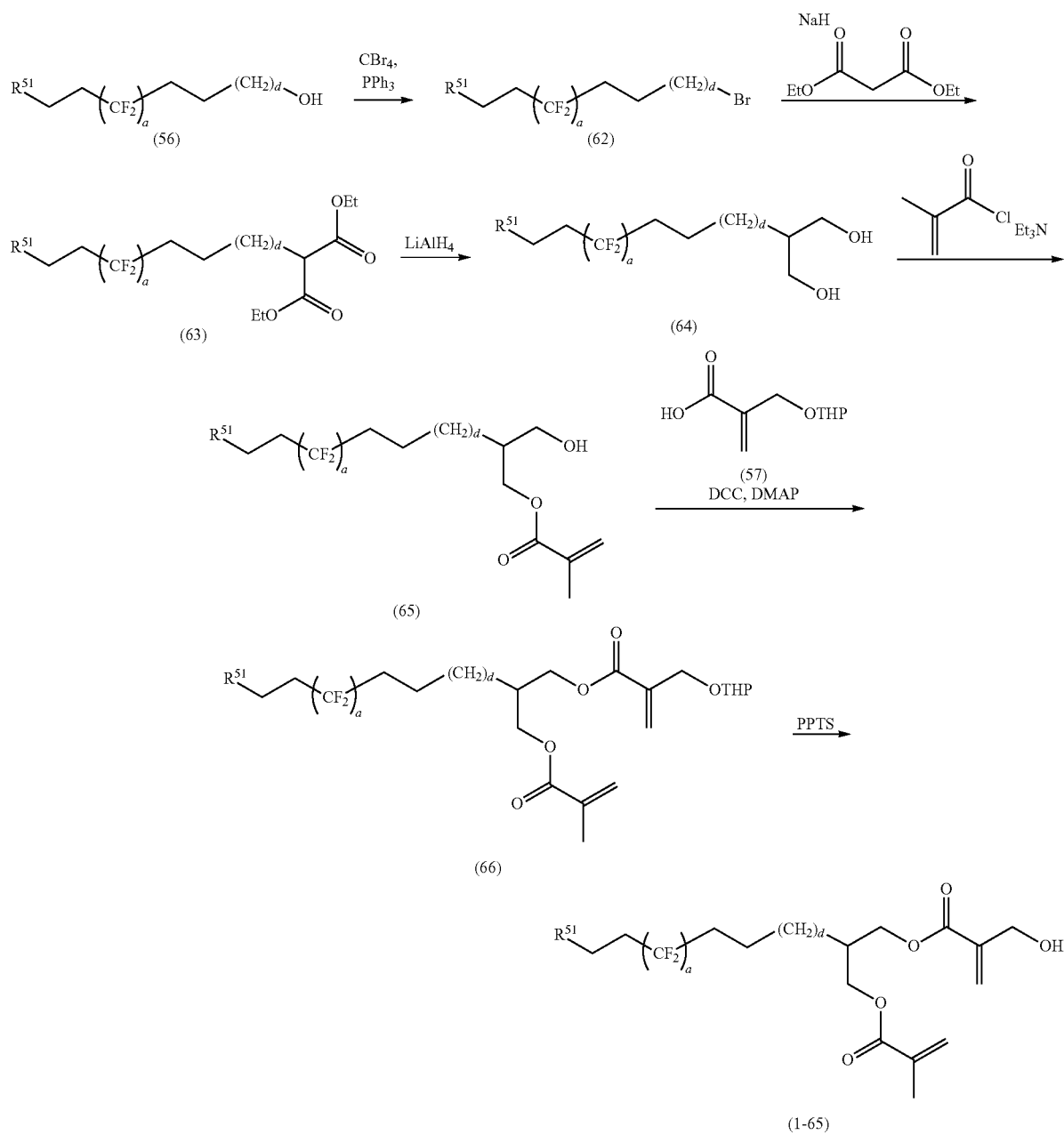

In these formulae, $R^{51}$ is an alkyl group having 1 to 13 carbon atoms, a is an integer of 2 to 12, and d is an integer of 0 to 11.

Compound (1-66) in which $R^1$ is an alkyl having more than 3 carbon atoms, $Sp^1$ is an alkylene group having more than 2 carbon atoms, $M^1$ and $M^2$ are a hydrogen atom, $R^2$ is a group represented by Formula (1-b), $Sp^2$ and $Sp^3$ are —$CH_2$—, $R^3$ is a hydrogen atom, and both of $X^1$ are —OH in Formula (1) can be synthesized by the following method.

Compound (67) is iodinated with iodine, triphenylphosphine, and imidazole to obtain Compound (68), and then Compound (69) and sodium hydride, paraformaldehyde, and potassium carbonate are sequentially reacted to obtain Compound (70). Compound (70) is hydrolyzed using lithium hydroxide to obtain Compound (71). Compound (56) and Compound (71) are reacted in the presence of DCC and DMAP to obtain Compound (72) and then deprotected using PPTS, and thereby Compound (1-66) can be derived.

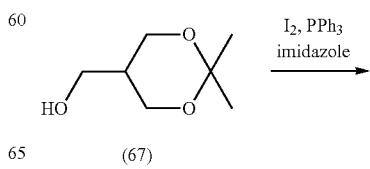
(67)

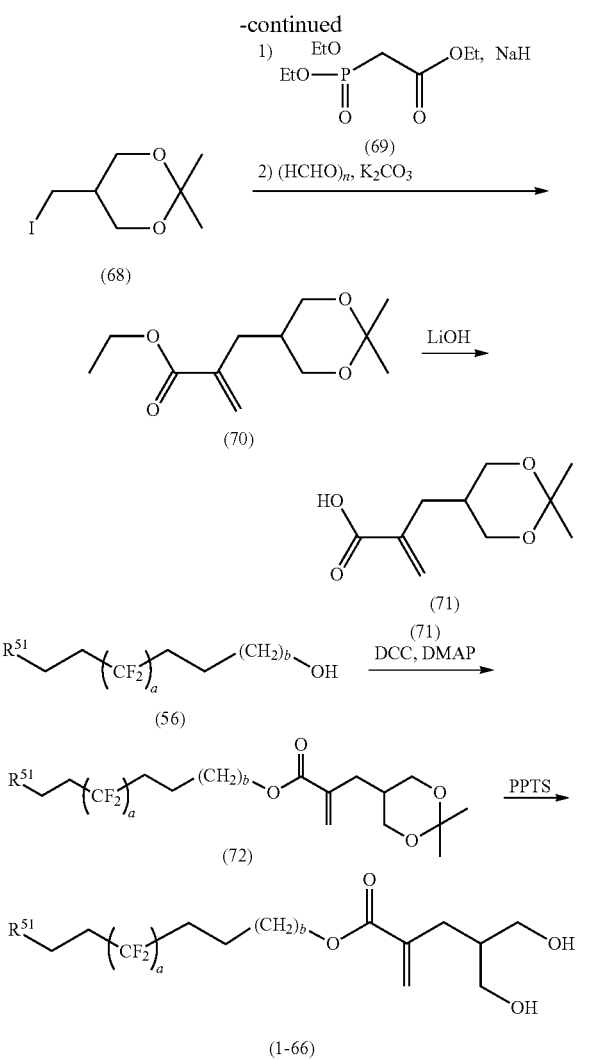

In these formulae, $R^{51}$ is an alkyl group having 1 to 13 carbon atoms, a is an integer of 2 to 12, and b is an integer of 0 to 13.

3. Liquid Crystal Composition

3-1. Component Compounds

A liquid crystal composition of the disclosure includes Compound (1) as a component A. Compound (1) can control the alignment of liquid crystal molecules according to a noncovalent interaction with a substrate of an element. This composition contains Compound (1) as a component A, and preferably further contains at least one liquid crystalline compound selected from the following components B, C, D, and E. The component B is Compounds (2) to (4). The component C is Compounds (5) to (7). The component D is Compound (8). The component E is Compounds (11) to (19). This composition may contain other liquid crystalline compounds different from Compounds (2) to (8) and (11) to (19). When this composition is prepared, the components B, C, D, and E are preferably selected in consideration of a magnitude of positive or negative dielectric anisotropy. A composition containing components appropriately selected has a high upper limit temperature, a low lower limit temperature, a low viscosity, appropriate optical anisotropy (that is, large optical anisotropy or small optical anisotropy), large positive or negative dielectric anisotropy, a large specific resistance, stability with respect to heat or ultraviolet rays, and an appropriate elastic constant (that is, a large elastic constant or a small elastic constant).

Compound (1) is added to the composition in order to control the alignment of liquid crystal molecules. A preferable proportion of Compound (1) with respect to 100 weight % of a liquid crystal composition is 0.05 weight % or more in order to easily align liquid crystal molecules, and preferably 10 weight % or less in order to further prevent display defects of an element. A more preferably proportion is in a range of 0.1 weight % to 7 weight %, and a particularly preferable portion is in a range of 0.4 weight % to 5 weight %. These proportions also apply to a composition containing Compound (20).

The component B is a compound in which two terminal groups are an alkyl group. The component B has small dielectric anisotropy. Preferable examples of the component B include Compounds (2-1) to (2-11), Compounds (3-1) to (3-19), and Compounds (4-1) to (4-7). In these compounds, $R^{11}$ and $R^{12}$ are independently an alkyl group having 1 to 10 carbon atoms or an alkenyl group having 2 to 10 carbon atoms, and in this alkyl or alkenyl group, at least one —$CH_2$— is optionally substituted with —O—, and at least one hydrogen atom is optionally substituted with a fluorine atom.

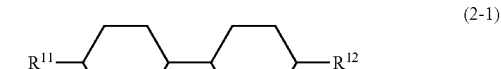
(2-1)

(2-2)

(2-3)

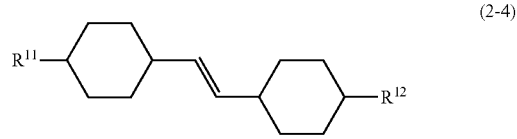
(2-4)

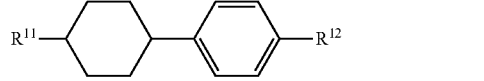
(2-5)

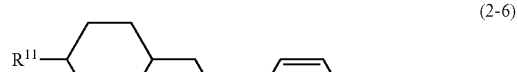
(2-6)

(2-7)

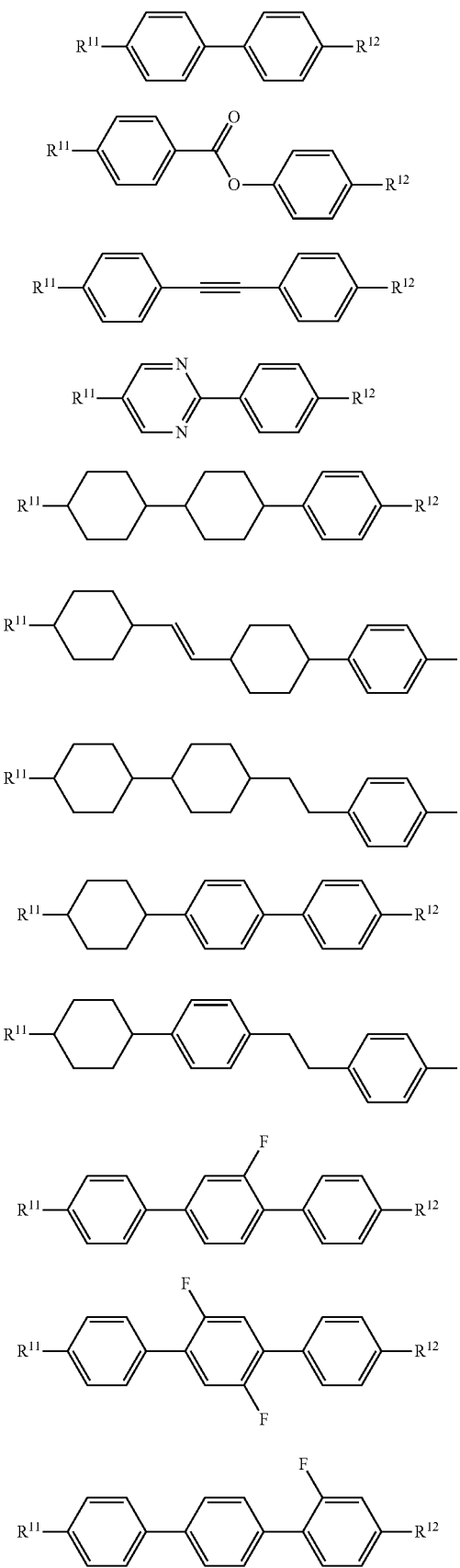
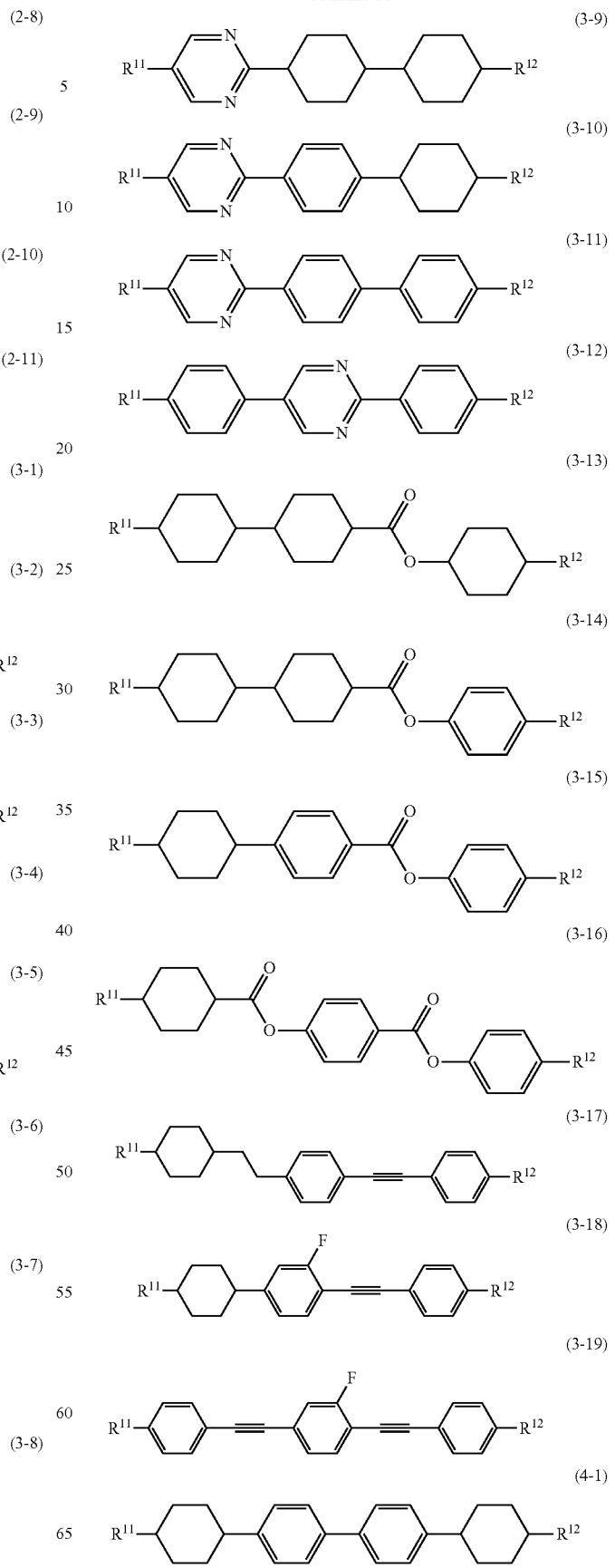

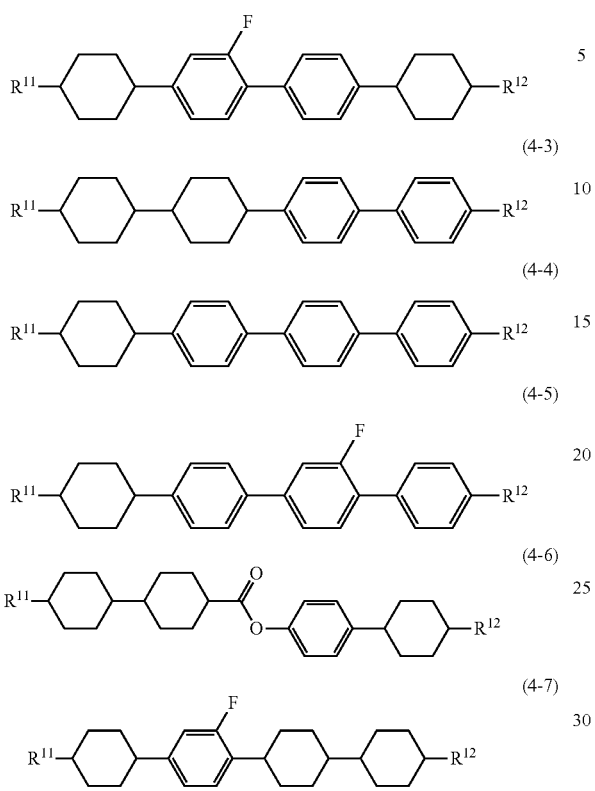

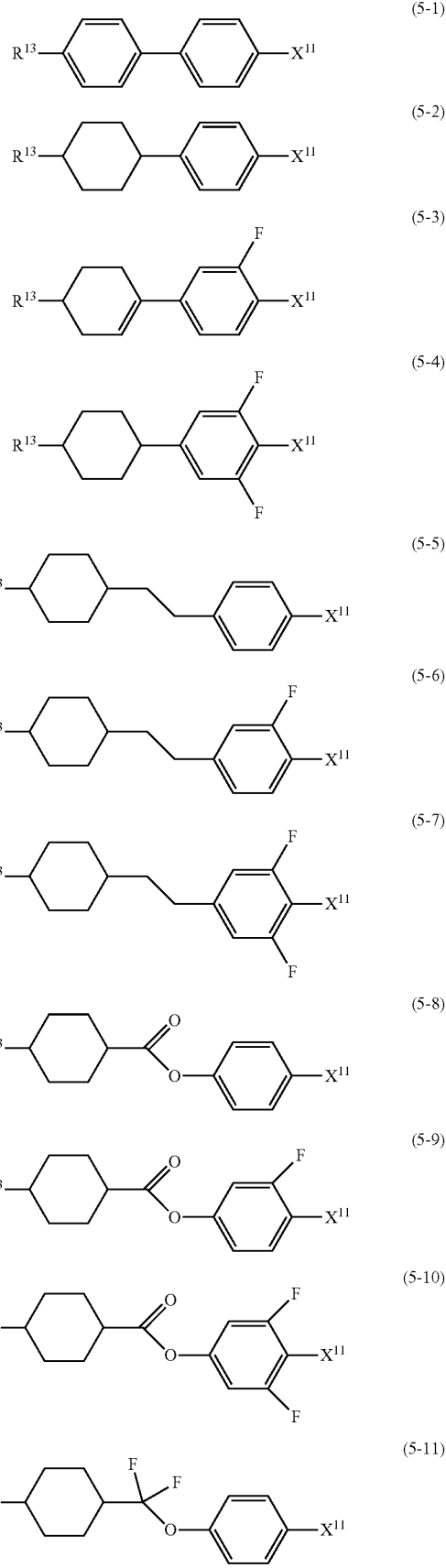

The component B is a compound close to being neutral because an absolute value of dielectric anisotropy is small. Compound (2) has an effect of mainly lowering the viscosity or adjusting the optical anisotropy. Compounds (3) and (4) have an effect of increasing an upper limit temperature and thus widening a temperature range of the nematic phase or an effect of adjusting the optical anisotropy.

As the content of the component B increases, the dielectric anisotropy of the composition decreases but the viscosity decreases. Therefore, a higher content of the component B is preferable as long as a threshold voltage of the element has a required value. The content of the component B is preferably 30 weight % or more, and more preferably 40 weight % or more with respect to 100 weight % of a liquid crystal composition and an upper limit thereof is not particularly limited, but may be, for example, 99.95 weight %.

The component C is a compound having a fluorine atom, a chlorine atom or a fluorine-containing group at at least one end. The component C has large positive dielectric anisotropy. Preferable examples of the component C include Compounds (5-1) to (5-16), Compounds (6-1) to (6-116), and Compounds (7-1) to (7-59). In a compound containing the component C, $R^{13}$ is an alkyl group having 1 to 10 carbon atoms or an alkenyl group having 2 to 10 carbon atoms, and in these alkyl and alkenyl groups, at least one —$CH_2$— is optionally substituted with —O—, at least one hydrogen atom is optionally substituted with a fluorine atom; and $X^{11}$ is a fluorine atom, a chlorine atom, —$OCF_3$, —$OCHF_2$, —$CF_3$, —$CHF_2$, —$CH_2F$, —$OCF_2CHF_2$, or —$OCF_2CHFCF_3$.

(5-12) 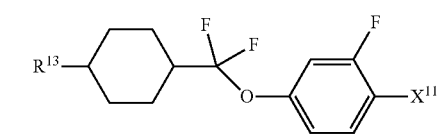
(5-13) 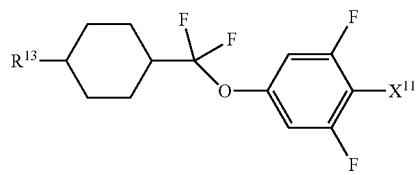
(5-14) 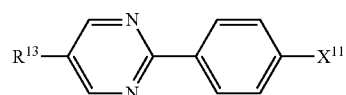
(5-15) 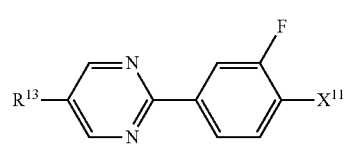
(5-16) 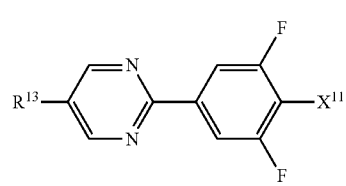
(6-1) 
(6-2) 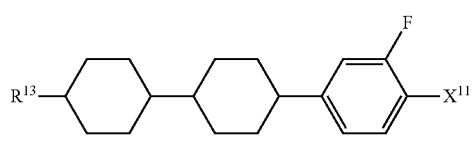
(6-3) 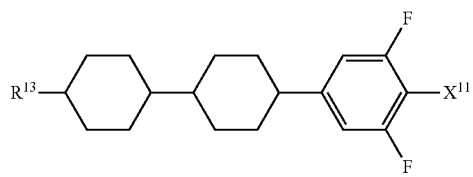
(6-4) 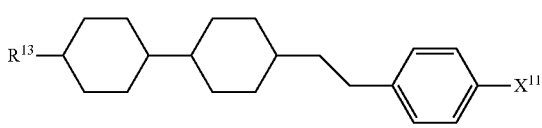
(6-5) 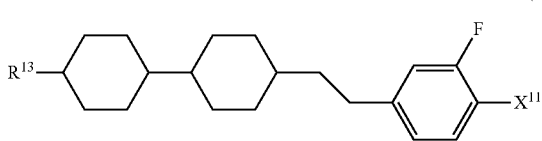
(6-6) 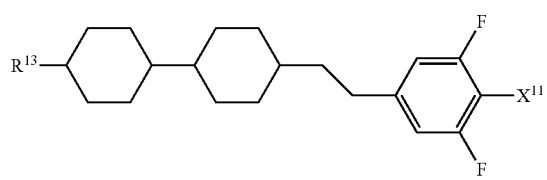
(6-7) 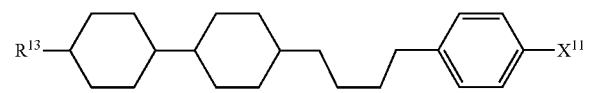
(6-8) 
(6-9) 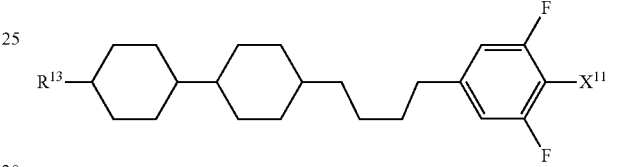
(6-10) 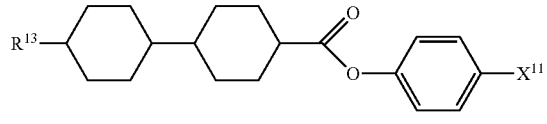
(6-11) 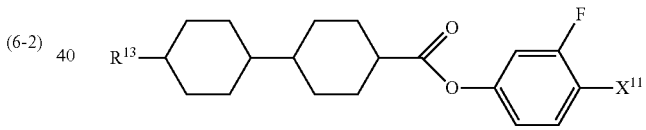
(6-12) 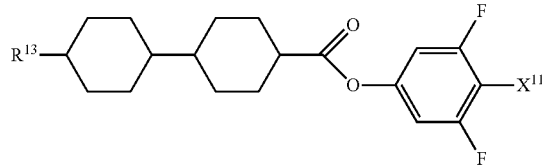
(6-13) 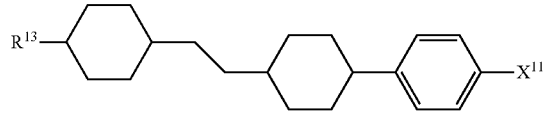
(6-14) 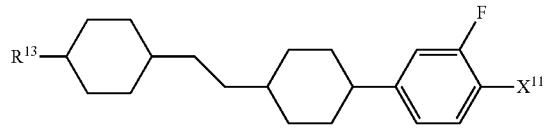

(6-15) 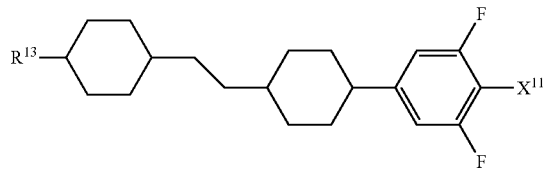
(6-16) 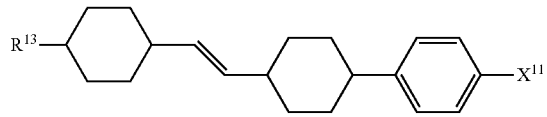
(6-17) 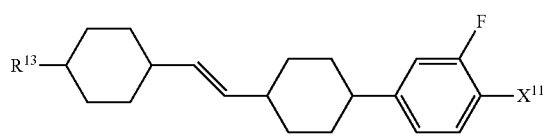
(6-18) 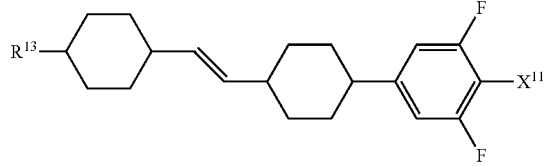
(6-19) 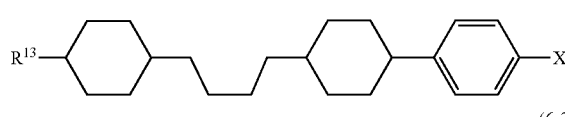
(6-20) 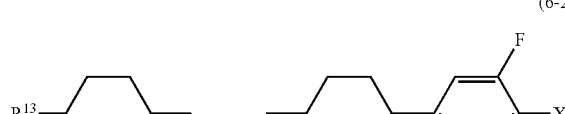
(6-21) 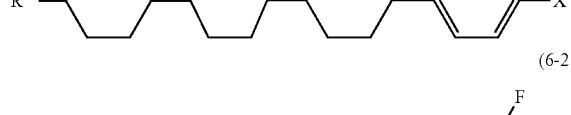
(6-22) 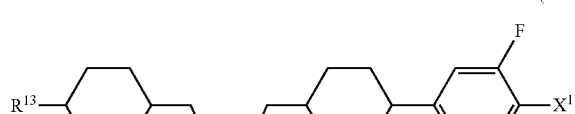
(6-23) 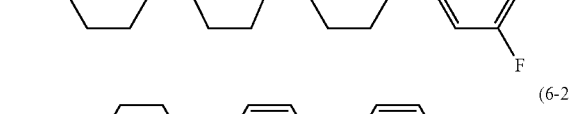
(6-24) 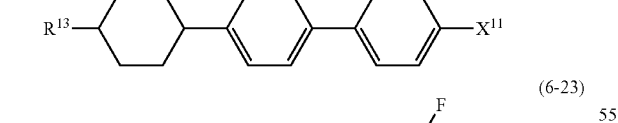
(6-25) 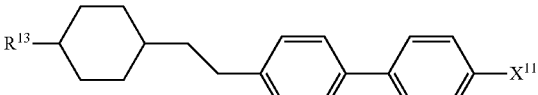
(6-26) 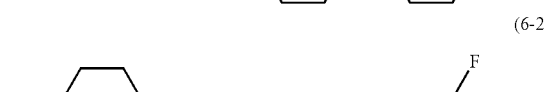
(6-27) 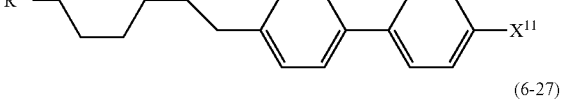
(6-28) 
(6-29) 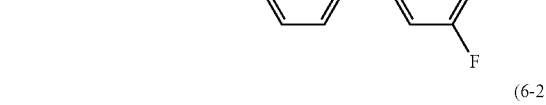
(6-30) 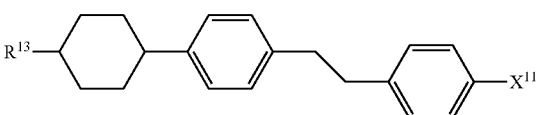
(6-31) 
(6-32) 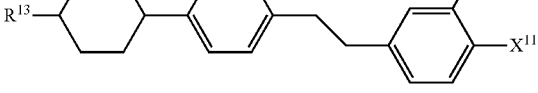
(6-33) 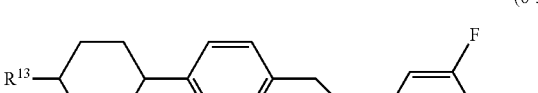
(6-34) 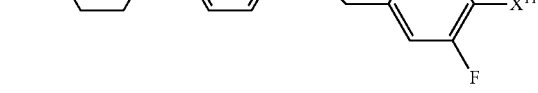

(6-35) 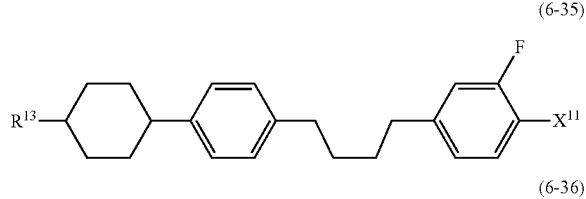
(6-36) 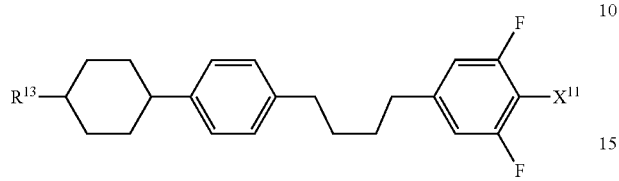
(6-37) 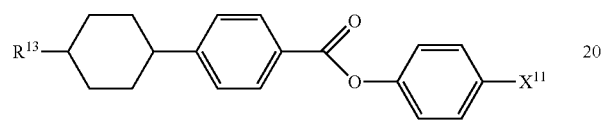
(6-38) 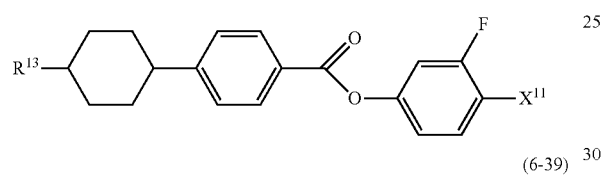
(6-39) 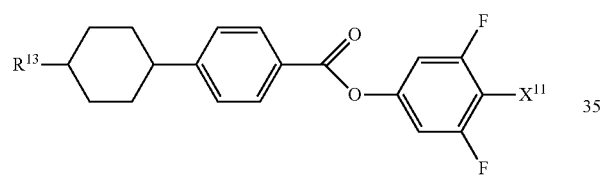
(6-40) 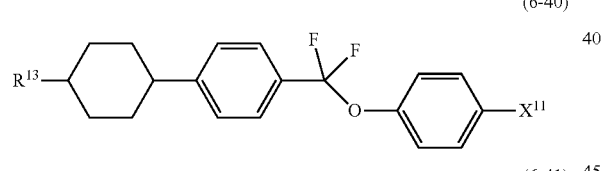
(6-41) 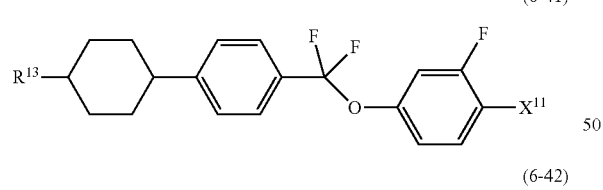
(6-42) 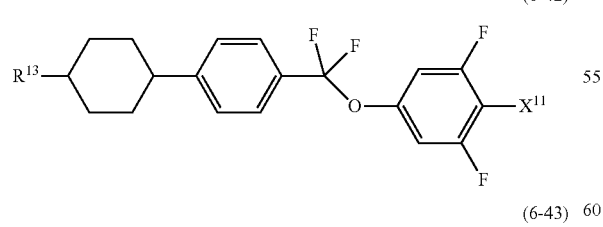
(6-43) 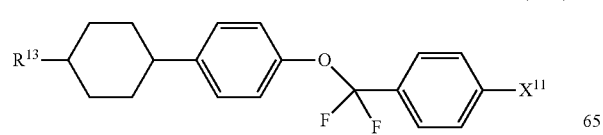
(6-44) 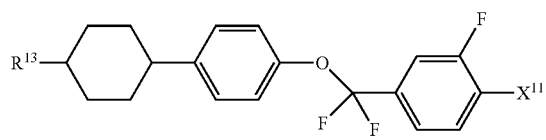
(6-45) 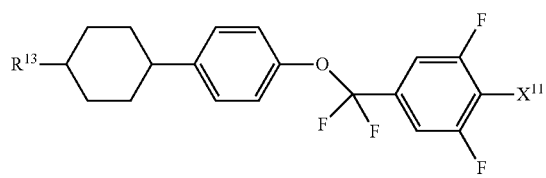
(6-46) 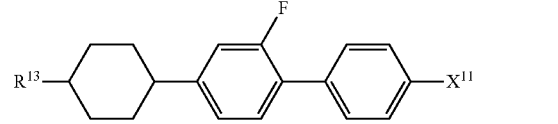
(6-47) 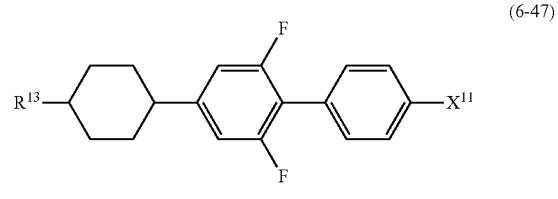
(6-48) 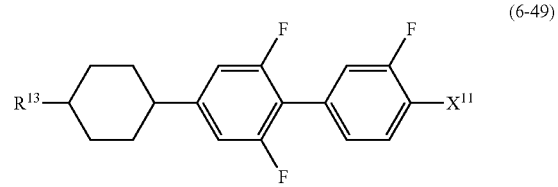
(6-49) 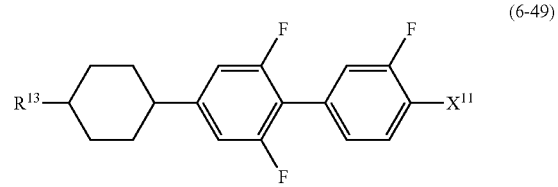
(6-50) 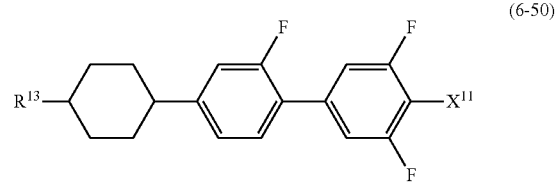
(6-51) 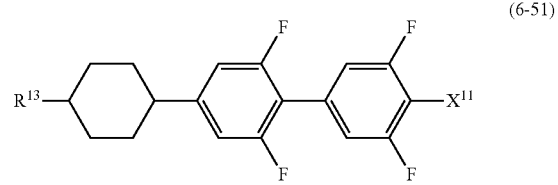
(6-52) 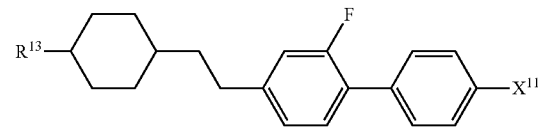

(6-53) 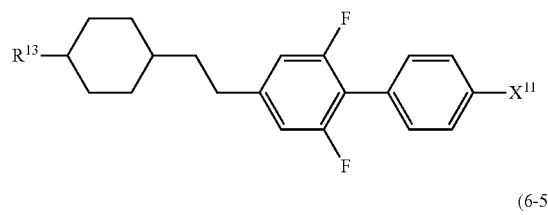
(6-54) 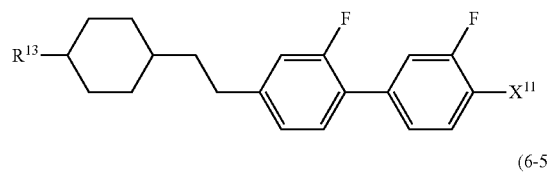
(6-55) 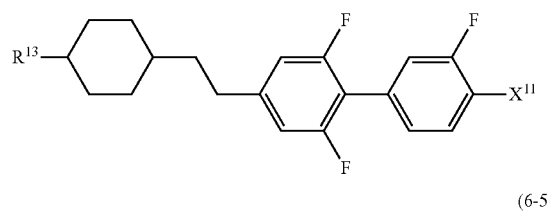
(6-56) 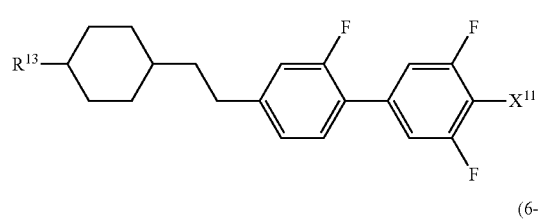
(6-57) 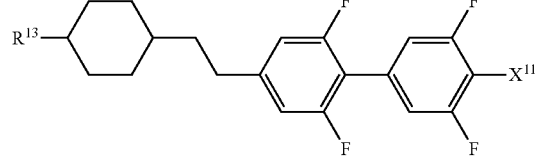
(6-58) 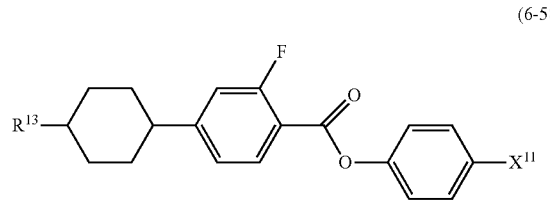
(6-59) 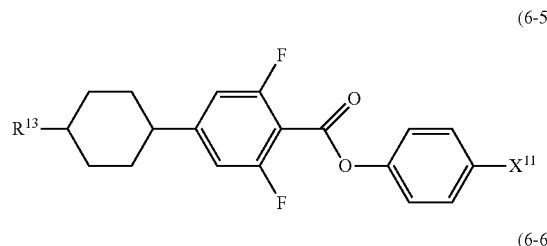
(6-60) 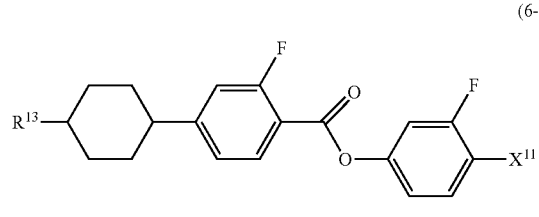
(6-61) 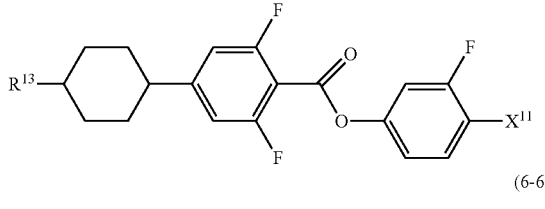
(6-62) 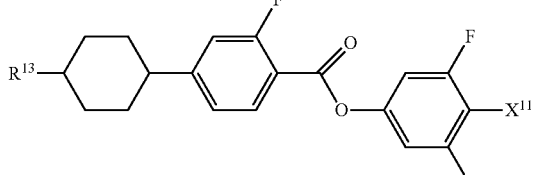
(6-63) 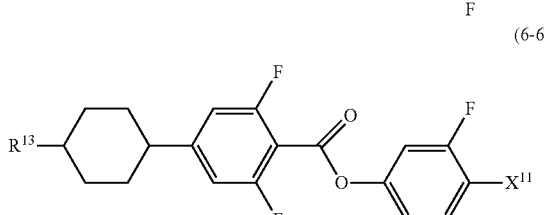
(6-64) 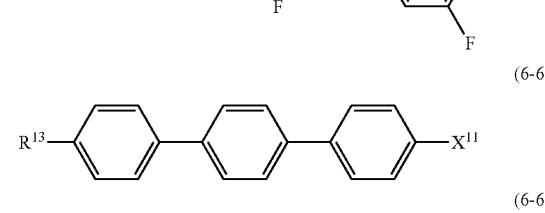
(6-65) 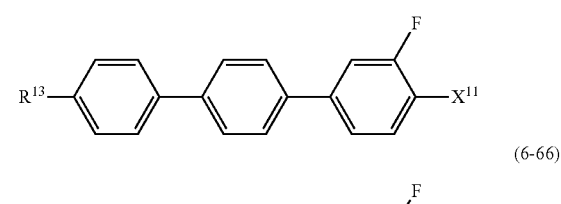
(6-66) 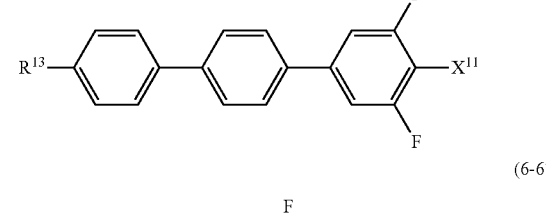
(6-67) 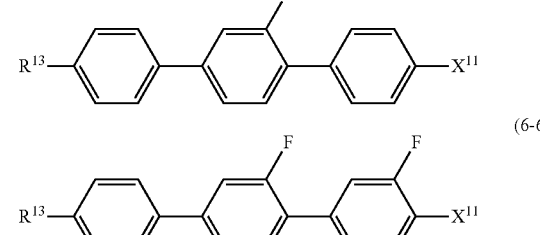
(6-68) 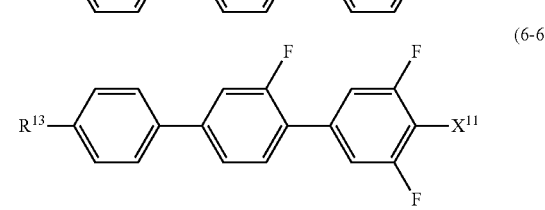

(6-70) 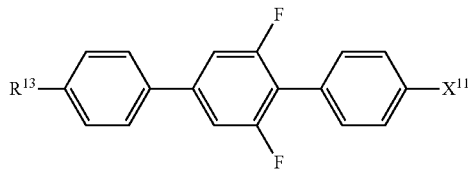
(6-71) 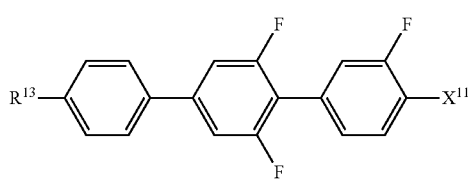
(6-72) 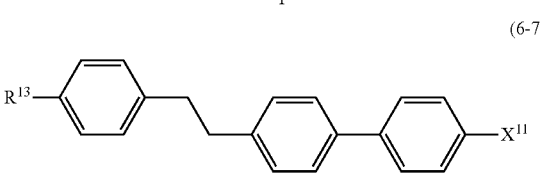
(6-73) 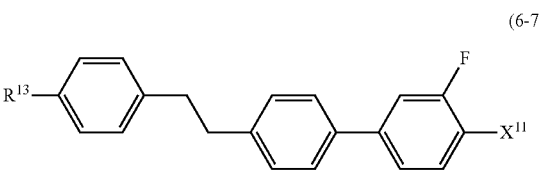
(6-74) 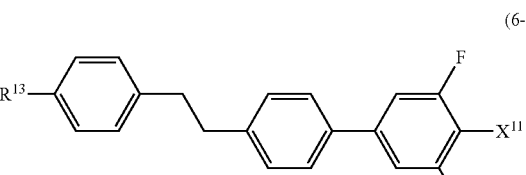
(6-75) 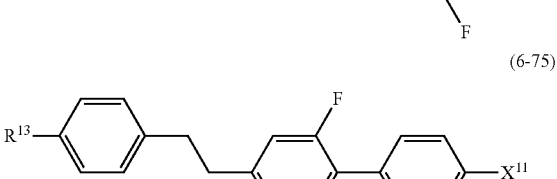
(6-76) 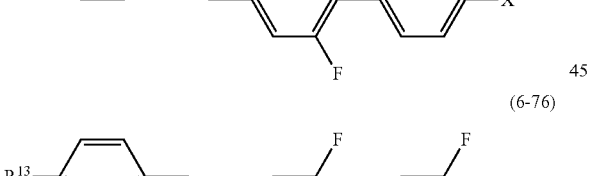
(6-77) 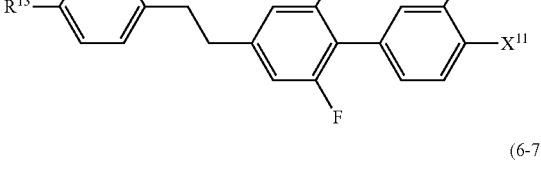
(6-78) 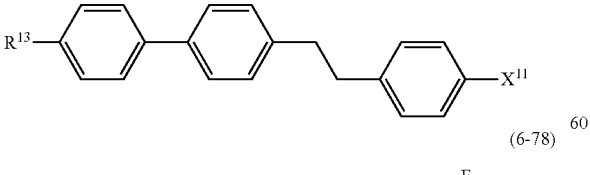
(6-79) 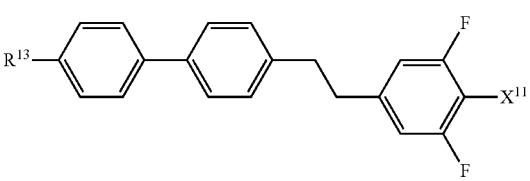
(6-80) 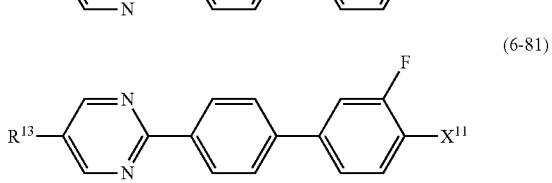
(6-81) 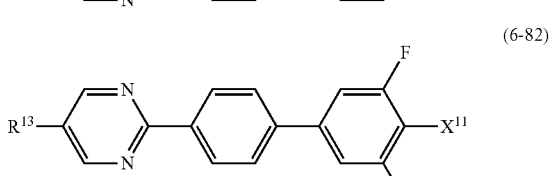
(6-82) 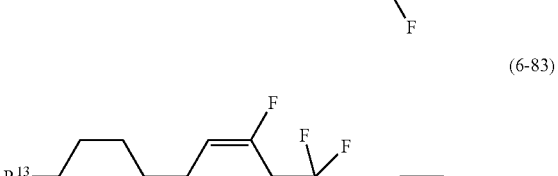
(6-83) 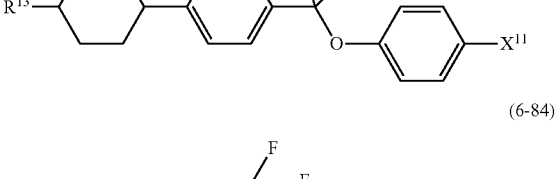
(6-84) 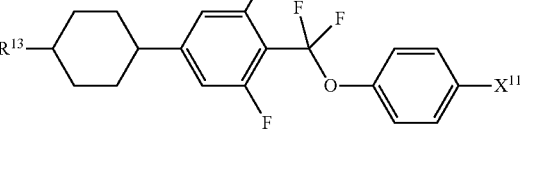
(6-85) 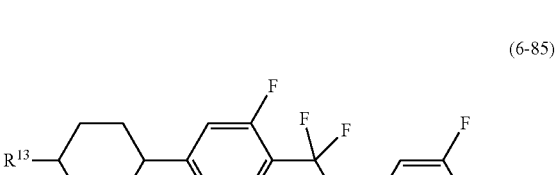
(6-86) 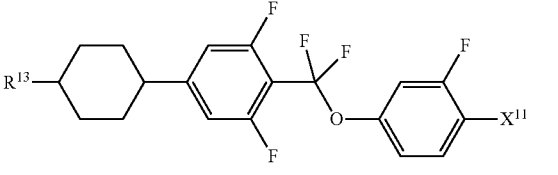

(6-104) 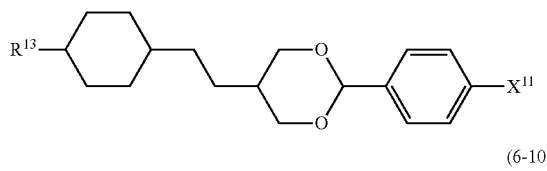
(6-105) 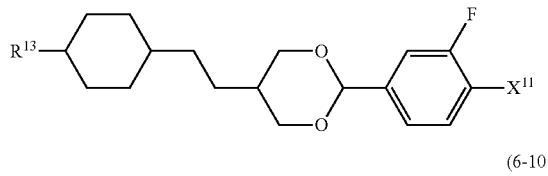
(6-106) 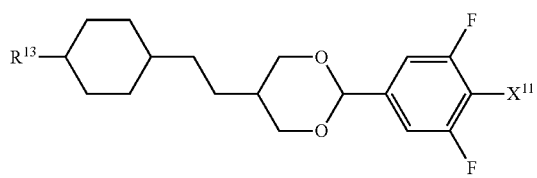
(6-107) 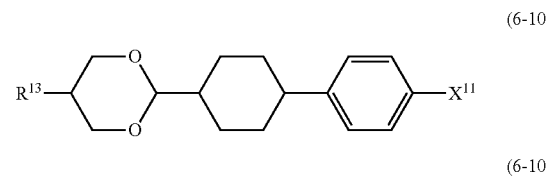
(6-108) 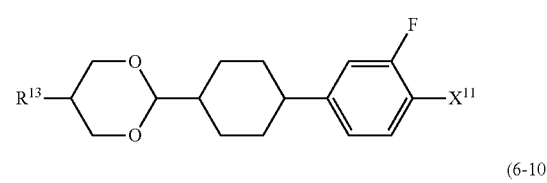
(6-109) 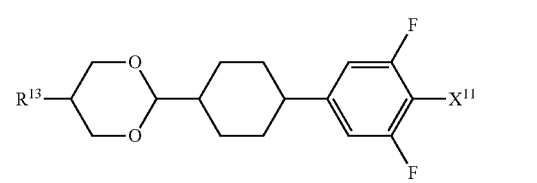
(6-110) 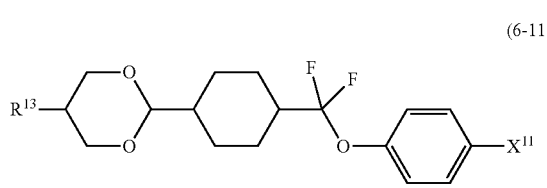
(6-111) 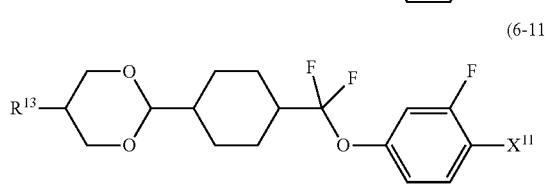
(6-112) 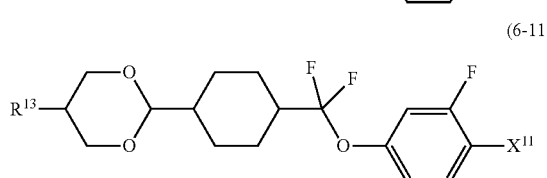
(6-113) 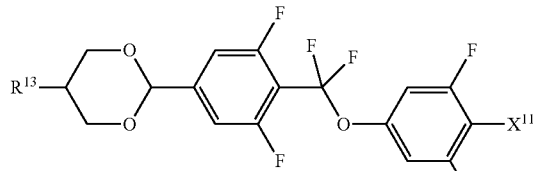
(6-114) 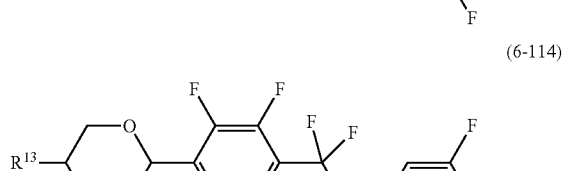
(6-115) 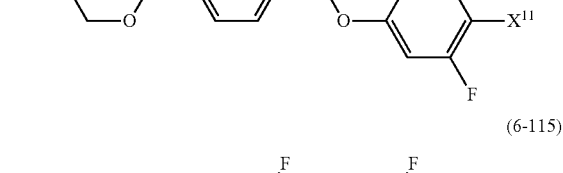
(6-116) 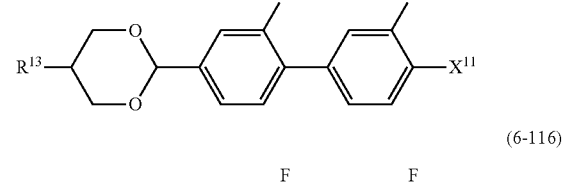
(7-1) 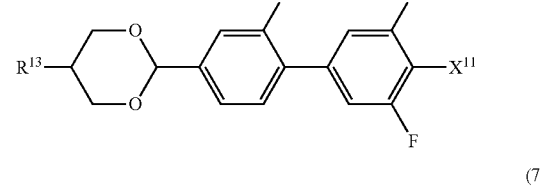
(7-2) 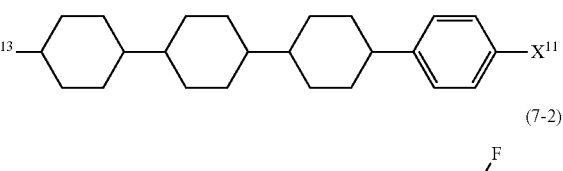
(7-3) 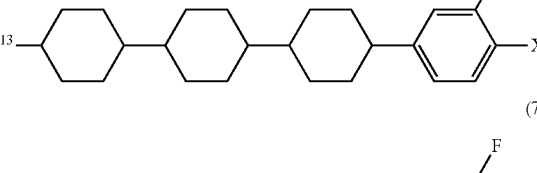
(7-4) 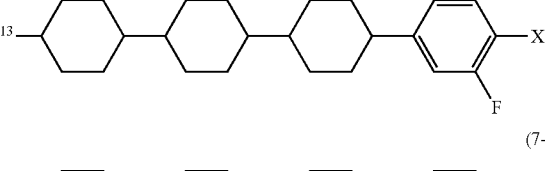
(7-5) 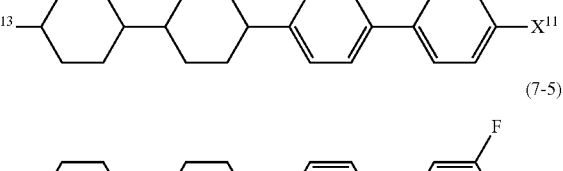

(7-6) 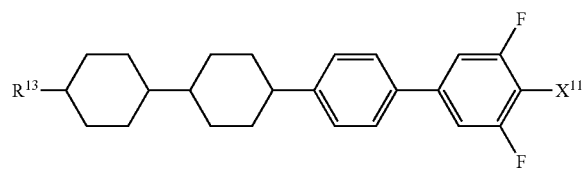
(7-7) 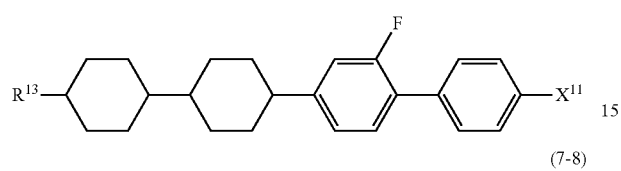
(7-8) 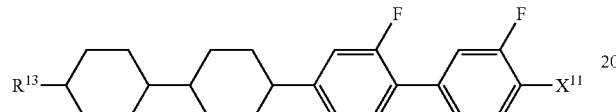
(7-9) 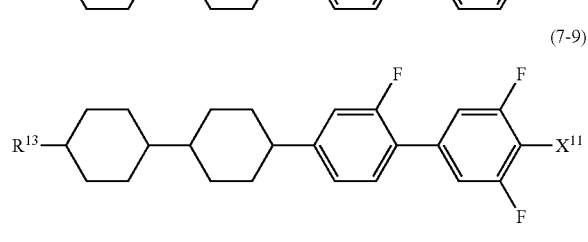
(7-10) 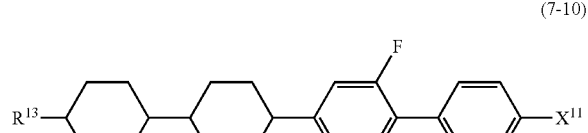
(7-11) 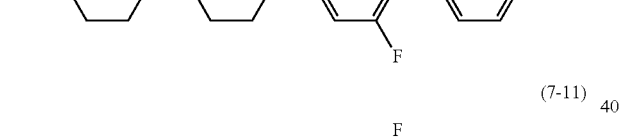
(7-12) 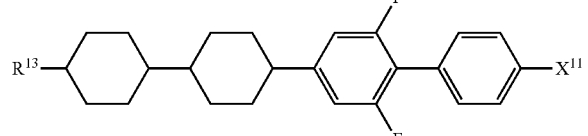
(7-13) 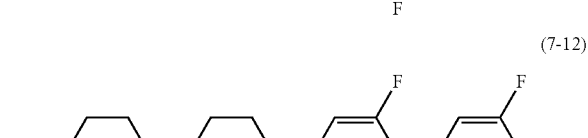
(7-14) 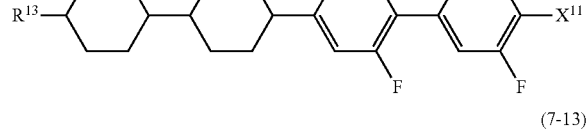
(7-15) 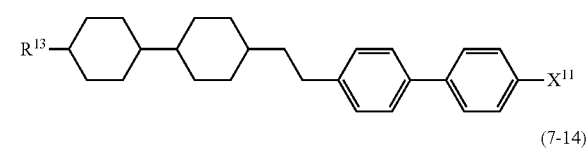
(7-16) 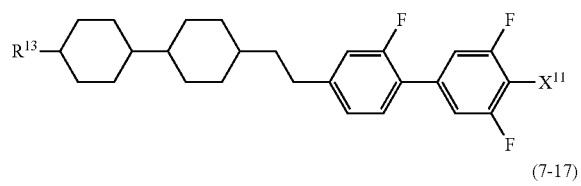
(7-17) 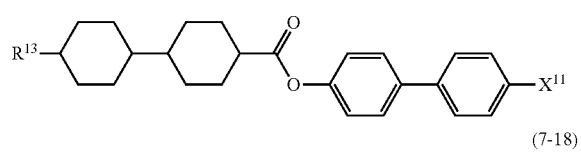
(7-18) 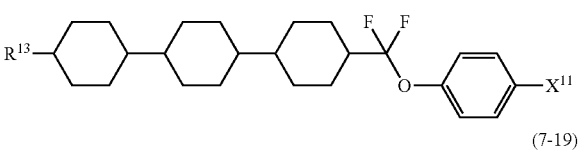
(7-19) 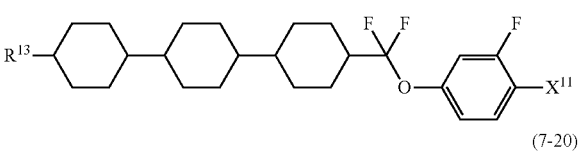
(7-20) 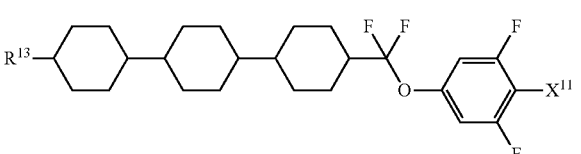
(7-21) 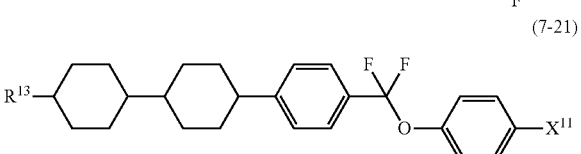
(7-22) 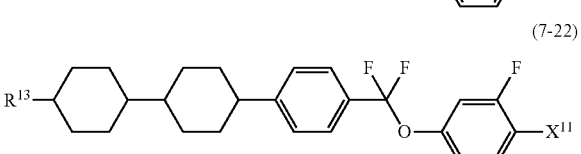
(7-23) 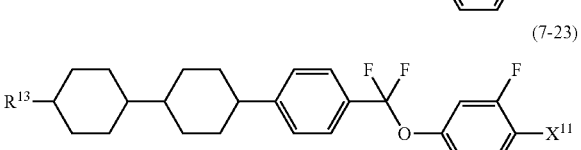
(7-24) 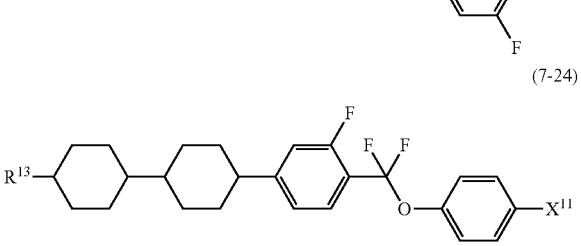

(7-25) 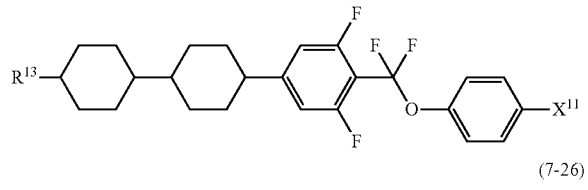
(7-26) 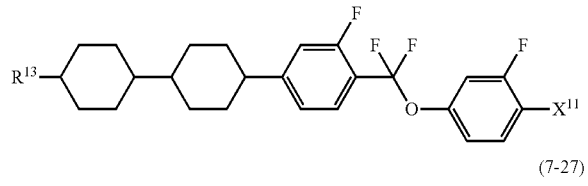
(7-27) 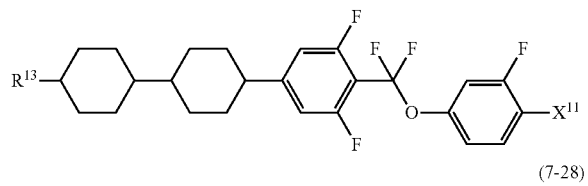
(7-28) 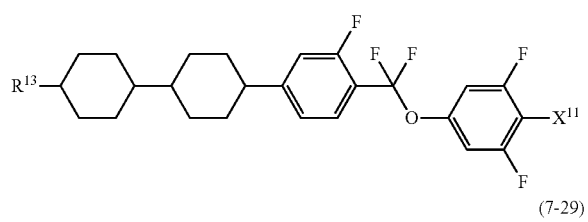
(7-29) 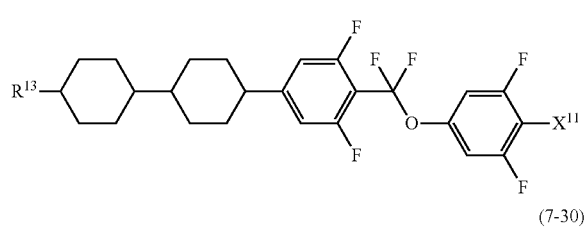
(7-30) 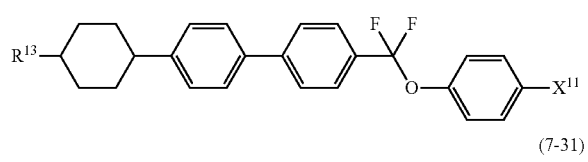
(7-31) 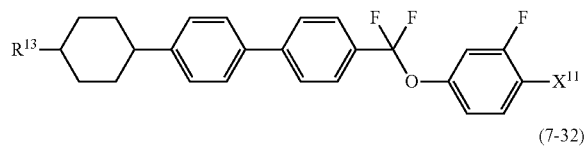
(7-32) 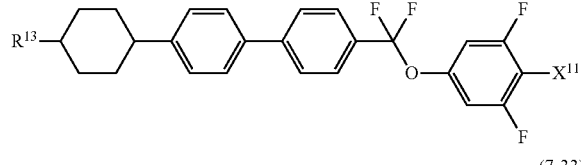
(7-33) 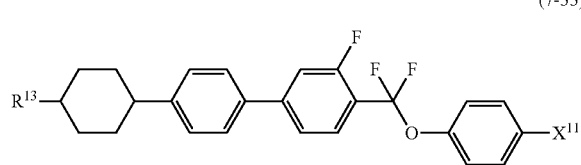
(7-34) 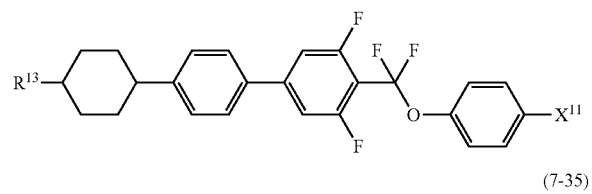
(7-35) 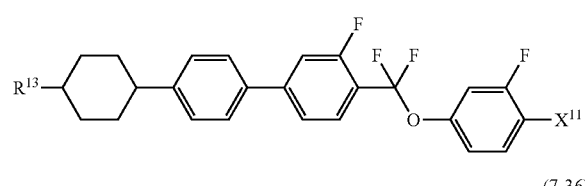
(7-36) 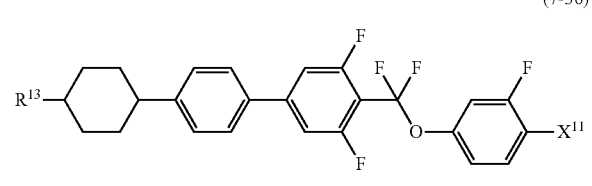
(7-37) 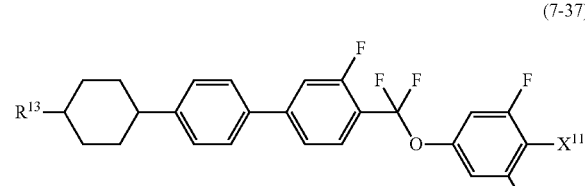
(7-38) 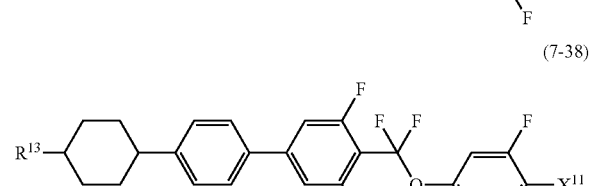
(7-39) 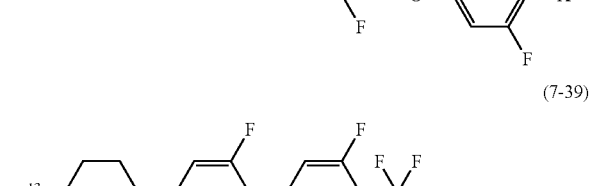
(7-40) 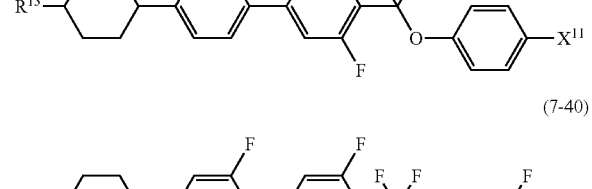
(7-41) 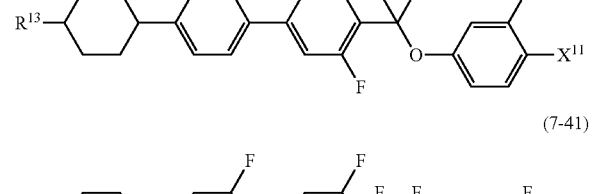
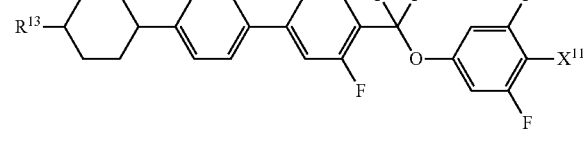

(7-42)
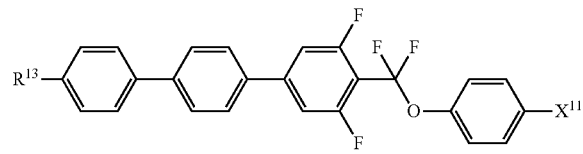
(7-50)
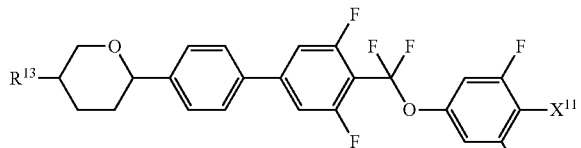
(7-43)
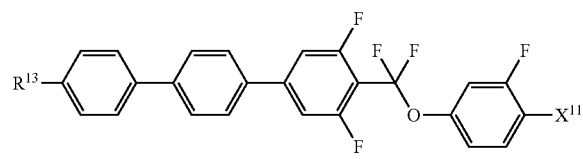
(7-51)
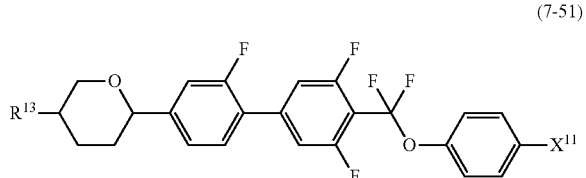
(7-44)
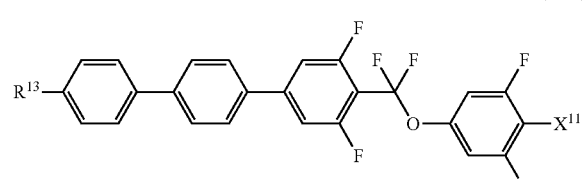
(7-52)
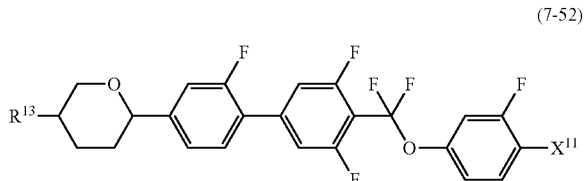
(7-45)
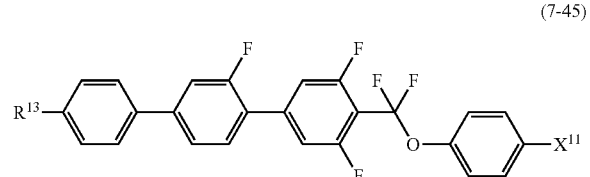
(7-53)
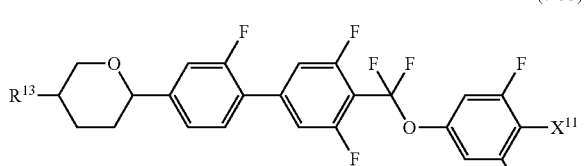
(7-46)
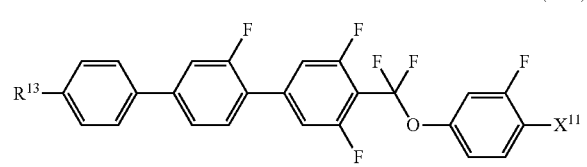
(7-54)
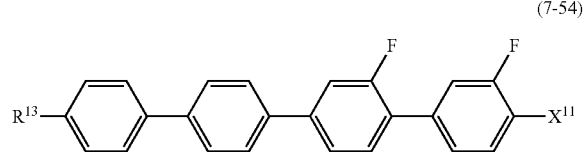
(7-47)
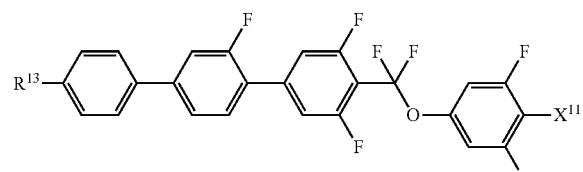
(7-55)
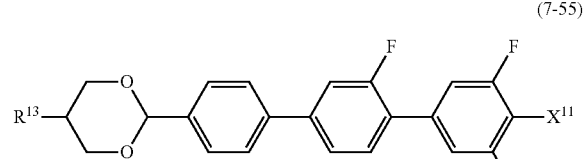
(7-48)
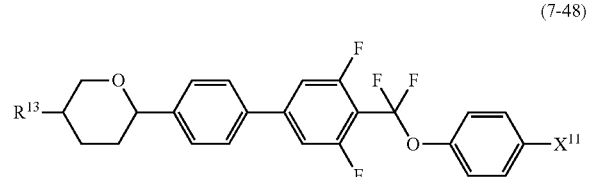
(7-56)
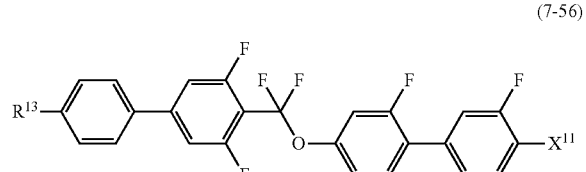
(7-49)
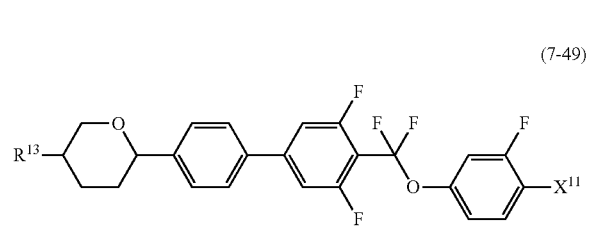
(7-57)
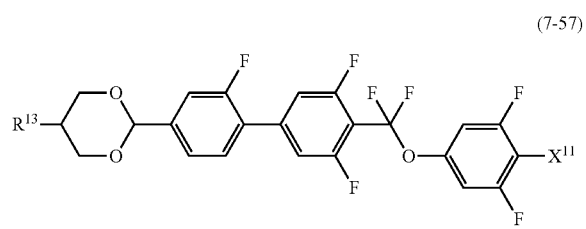

(7-58)
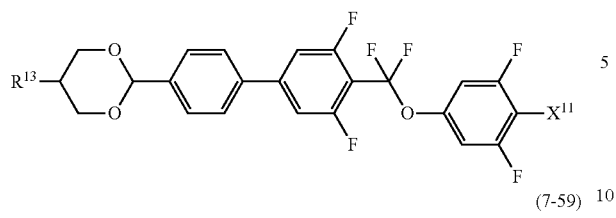

(7-59)
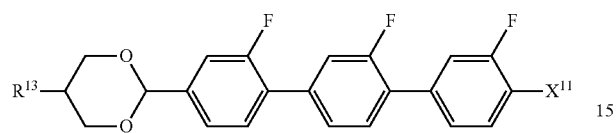

Since the component C has positive dielectric anisotropy and has very favorable stability with respect to heat and light, it is suitably used to prepare a composition for a mode such as IPS, FFS, and OCB. A content of the component C with respect to 100 weight % of a liquid crystal composition is suitably in a range of 1 weight % to 99 weight %, preferably in a range of 10 weight % to 97 weight %, and more preferably in a range of 40 weight % to 95 weight %. When the component C is added to a composition having negative dielectric anisotropy, the content of the component C with respect to 100 weight % of a liquid crystal composition is preferably 30 weight % or less. When the component C is added, it is possible to adjust an elastic constant of the composition and a voltage-transmittance curve of the element.

The component D is Compound (8) in which one terminal group is —C≡N or —C≡C—C≡N. The component D has larger positive dielectric anisotropy because it has a cyano group. Preferable examples of the component D include Compounds (8-1) to (8-64). In a compound containing the component D, $R^{14}$ is an alkyl group having 1 to 10 carbon atoms or an alkenyl group having 2 to 10 carbon atoms, and in these alkyl and alkenyl groups, at least one —CH$_2$— is optionally substituted with —O—, and at least one hydrogen atom is optionally substituted with a fluorine atom; —$X^{12}$ is —C≡N or —C≡C—C≡N.

(8-1)
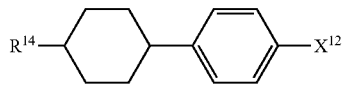

(8-2)
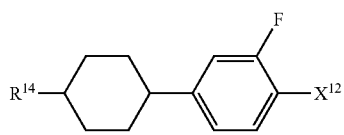

(8-3)
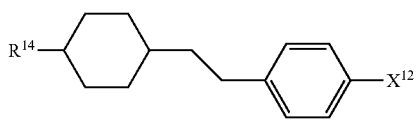

(8-4)
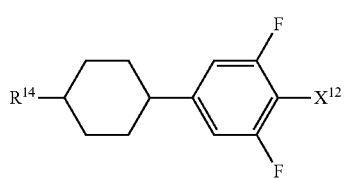

(8-5)
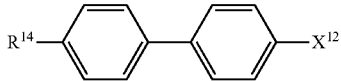

(8-6)
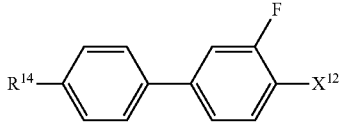

(8-7)
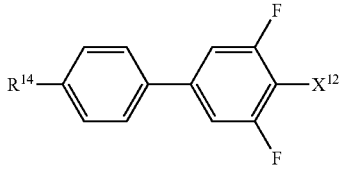

(8-8)
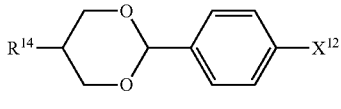

(8-9)
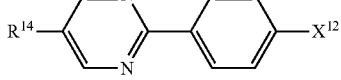

(8-10)
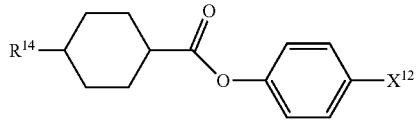

(8-11)
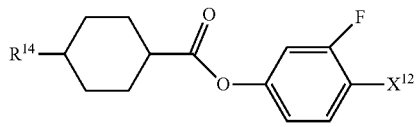

(8-12)
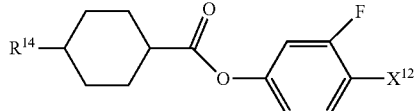

(8-13)
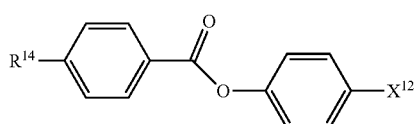

(8-14)
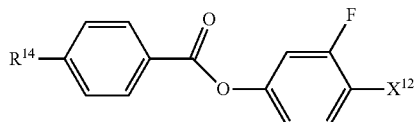

(8-15)
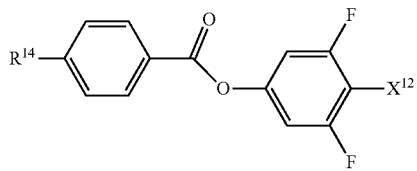

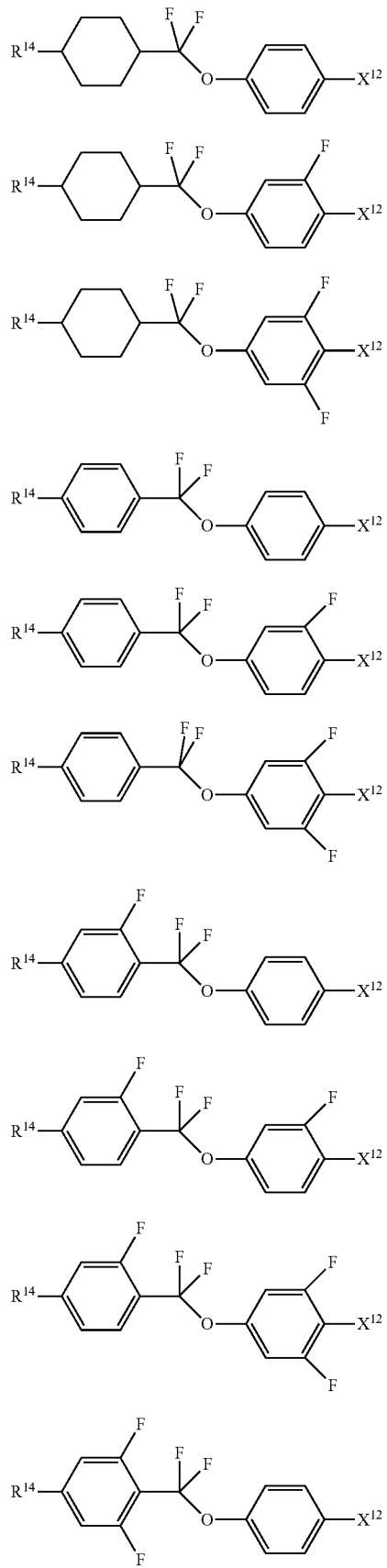
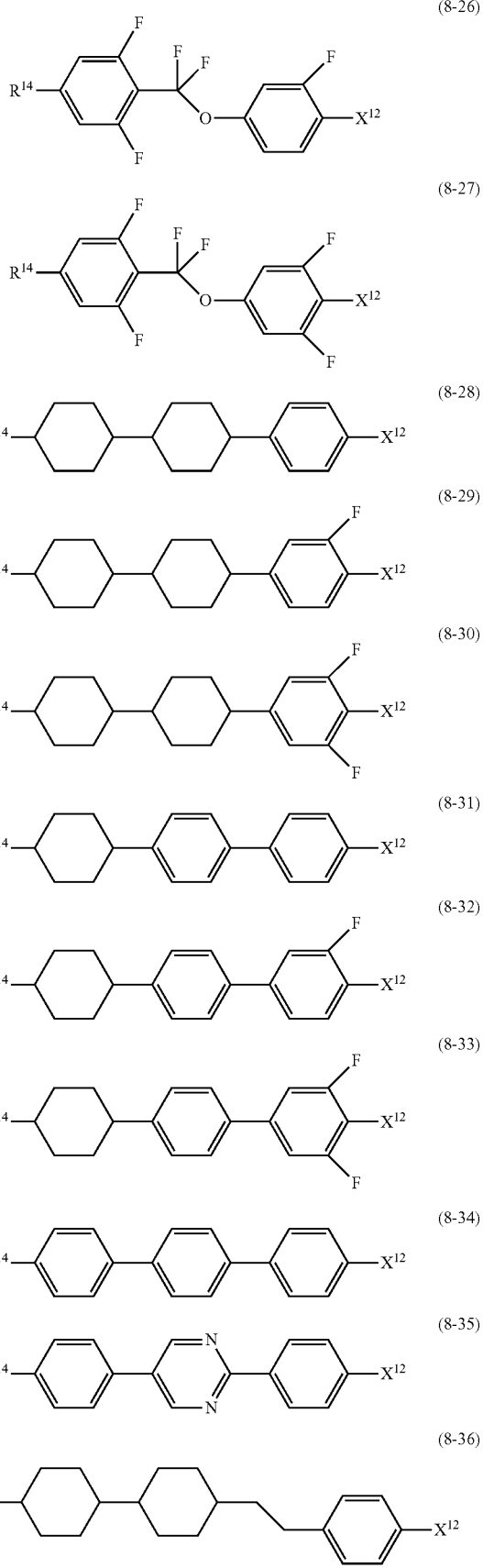

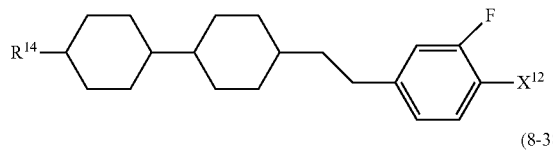
(8-37)
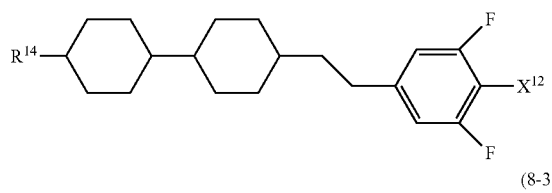
(8-38)
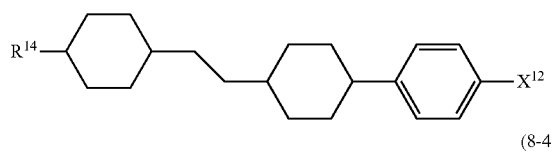
(8-39)
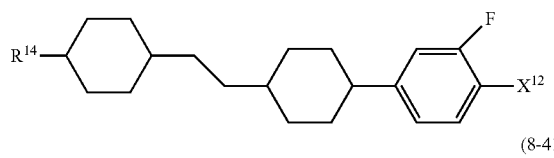
(8-40)
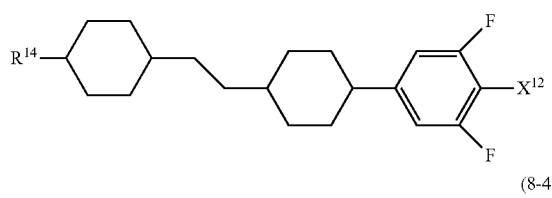
(8-41)
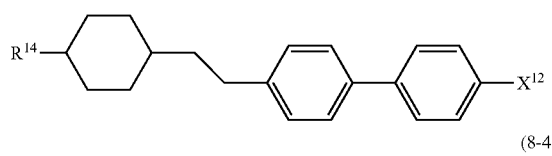
(8-42)
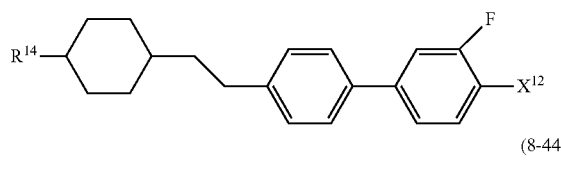
(8-43)
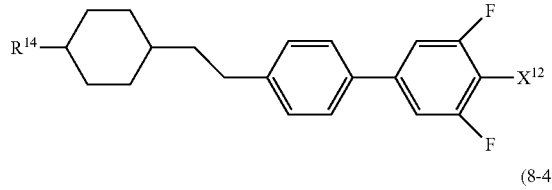
(8-44)
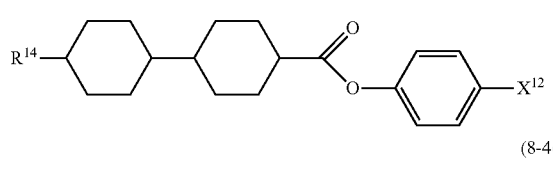
(8-45)
(8-46)
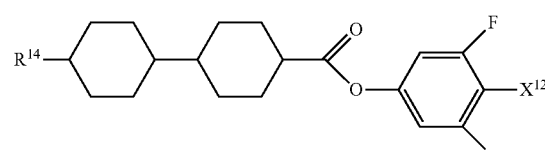
(8-47)
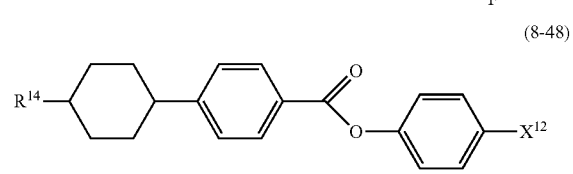
(8-48)
(8-49)
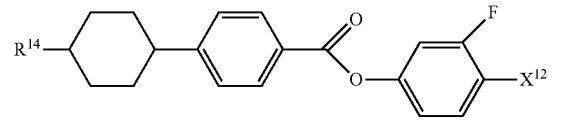
(8-50)
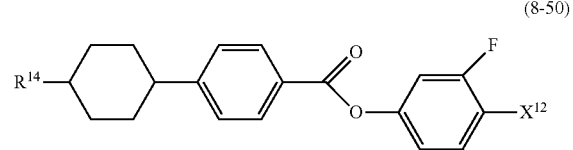
(8-51)
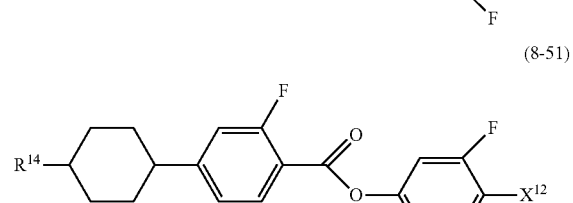
(8-52)
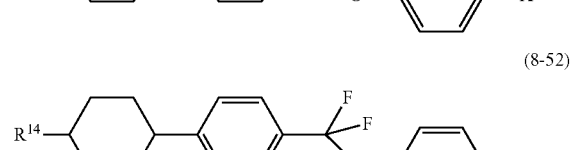
(8-53)
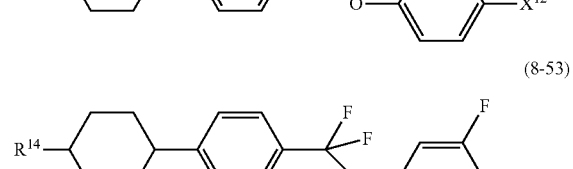
(8-54)
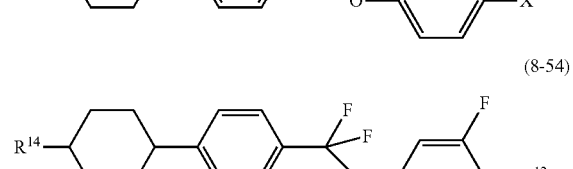
(8-55)
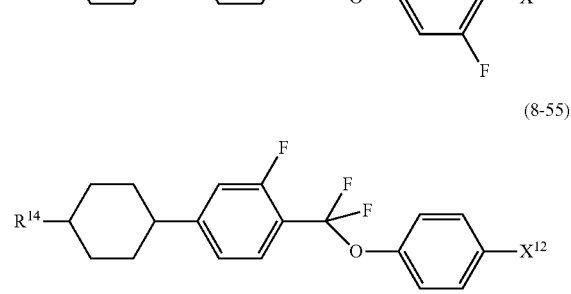

-continued

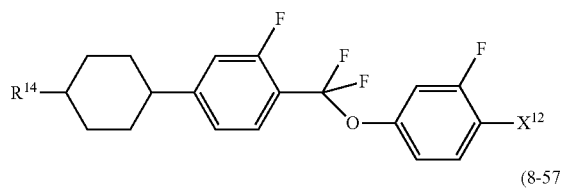
(8-56)

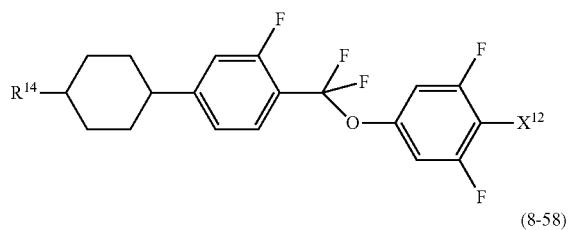
(8-57)

(8-58)

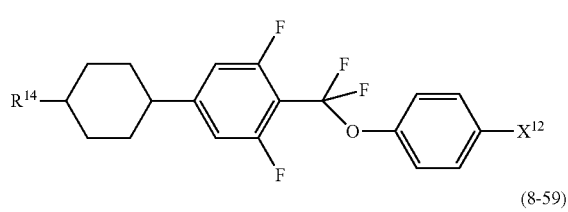
(8-59)

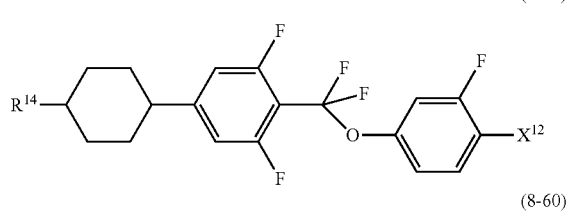
(8-60)

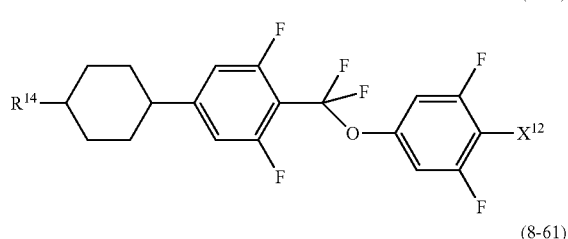
(8-61)

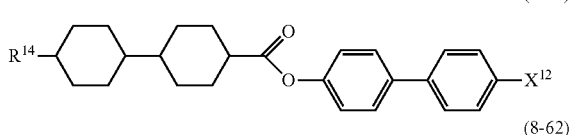
(8-62)

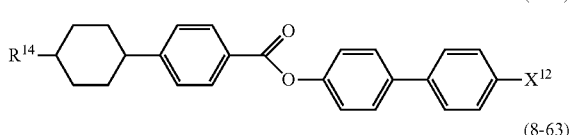
(8-63)

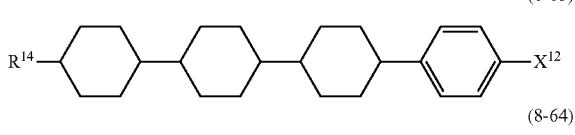
(8-64)

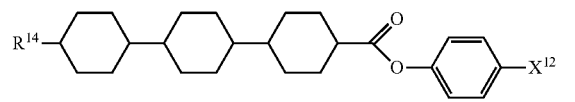

The component D has positive dielectric anisotropy and since its value is large, it is mainly used to prepare a composition for a mode such as TN. When the component D is added, it is possible to increase the dielectric anisotropy of the composition. The component D has an effect of widening a temperature range of the liquid crystal phase, adjusting the viscosity, or adjusting the optical anisotropy. The component D is also beneficial for adjusting a voltage-transmittance curve of the element.

A content of the component D with respect to 100 weight % of a liquid crystal composition is suitably in a range of 1 weight % to 99 weight %, preferably in a range of 10 weight % to 97 weight %, and more preferable in a range of 40 weight % to 95 weight %. When the component D is added to a composition having negative dielectric anisotropy, the content of the component D with respect to 100 weight % of a liquid crystal composition is preferably 30 weight % or less. When the component D is added, it is possible to adjust an elastic constant of the composition and adjust a voltage-transmittance curve of the element.

The component E is Compounds (11) to (19). The component E has large negative dielectric anisotropy. These compounds include a phenylene in which the lateral positions are substituted with two halogen atoms (fluorine or chlorine atoms) like 2,3-difluoro-1,4-phenylene. Preferable examples of the component E include Compounds (11-1) to (11-9), Compounds (12-1) to (12-19), Compounds (13-1) and (13-2), Compounds (14-1) to (14-3), Compounds (15-1) to (15-3), Compounds (16-1) to (16-11), Compounds (17-1) to (17-3), Compounds (18-1) to (18-3), and Compound (19-1). In these compounds, $R^{15}$, $R^{16}$, and $R^{17}$ are independently an alkyl group having 1 to 10 carbon atoms or an alkenyl group having 2 to 10 carbon atoms, and in the alkyl and alkenyl groups, at least one —CH$_2$— is optionally substituted with —O—, and in these groups, at least one hydrogen atom is optionally substituted with a fluorine atom, and $R^{17}$ may be a hydrogen atom or a fluorine atom.

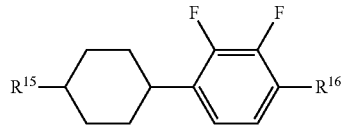
(11-1)

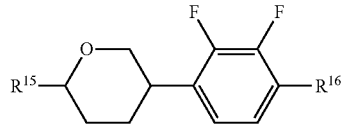
(11-2)

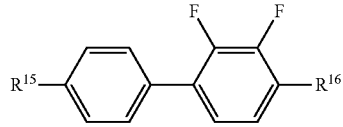
(11-3)

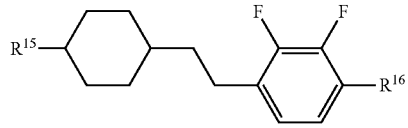
(11-4)

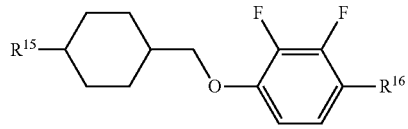
(11-5)

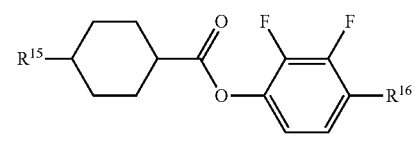 (11-6)
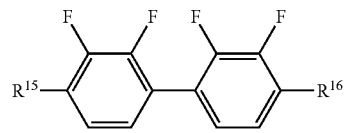 (11-7)
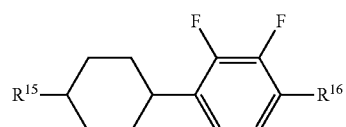 (11-8)
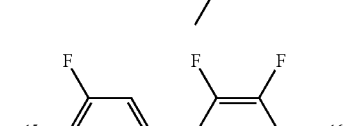 (11-9)
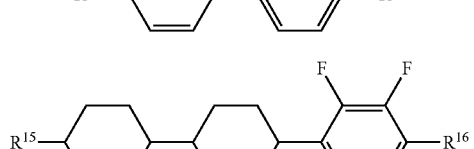 (12-1)
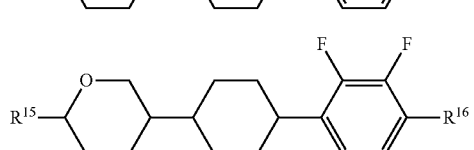 (12-2)
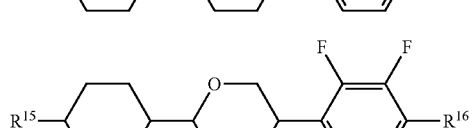 (12-3)
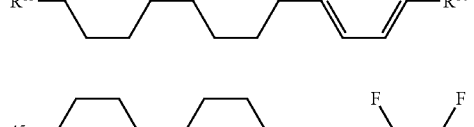 (12-4)
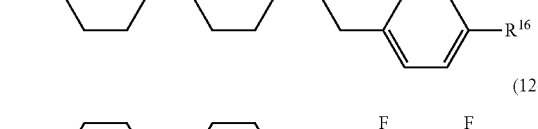 (12-5)
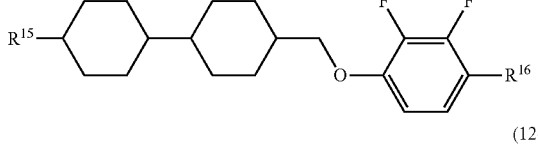 (12-6)
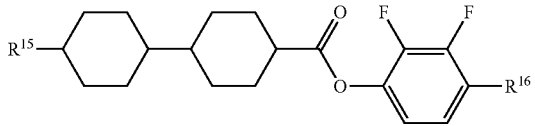 (12-7)
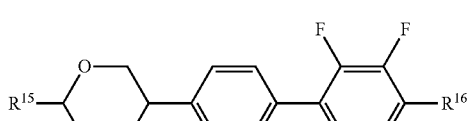 (12-8)
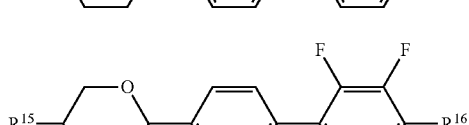 (12-9)
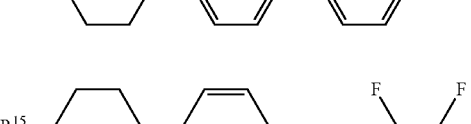 (12-10)
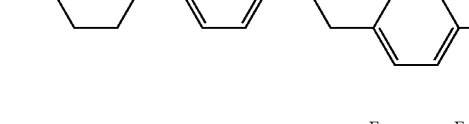 (12-11)
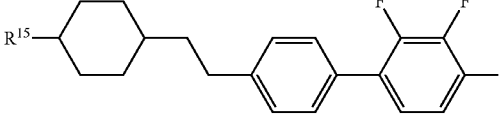 (12-12)
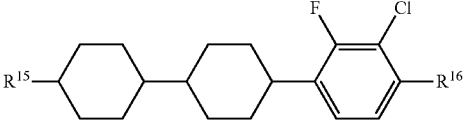 (12-13)
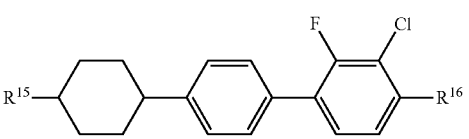 (12-14)
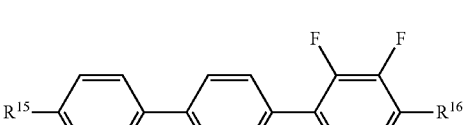 (12-15)
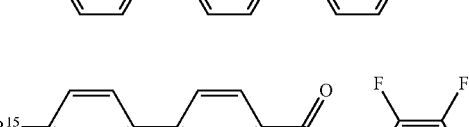 (12-16)
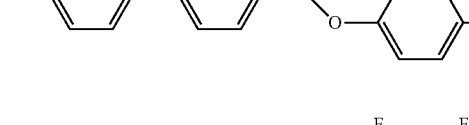 (12-17)
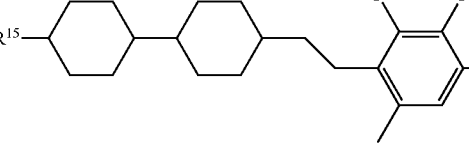

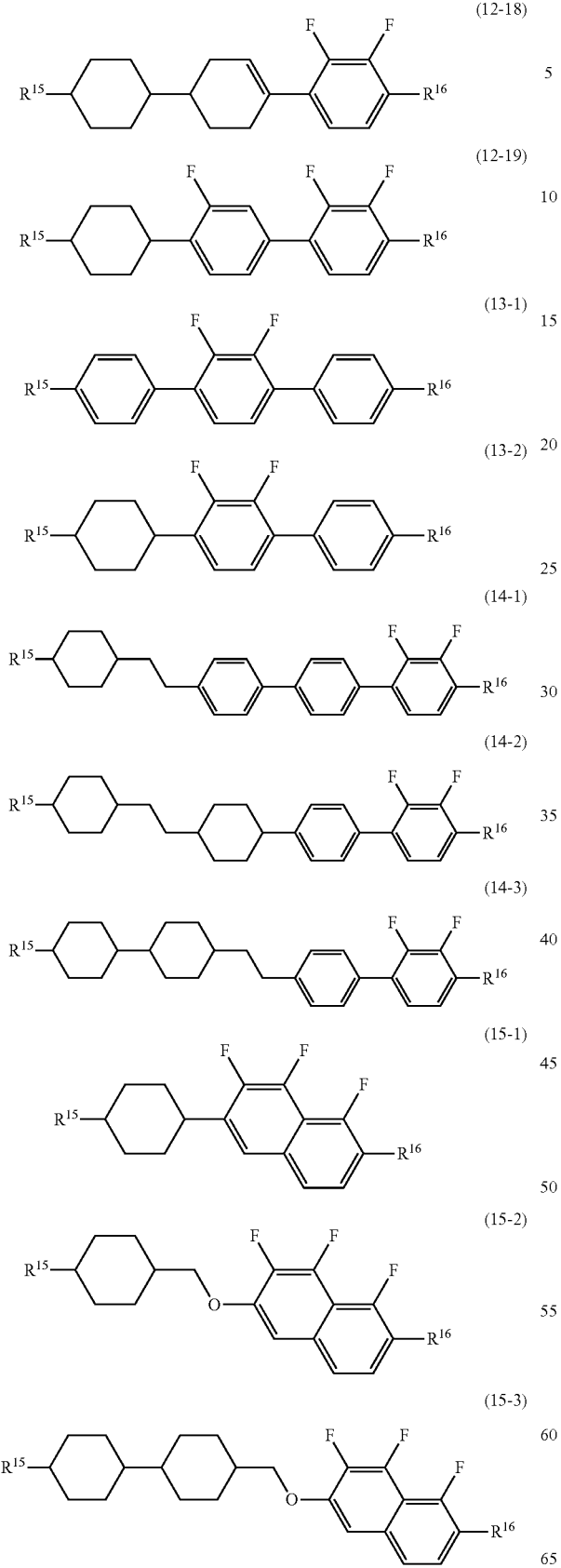
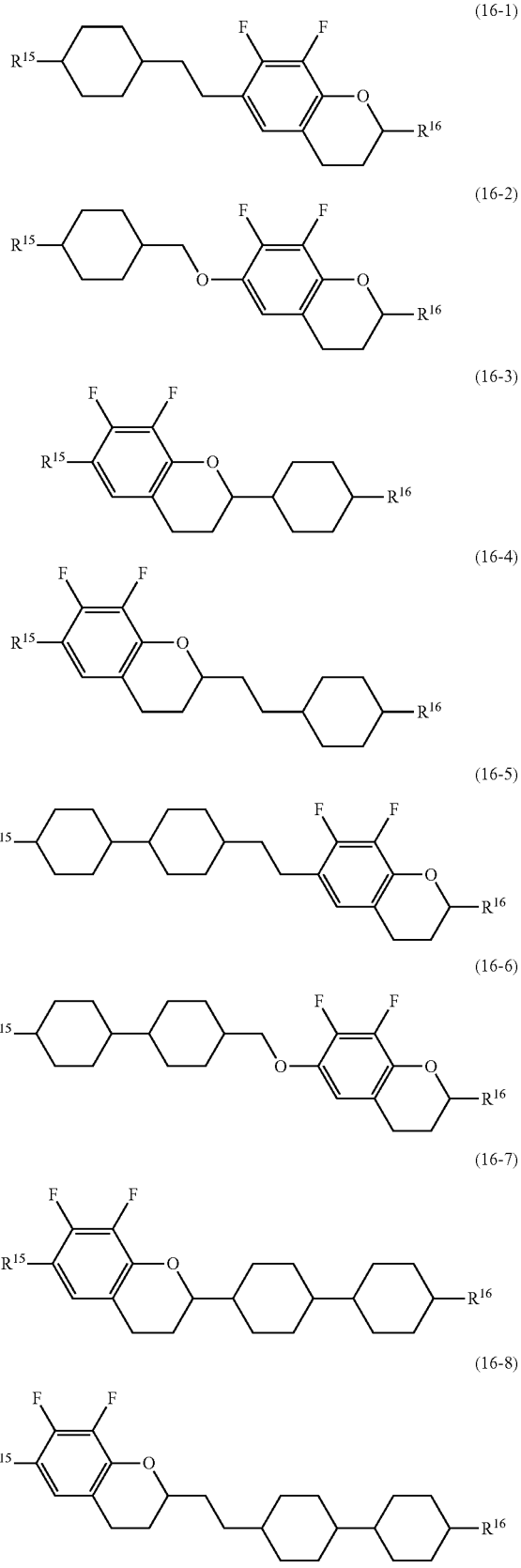

-continued

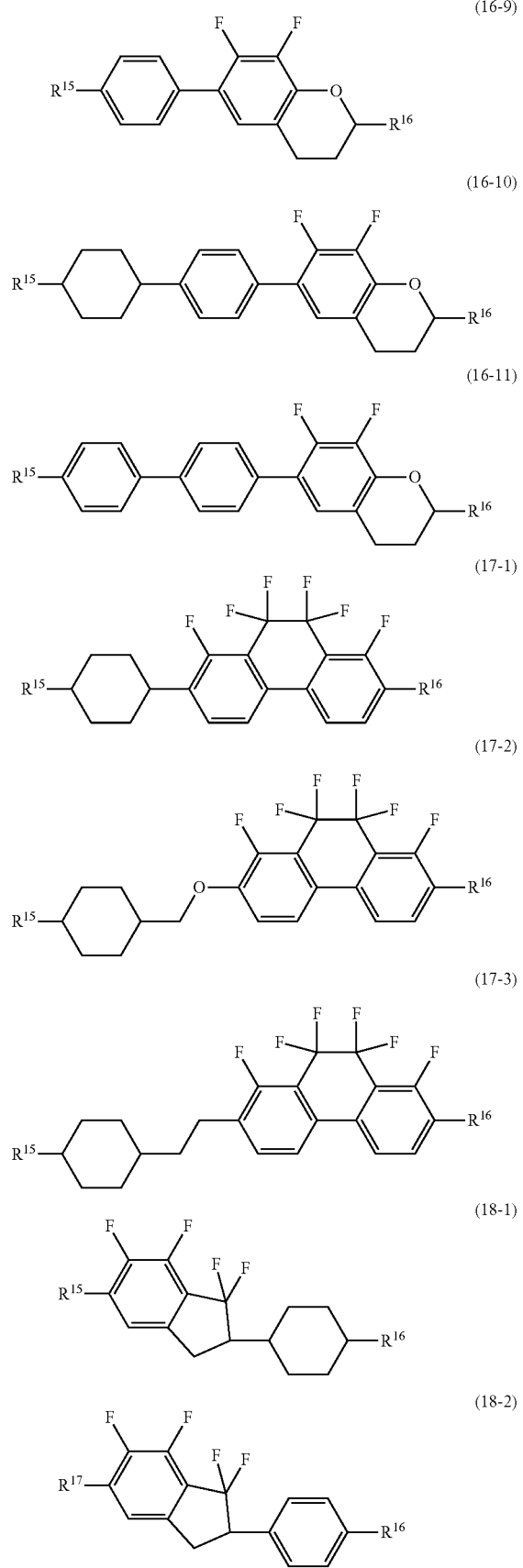

(16-9)
(16-10)
(16-11)
(17-1)
(17-2)
(17-3)
(18-1)
(18-2)

-continued

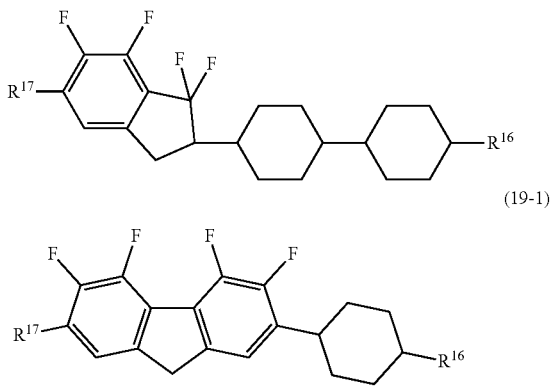

(18-3)
(19-1)

The component E has negative dielectric anisotropy. The component E is suitably used when a composition for a mode such as IPS, VA, and PSA is prepared. As the content of the component E increases, the dielectric anisotropy of the composition becomes negatively larger, but the viscosity increases. Therefore, the content is preferably as small as possible as long as a threshold voltage of the element has a required value. In consideration of the fact that the dielectric anisotropy is about −5, in order for driving at a sufficient voltage, the content of the component E with respect to 100 weight % of a liquid crystal composition is preferably 40 weight % or more.

Among the components E, since Compound (11) is a bicyclic compound, it has an effect of lowering the viscosity, adjusting the optical anisotropy, or increasing the dielectric anisotropy. Since Compounds (12) and (13) are tricyclic compounds and Compound (14) is a tetracyclic compound, they have an effect of increasing the upper limit temperature, increasing the optical anisotropy, or increasing the dielectric anisotropy. Compounds (15) to (19) have an effect of increasing the dielectric anisotropy.

The content of the component E with respect to 100 weight % of a liquid crystal composition is preferably 40 weight % or more, and more preferably in a range of 50 weight % to 95 weight %. When the component E is added to a composition having positive dielectric anisotropy, the content of the component E with respect to 100 weight % of a liquid crystal composition is preferably 30 weight % or less. When the component E is added, it is possible to adjust an elastic constant of the composition and a voltage-transmittance curve of the element.

When the components B, C, D, and E described above are appropriately combined, it is possible to prepare a liquid crystal composition which has at least one of characteristics such as a high upper limit temperature, a low lower limit temperature, a low viscosity, appropriate optical anisotropy, large positive or negative dielectric anisotropy, a large specific resistance, high stability with respect to ultraviolet rays, high stability with respect to heat, and a large elastic constant.

3-2. Additives

A liquid crystal composition is prepared by a known method. For example, there is a method in which the components are mixed together and then dissolved by heating. According to applications, an additive may be added to this composition. Examples of the additive include a polymerizable compound other than Compound (1), a polymerization initiator, a polymerization inhibitor, an optically active compound, an antioxidant, a UV absorber, a light stabilizer, a heat stabilizer, a dye, and an antifoaming agent. Such additives are well-known to those skilled in the art and described in documents.

The polymerizable compound is added in order to generate a polymer in the liquid crystal composition. While a voltage is applied between electrodes, when ultraviolet rays are emitted, and Compound (1) is polymerized, the polymer can be generated. In this case, Compound (1) is immobilized while its polar groups non-covalently interact with a surface of a glass (or a metal oxide) substrate. Accordingly, since an ability to control the alignment of liquid crystal molecules is further improved and an appropriate pretilt is obtained, a response time is shortened.

Preferable examples of the polymerizable compound include an acrylate, a methacrylate, a vinyl compound, a vinyloxy compound, propenyl ether, an epoxy compound (oxirane, oxetane), and vinyl ketone. More preferable examples include a compound having at least one acryloyloxy group and a compound having at least one methacryloyloxy group. Still more preferable examples include a compound having both acryloyloxy and methacryloyloxy groups.

Particularly preferable examples of the polymerizable compound include Compound (20). Compound (20) is a compound different from Compound (1). Compound (1) has a polar group. On the other hand, Compound (20) preferably has no polar group.

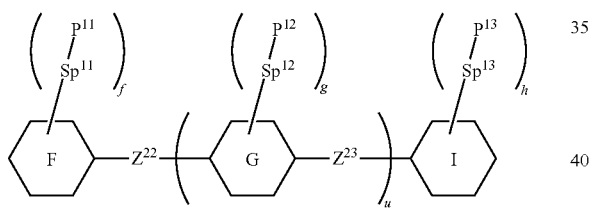

(20)

In Formula (20), the ring F and the ring I are independently cyclohexyl, cyclohexenyl, phenyl, 1-naphthyl, 2-naphthyl, tetrahydropyran-2-yl, 1,3-dioxan-2-yl, pyrimidin-2-yl, or pyridin-2-yl, and in these rings, at least one hydrogen atom is optionally substituted with a halogen atom, an alkyl group having 1 to 12 carbon atoms, an alkoxy group having 1 to 12 carbon atoms, or an alkyl group having 1 to 12 carbon atoms in which at least one hydrogen atom is substituted with a halogen atom.

Preferably, the ring F or the ring I is cyclohexyl, cyclohexenyl, phenyl, fluorophenyl, difluorophenyl, 1-naphthyl, or 2-naphthyl. More preferably, the ring F or the ring I is cyclohexyl, cyclohexenyl, or phenyl. Particularly preferably, the ring F or the ring I is phenyl.

In Formula (20), the ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, phenanthrene-2,7-diyl, tetrahydropyran-2,5-diyl, 1,3-dioxane-2,5-diyl, pyrimidine-2,5-diyl, or pyridine-2,5-diyl, and in these rings, at least one hydrogen atom is optionally substituted with a halogen atom, an alkyl group having 1 to 12 carbon atoms, an alkoxy group having 1 to 12 carbon atoms, or an alkyl group having 1 to 12 carbon atoms in which at least one hydrogen atom is substituted with a halogen atom.

Preferably, the ring G is 1,4-cyclohexylene, 1,4-cyclohexenylene, 1,4-phenylene, 2-fluoro-1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, or naphthalene-2,7-diyl. More preferably, the ring G is 1,4-cyclohexylene, 1,4-cyclohexenylene, 1,4-phenylene, or 2-fluoro-1,4-phenylene. Particularly preferably, the ring G is 1,4-phenylene or 2-fluoro-1,4-phenylene. Most preferably, the ring G is 1,4-phenylene.

In Formula (20), $Z^{22}$ and $Z^{23}$ are independently a single bond or an alkylene group having 1 to 10 carbon atoms, and in this alkylene group, at least one —CH$_2$— is optionally substituted with —O—, —CO—, —COO—, or —OCO—, and at least one —CH$_2$CH$_2$— is optionally substituted with —CH=CH—, —C(CH$_3$)=CH—, —CH=C(CH$_3$)—, or —C(CH$_3$)=C(CH$_3$)—, and in these groups, at least one hydrogen atom is optionally substituted with a fluorine or chlorine atom. Preferably, $Z^{22}$ or $Z^{23}$ is a single bond, —CH$_2$CH$_2$—, —CH$_2$O—, —OCH$_2$—, —COO—, or —OCO—. More preferably, $Z^{22}$ or $Z^{23}$ is a single bond.

In Compound (20), $P^{11}$, $P^{12}$, and $P^{13}$ are independently a polymerizable group. Preferably, $P^{11}$ to $P^{13}$ are a group selected from the group of polymerizable groups represented by Formula (P-1) to Formula (P-5). More preferably, $P^{11}$ to $P^{13}$ are a group represented by Formula (P-1), Formula (P-2), or Formula (P-3). Particularly preferably, $P^{11}$ to $P^{13}$ are a group represented by Formula (P-1). A preferable group represented by Formula (P-1) is acryloyloxy (—OCO—CH=CH$_2$) or methacryloyloxy (—OCO—C(CH$_3$)=CH$_2$). Wavy lines in Formula (P-1) to Formula (P-5) indicate bonding sites.

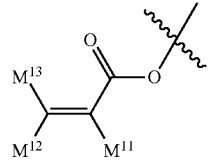

(P-1)

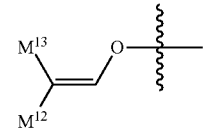

(P-2)

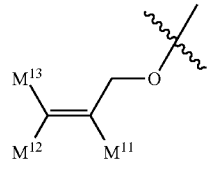

(P-3)

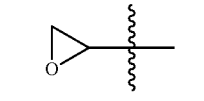

(P-4)

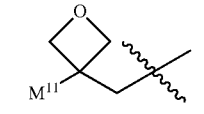

(P-5)

In Formula (P-1) to Formula (P-5), $M^{11}$, $M^{12}$, and $M^{13}$ are independently a hydrogen atom, a fluorine atom, an alkyl group having 1 to 5 carbon atoms, or an alkyl group having 1 to 5 carbon atoms in which at least one hydrogen atom is substituted with a halogen atom. Preferably, $M^{11}$, $M^{12}$, or $M^{13}$ is a hydrogen atom or a methyl group in order to increase the reactivity. More preferably, $M^{11}$ is a hydrogen atom or a methyl group, and most preferably, $M^{12}$ or $M^{13}$ is a hydrogen atom.

In Formula (20), $Sp^{11}$, $Sp^{12}$, and $Sp^{13}$ are independently a single bond or an alkylene group having 1 to 10 carbon atoms, and in this alkylene group, at least one —$CH_2$— is optionally substituted with —O—, —COO—, —OCO—, or —OCOO—, and at least one —$CH_2CH_2$— is optionally substituted with —CH=CH— or —C≡C—, and in these groups, at least one hydrogen atom is optionally substituted with a fluorine atom or a chlorine atom. Preferably, $Sp^{11}$, $Sp^{12}$, or $Sp^{13}$ is a single bond.

In Formula (20), u is 0, 1, or 2. Preferably, u is 0 or 1.

In Formula (20), f, g, and h are independently 0, 1, 2, 3, or 4, and a sum of f, g, and h is 1 or more. Preferably, f, g, or h is 1 or 2. Preferably, the sum is 2, 3 or 4. More preferably, the sum is 2 or 3.

Examples of a preferable Compound (20) include Compounds (20-1) to Compound (20-7) and Compounds (20-8) to (20-11) described in Item 15. More preferable examples include Compounds (20-1-1) to (20-1-5), Compounds (20-2-1) to (20-2-5), Compound (20-4-1), Compound (20-5-1), Compound (20-6-1), and Compound (20-7-1). In these compounds, $R^{25}$ to $R^{31}$ are independently a hydrogen atom or a methyl group, $R^{32}$, $R^{33}$, and $R^{34}$ are independently a hydrogen atom or an alkyl group having 1 to 5 carbon atoms, at least one of $R^{32}$, $R^{33}$, and $R^{34}$ is an alkyl group having 1 to 5 carbon atoms; v and x are independently 0 or 1; t and u are independently an integer of 1 to 10; t+v and x+u are a maximum of 10; $L^{31}$ to $L^{36}$ are independently a hydrogen atom or a fluorine atom, and $L^{37}$ and $L^{38}$ are independently a hydrogen atom, a fluorine atom, or a methyl group.

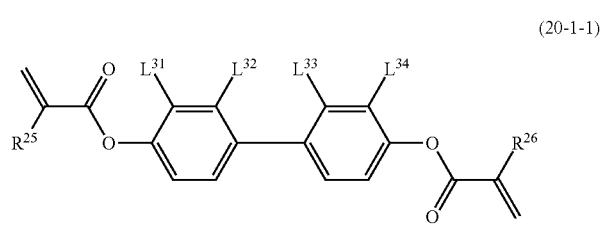

(20-1-1)

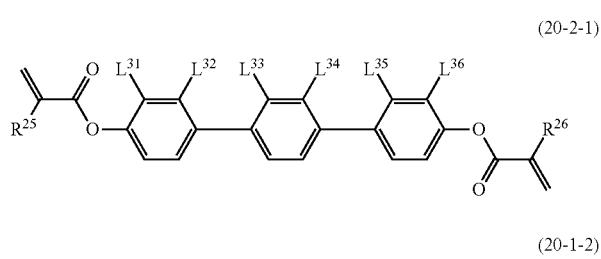

(20-2-1)

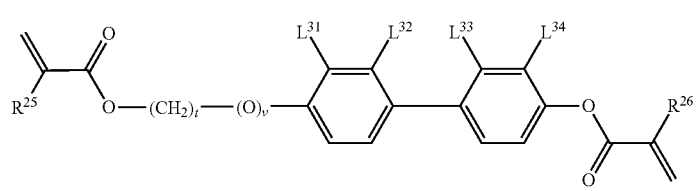

(20-1-2)

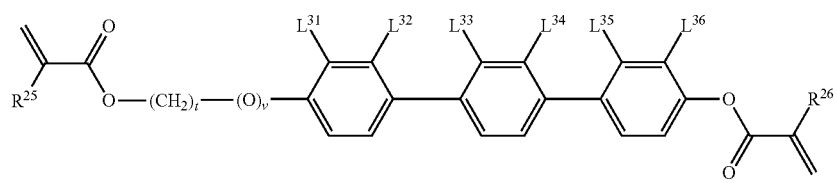

(20-2-2)

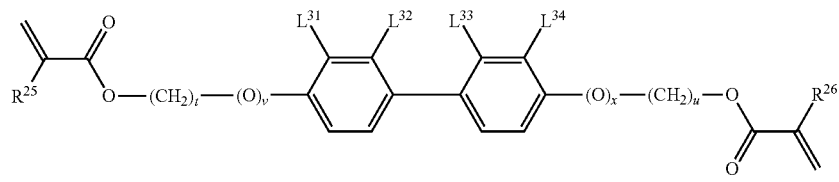

(20-1-3)

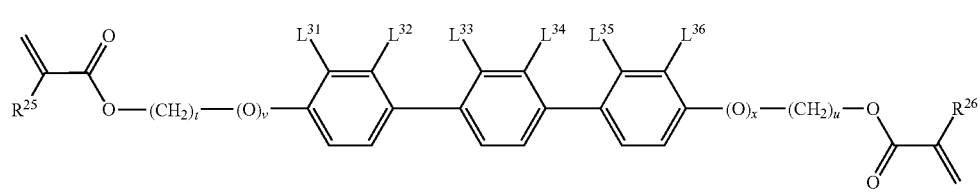

(20-2-3)

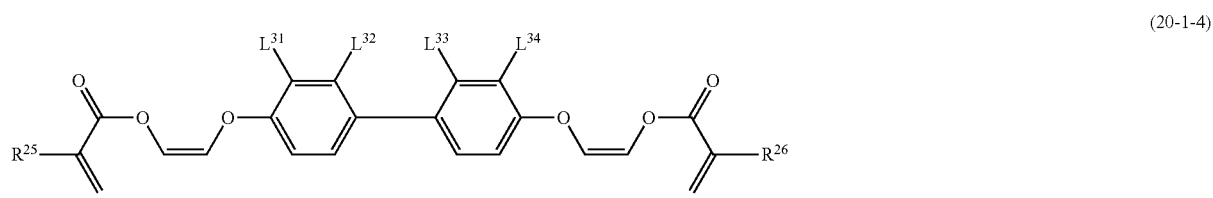

(20-1-4)

(20-2-4)
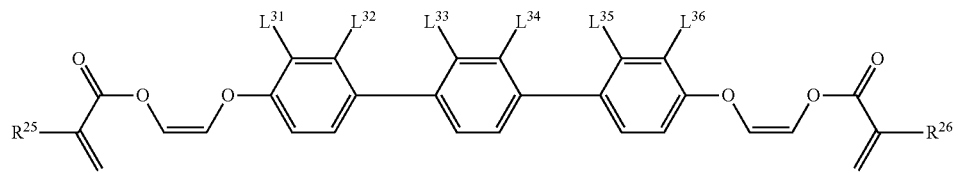
(20-1-5)
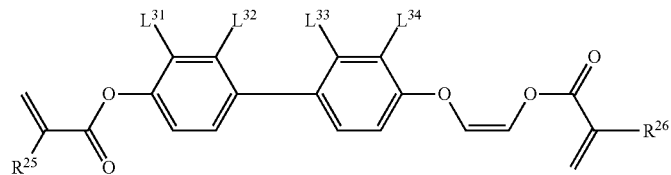
(20-2-5)
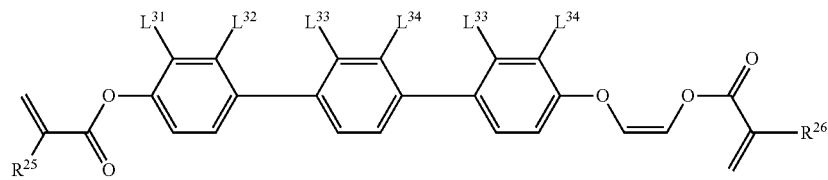
(20-4-1)
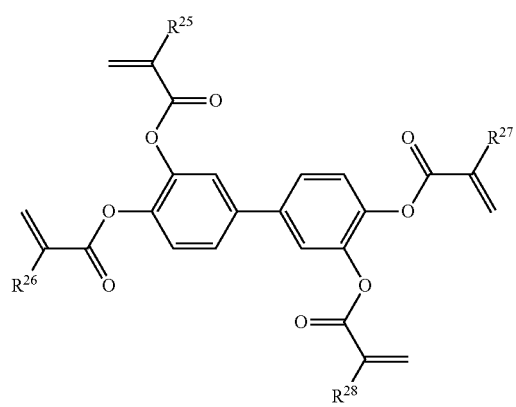
(20-5-1)
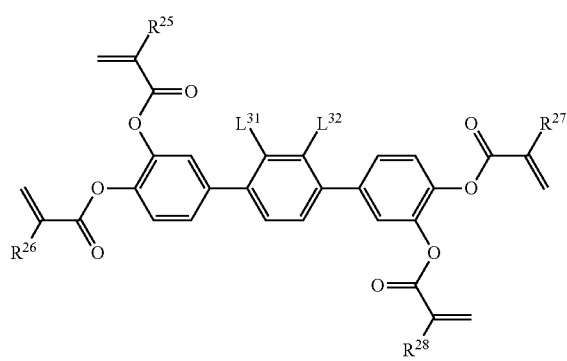
(20-6-1)
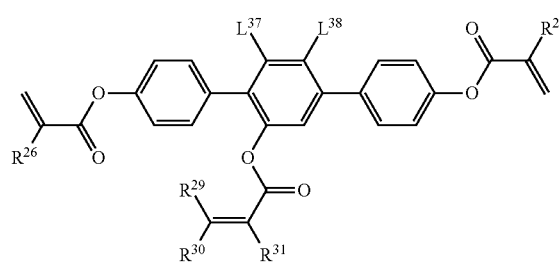
(20-7-1)
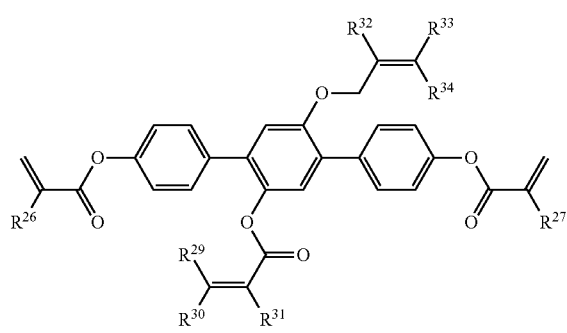
(20-8-1)
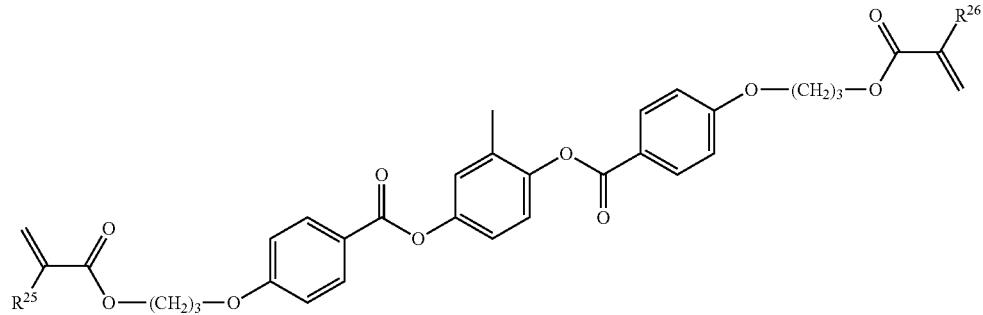

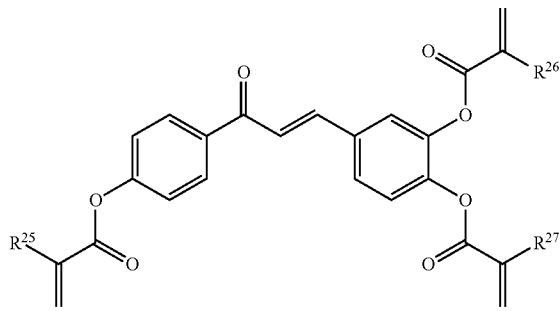

(20-9)

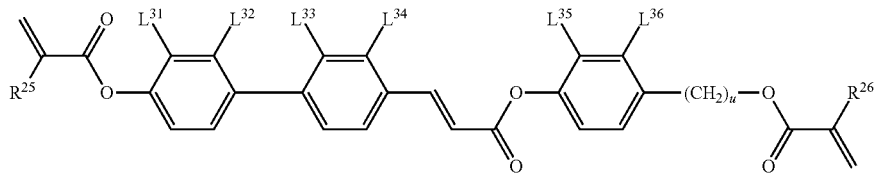

(20-10)

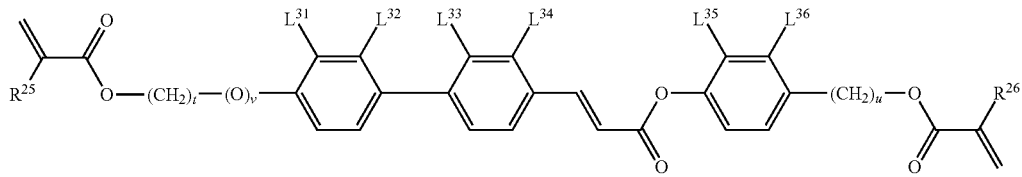

(20-11)

The polymerizable compound in the composition can be polymerized rapidly using a polymerization initiator such as a photoradical polymerization initiator. In addition, when reaction conditions during polymerization are optimized, it is possible to reduce an amount of the polymerizable compound remaining. Examples of a photoradical polymerization initiator include Darocur series TPO, 1173, and 4265, and Irgacure series 184, 369, 500, 651, 784, 819, 907, 1300, 1700, 1800, 1850, and 2959 which are commercially available from BASF.

Additional examples of the photoradical polymerization initiator include 4-methoxyphenyl-2,4-bis(trichloromethyl) triazine, 2-(4-butoxystyryl)-5-trichloromethyl-1,3,4-oxadiazole, 9-phenylacridine, 9,10-benzphenazine, a benzophenone/Michler's ketone mixture, a hexaarylbiimidazole/mercaptobenzimidazole mixture, 1-(4-isopropylphenyl)-2-hydroxy-2-methylpropan-1-one, benzyldimethylketal, 2-methyl-1-[4-(methylthio)phenyl]-2-morpholinopropan-1-one, 2,4-diethyl xanthone/methyl p-dimethylaminobenzoate mixture, and a benzophenone/methyltriethanolamine mixture.

After a photoradical polymerization initiator is added to the liquid crystal composition, ultraviolet rays are emitted while an electric field is applied, and thus polymerization can be performed. However, unreacted polymerization initiator or decomposition products of a polymerization initiator may cause display defects such as image burning in the element. In order to prevent this, photopolymerization may be performed without adding a polymerization initiator. A preferable wavelength of light to be emitted is in a range of 150 nm to 500 nm. A more preferable wavelength is in a range of 250 nm to 450 nm, and a most preferable wavelength is in a range of 300 nm to 400 nm.

When the polymerizable compound is stored, a polymerization inhibitor may be added in order to prevent polymerization. Generally, the polymerizable compound is added to the composition when the polymerization inhibitor has not been removed. Examples of the polymerization inhibitor include hydroquinone, hydroquinone derivatives such as methyl hydroquinone, 4-t-butyl catechol, 4-methoxyphenol, and phenothiazine.

The optically active compound has an effect of inducing a helical structure in liquid crystal molecules, imparting a required helix angle, and thus preventing reverse twist. When the optically active compound is added, it is possible to adjust a helical pitch. Two or more optically active compounds may be added in order to adjust temperature dependence of the helical pitch. Preferable examples of the optically active compound include the following Compounds (Op-1) to (Op-18). In Compound (Op-18), a ring J is 1,4-cyclohexylene or 1,4-phenylene, and $R^{28}$ is an alkyl group having 1 to 10 carbon atoms. The symbol * indicates an asymmetric carbon atom.

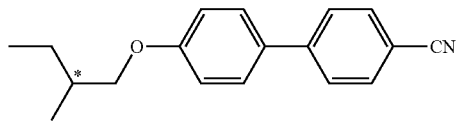

(Op-1)

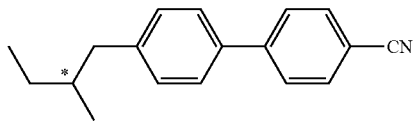

(Op-2)

-continued
(Op-3)
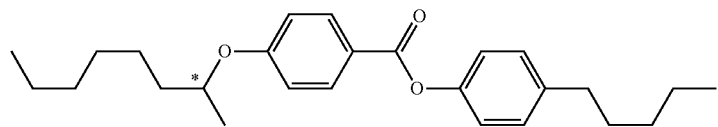
(Op-4)
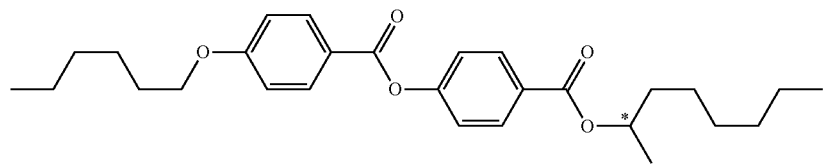
(Op-5)
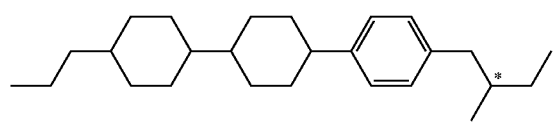
(Op-6)
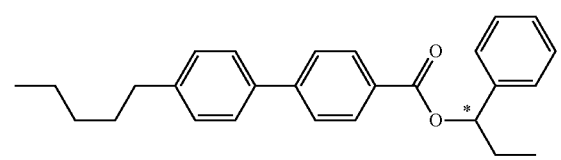
(Op-7)
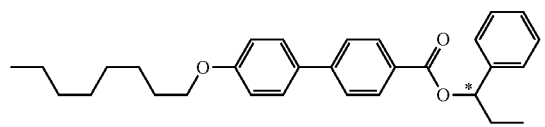
(Op-8)
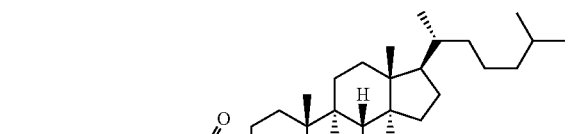
(Op-9)
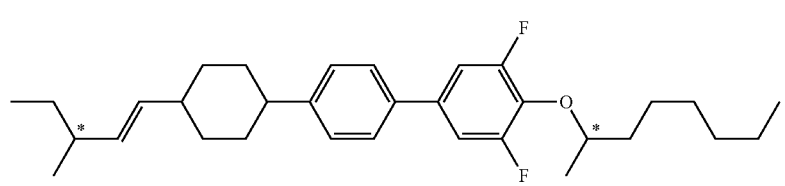
(Op-10)
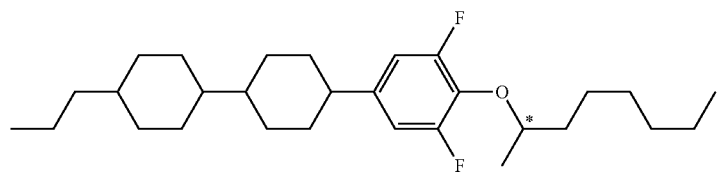
(Op-11)
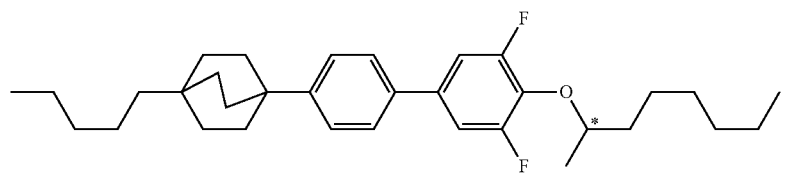
(Op-12)
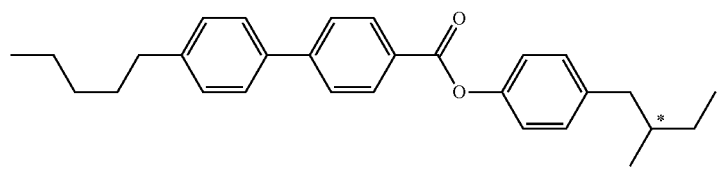

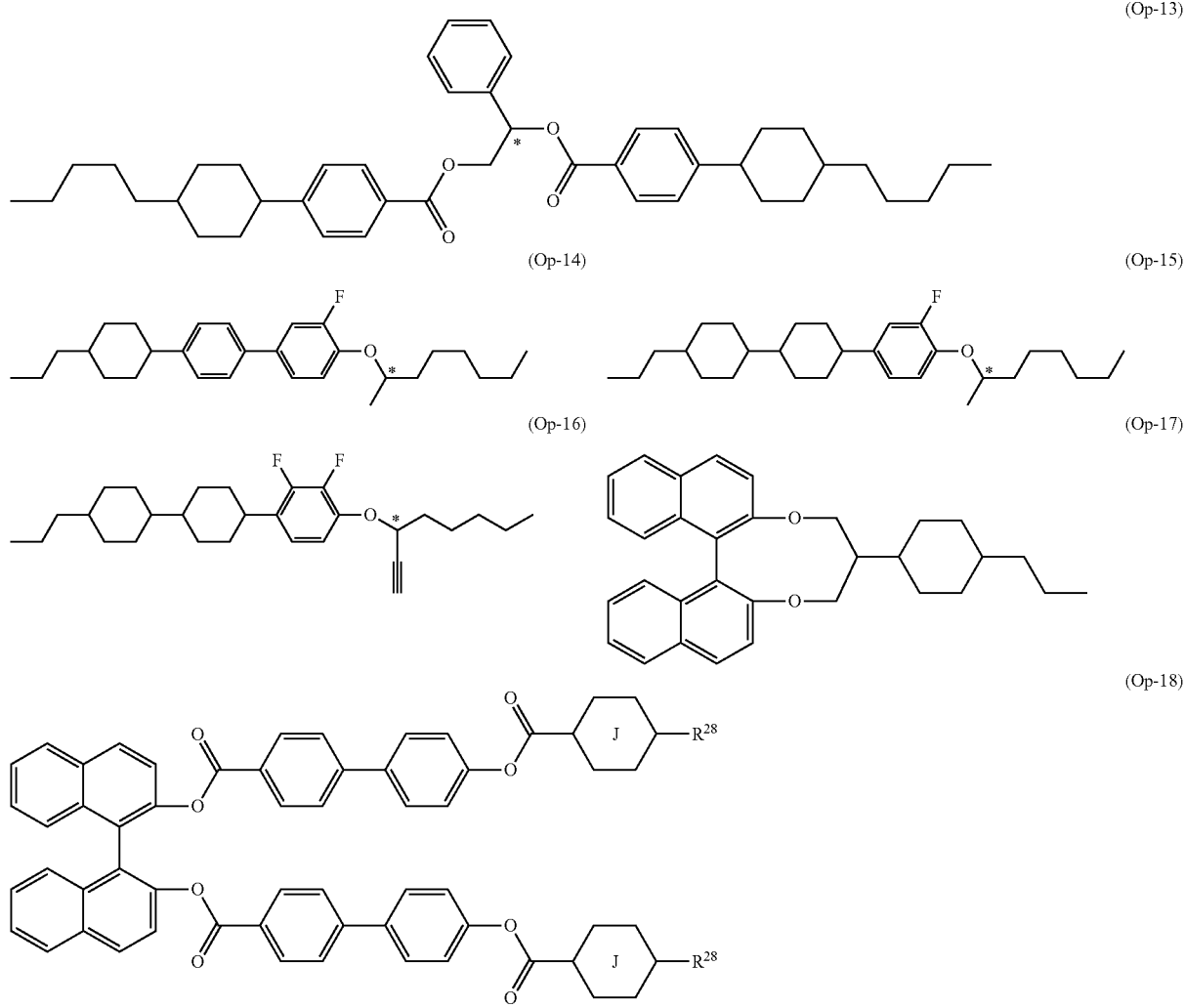

An antioxidant is effective for maintaining a high voltage holding ratio. Preferable examples of the antioxidant include the following Compounds (AO-1) and (AO-2); Irganox 415, Irganox 565, Irganox 1010, Irganox 1035, Irganox 3114, and Irganox 1098 (product name; commercially available from BASF).

A UV absorber is effective for preventing an upper limit temperature from decreasing. Preferable examples of the UV absorber include benzophenone derivatives, benzoate derivatives, and triazole derivatives. Specific examples include the following Compounds (AO-3) and (AO-4); Tinuvin 329, Tinuvin P, Tinuvin 326, Tinuvin 234, Tinuvin 213, Tinuvin 400, Tinuvin 328, and Tinuvin 99-2 (product name; commercially available from BASF); and 1,4-diazabicyclo[2.2.2]octane (DABCO).

A light stabilizer such as a sterically hindered amine is preferable in order to maintain a high voltage holding ratio. Preferable examples of the light stabilizer include the following Compounds (AO-5), (AO-6), and (AO-7); Tinuvin 144, Tinuvin 765, and Tinuvin 770DF (product name; commercially available from BASF); LA-77Y and LA-77G (product name; commercially available from ADEKA).

A heat stabilizer is also effective for maintaining a high voltage holding ratio. Preferable examples include Irgafos 168 (product name; commercially available from BASF).

In order to adapt the composition to an element in a guest host (GH) mode, a dichroic dye such as an azo dye or an anthraquinone dye is added to the composition as necessary.

The antifoaming agent is effective for preventing foaming. Preferable examples of the antifoaming agent include dimethyl silicone oil and methylphenyl silicone oil.

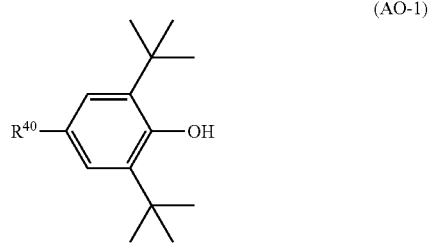

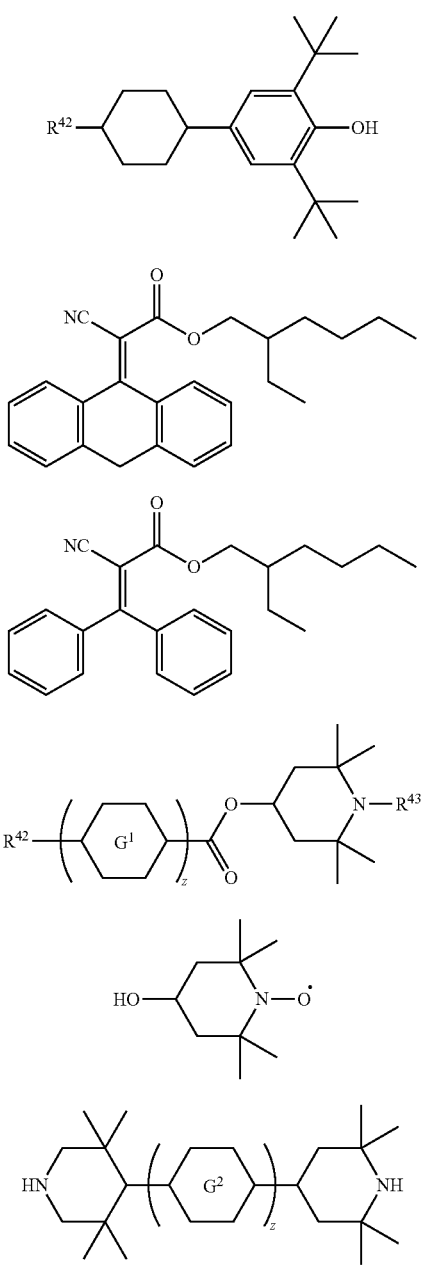

(AO-2)
(AO-3)
(AO-4)
(AO-5)
(AO-6)
(AO-7)

In Compound (AO-1), $R^{40}$ is an alkyl group having 1 to 20 carbon atoms, an alkoxy group having 1 to 20 carbon atoms, —COOR$^{41}$, or —CH$_2$CH$_2$COOR$^{41}$, here, $R^{41}$ is an alkyl group having 1 to 20 carbon atoms. In Compounds (AO-2) and (AO-5), $R^{42}$ is an alkyl group having 1 to 20 carbon atoms. In Compound (AO-5), $R^{43}$ is a hydrogen atom, a methyl group or O— (oxygen radical); a ring $G^1$ is 1,4-cyclohexylene or 1,4-phenylene; in Compound (AO-7), a ring $G^2$ is 1,4-cyclohexylene, 1,4-phenylene, or a group in which at least one hydrogen atom of 1,4-phenylene is substituted with a fluorine atom; and in Compounds (AO-5) and (AO-7), z is 1, 2, or 3.

4. Liquid Crystal Display Element

The liquid crystal composition can be suitably used for a liquid crystal display element that has an operation mode such as PC, TN, STN, OCB, and PSA, and is driven by an active matrix method. This composition can also be suitably used for a liquid crystal display element that has an operation mode such as PC, TN, STN, OCB, VA, and IPS, and is driven by a passive matrix method. These elements can be applied to any type of a reflective type, a transmissive type, and a semi-transmissive type.

This composition is also suitable for a nematic curvilinear aligned phase (NCAP) element, and here, the composition is microencapsulated. This composition can also be used for a polymer dispersed liquid crystal display element (PDLCD) and a polymer network liquid crystal display element (PN-LCD). In these compositions, a large amount of the polymerizable compound is added. On the other hand, in a composition using a liquid crystal display element in a PSA mode, a proportion of the polymerizable compound with respect to 100 weight % of a liquid crystal composition is preferably 10 weight % or less, a more preferable proportion is in a range of 0.1 weight % to 2 weight %, and a still more preferable proportion is in a range of 0.2 weight % to 1.0 weight %. An element in a PSA mode can be driven by a driving method such as an active matrix method and a passive matrix method. Such an element can be applied to any type of a reflective type, a transmissive type, and a semi-transmissive type.

In the polymer sustained alignment type element, the polymer contained in the composition causes liquid crystal molecules to be aligned. The polar compound assists the alignment of liquid crystal molecule. That is, the polar compound can be used in place of an alignment film. An example of a method of producing such an element is as follows. An element including two substrates called an array substrate and a color filter substrate is prepared. The substrates have no alignment film. At least one of the substrates has an electrode layer. Liquid crystalline compounds are mixed to prepare a liquid crystal composition. Compound (1), and additionally other polymerizable compounds and polar compounds are added as necessary to this composition. As necessary, an additive may be further added thereto. This composition is inserted into an element. Light is emitted while a voltage is applied to this element. Ultraviolet rays are preferable. The polymerizable compound is polymerized by emitting light. According to the polymerization, a composition containing a polymer is produced and an element having a PSA mode is produced.

In this procedure, since a polar group interacts with a surface of the substrate, the polar compound is disposed on the substrate. The polar compound causes liquid crystal molecules to be aligned. When there are a plurality of polar groups, interaction with a surface of the substrate becomes stronger and liquid crystal molecules can be aligned at a low concentration. When a voltage is applied, the alignment of liquid crystal molecules is further promoted according to an action of an electric field. According to the alignment, the polymerizable compound is also aligned. Since the polymerizable compound is polymerized by ultraviolet rays in this state, a polymer that maintains this alignment is produced. According to an effect of the polymer, the alignment of liquid crystal molecules is additionally stabilized, and thus a response time of the element is shortened. Since image burn is a malfunction of liquid crystal molecules, burn is also lessened by an effect of the polymer at the same time. Since Compound (1) is polymerizable, it is consumed by polymerization. Compound (1) is also consumed by copolymerization with other polymerizable compounds. Therefore, Compound (1) has a polar group but it is consumed, and thus a liquid crystal display element having a high voltage holding ratio is obtained. Here, when a polar compound having polymerizability is used, it is possible for one compound to exhibit effects of both a polar compound and a polymerizable compound. Therefore, a polymerizable compound having no polar group is not necessary in some cases.

EXAMPLES

The disclosure will be described in further detail with reference to examples (including synthesis examples and usage examples). The disclosure is not limited to such examples. The disclosure also includes a mixture prepared by mixing at least two of compositions of usage examples.

1. Example of Compound (1)

Unless otherwise described, the reactions occurred under a nitrogen atmosphere. Compound (1) was synthesized according to procedures shown in Example 1. A synthesized compound was identified by a method such as NMR analysis. Characteristics of Compound (1), liquid crystalline compounds, compositions, and elements were measured by the following methods.

NMR analysis: a DRX-500 (commercially available from Bruker BioSpin) was used for measurement. In $^1$H-NMR measurement, a sample was dissolved in a deuterated solvent such as $CDCl_3$ and measurement was performed under conditions of room temperature and 500 MHz with a cumulative number of 16 measurements. Tetramethylsilane was used as an internal standard. $^{19}$F-NMR measurement was performed using $CFCl_3$ as an internal standard and a cumulative number of measurements was 24. In the explanation of nuclear magnetic resonance spectrums, s denotes singlet, d denotes doublet, t denotes triplet, q denotes quartet, quin denotes quintet, sext denotes sextet, m denotes multiplet, and br denotes broad.

Gas chromatographic analysis: A GC-2010 type gas chromatography instrument (commercially available from Shimadzu Corporation) was used for measurement. As a column, a capillary column DB-1 (with a length 60 m, an inner diameter of 0.25 mm, and a film thickness of 0.25 μm, commercially available from Agilent Technologies Inc.) was used. Helium (1 ml/min) was used as a carrier gas. A temperature of a sample vaporization chamber was set to 300° C., and a temperature of a detector (FID) part was set to 300° C. A sample was dissolved in acetone to prepare a 1 weight % solution, and 1 μl of the obtained solution was injected into the sample vaporization chamber. As a recorder, a GC Solution system (commercially available from Shimadzu Corporation) was used.

HPLC analysis: a Prominence (LC-20AD; SPD-20A, commercially available from Shimadzu Corporation) was used for measurement. As a column, a YMC-Pack ODS-A (with a length of 150 mm, an inner diameter of 4.6 mm, and a particle size of 5 μm, commercially available from YMC Co., Ltd.) was used. As an eluent, acetonitrile and water were appropriately mixed and used. As a detector, a UV detector, an RI detector, a CORONA detector, or the like was appropriately used. When a UV detector was used, a detection wavelength was set to 254 nm. A sample was dissolved in acetonitrile to prepare a 0.1 weight % solution and 1 μL of the solution was introduced into a sample chamber. As a recorder, a C-R7Aplus (commercially available from Shimadzu Corporation) was used.

UV-visible spectroscopic analysis: a PharmaSpec UV-1700 (commercially available from Shimadzu Corporation) was used for measurement. A detection wavelength of 190 nm to 700 nm was set. A sample was dissolved in acetonitrile to prepare a 0.01 mmol/L solution, and put into a quartz cell (optical path length of 1 cm) for measurement.

Measurement sample: when a phase structure and a transition temperature (a clearing point, a melting point, a polymerization initiation temperature, etc.) were measured, a compound itself was used as a sample.

Measurement method: properties were measured by the following methods. Most of these are described in JEITA standards (JEITA-ED-2521B) discussed and established by the Japan Electronics and Information Technology Industries Association (JEITA) or modified methods thereof. No thin film transistor (TFT) was attached to a TN element used for measurement.

(1) Phase Structure

A sample was placed on a hot plate (FP-52 type hot stage commercially available from Mettler) of a melting point measuring device including a polarization microscope. While this sample was heated at a speed of 3° C./min, a phase state and a change thereof were observed under a polarization microscope, and a type of the phase was identified.

(2) Transition Temperature (° C.)

A scanning calorimeter Diamond DSC system (commercially available from PerkinElmer) or a high sensitivity differential scanning calorimeter X-DSC7000 (commercially available from Hitachi High-Tech Science Corporation) were used for measurement. The temperature of the sample was raised or lowered at a speed of 3° C./min, a starting point of an endothermic peak or an exothermic peak according to a phase change in the sample was obtained by extrapolation, and a transition temperature was determined. A melting point and a polymerization initiation temperature of the compound were measured using this device. A temperature at which the compound transitions from a solid phase to a liquid crystal phase such as a smectic phase or a nematic phase may be abbreviated as a "lower limit temperature of a liquid crystal phase." A temperature at which the compound transitions from a liquid crystal phase to a liquid phase may be abbreviated as a "clearing point.

A crystal is represented as C. When types of crystal are distinguished, they are denoted as $C_1$ and $C_2$. The smectic phase is represented as S and the nematic phase is represented as N. In the smectic phase, when phases are distinguished as a smectic A phase, a smectic B phase, a smectic C phase, and a smectic F phase, they are represented as $S_A$, $S_B$, $S_C$, and $S_F$, respectively. A liquid (isotropic) is represented as I. The transition temperature is expressed as, for example, "C 50.0 N 100.0 I." This indicates that a transition temperature from a crystal to a nematic phase is 50.0° C., and a transition temperature from a nematic phase to a liquid is 100.0° C.

(3) Upper Limit Temperature of Nematic Phase ($T_{NI}$ or NI; ° C.)

A sample was placed on a hot plate of a melting point measuring device including a polarization microscope and heated at a speed of 1° C./min. A temperature at which a part of the sample changed from a nematic phase to an isotropic liquid was measured. The upper limit temperature of a nematic phase may be abbreviated as an "upper limit temperature." When a sample is a mixture of Compound (1) and a mother liquid crystal, the sample is indicated by a symbol $T_{NI}$. When a sample is a mixture of Compound (1) and a compound of the components B, C, and D, the sample is indicated by a symbol NI.

(4) Lower Limit Temperature of Nematic Phase ($T_C$; ° C.)

A sample having a nematic phase was stored in a freezer at 0° C., −10° C., −20° C., −30° C., and −40° C. for 10 days, and then a liquid crystal phase was observed. For example, when the sample remained in a nematic phase at −20° C. and changed to a crystal or a smectic phase at −30° C., $T_C$ is described as ≤−20° C. A lower limit temperature of a nematic phase may be abbreviated as a "lower limit temperature."

(5) Viscosity (Bulk Viscosity; f; Measured at 20° C.; mPa·s)

An E type rotational viscometer (commercially available from Tokyo Keiki) was used for measurement.

(6) Optical Anisotropy (Refractive Index Anisotropy; Measured at 25° C.; Δn)

Measurement was performed by an Abbe refractometer in which a polarizing plate was attached to an eyepiece using light with a wavelength of 589 nm. A surface of a main prism was rubbed in one direction and the sample was then added dropwise on the main prism. A refractive index (n∥) was measured when a direction of polarized light was parallel to a rubbing direction. A refractive index (n⊥) was measured when a direction of polarized light was perpendicular to a rubbing direction. A value of optical anisotropy (Δn) was calculated from the equation Δn=n∥−n⊥.

(7) Specific Resistance (ρ; Measured at 25° C.; Ωcm)

1.0 mL of a sample was injected into a container including an electrode. A DC voltage (10 V) was applied to this container and a direct current was measured after 10 seconds. A specific resistance was computed from the following equation. (Specific resistance)={(voltage)×(electric capacitance of container)}/{(direct current)×(dielectric constant of vacuum)}.

Methods of measuring properties may be different between a sample having positive dielectric anisotropy and a sample having negative dielectric anisotropy. A measurement method when dielectric anisotropy is positive is described in Items (8a) to (12a). A measurement method when dielectric anisotropy is negative is described in Items (8b) to (12b).

(8a) Viscosity (Rotational Viscosity; γ1; Measured at 25° C.; mPa·s)

Positive dielectric anisotropy: Measurement was performed according to a method described in M. Imai et al., Molecular Crystals and Liquid Crystals, Vol. 259, 37 (1995). A sample was inserted into a TN element in which a twist angle was 0 degrees and an interval (cell gap) between two glass substrates was 5 μm. Voltages in a range of 16 V to 19.5 V were gradually applied at 0.5 V intervals to this element. After no voltage was applied for 0.2 seconds, application was repeated under conditions of one square wave (rectangular pulse; 0.2 seconds) and no voltage application (2 seconds). A peak current and a peak time of a transient current generated by this application were measured. A value of the rotational viscosity was obtained from these measured values and Calculation Formula (8) on page 40 in the paper (M. Imai et al.). A value of the dielectric anisotropy necessary for this calculation was obtained by the method described below using an element for which the rotational viscosity was measured.

(8b) Viscosity (Rotational Viscosity; γ1; Measured at 25° C.; mPa·s)

Negative dielectric anisotropy: Measurement was performed according to a method described in M. Imai et al., Molecular Crystals and Liquid Crystals, Vol. 259, 37 (1995). A sample was inserted into a VA element in which an interval (cell gap) between two glass substrates was 20 μm. Voltages in a range of 39 V to 50 V were gradually applied at 1 V intervals to this element. After no voltage was applied for 0.2 seconds, application was repeated under conditions of one square wave (rectangular pulse; 0.2 seconds) and no voltage application (2 seconds). A peak current and a peak time of a transient current generated by this application were measured. A value of the rotational viscosity was obtained from these measured values and Calculation Formula (8) on page 40 in the paper (M. Imai et al.). The dielectric anisotropy necessary for this calculation was obtained using a value measured in the following dielectric anisotropy section.

(9a) Dielectric Anisotropy (Δε; Measured at 25° C.)

Positive dielectric anisotropy: A sample was inserted into a TN element in which an interval (cell gap) between two glass substrates was 9 μm and a twist angle was 80 degrees. A sine wave (10 V, 1 kHz) was applied to this element, and after 2 seconds, a dielectric constant (ε∥) in a long axis direction of liquid crystal molecules was measured. A sine wave (0.5 V, 1 kHz) was applied to this element, and after 2 seconds, a dielectric constant (ε⊥) in a short axis direction of liquid crystal molecules was measured. A value of the dielectric anisotropy was calculated from Formula Δε=ε∥−ε⊥.

(9b) Dielectric Anisotropy (Δε; Measured at 25° C.)

Negative dielectric anisotropy: A value of dielectric anisotropy was calculated from Formula Δε=ε∥−ε⊥. A dielectric constant (ε∥ and ε⊥) was measured as follows.

1) Measurement of dielectric constant (ε∥): An ethanol (20 mL) solution containing octadecyltriethoxysilane (0.16 mL) was applied to a well-washed glass substrate. The glass substrate was rotated by a spinner and then heated at 150° C. for 1 hour. A sample was inserted into a VA element in which an interval (cell gap) between two glass substrates was 4 μm, and this element was sealed using an adhesive that was cured with ultraviolet rays. A sine wave (0.5 V, 1 kHz) was applied to this element and after 2 seconds, a dielectric constant (ε∥) in a long axis direction of liquid crystal molecules was measured.

2) Measurement of dielectric constant (ε⊥): A polyimide solution was applied to a well-washed glass substrate. The glass substrate was fired and a rubbing treatment was then performed on the obtained alignment film. A sample was inserted into a TN element in which an interval (cell gap) between two glass substrates was 9 μm and a twist angle was 80 degrees. A sine wave (0.5 V, 1 kHz) was applied to this element, and after 2 seconds, a dielectric constant (ε⊥) in a short axis direction of liquid crystal molecules was measured.

(10a) Elastic Constant (K; Measured at 25° C.; pN)

Positive dielectric anisotropy: An HP4284A type LCR meter (commercially available from Agilent Technologies) was used for measurement. A sample was inserted into a horizontally aligned element in which an interval (cell gap) between two glass substrates was 20 μm. A charge of 0 V to 20 V was applied to this element, and an electrostatic capacitance and an applied voltage were measured. These measured electrostatic capacitance (C) and applied voltage (V) values were fitted into Formula (2.98) and Formula (2.101) on page 75 in "Liquid Crystal Device Handbook" (commercially available from Nikkan Kogyo Shimbun, Ltd.), and values of $K_{11}$ and $K_{33}$ were obtained from Formula (2.99). Next, in Formula (3.18) on page 171, $K_{22}$ was computed using the values of $K_{11}$ and $K_{33}$ obtained above. An elastic constant K was expressed as an average value of $K_{11}$, $K_{22}$ and $K_{33}$ obtained in this manner.

(10b) Elastic Constant ($K_{11}$ and $K_{33}$; Measured at 25° C.; pN)

Negative dielectric anisotropy: An EC-1 elastic constant measuring instrument (commercially available from TOYO Corporation) was used for measurement. A sample was inserted into a vertically aligned element in which an interval (cell gap) between two glass substrates was 20 µm. A charge of 20 V to 0 V was applied to this element and an electrostatic capacitance and an applied voltage were measured. Values of an electrostatic capacitance (C) and an applied voltage (V) were fitted into Formula (2.98) and Formula (2.101) on page 75 in "Liquid Crystal Device Handbook" (commercially available from Nikkan Kogyo Shimbun, Ltd.) and a value of the elastic constant was obtained from Formula (2.100).

(11a) Threshold Voltage (Vth; Measured at 25° C.; V)

Positive dielectric anisotropy: An LCD5100 type luminance meter (commercially available from Otsuka Electronics) was used for measurement. A light source was a halogen lamp. A sample was inserted into a TN element in a normally white mode in which an interval (cell gap) between two glass substrates was 0.45/An (am) and a twist angle was 80 degrees. A voltage (32 Hz, square wave) applied to this element was gradually increased by 0.02 V from 0 V to 10 V. In this case, light was emitted to the element in a vertical direction and a quantity of light that had passed through the element was measured. A voltage-transmittance curve in which the transmittance was 100% when the quantity of light was a maximum and the transmittance was 0% when the quantity of light was a minimum was created. A threshold voltage was a voltage when the transmittance was 90%.

(11b) Threshold Voltage (Vth; Measured at 25° C.; V)

Negative dielectric anisotropy: An LCD5100 type luminance meter (commercially available from Otsuka Electronics) was used for measurement. A light source was a halogen lamp. A sample was inserted into a VA element in a normally black mode in which an interval (cell gap) between two glass substrates was 4 am and a rubbing direction was antiparallel, and this element was sealed using an adhesive that was cured with ultraviolet rays. A voltage (60 Hz, square wave) applied to this element was gradually increased by 0.02 V from 0 V to 20 V. In this case, light was emitted to the element in a vertical direction and a quantity of light that had passed through the element was measured. A voltage-transmittance curve in which the transmittance was 100% when the quantity of light was a maximum and the transmittance was 0% when the quantity of light was a minimum was created. A threshold voltage was a voltage when the transmittance was 10%.

(12a) Response Time ($\tau$; Measured at 25° C.; ms)

Positive dielectric anisotropy: An LCD5100 type luminance meter (commercially available from Otsuka Electronics) was used for measurement. A light source was a halogen lamp. A low-pass filter was set at 5 kHz. A sample was inserted into a TN element in a normally white mode in which an interval (cell gap) between two glass substrates was 5.0 µm and a twist angle was 80 degrees. A square wave (60 Hz, 5 V, 0.5 seconds) was applied to this element. In this case, light was emitted to the element in a vertical direction and a quantity of light that had passed through the element was measured. The transmittance was 100% when the quantity of light was a maximum, and the transmittance was 0% when the quantity of light was a minimum. A rise time ($\tau r$; millisecond) was a time required for the transmittance to change from 90% to 10%. A fall time ($\tau f$; millisecond) was a time for the transmittance to change from 10% to 90%. A response time was a sum of the rise time and the fall time obtained in this manner.

(12b) Response Time ($\tau$; Measured at 25° C.; ms)

Negative dielectric anisotropy: An LCD5100 type luminance meter (commercially available from Otsuka Electronics) was used for measurement. A light source was a halogen lamp. A low-pass filter was set at 5 kHz. A low-pass filter was set at 5 kHz. A sample was inserted into a PVA element in a normally black mode in which an interval (cell gap) between two glass substrates was 3.2 µm and a rubbing direction was antiparallel. This element was sealed using an adhesive that was cured with ultraviolet rays. A voltage that was slightly higher than a threshold voltage was applied to this element for 1 minute, and next ultraviolet rays of 23.5 mW/cm$^2$ were emitted for 8 minutes while a voltage of 5.6 V was applied. A square wave (60 Hz, 10 V, 0.5 seconds) was applied to this element. In this case, light was emitted to the element in a vertical direction and a quantity of light that had passed through the element was measured. The transmittance was 100% when the quantity of light was a maximum, and the transmittance was 0% when the quantity of light was a minimum. A response time was a time (fall time; milliseconds) required for the transmittance to change from 90% to 10%.

(13) Voltage Holding Ratio

A polymerizable compound was polymerized by emitting ultraviolet rays using a Black light, F40T10/BL (peak wavelength of 369 nm, commercially available from Eye Graphics Co., Ltd.). A pulse voltage (at 1 V for 60 microseconds) was applied to this element at 60° C. for charging. An attenuating voltage was measured for 1.67 seconds using a high-speed voltmeter, and an area A between a voltage curve in a unit cycle and the horizontal axis was obtained. An area B was an area when the voltage was not attenuated. A voltage holding ratio was expressed as a percentage of the area A with respect to the area B.

Synthesis Example 1

Synthesis of Compound (1-1-5)

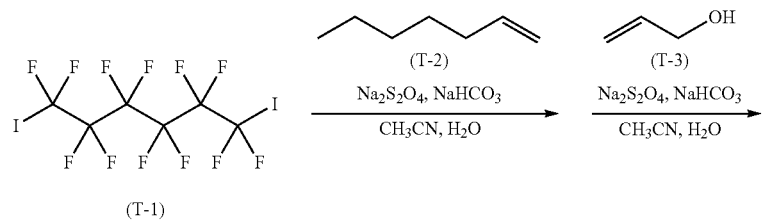

-continued

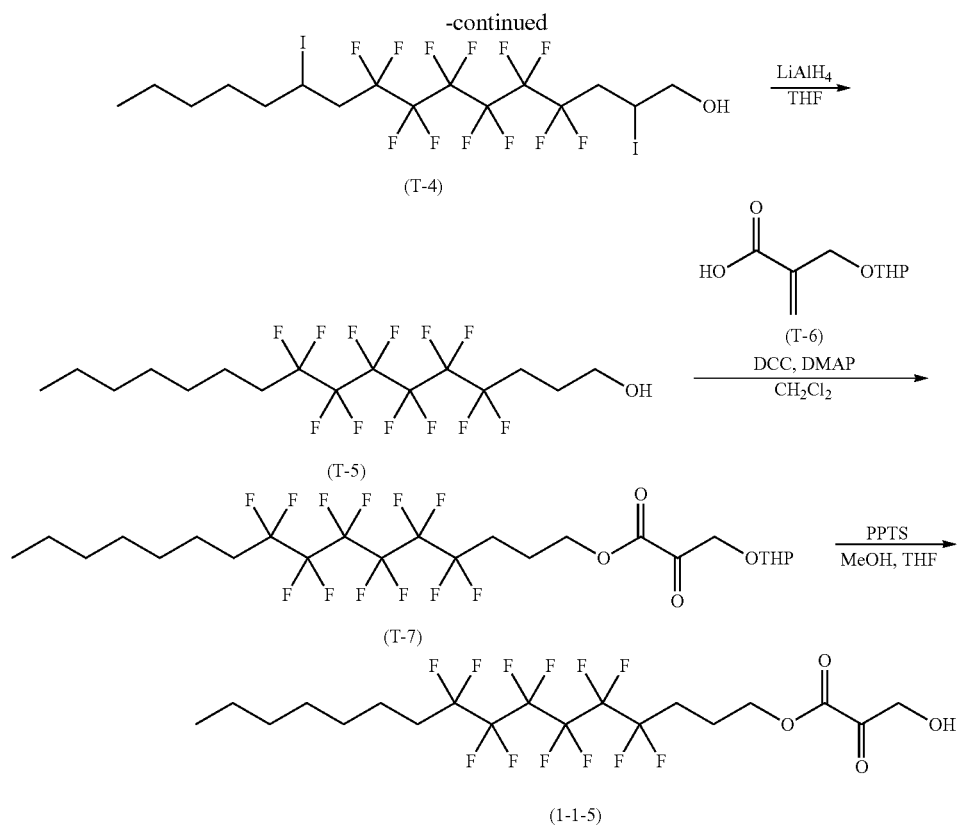

First Process

Compound (T-1) (35.0 g), Compound (T-2) (8.86 ml), and acetonitrile (525 ml) were put into a reaction vessel and cooled to 0° C. An aqueous (70.0 ml) solution containing sodium dithionite (7.34 g) and sodium hydrogen carbonate (2.65 g) was slowly added dropwise thereto and additionally the mixture was stirred for 1 hour. Compound (T-3) (4.32 ml) was added and an aqueous (140 ml) solution containing sodium dithionite (14.7 g) and sodium hydrogen carbonate (5.30 g) was then slowly added dropwise, and the reaction mixture was stirred for 2 hours while the temperature returned to room temperature. The reaction mixture was poured into ice water, and an aqueous layer was extracted with ethyl acetate. The combined organic layer was washed with brine and dried with anhydrous magnesium sulfate. This solution was concentrated under a reduced pressure, the residue was purified through silica gel chromatography (volume ratio, toluene:ethyl acetate=20:1), and thereby Compound (T-4) (8.69 g; 19%) was obtained.

Second Process

Lithium aluminum hydride (1.63 g) and THF (220 ml) were put into a reaction vessel and cooled to −10° C. A THF (80.0 ml) solution containing Compound (T-4) (8.69 g) was slowly added dropwise thereto and the reaction mixture was stirred for 8 hours while the temperature returned to room temperature. The reaction mixture was poured into a saturated aqueous ammonium chloride solution, insoluble substances were filtered off, and an aqueous layer was then extracted with ethyl acetate. The combined organic layer was washed with water and dried with anhydrous magnesium sulfate. This solution was concentrated under a reduced pressure, and the residue was purified through silica gel chromatography (volume ratio, toluene:ethyl acetate=10:1).

In addition, the residue was purified by re-crystallization from heptane, and thereby Compound (T-5) (3.70 g; 66%) was obtained.

Third Process

Compound (T-5) (3.70 g), Compound (T-6) (1.80 g) synthesized by the method described in WO2017209161A1, DMAP (0.493 g), and dichloromethane (40.0 ml) were put into a reaction vessel and cooled to 0° C. A dichloromethane (15.0 ml) solution containing DCC (2.50 g) was slowly added dropwise thereto and the mixture was stirred for 12 hours while the temperature returned to room temperature. Insoluble substances were filtered off and the reaction mixture was then poured into water, and an aqueous layer was extracted with dichloromethane. The obtained organic layer was washed with water and dried with anhydrous magnesium sulfate. This solution was concentrated under a reduced pressure, the residue was purified through silica gel chromatography (volume ratio, heptane:ethyl acetate=8:1), and thereby Compound (T-7) (4.66 g; 92%) was obtained.

Fourth Process

Compound (T-7) (4.66 g), PPTS (0.93 g), THF (25.0 ml), and methanol (25.0 ml) were put into a reaction vessel and the mixture was stirred at 50° C. for 4 hours. The reaction mixture was poured into water and an aqueous layer was extracted with ethyl acetate. The obtained organic layer was washed with water and dried with anhydrous magnesium sulfate. This solution was concentrated under a reduced pressure, and the residue was purified through silica gel chromatography (volume ratio, heptane:ethyl acetate=3:1). In addition, the residue was purified by re-crystallization from heptane, and thereby Compound (1-1-5) (3.44 g; 85%) was obtained.

NMR analysis values the obtained Compound (1-1-5) were as follows.

$^1$H-NMR: chemical shift δ (ppm; CDCl$_3$): 6.27 (s, 1H), 5.89 (s, 1H), 4.35 (d, J=6.8 Hz, 2H), 4.27 (t, J=6.3 Hz, 2H), 2.28-2.12 (m, 3H), 2.11-1.98 (m, 4H), 1.65-1.56 (m, 2H), 1.42-1.24 (m, 8H), 0.89 (t, J=7.1 Hz, 3H).

Synthesis Example 2

Synthesis of Compound (1-1-19)

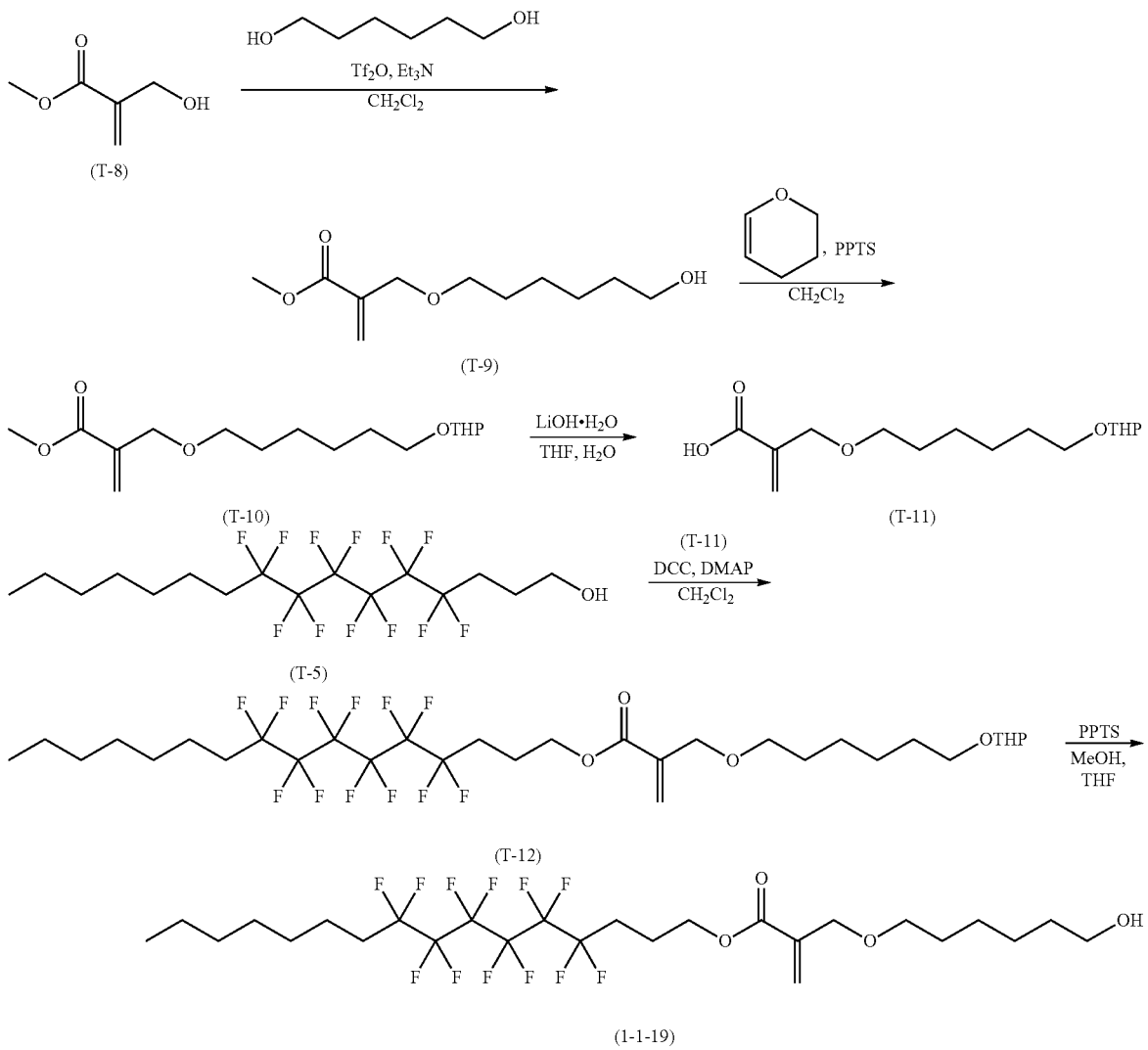

First Process

Trifluoromethanesulfonic anhydride (25.0 g) and dichloromethane (80.0 ml) were put into a reaction vessel and cooled to 0° C. Compound (T-8) (10.3 g) and a dichloromethane (160 ml) solution containing trimethylamine (8.97 g) were slowly added dropwise thereto. The obtained solution was poured into 1,6-hexanediol (314 g) and the mixture was stirred at room temperature for 12 hours. The reaction mixture was poured into water, and an aqueous layer was extracted with dichloromethane. The obtained organic layer was washed with water and dried with anhydrous magnesium sulfate. This solution was concentrated under a reduced pressure, and the residue was purified through silica gel chromatography (volume ratio, heptane:ethyl acetate=3:2), and thereby Compound (T-9) (11.3 g; 59%) was obtained.

Second Process

Compound (T-9) (11.3 g), 3,4-dihydro-2H-pyran (4.83 g), and dichloromethane (115 ml) were put into a reaction vessel and cooled to 0° C. PPTS (1.31 g) was added thereto and the mixture was stirred for 12 hours while the temperature returned to room temperature. The reaction mixture was poured into water, and an aqueous layer was extracted with dichloromethane. The obtained organic layer was washed with water and dried with anhydrous magnesium sulfate. This solution was concentrated under a reduced pressure, and the residue was purified through silica gel chromatography (volume ratio, heptane:ethyl acetate=7:1), and thereby Compound (T-10) (15.0 g; 96%) was obtained. Here, THP indicates a tetrahydropyranyl group.

Third Process

Compound (T-10) (15.0 g), THF (75.0 ml), and water (75.0 ml) were put into a reaction vessel and cooled to 0° C. Lithium hydroxide monohydrate (4.19 g) was added thereto and the mixture was stirred for 7 hours while the temperature returned to room temperature. The reaction mixture was poured into water, and 1 N hydrochloric acid (112 ml) was slowly added thereto so that it became acidic and an aqueous layer was then extracted with ethyl acetate. The obtained organic layer was washed with water and dried with anhydrous magnesium sulfate. This solution was concentrated under a reduced pressure, and thereby Compound (T-11) (13.0 g; 91%) was obtained.

Fourth Process

Compound (T-5) (3.00 g) and Compound (T-11) (2.25 g) were used as raw materials, and Compound (T-12) (4.44 g; 93%) was obtained in the same manner as in the third process of Synthesis Example 1.

Fifth Process

Compound (T-12) (4.44 g) was used as a raw material, and Compound (1-1-19) (3.54 g; 90%) was obtained in the same manner as in the fourth process of Synthesis Example 1.

NMR analysis values of the obtained Compound (1-1-19) were as follows.

$^1$H-NMR: chemical shift δ (ppm; CDCl$_3$): 6.30 (d, J=0.8 Hz, 1H), 5.90 (d, J=1.6 Hz, 1H), 4.25 (t, J=6.2 Hz, 2H), 4.17 (s, 2H), 3.68-3.61 (m, 2H), 3.49 (t, J=6.6 Hz, 2H), 2.26-2.12 (m, 2H), 2.12-1.97 (m, 4H), 1.67-1.57 (m, 6H), 1.42-1.22 (m, 13H), 0.89 (t, J=7.1 Hz, 3H).

[Comparative Example 1] Compound (S-1) was synthesized as a comparative compound and properties thereof were measured because this compound is described in Japanese Unexamined Patent Application Publication No. 2016-108310 and similar to a compound of the disclosure.

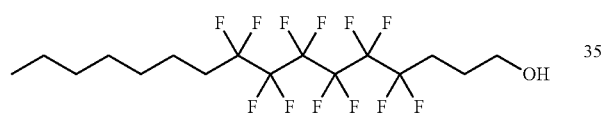
(S-1)

NMR analysis values of the obtained Comparative Compound (S-1) were as follows.

$^1$H-NMR: chemical shift δ (ppm; CDCl$_3$): 3.75 (t, J=6.1 Hz, 2H), 2.28-2.14 (m, 2H), 2.12-1.98 (m, 2H), 1.92-1.82 (m, 2H), 1.64-1.53 (m, 2H), 1.42-1.23 (m, 8H), 0.89 (t, J=7.0 Hz, 3H).

Vertical alignment properties and voltage holding ratios (VHR) of Compound (1-1-5) and Comparative Compound (S-1) were compared. Here, Composition (i) and Polymerizable Compound (M-1-1) were used for evaluation.

A proportion of a component of Composition (i) is indicated by weight %.

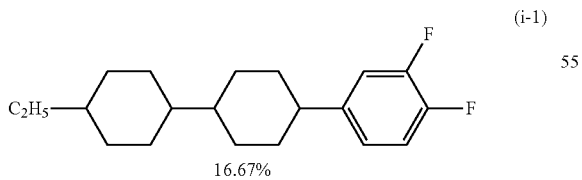
(i-1)
16.67%

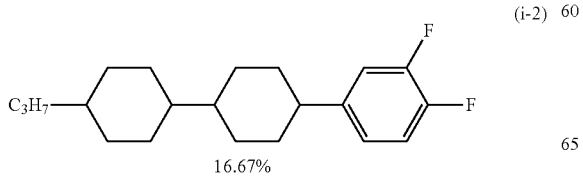
(i-2)
16.67%

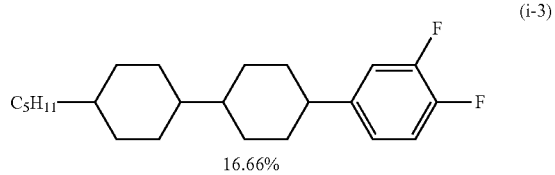
(i-3)
16.66%

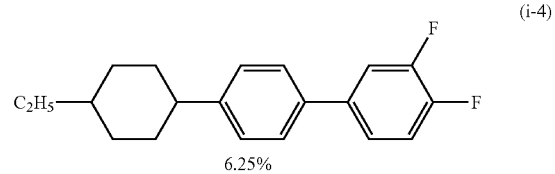
(i-4)
6.25%

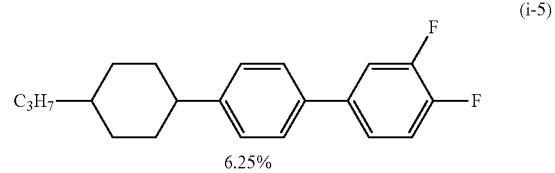
(i-5)
6.25%

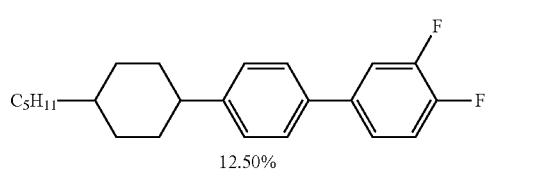
(i-6)
12.50%

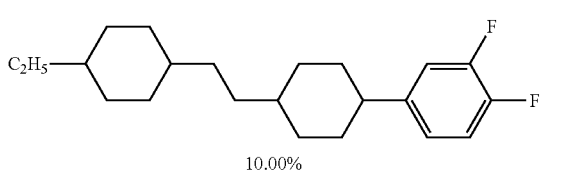
(i-7)
10.00%

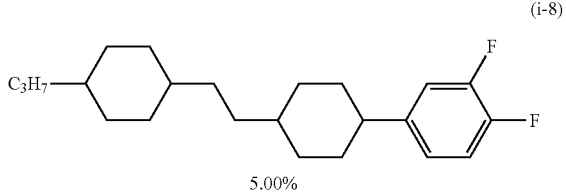
(i-8)
5.00%

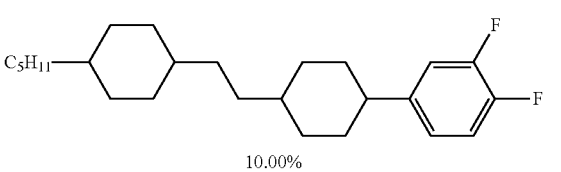
(i-9)
10.00%

Polymerizable Compound (M-1-1) is shown below.

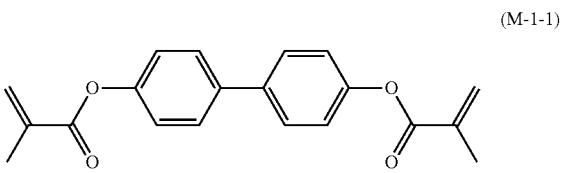 [SMILES: C=C(C)C(=O)Oc1ccc(-c2ccc(OC(=O)C(=C)C)cc2)cc1]
(M-1-1)

Vertical Alignment Property

Polymerizable Compound (M-1-1) in a proportion of 0.4 weight % was added to Composition (i). Compound (1-1-5) or Comparative Compound (S-1) in a proportion of 3.5 weight % was added thereto. This mixture was injected into an element in which an interval (cell gap) between two glass substrates was 3.5 μm and which has no alignment film. This element was set in a polarizing microscope, light was emitted to the element from below and it was observed whether light leaked. When sufficient liquid crystal molecules were aligned and light did not pass through the element, a vertical alignment property was determined as "favorable." When light that passed through the element was observed, this was determined as "poor."

Voltage Holding Ratio (VHR)

A polymerizable compound was polymerized by emitting ultraviolet rays (20 J) to the element prepared above using a Black light, F40T10/BL (peak wavelength of 355 nm, commercially available from Eye Graphics Co., Ltd). A pulse voltage (at 1 V for 60 microseconds) was applied to this element at 60° C. for charging. An attenuating voltage was measured for 1.67 milliseconds using a high-speed voltmeter, and an area A between a voltage curve in a unit cycle and the horizontal axis was obtained. An area B was an area when the voltage was not attenuated. A voltage holding ratio was expressed as a percentage of the area A with respect to the area B.

TABLE 2

Physical Properties of Compound (1-1-5) and Comparative Compound (S-1)

| | Compound (1-1-5) | Comparative Compound (S-1) |
|---|---|---|
| Vertical alignment property | Favorable | Favorable |
| Voltage holding ratio (VHR) | 95.92% | 71.20% |

Physical properties of Compound (No. 1-1-5) of Synthesis Example 1 and Comparative Compound (S-1) are summarized in Table 2. Both exhibited a favorable vertical alignment property in an element having no alignment film. On the other hand, a voltage holding ratio was higher in a case in which Compound (1-1-5) was used than a case in which Comparative Compound (S-1) was used. This is because a polar compound having an —OH group such as Comparative Compound (S-1) greatly reduced a voltage holding ratio of an element, but when polymerizability was imparted as in Compound (1-1-5), a polar compound was incorporated into a polymer produced using a polymerizable compound and a decrease in the voltage holding ratio was reduced. Therefore, it can be said that Compound (1-1-5) is an excellent compound which exhibits a favorable vertical alignment property without lowering a voltage holding ratio of an element.

The following Compounds (1-1-1) to (1-6-20) can be synthesized with reference to methods described in synthesis examples and the section of "2. Synthesis of Compound (1)."

| No. | |
|---|---|
| 1-1-1 | 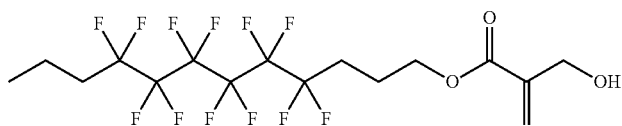 [SMILES: C=C(CO)C(=O)OCCCC(F)(F)C(F)(F)C(F)(F)C(F)(F)C(F)(F)C(F)(F)CCC] |
| 1-1-2 | 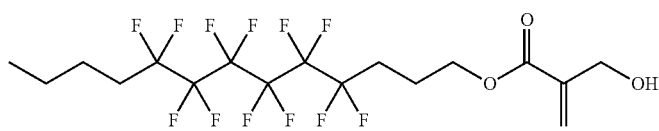 [SMILES: C=C(CO)C(=O)OCCCC(F)(F)C(F)(F)C(F)(F)C(F)(F)C(F)(F)C(F)(F)CCCC] |

-continued
| No. | |
|---|---|
| 1-1-3 | 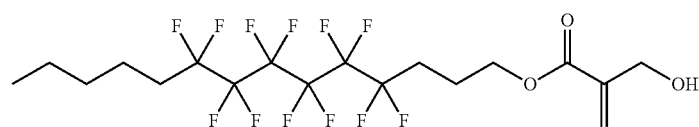 [SMILES: C=C(CO)C(=O)OCCCC(F)(F)C(F)(F)C(F)(F)C(F)(F)C(F)(F)C(F)(F)CCCCC] |
| 1-1-4 | 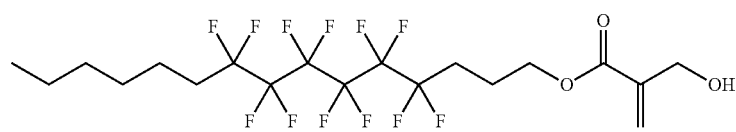 [SMILES: C=C(CO)C(=O)OCCCC(F)(F)C(F)(F)C(F)(F)C(F)(F)C(F)(F)C(F)(F)CCCCCC] |
| 1-1-5 | 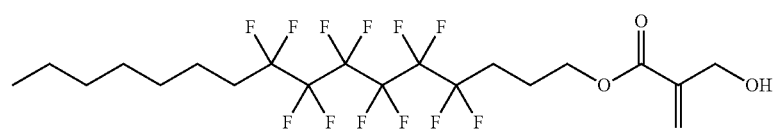 [SMILES: C=C(CO)C(=O)OCCCC(F)(F)C(F)(F)C(F)(F)C(F)(F)C(F)(F)C(F)(F)CCCCCCC] |
| 1-1-6 | 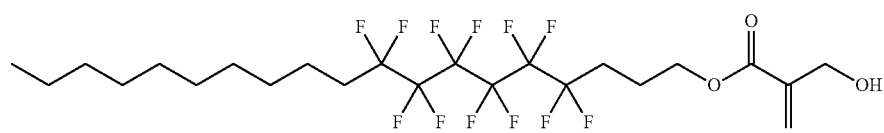 [SMILES: C=C(CO)C(=O)OCCCC(F)(F)C(F)(F)C(F)(F)C(F)(F)C(F)(F)C(F)(F)CCCCCCCCCC] |
| 1-1-7 | 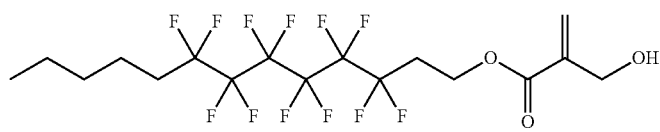 [SMILES: C=C(CO)C(=O)OCCC(F)(F)C(F)(F)C(F)(F)C(F)(F)C(F)(F)C(F)(F)CCCCC] |
| 1-1-8 | 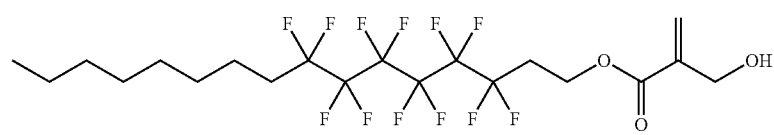 [SMILES: C=C(CO)C(=O)OCCC(F)(F)C(F)(F)C(F)(F)C(F)(F)C(F)(F)C(F)(F)CCCCCCCC] |
| 1-1-9 | 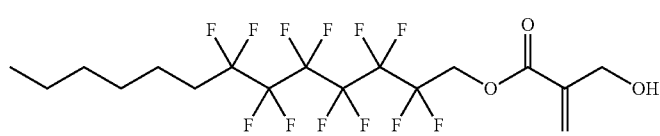 [SMILES: C=C(CO)C(=O)OCC(F)(F)C(F)(F)C(F)(F)C(F)(F)C(F)(F)C(F)(F)CCCCCC] |
| 1-1-10 | 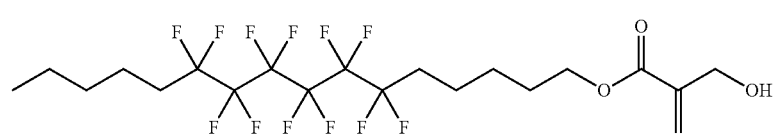 [SMILES: C=C(CO)C(=O)OCCCCCC(F)(F)C(F)(F)C(F)(F)C(F)(F)C(F)(F)C(F)(F)CCCCC] |
| 1-1-11 | 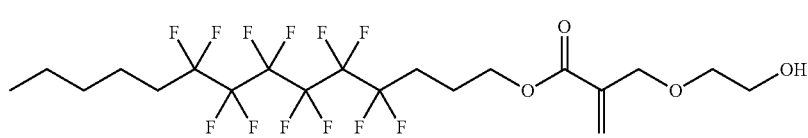 [SMILES: C=C(COCCO)C(=O)OCCCC(F)(F)C(F)(F)C(F)(F)C(F)(F)C(F)(F)C(F)(F)CCCCC] |
| 1-1-12 | 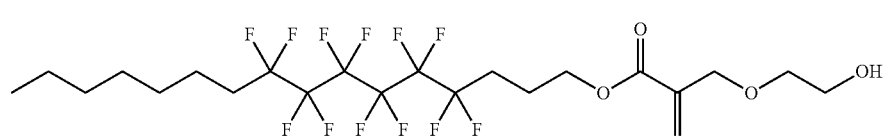 [SMILES: C=C(COCCO)C(=O)OCCCC(F)(F)C(F)(F)C(F)(F)C(F)(F)C(F)(F)C(F)(F)CCCCCCC] |
| 1-1-13 | 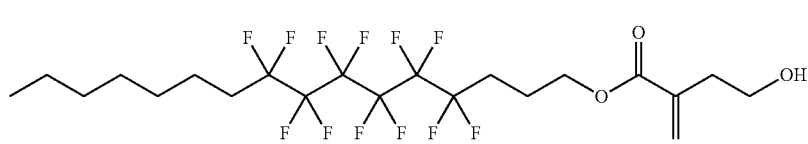 [SMILES: C=C(CCO)C(=O)OCCCC(F)(F)C(F)(F)C(F)(F)C(F)(F)C(F)(F)C(F)(F)CCCCCCC] |

-continued
| No. | |
|---|---|
| 1-1-14 | 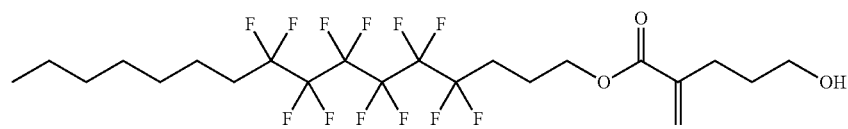 [SMILES: C=C(CCCO)C(=O)OCCCC(F)(F)C(F)(F)C(F)(F)C(F)(F)C(F)(F)C(F)(F)CCCCCCC] |
| 1-1-15 | 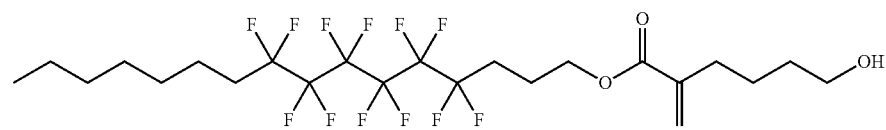 [SMILES: C=C(CCCCO)C(=O)OCCCC(F)(F)C(F)(F)C(F)(F)C(F)(F)C(F)(F)C(F)(F)CCCCCCC] |
| 1-1-16 | 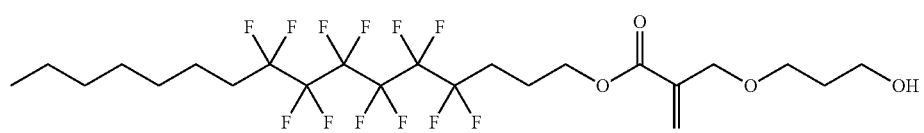 [SMILES: C=C(COCCCO)C(=O)OCCCC(F)(F)C(F)(F)C(F)(F)C(F)(F)C(F)(F)C(F)(F)CCCCCCC] |
| 1-1-17 | 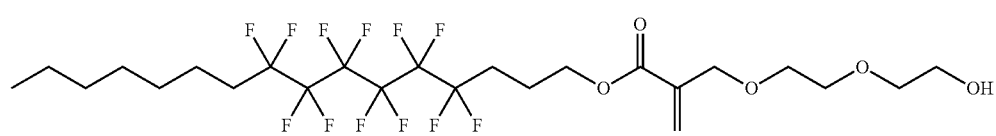 [SMILES: C=C(COCCOCCO)C(=O)OCCCC(F)(F)C(F)(F)C(F)(F)C(F)(F)C(F)(F)C(F)(F)CCCCCCC] |
| 1-1-18 | 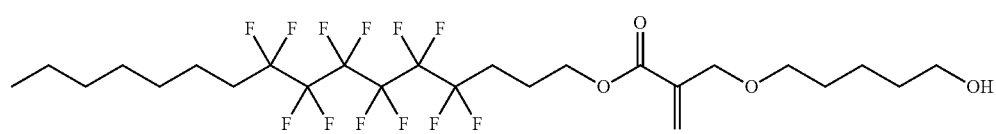 [SMILES: C=C(COCCCCCO)C(=O)OCCCC(F)(F)C(F)(F)C(F)(F)C(F)(F)C(F)(F)C(F)(F)CCCCCCC] |
| 1-1-19 | 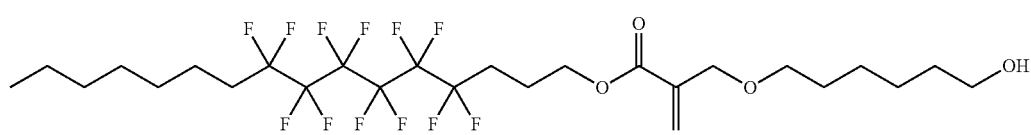 [SMILES: C=C(COCCCCCCO)C(=O)OCCCC(F)(F)C(F)(F)C(F)(F)C(F)(F)C(F)(F)C(F)(F)CCCCCCC] |
| 1-1-20 | 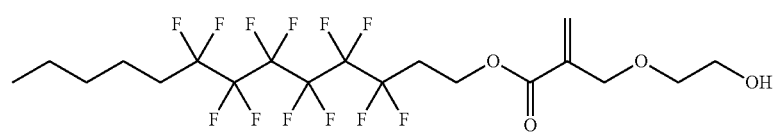 [SMILES: C=C(COCCO)C(=O)OCCC(F)(F)C(F)(F)C(F)(F)C(F)(F)C(F)(F)C(F)(F)CCCCC] |
| 1-1-21 | 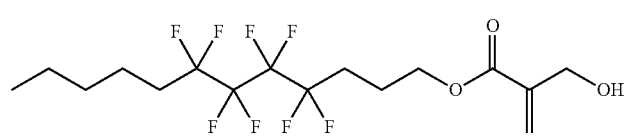 [SMILES: C=C(CO)C(=O)OCCCC(F)(F)C(F)(F)C(F)(F)C(F)(F)CCCCC] |
| 1-1-22 | 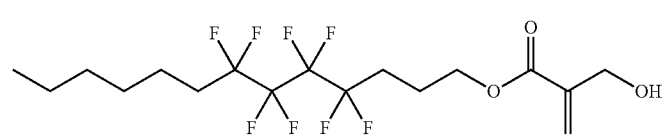 [SMILES: C=C(CO)C(=O)OCCCC(F)(F)C(F)(F)C(F)(F)C(F)(F)CCCCCC] |
| 1-1-23 | 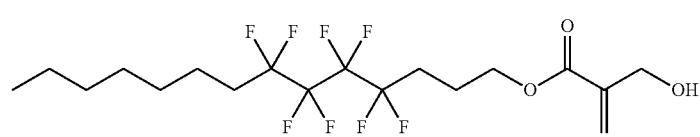 [SMILES: C=C(CO)C(=O)OCCCC(F)(F)C(F)(F)C(F)(F)C(F)(F)CCCCCCC] |
| 1-1-24 | 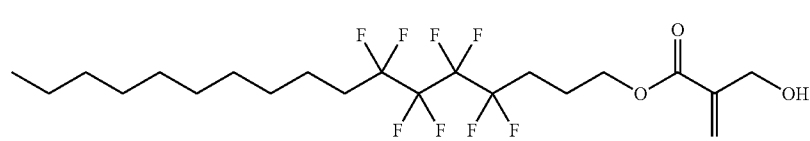 [SMILES: C=C(CO)C(=O)OCCCC(F)(F)C(F)(F)C(F)(F)C(F)(F)CCCCCCCCCC] |

-continued
| No. | |
|---|---|
| 1-1-25 | 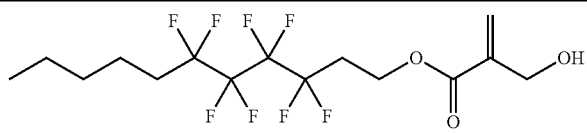 |
| 1-1-26 | 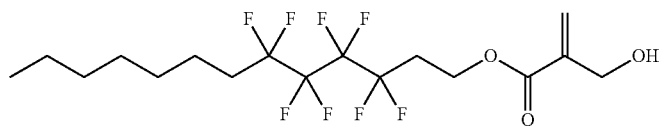 [SMILES: C=C(CO)C(=O)OCCC(F)(F)C(F)(F)C(F)(F)C(F)(F)CCCCCCC] |
| 1-1-27 | 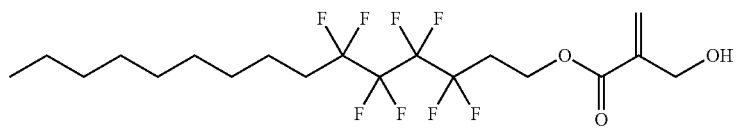 [SMILES: C=C(CO)C(=O)OCCC(F)(F)C(F)(F)C(F)(F)C(F)(F)CCCCCCCCC] |
| 1-1-28 | 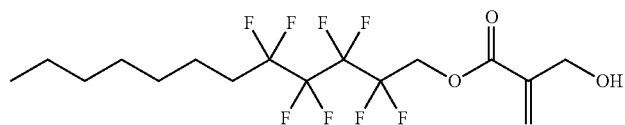 [SMILES: C=C(CO)C(=O)OCC(F)(F)C(F)(F)C(F)(F)C(F)(F)CCCCCCC] |
| 1-1-29 | 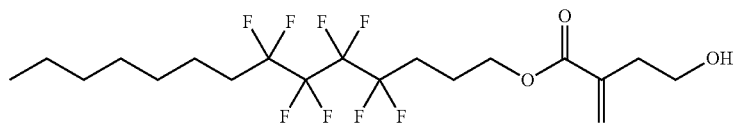 [SMILES: C=C(CCO)C(=O)OCCCC(F)(F)C(F)(F)C(F)(F)C(F)(F)CCCCCCC] |
| 1-1-30 | 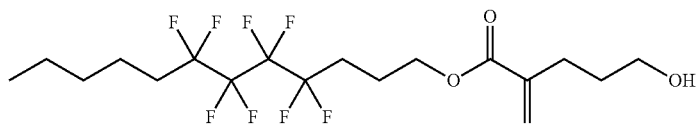 [SMILES: C=C(CCCO)C(=O)OCCCC(F)(F)C(F)(F)C(F)(F)C(F)(F)CCCCC] |
| 1-1-31 | 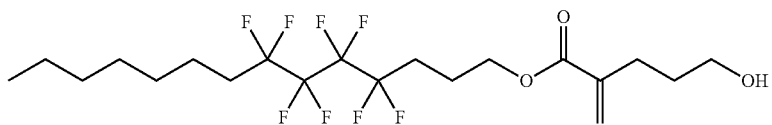 [SMILES: C=C(CCCO)C(=O)OCCCC(F)(F)C(F)(F)C(F)(F)C(F)(F)CCCCCCC] |
| 1-1-32 | 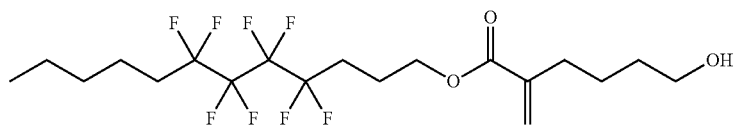 [SMILES: C=C(CCCCO)C(=O)OCCCC(F)(F)C(F)(F)C(F)(F)C(F)(F)CCCCC] |
| 1-1-33 | 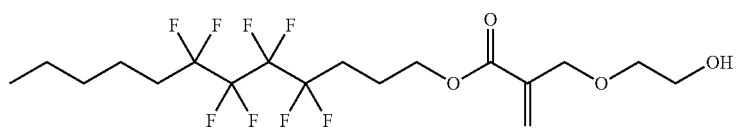 [SMILES: C=C(COCCO)C(=O)OCCCC(F)(F)C(F)(F)C(F)(F)C(F)(F)CCCCC] |
| 1-1-34 | 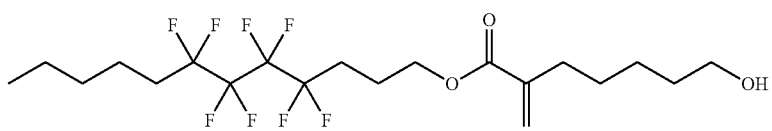 [SMILES: C=C(CCCCCO)C(=O)OCCCC(F)(F)C(F)(F)C(F)(F)C(F)(F)CCCCC] |
| 1-1-35 | 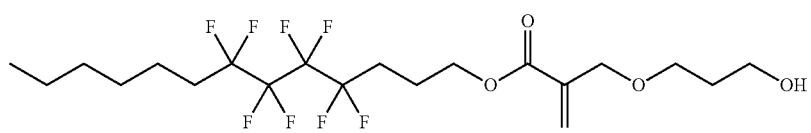 [SMILES: C=C(COCCCO)C(=O)OCCCC(F)(F)C(F)(F)C(F)(F)C(F)(F)CCCCCC] |

-continued
| No. | |
|---|---|
| 1-1-36 | 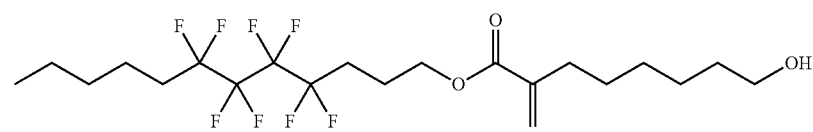 [SMILES: C=C(CCCCCCO)C(=O)OCCCC(F)(F)C(F)(F)C(F)(F)C(F)(F)CCCCC] |
| 1-1-37 | 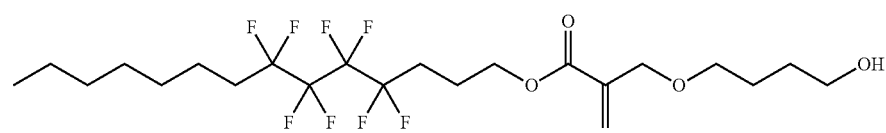 [SMILES: C=C(COCCCCO)C(=O)OCCCC(F)(F)C(F)(F)C(F)(F)C(F)(F)CCCCCCC] |
| 1-1-38 | 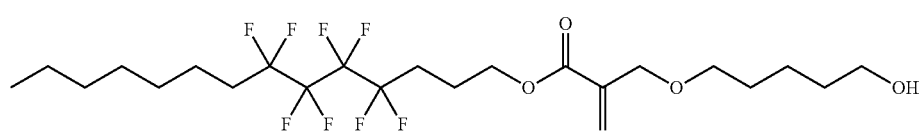 [SMILES: C=C(COCCCCCO)C(=O)OCCCC(F)(F)C(F)(F)C(F)(F)C(F)(F)CCCCCCC] |
| 1-1-39 | 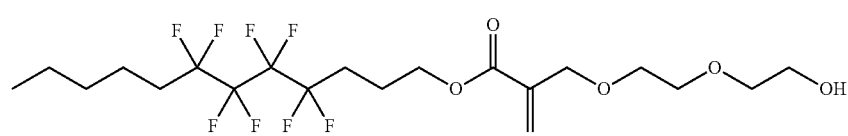 [SMILES: C=C(COCCOCCO)C(=O)OCCCC(F)(F)C(F)(F)C(F)(F)C(F)(F)CCCCC] |
| 1-1-40 | 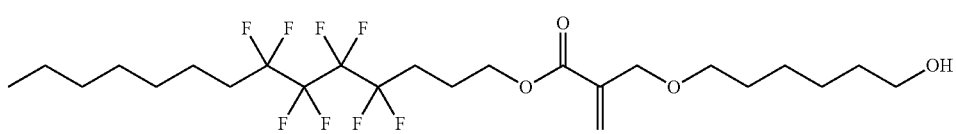 [SMILES: C=C(COCCCCCCO)C(=O)OCCCC(F)(F)C(F)(F)C(F)(F)C(F)(F)CCCCCCC] |
| 1-1-41 | 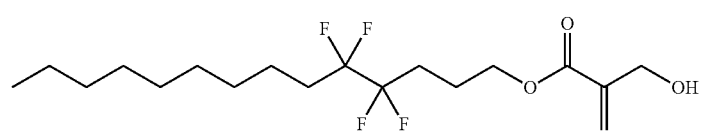 [SMILES: C=C(CO)C(=O)OCCCC(F)(F)C(F)(F)CCCCCCCCC] |
| 1-1-42 | 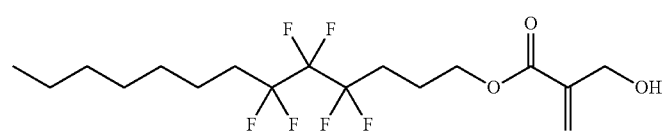 [SMILES: C=C(CO)C(=O)OCCCC(F)(F)C(F)(F)C(F)(F)CCCCCCC] |
| 1-1-43 | 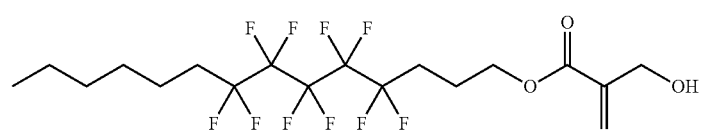 [SMILES: C=C(CO)C(=O)OCCCC(F)(F)C(F)(F)C(F)(F)C(F)(F)C(F)(F)CCCCCC] |
| 1-1-44 | 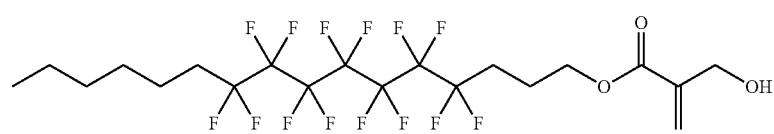 [SMILES: C=C(CO)C(=O)OCCCC(F)(F)C(F)(F)C(F)(F)C(F)(F)C(F)(F)C(F)(F)C(F)(F)CCCCCC] |
| 1-1-45 | 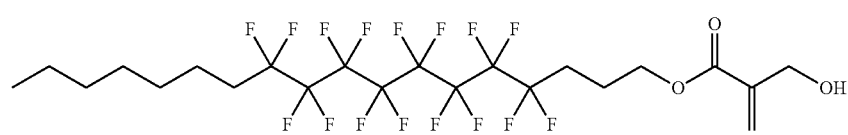 [SMILES: C=C(CO)C(=O)OCCCC(F)(F)C(F)(F)C(F)(F)C(F)(F)C(F)(F)C(F)(F)C(F)(F)C(F)(F)CCCCCCC] |
| 1-1-46 | 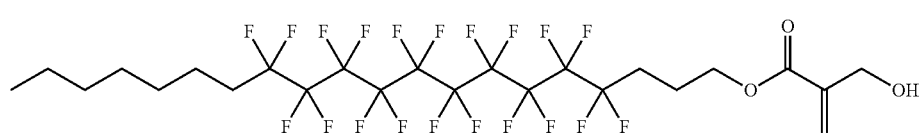 [SMILES: C=C(CO)C(=O)OCCCC(F)(F)C(F)(F)C(F)(F)C(F)(F)C(F)(F)C(F)(F)C(F)(F)C(F)(F)C(F)(F)C(F)(F)CCCCCCC] |

-continued
| No. | |
|---|---|
| 1-1-47 | 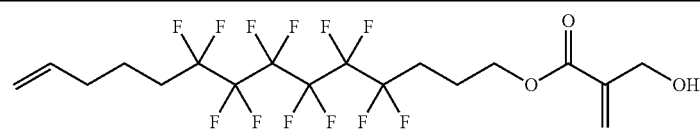 |
| 1-1-48 | 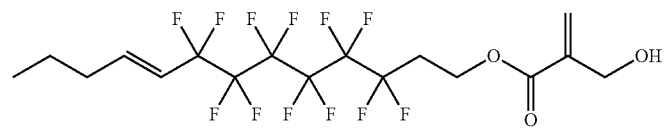 [SMILES: C=C(CO)C(=O)OCCC(F)(F)C(F)(F)C(F)(F)C(F)(F)C(F)(F)C(F)(F)/C=C/CCC] |
| 1-1-49 | 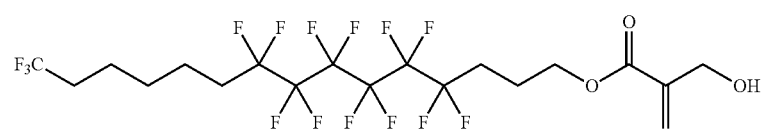 [SMILES: C=C(CO)C(=O)OCCCC(F)(F)C(F)(F)C(F)(F)C(F)(F)C(F)(F)C(F)(F)CCCCCC(F)(F)F] |
| 1-1-50 | 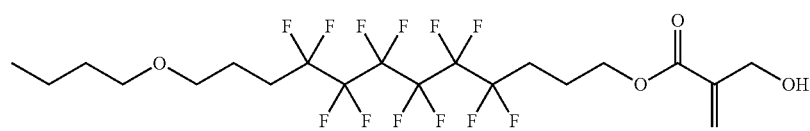 [SMILES: C=C(CO)C(=O)OCCCC(F)(F)C(F)(F)C(F)(F)C(F)(F)C(F)(F)C(F)(F)CCCOCCCC] |
| 1-1-51 | 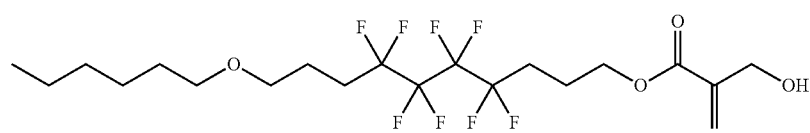 [SMILES: C=C(CO)C(=O)OCCCC(F)(F)C(F)(F)C(F)(F)C(F)(F)CCCOCCCCCC] |
| 1-1-52 | 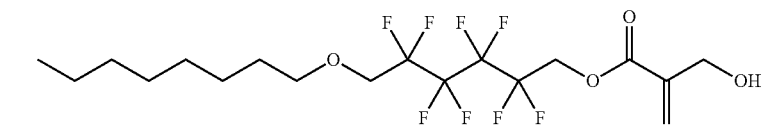 [SMILES: C=C(CO)C(=O)OCC(F)(F)C(F)(F)C(F)(F)C(F)(F)COCCCCCCCC] |
| 1-1-53 | 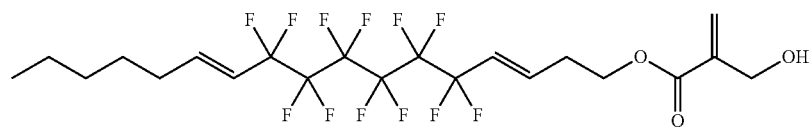 [SMILES: C=C(CO)C(=O)OCC/C=C/C(F)(F)C(F)(F)C(F)(F)C(F)(F)C(F)(F)C(F)(F)/C=C/CCCCC] |
| 1-1-54 | 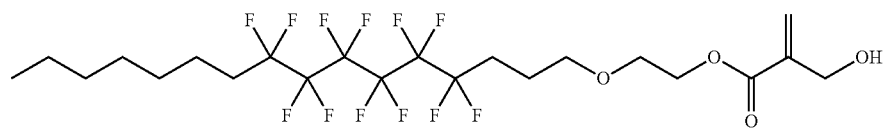 [SMILES: C=C(CO)C(=O)OCCOCCCC(F)(F)C(F)(F)C(F)(F)C(F)(F)C(F)(F)C(F)(F)CCCCCCC] |
| 1-1-55 | 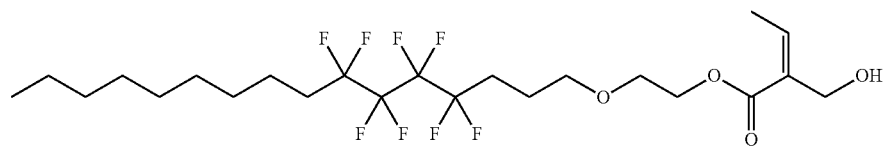 [SMILES: C/C=C(/CO)C(=O)OCCOCCCC(F)(F)C(F)(F)C(F)(F)C(F)(F)CCCCCCCCC] |
| 1-1-56 | 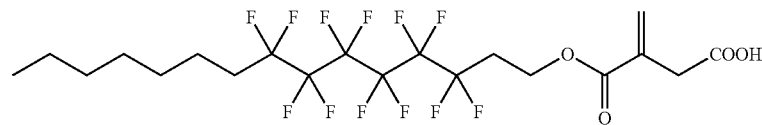 [SMILES: C=C(CC(=O)O)C(=O)OCCC(F)(F)C(F)(F)C(F)(F)C(F)(F)C(F)(F)C(F)(F)CCCCCCC] |
| 1-1-57 | 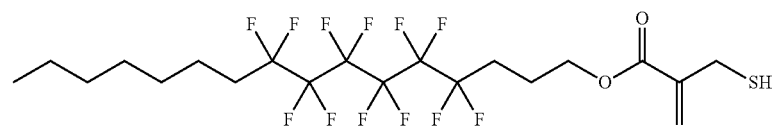 [SMILES: C=C(CS)C(=O)OCCCC(F)(F)C(F)(F)C(F)(F)C(F)(F)C(F)(F)C(F)(F)CCCCCCC] |

-continued
| No. | |
|---|---|
| 1-1-58 | 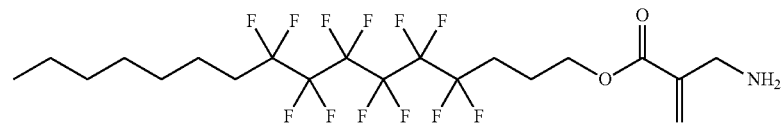 [SMILES: C=C(CN)C(=O)OCCCC(F)(F)C(F)(F)C(F)(F)C(F)(F)C(F)(F)C(F)(F)CCCCCCC] |
| 1-1-59 | 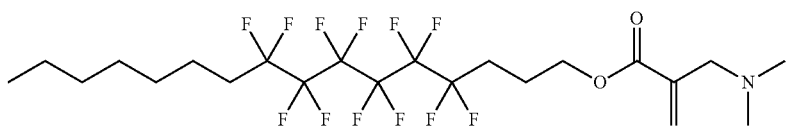 [SMILES: C=C(CN(C)C)C(=O)OCCCC(F)(F)C(F)(F)C(F)(F)C(F)(F)C(F)(F)C(F)(F)CCCCCCC] |
| 1-1-60 | 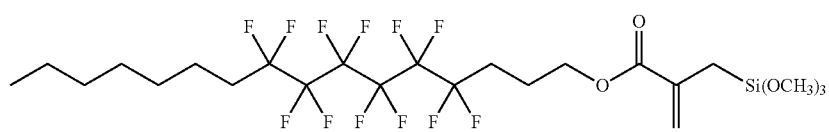 |
| 1-2-1 | 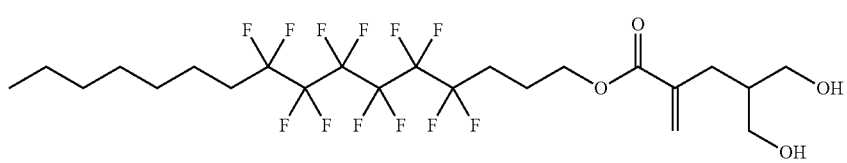 [SMILES: C=C(CC(CO)CO)C(=O)OCCCC(F)(F)C(F)(F)C(F)(F)C(F)(F)C(F)(F)C(F)(F)CCCCCCC] |
| 1-2-2 | 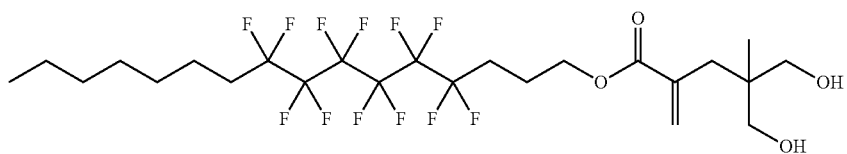 [SMILES: C=C(CC(C)(CO)CO)C(=O)OCCCC(F)(F)C(F)(F)C(F)(F)C(F)(F)C(F)(F)C(F)(F)CCCCCCC] |
| 1-2-3 | 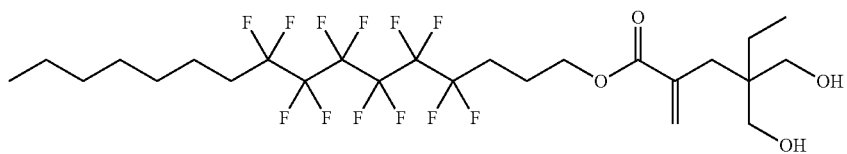 [SMILES: C=C(CC(CC)(CO)CO)C(=O)OCCCC(F)(F)C(F)(F)C(F)(F)C(F)(F)C(F)(F)C(F)(F)CCCCCCC] |
| 1-2-4 | 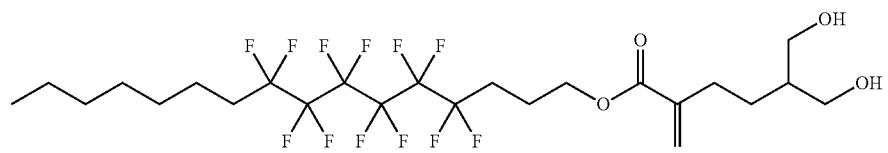 [SMILES: C=C(CCC(CO)CO)C(=O)OCCCC(F)(F)C(F)(F)C(F)(F)C(F)(F)C(F)(F)C(F)(F)CCCCCCC] |
| 1-2-5 | 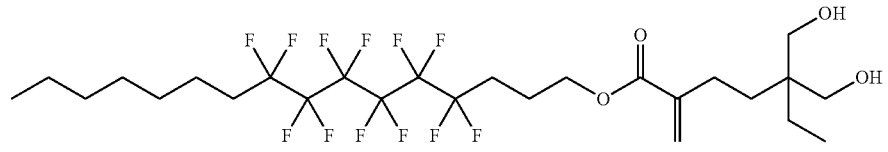 [SMILES: C=C(CCC(CC)(CO)CO)C(=O)OCCCC(F)(F)C(F)(F)C(F)(F)C(F)(F)C(F)(F)C(F)(F)CCCCCCC] |
| 1-2-6 | 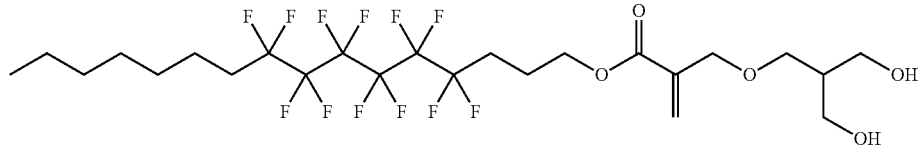 [SMILES: C=C(COCC(CO)CO)C(=O)OCCCC(F)(F)C(F)(F)C(F)(F)C(F)(F)C(F)(F)C(F)(F)CCCCCCC] |
| 1-2-7 | 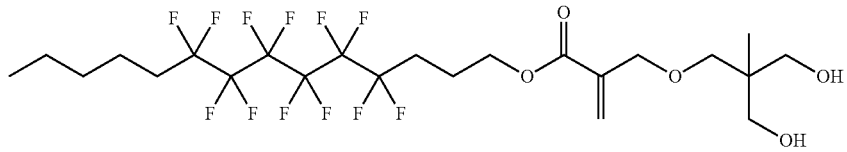 [SMILES: C=C(COCC(C)(CO)CO)C(=O)OCCCC(F)(F)C(F)(F)C(F)(F)C(F)(F)C(F)(F)C(F)(F)CCCCC] |

| No. | |
|---|---|
| 1-2-8 | 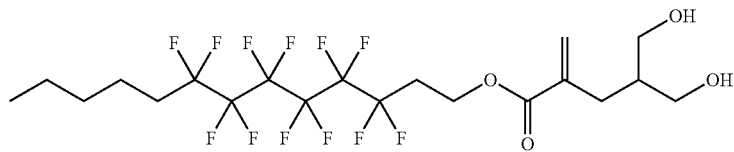 [SMILES: C=C(CC(CO)CO)C(=O)OCCC(F)(F)C(F)(F)C(F)(F)C(F)(F)C(F)(F)C(F)(F)CCCCC] |
| 1-2-9 | 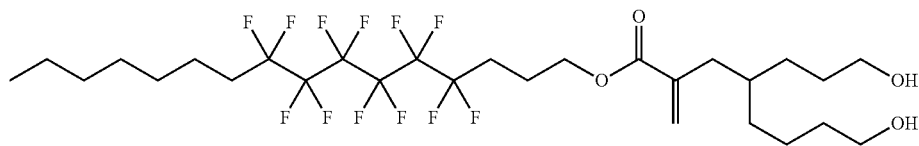 [SMILES: C=C(CC(CCCO)CCCCO)C(=O)OCCCC(F)(F)C(F)(F)C(F)(F)C(F)(F)C(F)(F)C(F)(F)CCCCCCC] |
| 1-2-10 | 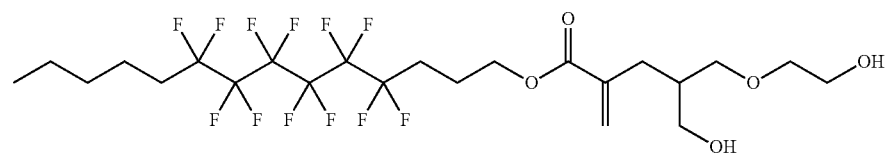 [SMILES: C=C(CC(CO)COCCO)C(=O)OCCCC(F)(F)C(F)(F)C(F)(F)C(F)(F)C(F)(F)C(F)(F)CCCCC] |
| 1-2-11 | 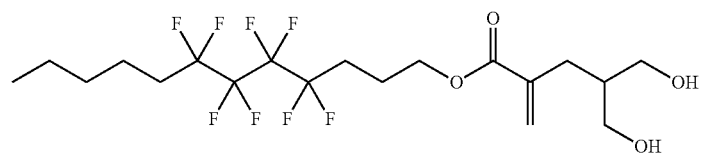 [SMILES: C=C(CC(CO)CO)C(=O)OCCCC(F)(F)C(F)(F)C(F)(F)C(F)(F)CCCCC] |
| 1-2-12 | 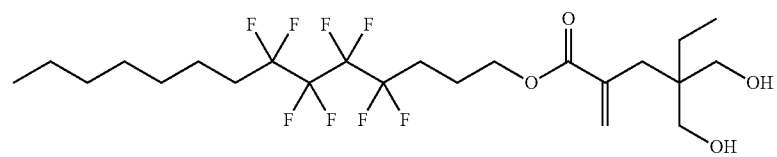 [SMILES: C=C(CC(CC)(CO)CO)C(=O)OCCCC(F)(F)C(F)(F)C(F)(F)C(F)(F)CCCCCCC] |
| 1-2-13 | 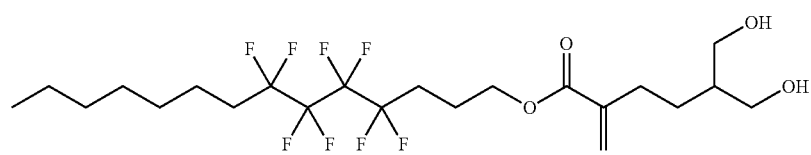 [SMILES: C=C(CCC(CO)CO)C(=O)OCCCC(F)(F)C(F)(F)C(F)(F)C(F)(F)CCCCCCC] |
| 1-2-14 | 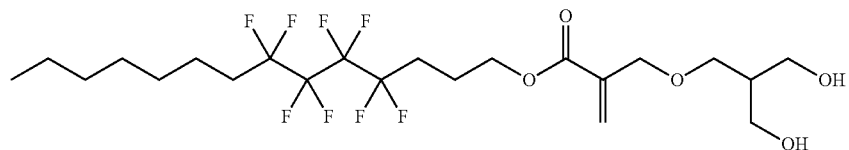 [SMILES: C=C(COCC(CO)CO)C(=O)OCCCC(F)(F)C(F)(F)C(F)(F)C(F)(F)CCCCCCC] |
| 1-2-15 | 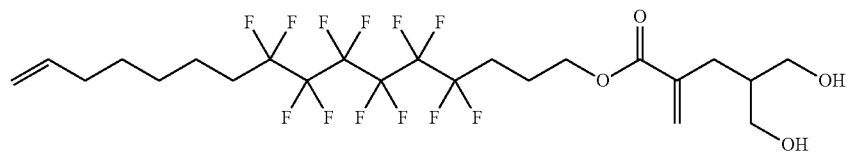 [SMILES: C=CCCCCCC(F)(F)C(F)(F)C(F)(F)C(F)(F)C(F)(F)C(F)(F)CCCOC(=O)C(=C)CC(CO)CO] |
| 1-2-16 | 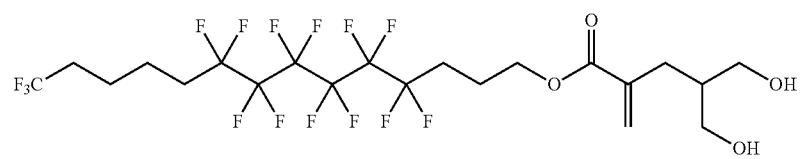 [SMILES: C=C(CC(CO)CO)C(=O)OCCCC(F)(F)C(F)(F)C(F)(F)C(F)(F)C(F)(F)C(F)(F)CCCCC(F)(F)F] |

-continued
| No. | |
|---|---|
| 1-2-17 | 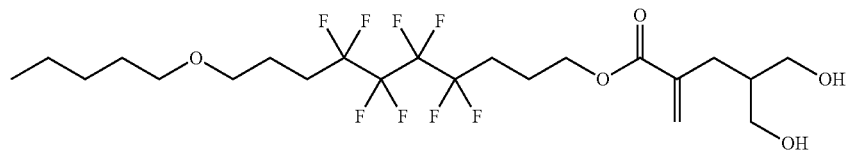 [SMILES: C=C(CC(CO)CO)C(=O)OCCCC(F)(F)C(F)(F)C(F)(F)C(F)(F)CCCOCCCCC] |
| 1-2-18 | 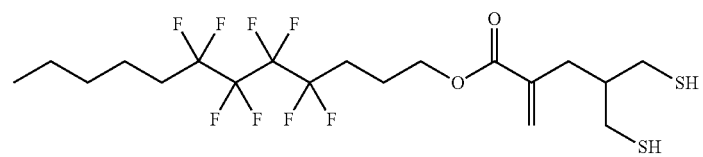 [SMILES: C=C(CC(CS)CS)C(=O)OCCCC(F)(F)C(F)(F)C(F)(F)C(F)(F)CCCCC] |
| 1-2-19 | 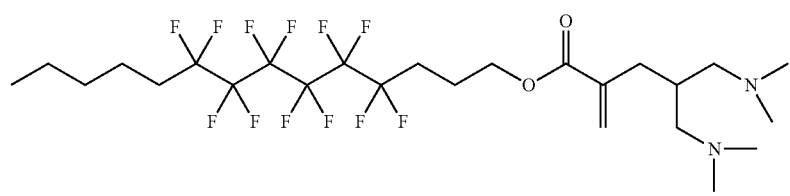 [SMILES: C=C(CC(CN(C)C)CN(C)C)C(=O)OCCCC(F)(F)C(F)(F)C(F)(F)C(F)(F)C(F)(F)C(F)(F)CCCCC] |
| 1-2-20 | 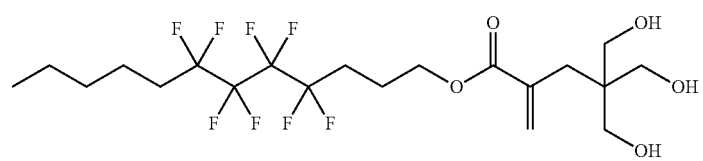 [SMILES: C=C(CC(CO)(CO)CO)C(=O)OCCCC(F)(F)C(F)(F)C(F)(F)C(F)(F)CCCCC] |
| 1-3-1 | 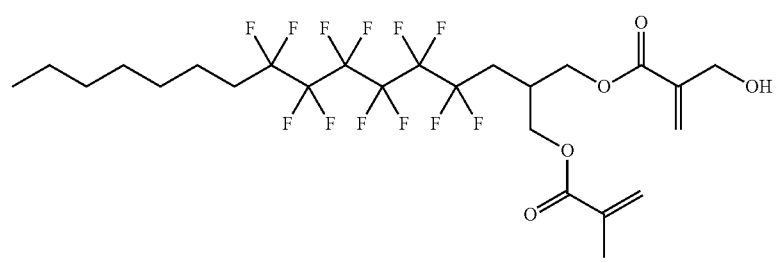 [SMILES: C=C(C)C(=O)OCC(COC(=O)C(=C)CO)CC(F)(F)C(F)(F)C(F)(F)C(F)(F)C(F)(F)C(F)(F)CCCCCCC] |
| 1-3-2 | 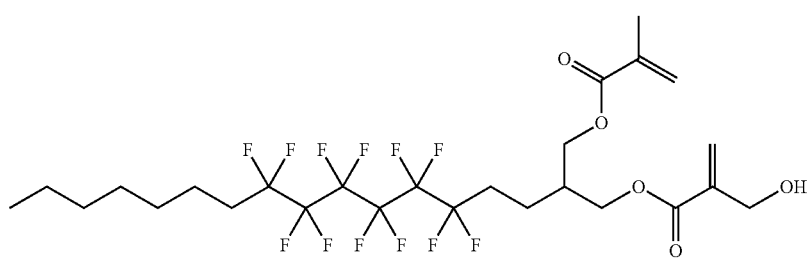 [SMILES: C=C(C)C(=O)OCC(CCC(F)(F)C(F)(F)C(F)(F)C(F)(F)C(F)(F)C(F)(F)CCCCCCC)COC(=O)C(=C)CO] |
| 1-3-3 | 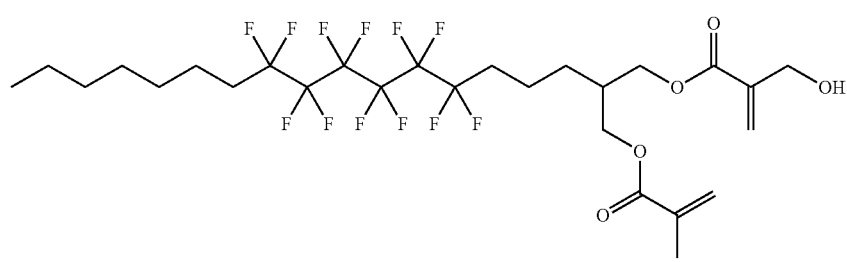 [SMILES: C=C(C)C(=O)OCC(CCCC(F)(F)C(F)(F)C(F)(F)C(F)(F)C(F)(F)C(F)(F)CCCCCCC)COC(=O)C(=C)CO] |

-continued
| No. |
|---|
| 1-3-4 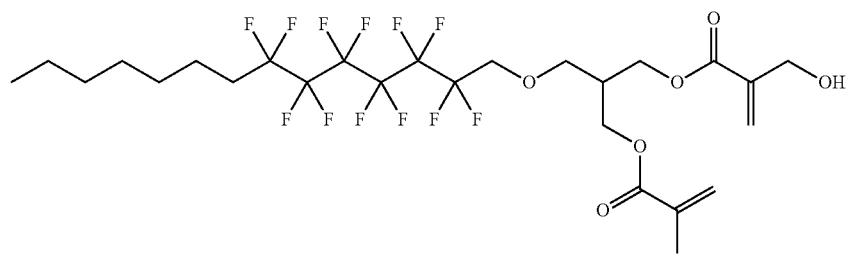 [SMILES: C=C(C)C(=O)OCC(COCC(F)(F)C(F)(F)C(F)(F)C(F)(F)C(F)(F)C(F)(F)CCCCCCC)COC(=O)C(=C)CO] |
| 1-3-5 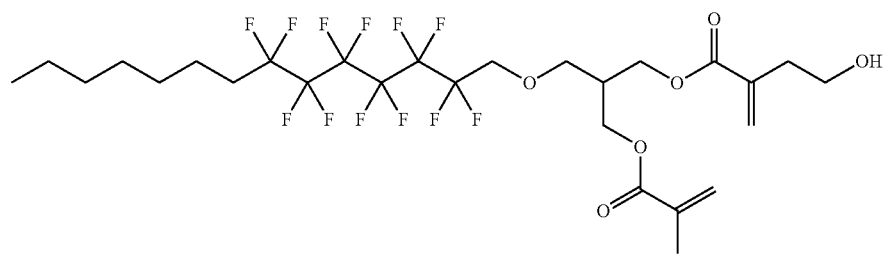 [SMILES: C=C(C)C(=O)OCC(COCC(F)(F)C(F)(F)C(F)(F)C(F)(F)C(F)(F)C(F)(F)CCCCCCC)COC(=O)C(=C)CCO] |
| 1-3-6 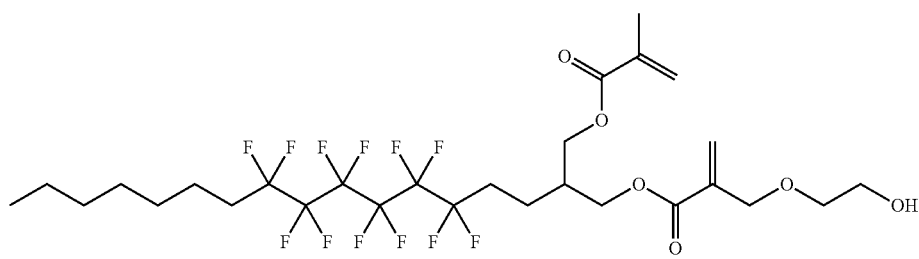 [SMILES: C=C(C)C(=O)OCC(CCC(F)(F)C(F)(F)C(F)(F)C(F)(F)C(F)(F)C(F)(F)CCCCCCC)COC(=O)C(=C)COCCO] |
| 1-3-7 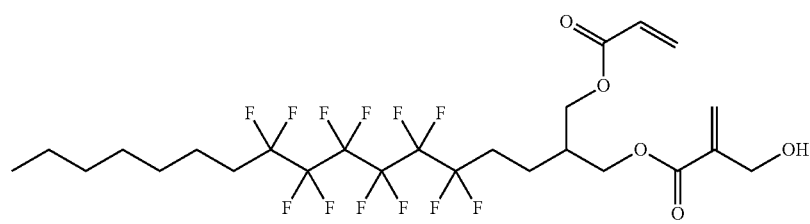 [SMILES: C=CC(=O)OCC(CCC(F)(F)C(F)(F)C(F)(F)C(F)(F)C(F)(F)C(F)(F)CCCCCCC)COC(=O)C(=C)CO] |
| 1-3-8 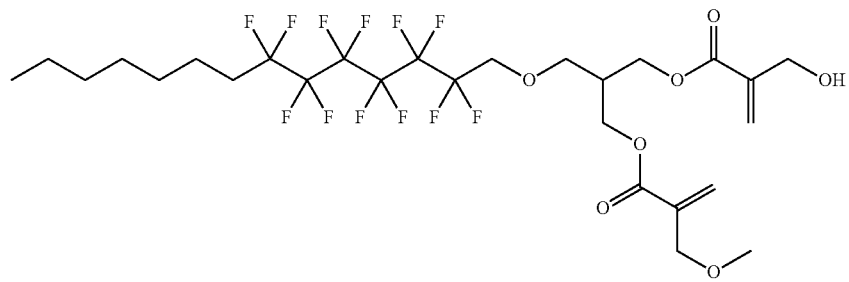 [SMILES: C=C(CO)C(=O)OCC(COCC(F)(F)C(F)(F)C(F)(F)C(F)(F)C(F)(F)C(F)(F)CCCCCCC)COC(=O)C(=C)COC] |
| 1-3-9 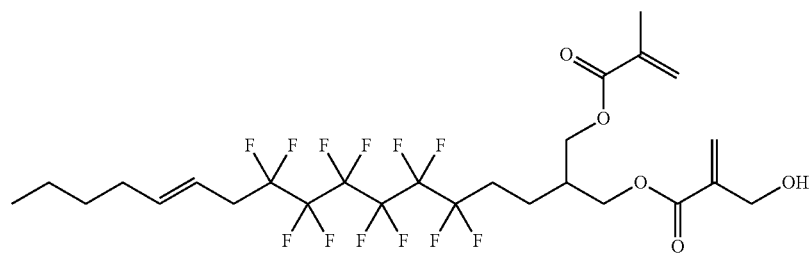 [SMILES: C=C(C)C(=O)OCC(CCC(F)(F)C(F)(F)C(F)(F)C(F)(F)C(F)(F)C(F)(F)C/C=C/CCCC)COC(=O)C(=C)CO] |

| No. | |
|---|---|
| 1-3-10 | 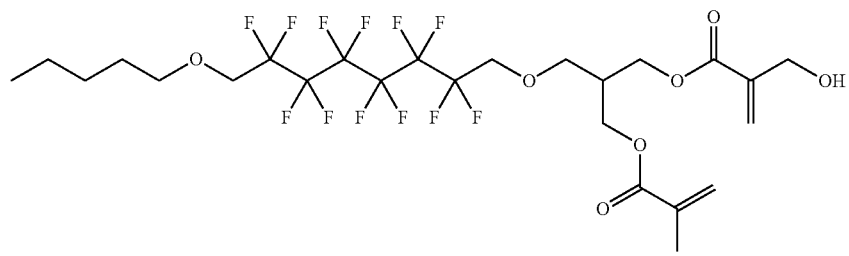 [SMILES: C=C(C)C(=O)OCC(COCC(F)(F)C(F)(F)C(F)(F)C(F)(F)C(F)(F)C(F)(F)COCCCCC)COC(=O)C(=C)CO] |
| 1-3-11 | 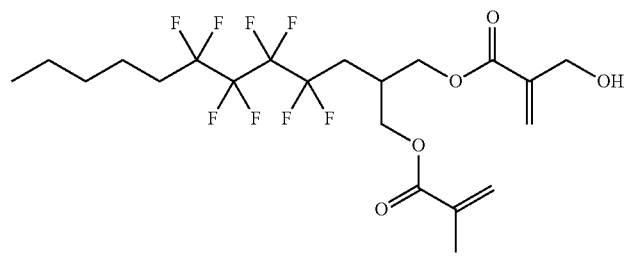 [SMILES: C=C(C)C(=O)OCC(COC(=O)C(=C)CO)CC(F)(F)C(F)(F)C(F)(F)C(F)(F)CCCCC] |
| 1-3-12 | 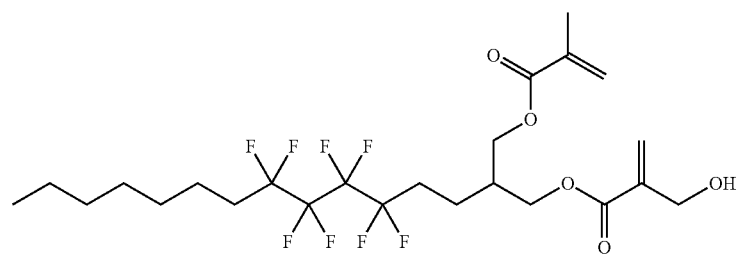 [SMILES: C=C(C)C(=O)OCC(CCC(F)(F)C(F)(F)C(F)(F)C(F)(F)CCCCCCC)COC(=O)C(=C)CO] |
| 1-3-13 | 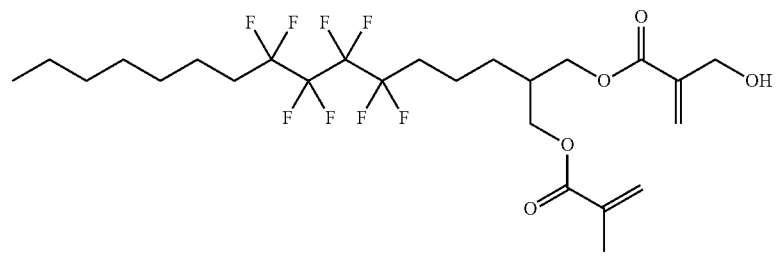 [SMILES: C=C(C)C(=O)OCC(CCCC(F)(F)C(F)(F)C(F)(F)C(F)(F)CCCCCCC)COC(=O)C(=C)CO] |
| 1-3-14 | 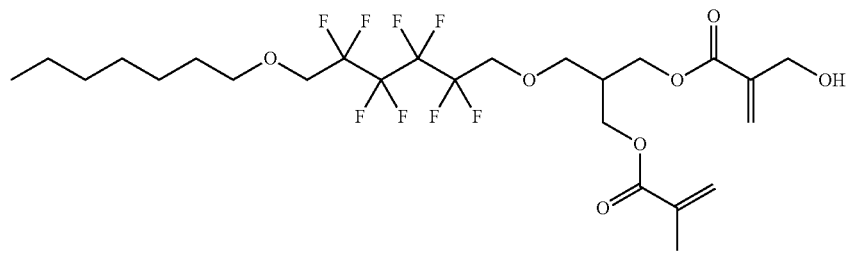 [SMILES: C=C(C)C(=O)OCC(COCC(F)(F)C(F)(F)C(F)(F)C(F)(F)COCCCCCCC)COC(=O)C(=C)CO] |
| 1-3-15 | 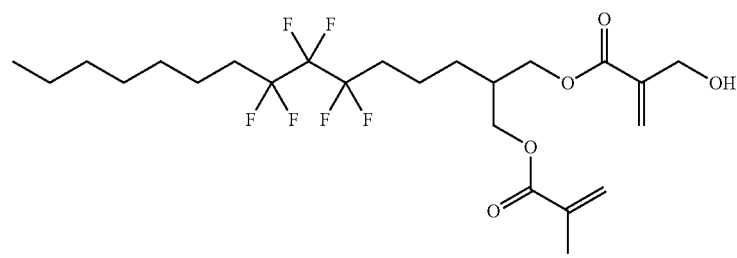 [SMILES: C=C(C)C(=O)OCC(CCCC(F)(F)C(F)(F)C(F)(F)CCCCCCC)COC(=O)C(=C)CO] |

-continued
| No. | |
|---|---|
| 1-3-16 | 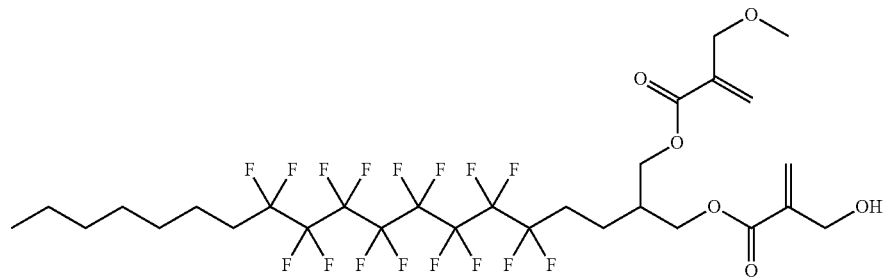 [SMILES: C=C(CO)C(=O)OCC(CCC(F)(F)C(F)(F)C(F)(F)C(F)(F)C(F)(F)C(F)(F)C(F)(F)C(F)(F)CCCCCCC)COC(=O)C(=C)COC] |
| 1-3-17 | 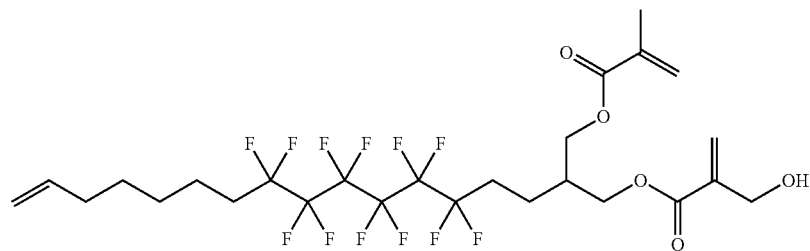 [SMILES: C=CCCCCCC(F)(F)C(F)(F)C(F)(F)C(F)(F)C(F)(F)C(F)(F)CCC(COC(=O)C(=C)C)COC(=O)C(=C)CO] |
| 1-3-18 | 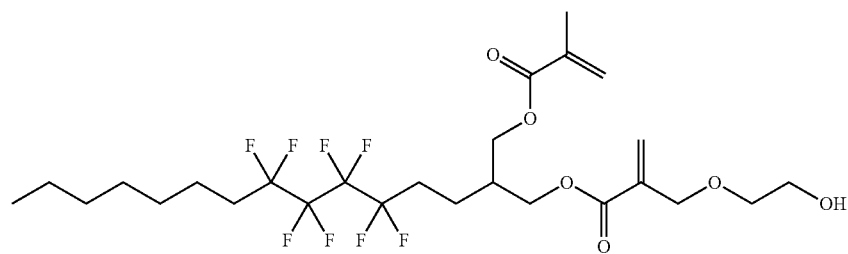 [SMILES: C=C(C)C(=O)OCC(CCC(F)(F)C(F)(F)C(F)(F)C(F)(F)CCCCCCC)COC(=O)C(=C)COCCO] |
| 1-3-19 | 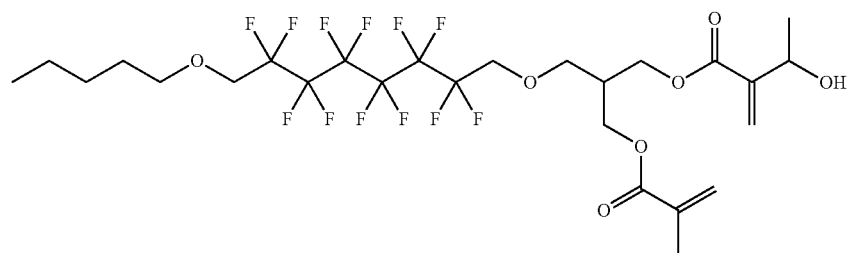 [SMILES: C=C(C)C(=O)OCC(COCC(F)(F)C(F)(F)C(F)(F)C(F)(F)C(F)(F)C(F)(F)COCCCCC)COC(=O)C(=C)C(C)O] |
| 1-3-20 | 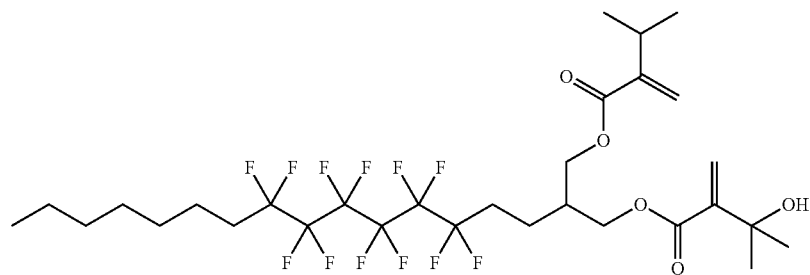 [SMILES: C=C(C(=O)OCC(CCC(F)(F)C(F)(F)C(F)(F)C(F)(F)C(F)(F)C(F)(F)CCCCCCC)COC(=O)C(=C)C(C)(C)O)C(C)C] |
| 1-4-1 | 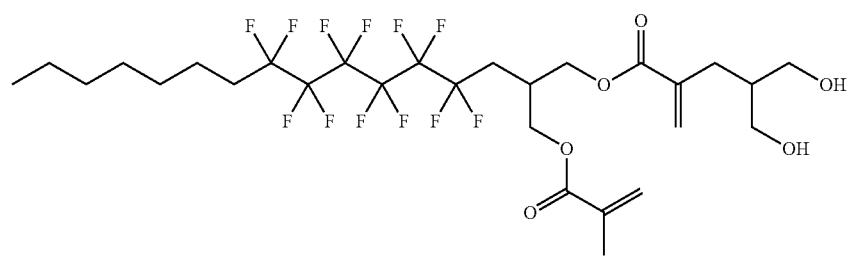 [SMILES: C=C(C)C(=O)OCC(COC(=O)C(=C)CC(CO)CO)CC(F)(F)C(F)(F)C(F)(F)C(F)(F)C(F)(F)C(F)(F)CCCCCCC] |

| No. | |
|---|---|
| 1-4-2 | 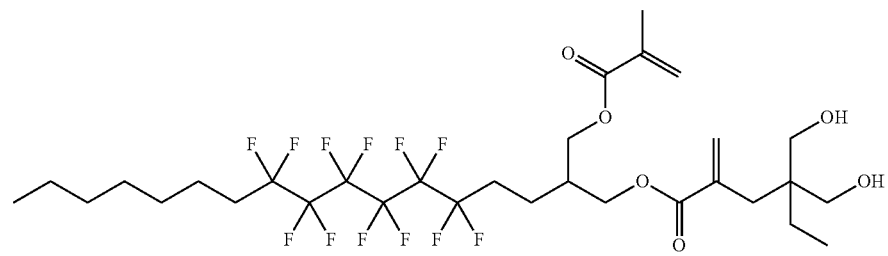 [SMILES: C=C(C)C(=O)OCC(CCC(F)(F)C(F)(F)C(F)(F)C(F)(F)C(F)(F)C(F)(F)CCCCCCC)COC(=O)C(=C)CC(CC)(CO)CO] |
| 1-4-3 | 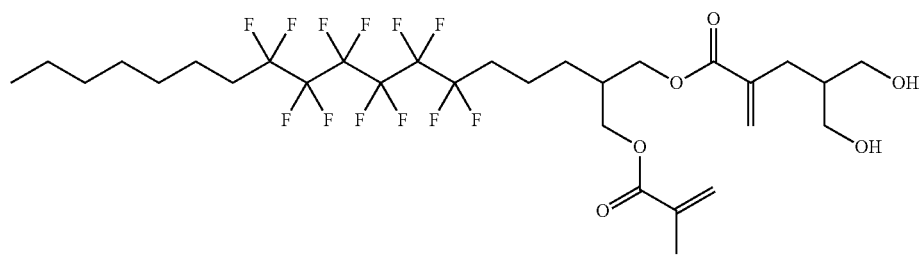 [SMILES: C=C(C)C(=O)OCC(CCCC(F)(F)C(F)(F)C(F)(F)C(F)(F)C(F)(F)C(F)(F)CCCCCCC)COC(=O)C(=C)CC(CO)CO] |
| 1-4-4 | 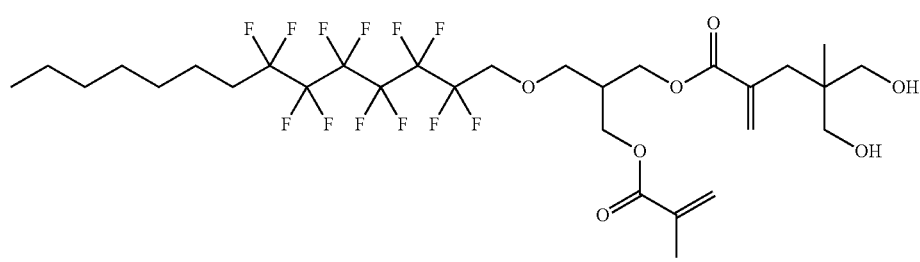 [SMILES: C=C(C)C(=O)OCC(COCC(F)(F)C(F)(F)C(F)(F)C(F)(F)C(F)(F)C(F)(F)CCCCCCC)COC(=O)C(=C)CC(C)(CO)CO] |
| 1-4-5 | 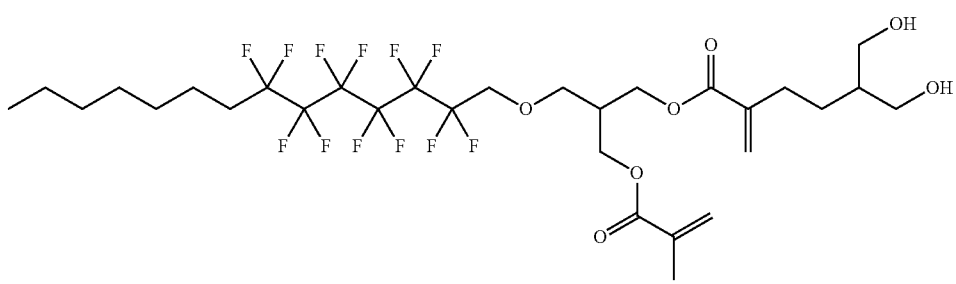 [SMILES: C=C(C)C(=O)OCC(COCC(F)(F)C(F)(F)C(F)(F)C(F)(F)C(F)(F)C(F)(F)CCCCCCC)COC(=O)C(=C)CCC(CO)CO] |
| 1-4-6 | 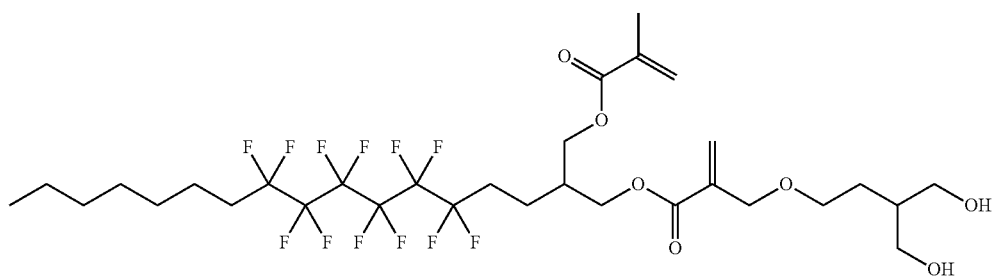 [SMILES: C=C(C)C(=O)OCC(CCC(F)(F)C(F)(F)C(F)(F)C(F)(F)C(F)(F)C(F)(F)CCCCCCC)COC(=O)C(=C)COCCC(CO)CO] |
| 1-4-7 | 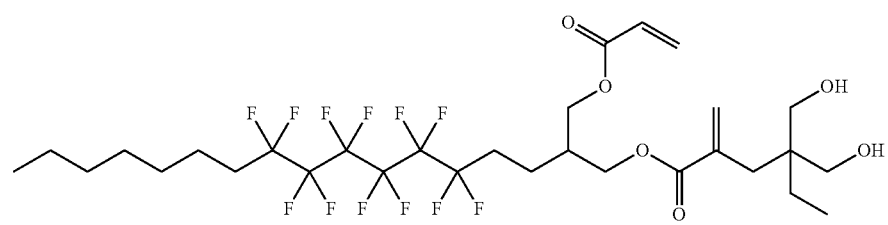 [SMILES: C=CC(=O)OCC(CCC(F)(F)C(F)(F)C(F)(F)C(F)(F)C(F)(F)C(F)(F)CCCCCCC)COC(=O)C(=C)CC(CC)(CO)CO] |

-continued
| No. | |
|---|---|
| 1-4-8 | 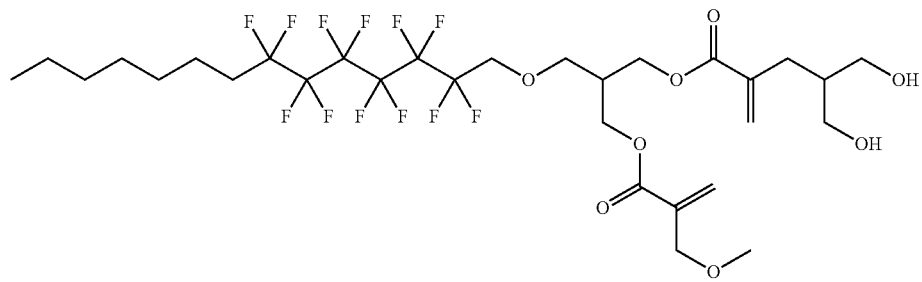 [SMILES: C=C(COC)C(=O)OCC(COCC(F)(F)C(F)(F)C(F)(F)C(F)(F)C(F)(F)C(F)(F)CCCCCCC)COC(=O)C(=C)CC(CO)CO] |
| 1-4-9 | 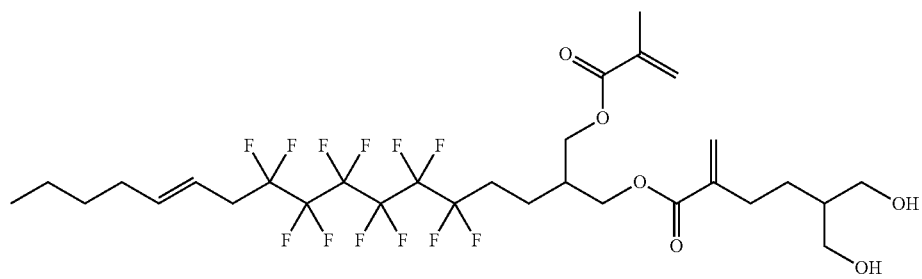 [SMILES: C=C(C)C(=O)OCC(CCC(F)(F)C(F)(F)C(F)(F)C(F)(F)C(F)(F)C(F)(F)C/C=C/CCCC)COC(=O)C(=C)CCC(CO)CO] |
| 1-4-10 | 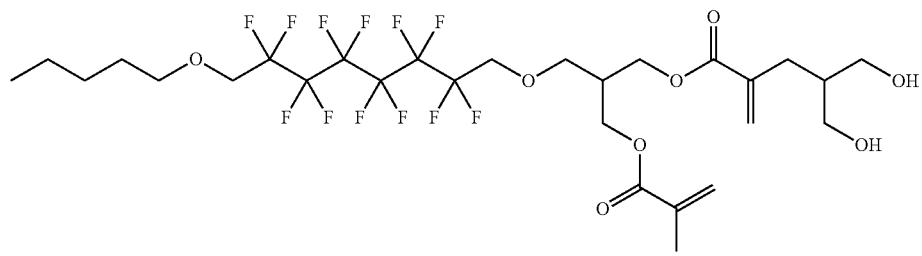 [SMILES: C=C(C)C(=O)OCC(COCC(F)(F)C(F)(F)C(F)(F)C(F)(F)C(F)(F)C(F)(F)COCCCCC)COC(=O)C(=C)CC(CO)CO] |
| 1-4-11 | 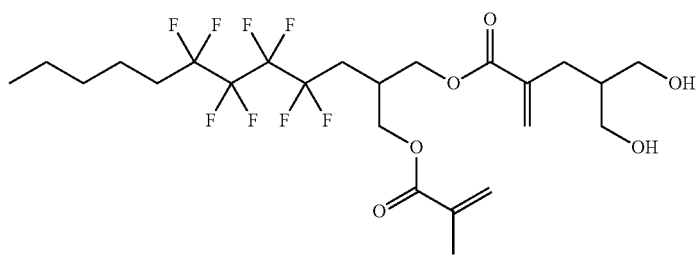 [SMILES: C=C(C)C(=O)OCC(COC(=O)C(=C)CC(CO)CO)CC(F)(F)C(F)(F)C(F)(F)C(F)(F)CCCCC] |
| 1-4-12 | 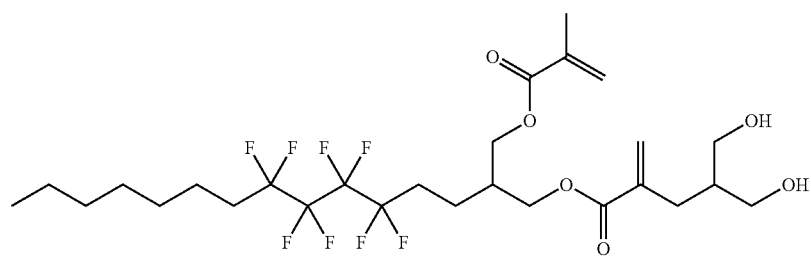 [SMILES: C=C(C)C(=O)OCC(CCC(F)(F)C(F)(F)C(F)(F)C(F)(F)CCCCCCC)COC(=O)C(=C)CC(CO)CO] |
| 1-4-13 | 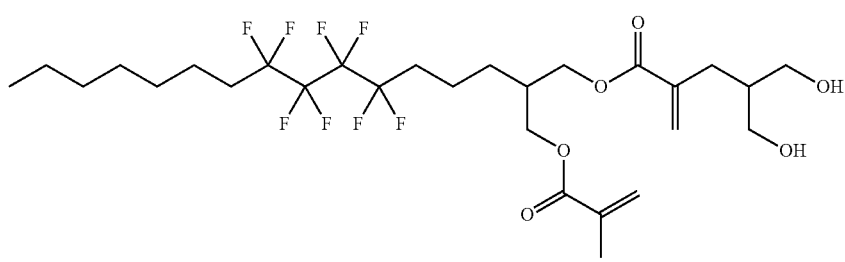 [SMILES: C=C(C)C(=O)OCC(CCCC(F)(F)C(F)(F)C(F)(F)C(F)(F)CCCCCCC)COC(=O)C(=C)CC(CO)CO] |

-continued
No.
1-4-14
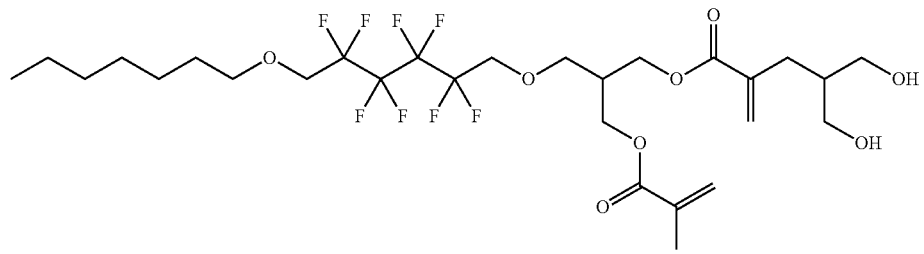 [SMILES: C=C(C)C(=O)OCC(COCC(F)(F)C(F)(F)C(F)(F)C(F)(F)COCCCCCCC)COC(=O)C(=C)CC(CO)CO]
1-4-15
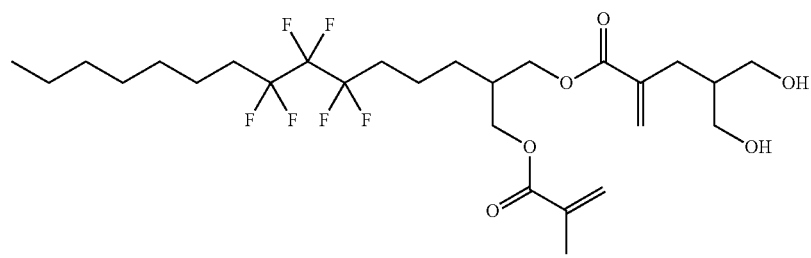 [SMILES: C=C(C)C(=O)OCC(CCCC(F)(F)C(F)(F)C(F)(F)CCCCCCC)COC(=O)C(=C)CC(CO)CO]
1-4-16
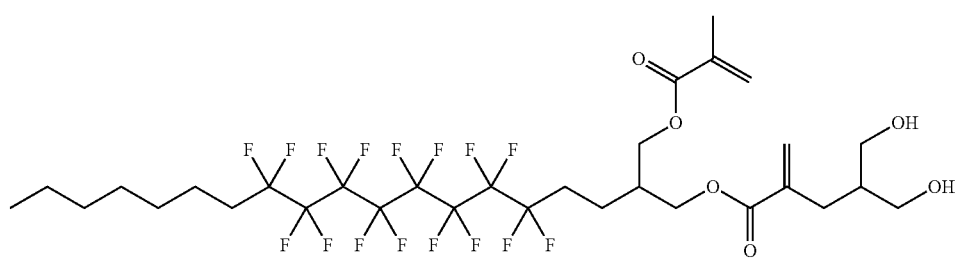 [SMILES: C=C(C)C(=O)OCC(CCC(F)(F)C(F)(F)C(F)(F)C(F)(F)C(F)(F)C(F)(F)C(F)(F)C(F)(F)CCCCCCC)COC(=O)C(=C)CC(CO)CO]
1-4-17
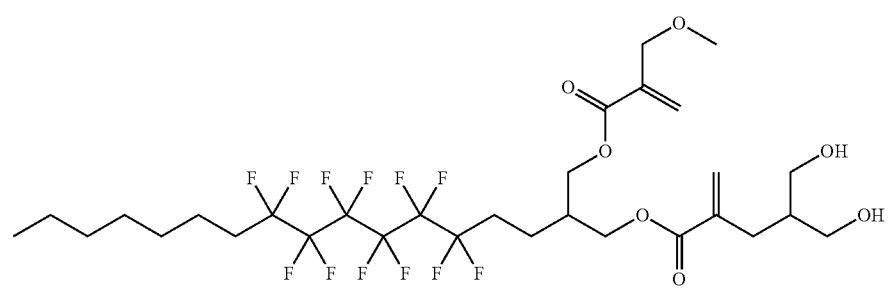 [SMILES: C=C(COC)C(=O)OCC(CCC(F)(F)C(F)(F)C(F)(F)C(F)(F)C(F)(F)C(F)(F)CCCCCCC)COC(=O)C(=C)CC(CO)CO]
1-4-18
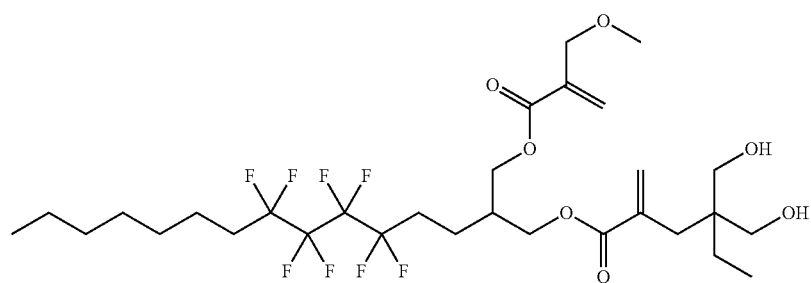 [SMILES: C=C(COC)C(=O)OCC(CCC(F)(F)C(F)(F)C(F)(F)C(F)(F)CCCCCCC)COC(=O)C(=C)CC(CC)(CO)CO]

| No. | |
|---|---|
| 1-4-19 | 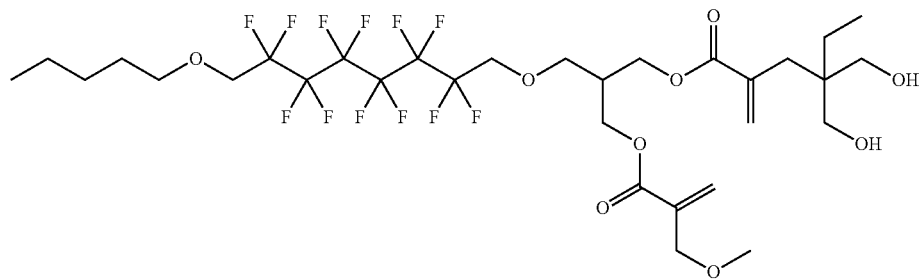 [SMILES: C=C(COC)C(=O)OCC(COCC(F)(F)C(F)(F)C(F)(F)C(F)(F)C(F)(F)C(F)(F)COCCCCC)COC(=O)C(=C)CC(CC)(CO)CO] |
| 1-4-20 | 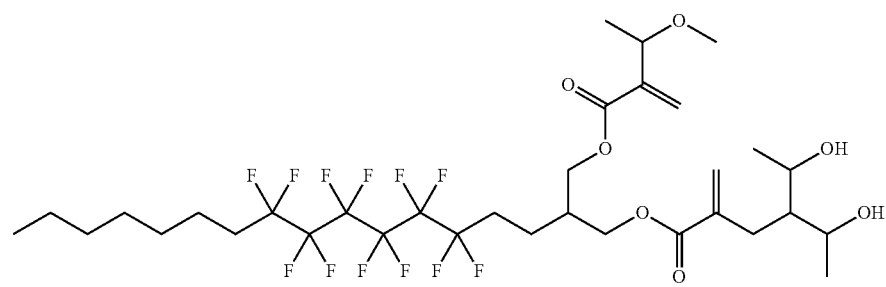 [SMILES: C=C(CC(C(C)O)C(C)O)C(=O)OCC(CCC(F)(F)C(F)(F)C(F)(F)C(F)(F)C(F)(F)C(F)(F)CCCCCCC)COC(=O)C(=C)C(C)OC] |
| 1-5-1 | 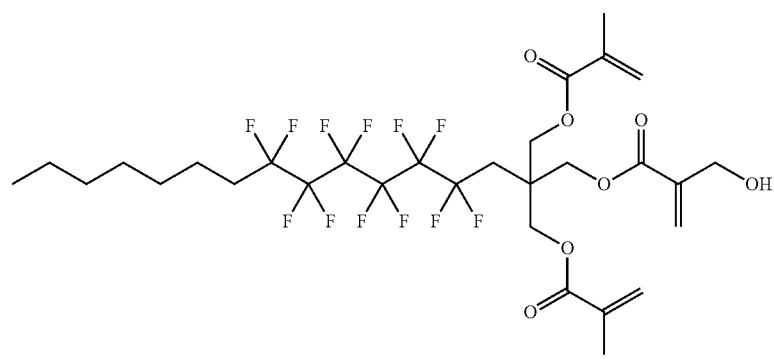 [SMILES: C=C(C)C(=O)OCC(COC(=O)C(=C)C)(COC(=O)C(=C)CO)CC(F)(F)C(F)(F)C(F)(F)C(F)(F)C(F)(F)C(F)(F)CCCCCCC] |
| 1-5-2 | 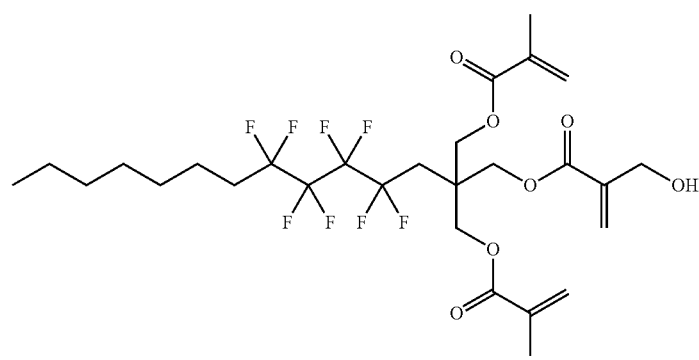 [SMILES: C=C(C)C(=O)OCC(COC(=O)C(=C)C)(COC(=O)C(=C)CO)CC(F)(F)C(F)(F)C(F)(F)C(F)(F)CCCCCCC] |

| No. | |
|---|---|
| 1-5-3 | 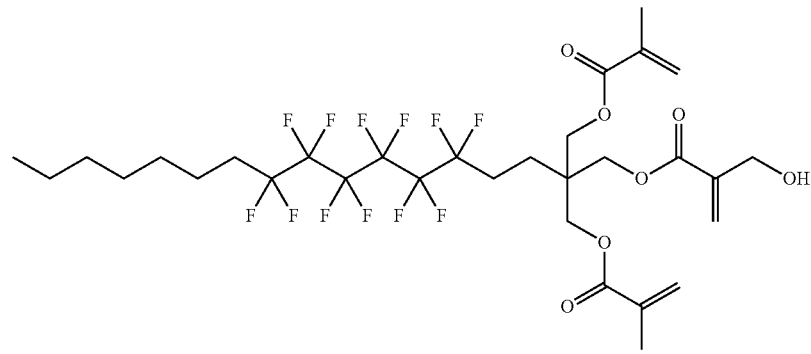 [SMILES: C=C(C)C(=O)OCC(CCC(F)(F)C(F)(F)C(F)(F)C(F)(F)C(F)(F)C(F)(F)CCCCCCC)(COC(=O)C(=C)C)COC(=O)C(=C)CO] |
| 1-5-4 | 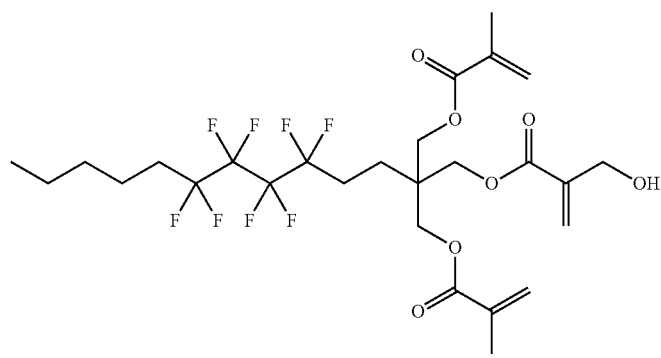 [SMILES: C=C(C)C(=O)OCC(CCC(F)(F)C(F)(F)C(F)(F)C(F)(F)CCCCC)(COC(=O)C(=C)C)COC(=O)C(=C)CO] |
| 1-5-5 | 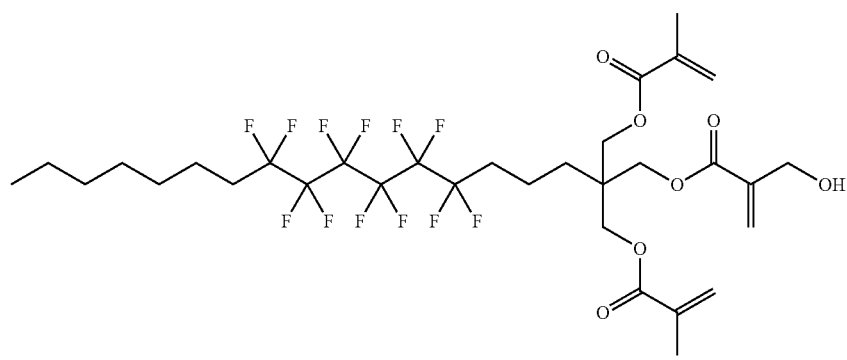 [SMILES: C=C(C)C(=O)OCC(CCCC(F)(F)C(F)(F)C(F)(F)C(F)(F)C(F)(F)C(F)(F)CCCCCCC)(COC(=O)C(=C)C)COC(=O)C(=C)CO] |
| 1-5-6 | 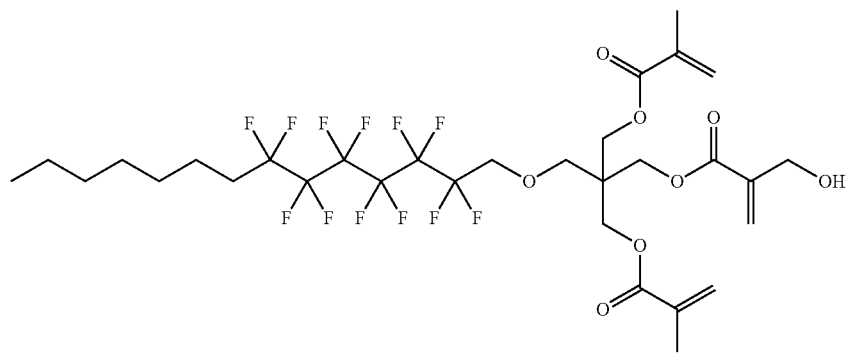 [SMILES: C=C(C)C(=O)OCC(COCC(F)(F)C(F)(F)C(F)(F)C(F)(F)C(F)(F)C(F)(F)CCCCCCC)(COC(=O)C(=C)C)COC(=O)C(=C)CO] |

| No. |
| --- |
| 1-5-7 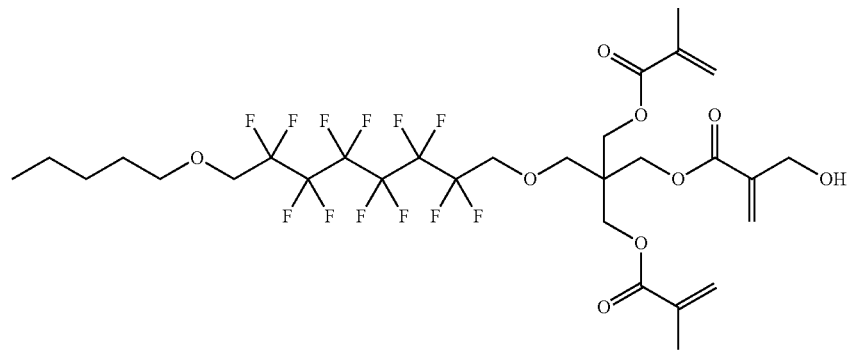 [SMILES: C=C(C)C(=O)OCC(COCC(F)(F)C(F)(F)C(F)(F)C(F)(F)C(F)(F)C(F)(F)COCCCCC)(COC(=O)C(=C)C)COC(=O)C(=C)CO] |
| 1-5-8 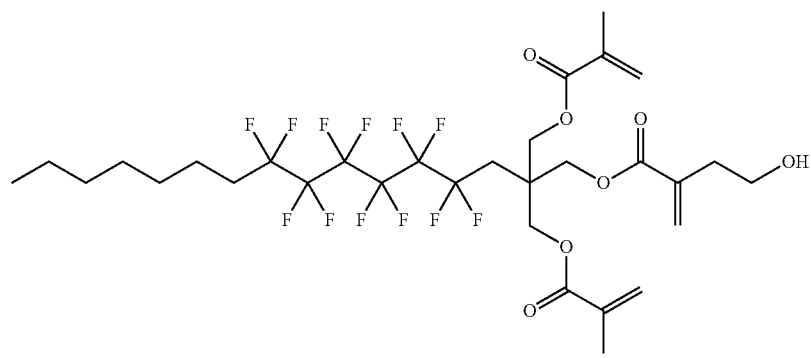 [SMILES: C=C(C)C(=O)OCC(COC(=O)C(=C)C)(COC(=O)C(=C)CCO)CC(F)(F)C(F)(F)C(F)(F)C(F)(F)C(F)(F)C(F)(F)CCCCCCC] |
| 1-5-9 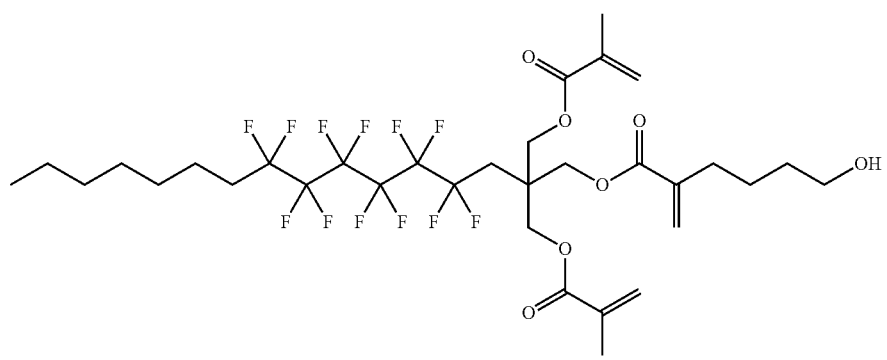 [SMILES: C=C(C)C(=O)OCC(COC(=O)C(=C)C)(COC(=O)C(=C)CCCCO)CC(F)(F)C(F)(F)C(F)(F)C(F)(F)C(F)(F)C(F)(F)CCCCCCC] |
| 1-5-10 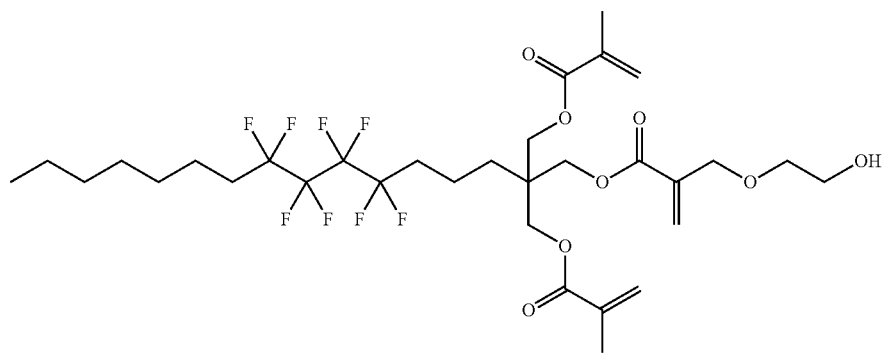 [SMILES: C=C(C)C(=O)OCC(CCCC(F)(F)C(F)(F)C(F)(F)C(F)(F)CCCCCCC)(COC(=O)C(=C)C)COC(=O)C(=C)COCCO] |

-continued
| No. |
|---|
| 1-5-11 |
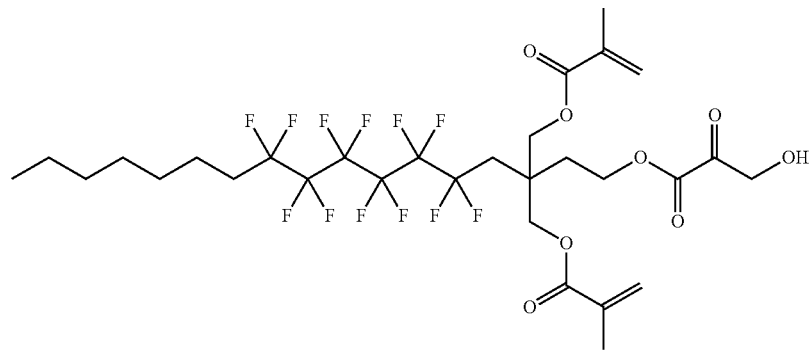 [SMILES: C=C(C)C(=O)OCC(CCOC(=O)C(=O)CO)(COC(=O)C(=C)C)CC(F)(F)C(F)(F)C(F)(F)C(F)(F)C(F)(F)C(F)(F)CCCCCCC]
1-5-12
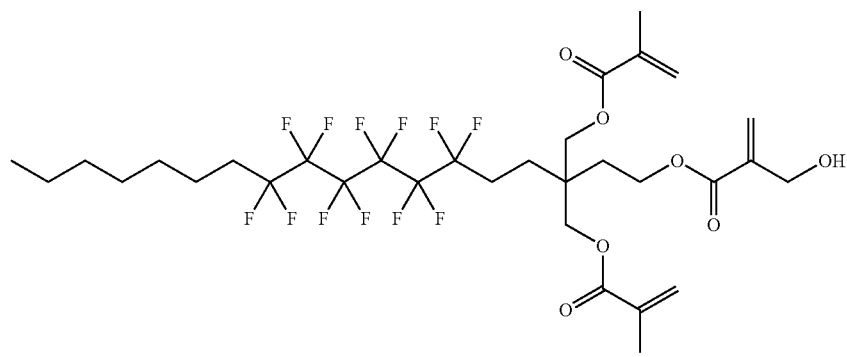 [SMILES: C=C(C)C(=O)OCC(CCOC(=O)C(=C)CO)(CCC(F)(F)C(F)(F)C(F)(F)C(F)(F)C(F)(F)C(F)(F)CCCCCCC)COC(=O)C(=C)C]
1-5-13
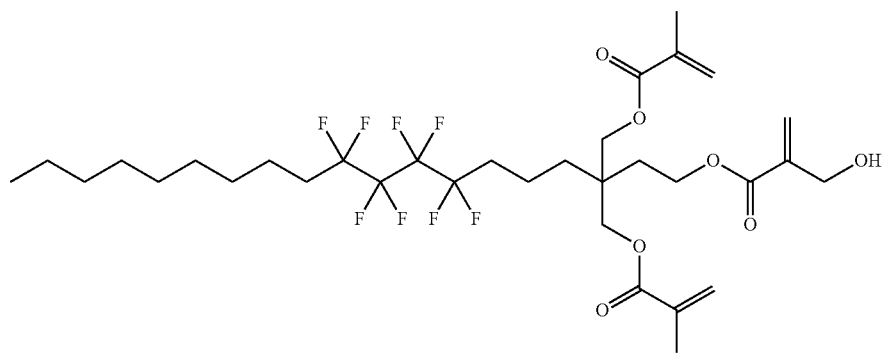 [SMILES: C=C(C)C(=O)OCC(CCCC(F)(F)C(F)(F)C(F)(F)C(F)(F)CCCCCCCCC)(CCOC(=O)C(=C)CO)COC(=O)C(=C)C]
1-5-14
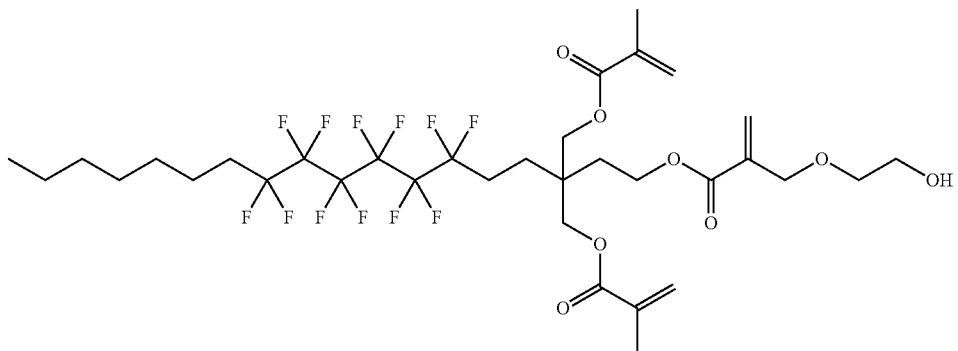 [SMILES: C=C(C)C(=O)OCC(CCOC(=O)C(=C)COCCO)(CCC(F)(F)C(F)(F)C(F)(F)C(F)(F)C(F)(F)C(F)(F)CCCCCCC)COC(=O)C(=C)C]

| No. |
|---|
| 1-5-15 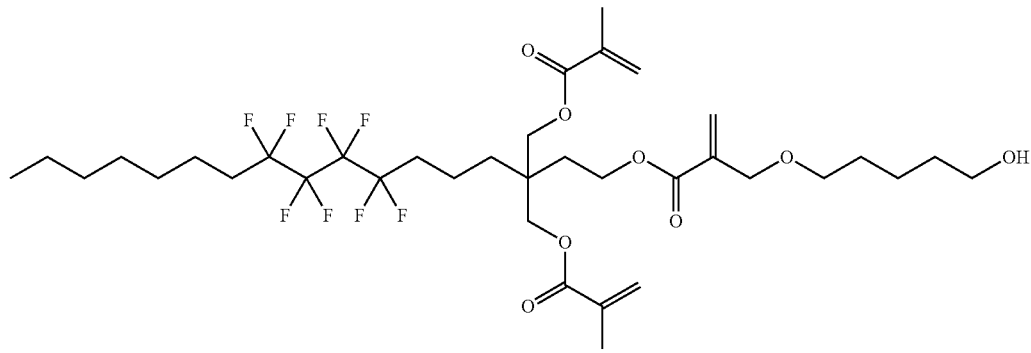 [SMILES: C=C(C)C(=O)OCC(CCCC(F)(F)C(F)(F)C(F)(F)C(F)(F)CCCCCCC)(CCOC(=O)C(=C)COCCCCCO)COC(=O)C(=C)C] |
| 1-5-16 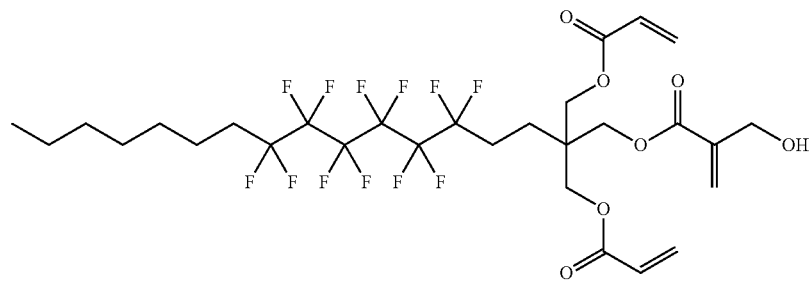 [SMILES: C=CC(=O)OCC(CCC(F)(F)C(F)(F)C(F)(F)C(F)(F)C(F)(F)C(F)(F)CCCCCCC)(COC(=O)C=C)COC(=O)C(=C)CO] |
| 1-5-17 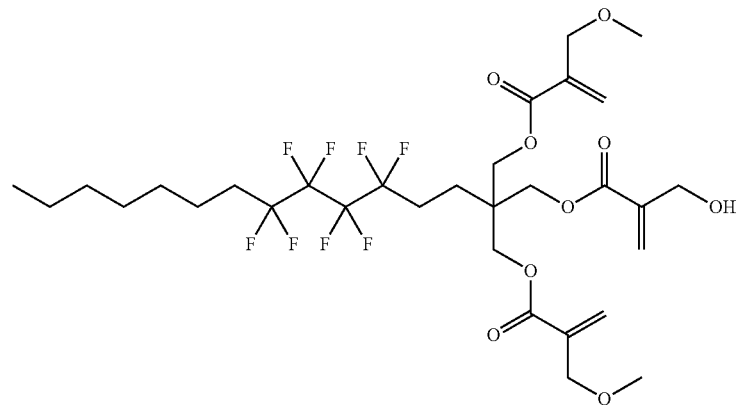 [SMILES: C=C(CO)C(=O)OCC(CCC(F)(F)C(F)(F)C(F)(F)C(F)(F)CCCCCCC)(COC(=O)C(=C)COC)COC(=O)C(=C)COC] |
| 1-5-18 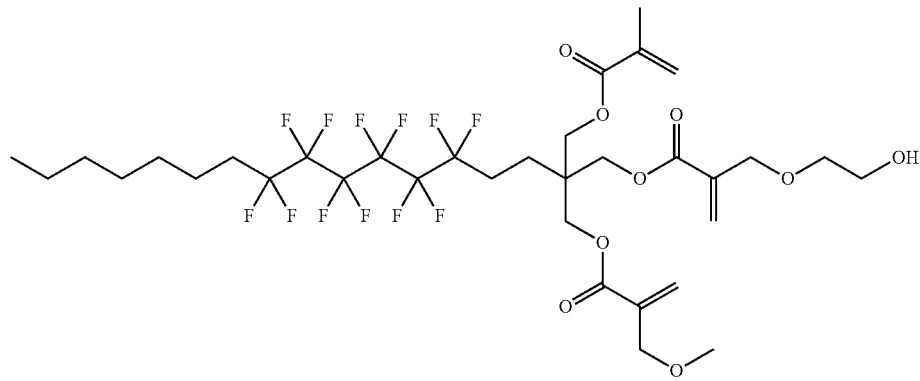 [SMILES: C=C(C)C(=O)OCC(CCC(F)(F)C(F)(F)C(F)(F)C(F)(F)C(F)(F)C(F)(F)CCCCCCC)(COC(=O)C(=C)COC)COC(=O)C(=C)COCCO] |

| No. |
|---|
| 1-5-19 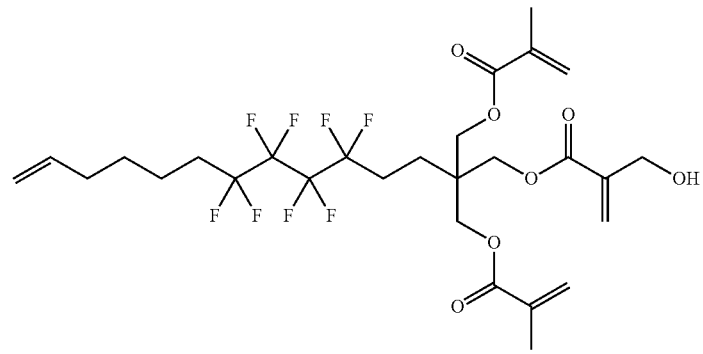 [SMILES: C=CCCCCC(F)(F)C(F)(F)C(F)(F)C(F)(F)CCC(COC(=O)C(=C)C)(COC(=O)C(=C)C)COC(=O)C(=C)CO] |
| 1-5-20 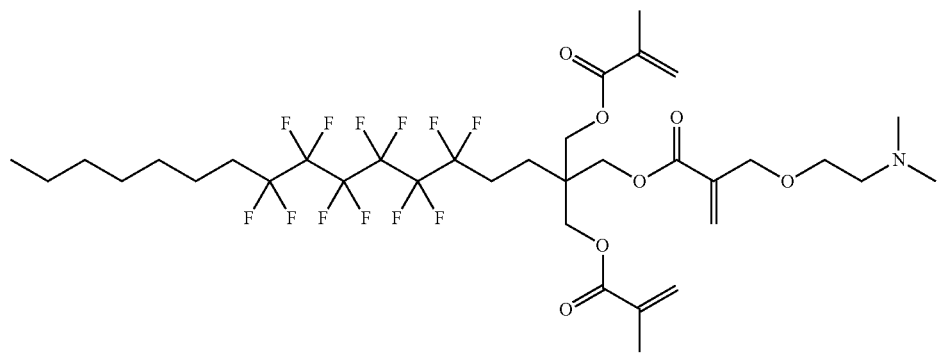 [SMILES: C=C(C)C(=O)OCC(CCC(F)(F)C(F)(F)C(F)(F)C(F)(F)C(F)(F)C(F)(F)CCCCCCC)(COC(=O)C(=C)C)COC(=O)C(=C)COCCN(C)C] |
| 1-6-1 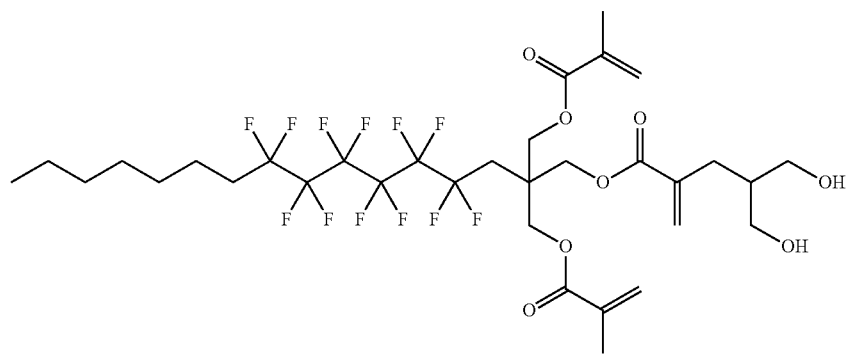 [SMILES: C=C(C)C(=O)OCC(COC(=O)C(=C)C)(COC(=O)C(=C)CC(CO)CO)CC(F)(F)C(F)(F)C(F)(F)C(F)(F)C(F)(F)C(F)(F)CCCCCCC] |
| 1-6-2 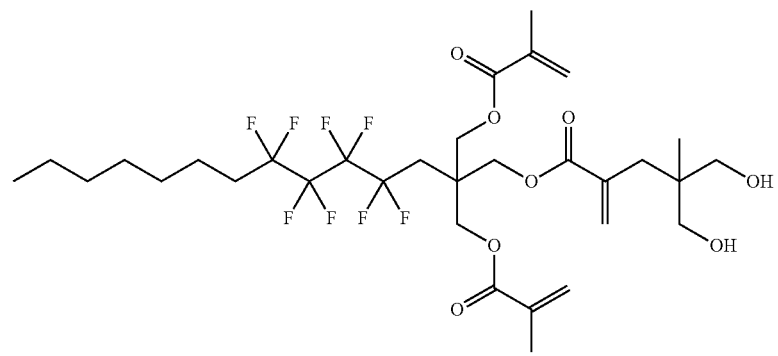 [SMILES: C=C(C)C(=O)OCC(COC(=O)C(=C)C)(COC(=O)C(=C)CC(C)(CO)CO)CC(F)(F)C(F)(F)C(F)(F)C(F)(F)CCCCCCC] |

| No. |
|---|
| 1-6-3 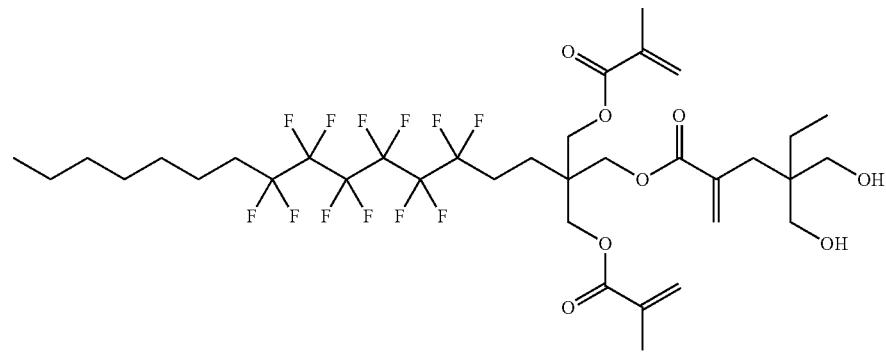 [SMILES: C=C(C)C(=O)OCC(CCC(F)(F)C(F)(F)C(F)(F)C(F)(F)C(F)(F)C(F)(F)CCCCCCC)(COC(=O)C(=C)C)COC(=O)C(=C)CC(CC)(CO)CO] |
| 1-6-4 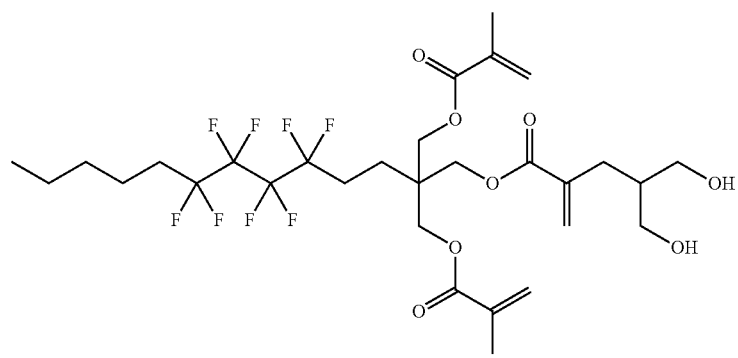 [SMILES: C=C(C)C(=O)OCC(CCC(F)(F)C(F)(F)C(F)(F)C(F)(F)CCCCC)(COC(=O)C(=C)C)COC(=O)C(=C)CC(CO)CO] |
| 1-6-5 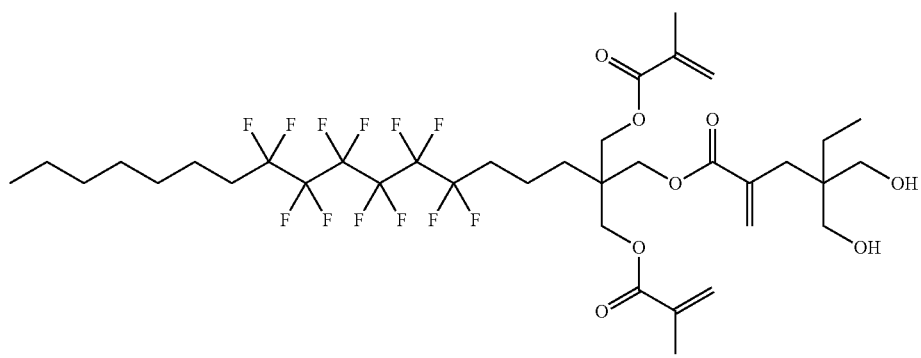 [SMILES: C=C(C)C(=O)OCC(CCCC(F)(F)C(F)(F)C(F)(F)C(F)(F)C(F)(F)C(F)(F)CCCCCCC)(COC(=O)C(=C)C)COC(=O)C(=C)CC(CC)(CO)CO] |
| 1-6-6 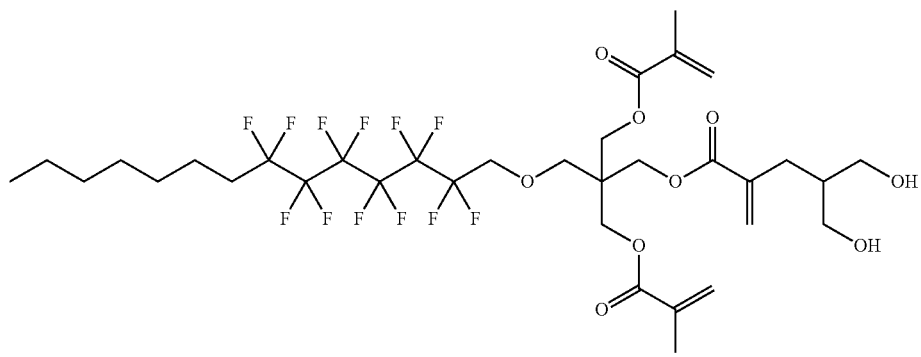 [SMILES: C=C(C)C(=O)OCC(COCC(F)(F)C(F)(F)C(F)(F)C(F)(F)C(F)(F)C(F)(F)CCCCCCC)(COC(=O)C(=C)C)COC(=O)C(=C)CC(CO)CO] |

| No. | |
|---|---|
| 1-6-7 | 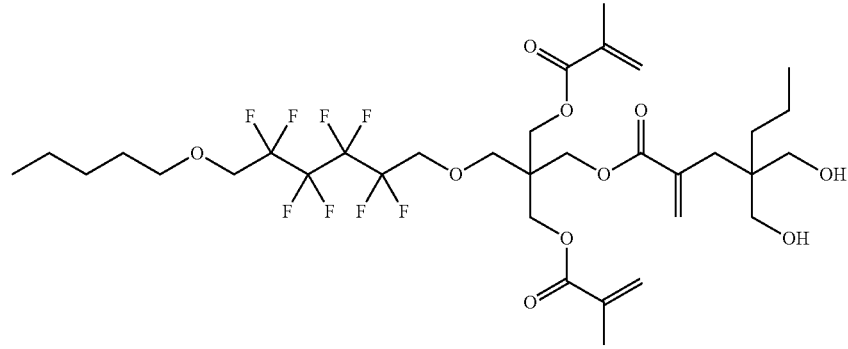 [SMILES: C=C(C)C(=O)OCC(COCC(F)(F)C(F)(F)C(F)(F)C(F)(F)COCCCCC)(COC(=O)C(=C)C)COC(=O)C(=C)CC(CO)(CO)CCC] |
| 1-6-8 | 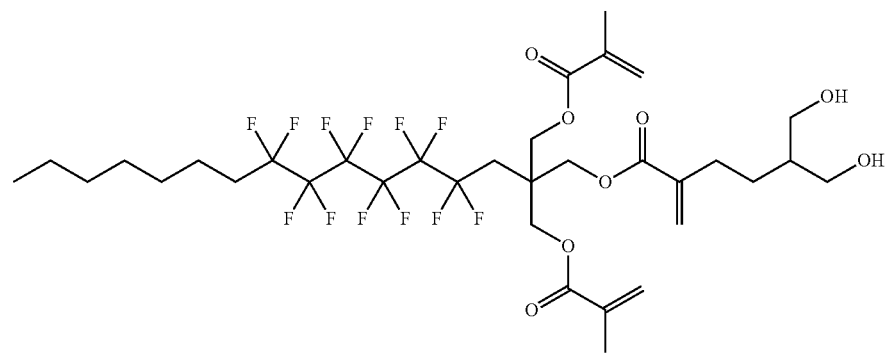 [SMILES: C=C(C)C(=O)OCC(COC(=O)C(=C)C)(COC(=O)C(=C)CCC(CO)CO)CC(F)(F)C(F)(F)C(F)(F)C(F)(F)C(F)(F)C(F)(F)CCCCCCC] |
| 1-6-9 | 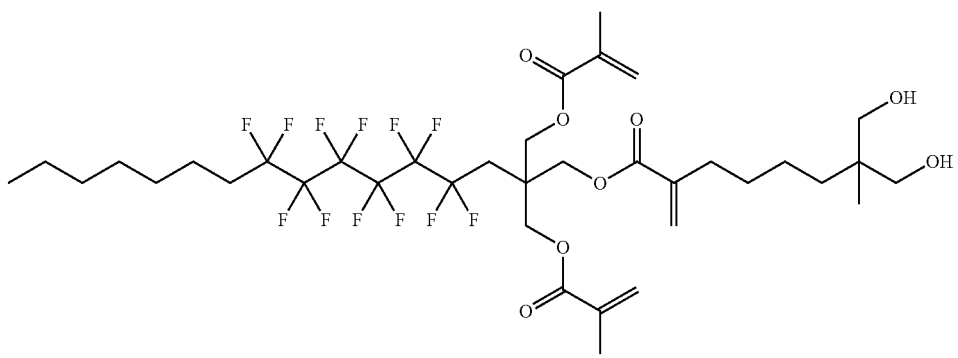 [SMILES: C=C(C)C(=O)OCC(COC(=O)C(=C)C)(COC(=O)C(=C)CCCCC(C)(CO)CO)CC(F)(F)C(F)(F)C(F)(F)C(F)(F)C(F)(F)C(F)(F)CCCCCCC] |
| 1-6-10 | 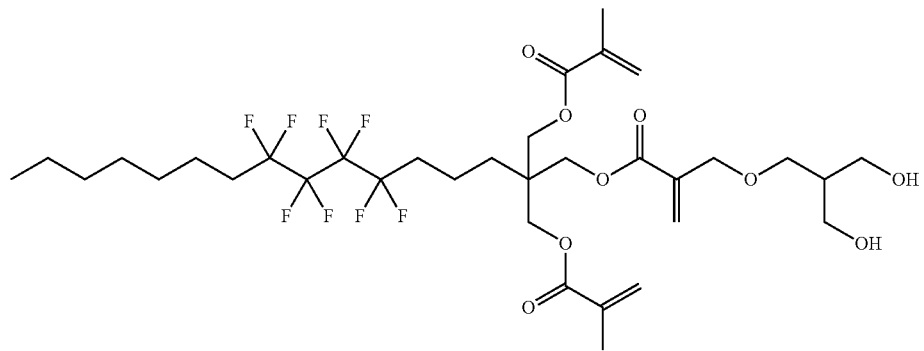 [SMILES: C=C(C)C(=O)OCC(CCCC(F)(F)C(F)(F)C(F)(F)C(F)(F)CCCCCCC)(COC(=O)C(=C)C)COC(=O)C(=C)COCC(CO)CO] |

| No. |
|---|
| 1-6-11 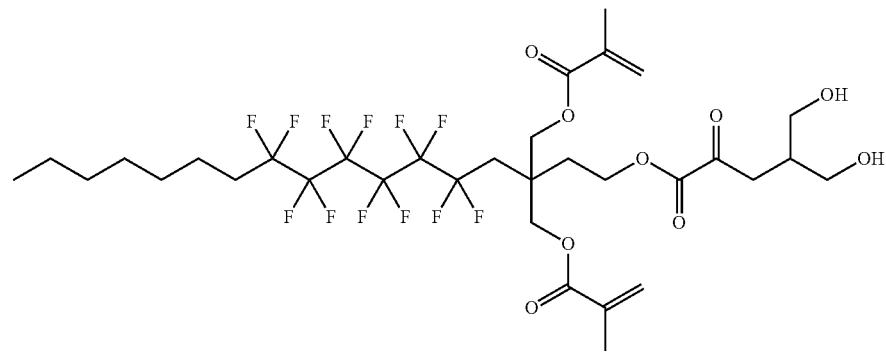 [SMILES: C=C(C)C(=O)OCC(CCOC(=O)C(=O)CC(CO)CO)(COC(=O)C(=C)C)CC(F)(F)C(F)(F)C(F)(F)C(F)(F)C(F)(F)C(F)(F)CCCCCCC] |
| 1-6-12 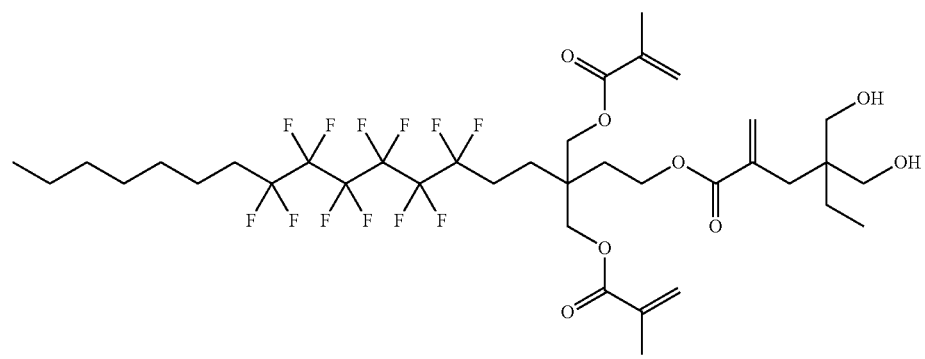 [SMILES: C=C(C)C(=O)OCC(CCOC(=O)C(=C)CC(CC)(CO)CO)(CCC(F)(F)C(F)(F)C(F)(F)C(F)(F)C(F)(F)C(F)(F)CCCCCCC)COC(=O)C(=C)C] |
| 1-6-13 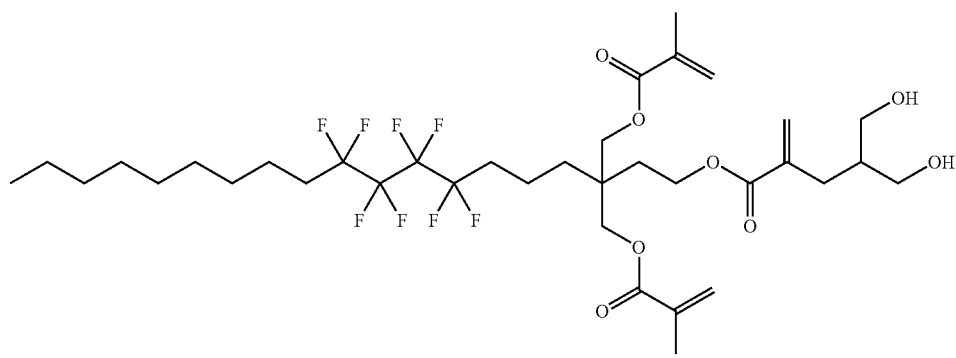 [SMILES: C=C(C)C(=O)OCC(CCCC(F)(F)C(F)(F)C(F)(F)C(F)(F)CCCCCCCCC)(CCOC(=O)C(=C)CC(CO)CO)COC(=O)C(=C)C] |
| 1-6-14 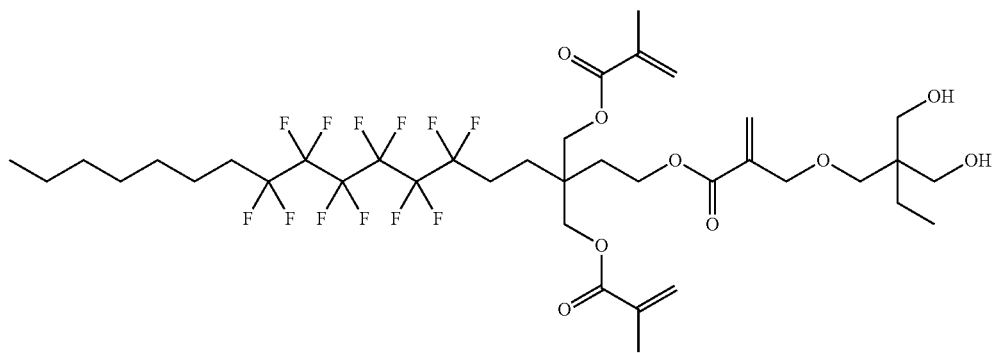 [SMILES: C=C(C)C(=O)OCC(CCOC(=O)C(=C)COCC(CC)(CO)CO)(CCC(F)(F)C(F)(F)C(F)(F)C(F)(F)C(F)(F)C(F)(F)CCCCCCC)COC(=O)C(=C)C] |

| No. | |
|---|---|
| 1-6-15 | 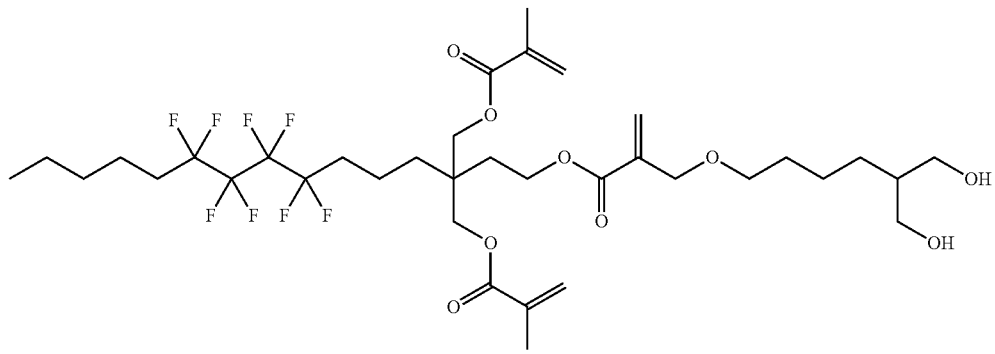 [SMILES: C=C(C)C(=O)OCC(CCCC(F)(F)C(F)(F)C(F)(F)C(F)(F)CCCCC)(CCOC(=O)C(=C)COCCCCC(CO)CO)COC(=O)C(=C)C] |
| 1-6-16 | 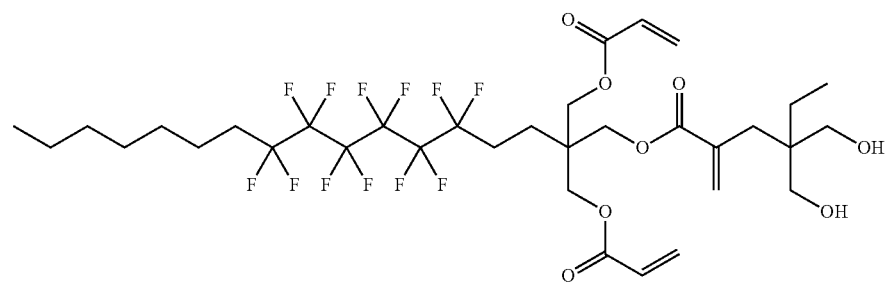 [SMILES: C=CC(=O)OCC(CCC(F)(F)C(F)(F)C(F)(F)C(F)(F)C(F)(F)C(F)(F)CCCCCCC)(COC(=O)C=C)COC(=O)C(=C)CC(CC)(CO)CO] |
| 1-6-17 | 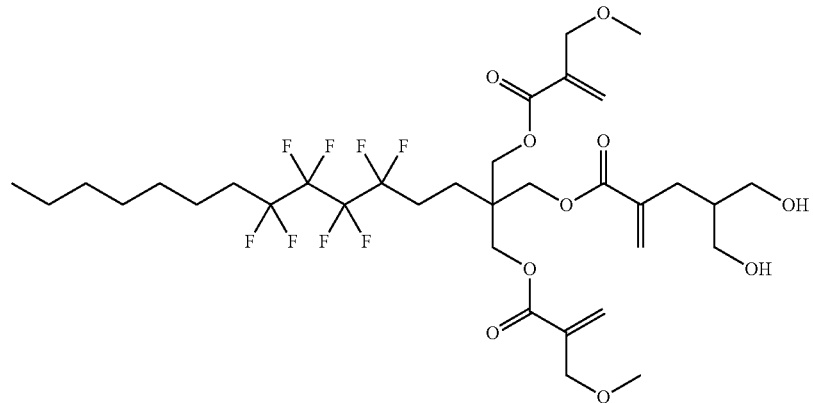 [SMILES: C=C(COC)C(=O)OCC(CCC(F)(F)C(F)(F)C(F)(F)C(F)(F)CCCCCCC)(COC(=O)C(=C)COC)COC(=O)C(=C)CC(CO)CO] |
| 1-6-18 | 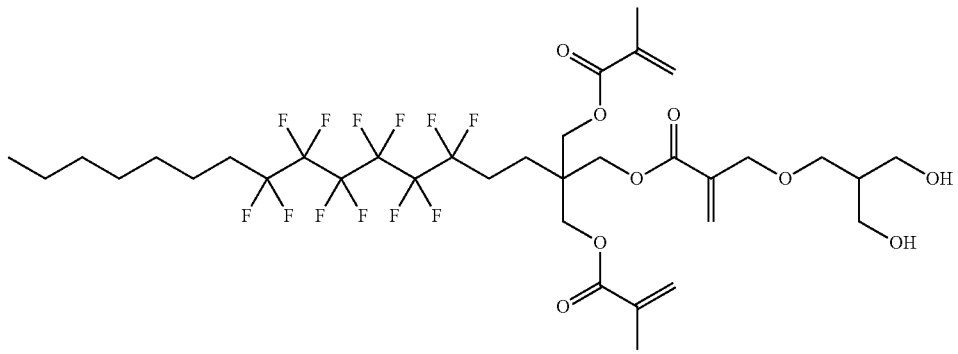 [SMILES: C=C(C)C(=O)OCC(CCC(F)(F)C(F)(F)C(F)(F)C(F)(F)C(F)(F)C(F)(F)CCCCCCC)(COC(=O)C(=C)C)COC(=O)C(=C)COCC(CO)CO] |

| No. | |
|---|---|
| 1-6-19 | 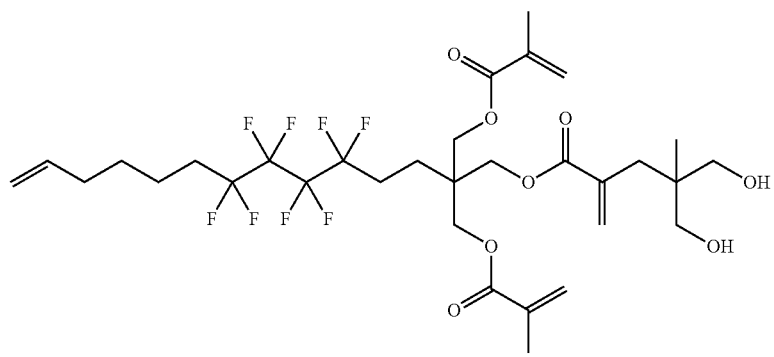 [SMILES: C=CCCCCC(F)(F)C(F)(F)C(F)(F)C(F)(F)CCC(COC(=O)C(=C)C)(COC(=O)C(=C)C)COC(=O)C(=C)CC(C)(CO)CO] |
| 1-6-20 | 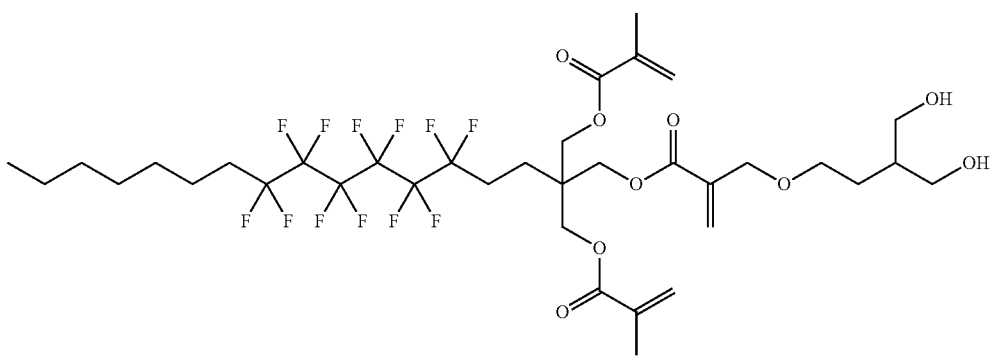 [SMILES: C=C(C)C(=O)OCC(CCC(F)(F)C(F)(F)C(F)(F)C(F)(F)C(F)(F)C(F)(F)CCCCCCC)(COC(=O)C(=C)C)COC(=O)C(=C)COCCC(CO)CO] |

2. Examples of Composition

Compounds in the examples are indicated by symbols based on definitions of the following Table 3. In Table 3, the configuration related to 1,4-cyclohexylene is trans. A number in parentheses after a symbol indicates a number of a compound. The symbol (-) refers to other liquid crystalline compounds. A proportion (percentage) of the liquid crystalline compound is a weight percentage (weight %) based on the weight of the liquid crystal composition. Finally, values of properties of the liquid crystal compositions are summarized. The properties were measured according to the methods described above and measured values (without extrapolation) are shown without change.

TABLE 3

| Method of representing compound using symbols $R—(A_1)—Z_1—\ldots—Z_n—(A_n)—R'$ | |
|---|---|
| 1) Left terminal group R— | symbols |
| $C_nH_{2n+1}—$ | n— |
| $C_nH_{2n+1}O—$ | nO— |
| $C_mH_{2m+1}OC_nH_{2n}—$ | mOn— |
| $CH_2=CH—$ | V— |
| $C_nH_{2n+1}—CH=CH—$ | nV— |
| $CH_2=CH—C_nH_{2n}—$ | Vn— |
| $C_mH_{2m+1}—CH=CH—C_nH_{2n}—$ | mVn— |
| $CF_2=CH—$ | VFF— |
| $CF_2=CH—C_nH_{2n}—$ | VFFn— |
| 2) Right terminal group —R' | symbols |
| $—C_nH_{2n+1}$ | —n |
| $—OC_nH_{2n+1}$ | —On |
| $—COOCH_3$ | —EMe |
| $—CH=CH_2$ | —V |

TABLE 3-continued

| Method of representing compound using symbols $R—(A_1)—Z_1—\ldots—Z_n—(A_n)—R'$ | |
|---|---|
| $—CH=CH—C_nH_{2n+1}$ | —Vn |
| $—C_nH_{2n}—CH=CH_2$ | —nV |
| $—C_mH_{2m}—CH=CH—C_nH_{2n+1}$ | —mVn |
| $—CH=CF_2$ | —VFF |
| —F | —F |
| —Cl | —CL |
| $—OCF_3$ | —OCF3 |
| $—OCF_2H$ | —OCF2H |
| $—CF_3$ | —CF3 |
| $—OCH=CH—CF_3$ | —OVCF3 |
| $—C≡N$ | —C |

| 3) Bond group —$Z_n$— | symbols |
|---|---|
| $—C_nH_{2n}—$ | n |
| —COO— | E |
| —CH=CH— | V |
| —$CH_2O$— | 10 |
| —$OCH_2$— | 01 |
| —$CF_2O$— | X |
| —C≡C— | T |

| 4) Ring structure —$A_n$— | symbols |
|---|---|
| cyclohexylene ring | H |
| phenylene ring | B |

TABLE 3-continued

Method of representing compound using symbols
R—(A₁)—Z₁—...—Zₙ—(Aₙ)—R'

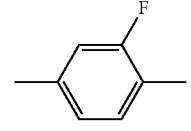 B(F)

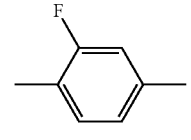 B(2F)

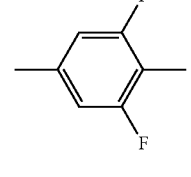 B(F,F)

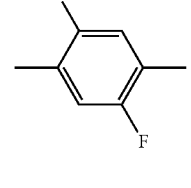 B(2F,5F)

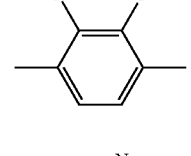 B(2F,3F)

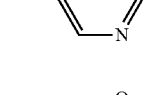 Py

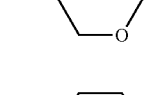 G

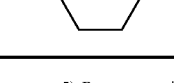 ch

5) Representative Examples

Example 1  3-HB—CL

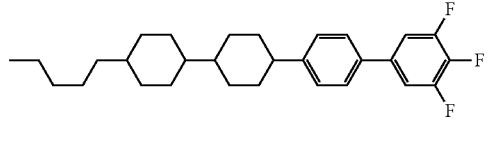 [SMILES: CCCCCC1CCC(C2CCC(c3ccc(-c4cc(F)c(F)c(F)c4)cc3)CC2)CC1]

TABLE 3-continued

Method of representing compound using symbols
R—(A₁)—Z₁—...—Zₙ—(Aₙ)—R'

Example 2  5-HHBB(F,F)—F

Example 3  3-HB—O2

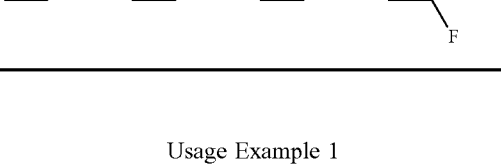

Example 4  3-HBB(F,F)—F

Usage Example 1

| | | |
|---|---|---|
| 1-BB-3 | (2-8) | 7% |
| 1-BB-5 | (2-8) | 8% |
| 2-BTB-1 | (2-10) | 3% |
| 3-HHB-1 | (3-1) | 8% |
| 3-HHB-3 | (3-1) | 14% |
| 3-HHB-O1 | (3-1) | 5% |
| 3-HHB-F | (6-1) | 4% |
| 2-HHB(F)-F | (6-2) | 6% |
| 3-HHB(F)-F | (6-2) | 7% |
| 5-HHB(F)-F | (6-2) | 7% |
| 3-HHB(F,F)-F | (6-3) | 5% |
| 3-HHEB-F | (6-10) | 5% |
| 5-HHEB-F | (6-10) | 4% |
| 2-HB-C | (8-1) | 7% |
| 3-HB-C | (8-1) | 10% |

The following Compound (1-1-5) in a proportion of 3 weight % was added to the above composition.

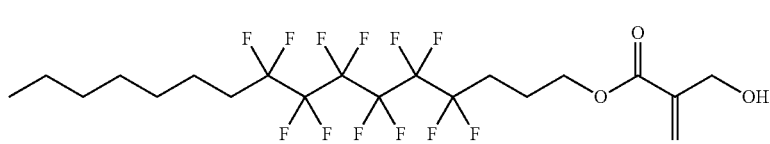

(1-1-5)

NI=96.7° C.; η=17.2 mPa·s; Δn=0.108; Δε=4.8.

Usage Example 2

| 3-HH-4 | (2-1) | 13% |
| 5-HB-O2 | (2-5) | 4% |
| 7-HB-1 | (2-5) | 3% |
| 5-HBB(F)B-2 | (4-5) | 5% |
| 5-HBB(F)B-3 | (4-5) | 5% |
| 3-HB-CL | (5-2) | 13% |
| 3-HHB(F,F)-F | (6-3) | 4% |
| 3-HBB(F,F)-F | (6-24) | 29% |
| 5-HBB(F,F)-F | (6-24) | 24% |

The following Compound (1-1-19) in a proportion of 5 weight % was added to the above composition.

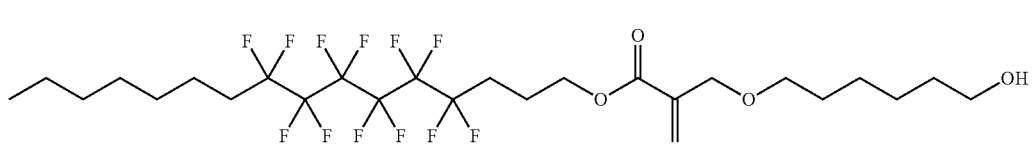

(1-1-19)

NI=70.6° C.; η=19.3 mPa·s; Δn=0.113; Δε=5.7.

Usage Example 3

| 1V2-HH-1 | (2-1) | 3% |
| 1V2-HH-3 | (2-1) | 4% |
| 7-HB(F,F)-F | (5-4) | 3% |
| 2-HHB(F)-F | (6-2) | 10% |
| 3-HHB(F)-F | (6-2) | 9% |
| 5-HHB(F)-F | (6-2) | 9% |
| 2-HBB-F | (6-22) | 5% |
| 3-HBB-F | (6-22) | 5% |
| 5-HBB-F | (6-22) | 3% |
| 2-HBB(F)-F | (6-23) | 9% |
| 3-HBB(F)-F | (6-23) | 9% |
| 5-HBB(F)-F | (6-23) | 16% |
| 3-HBB(F,F)-F | (6-24) | 5% |
| 5-HBB(F,F)-F | (6-24) | 10% |

The following Compound (1-1-7) in a proportion of 2.5 weight % was added to the above composition.

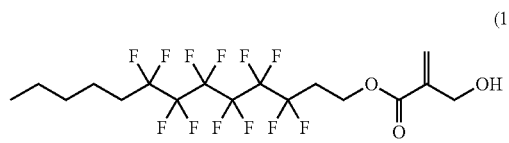

(1-1-7)

NI=84.7° C.; η=25.0 mPa·s; Δn=0.112; Δε=5.7.

Usage Example 4

| 2-HH-3 | (2-1) | 4% |
| 3-HH-4 | (2-1) | 12% |
| 1O1-HBBH-5 | (4-1) | 5% |
| 5-HB-CL | (5-2) | 14% |
| 3-HHB-F | (6-1) | 4% |
| 3-HHB-CL | (6-1) | 4% |
| 4-HHB-CL | (6-1) | 4% |
| 3-HHB(F)-F | (6-2) | 10% |
| 4-HHB(F)-F | (6-2) | 9% |
| 5-HHB(F)-F | (6-2) | 8% |
| 7-HHB(F)-F | (6-2) | 8% |
| 5-HBB(F)-F | (6-23) | 3% |
| 3-HHBB(F,F)-F | (7-6) | 2% |
| 4-HHBB(F,F)-F | (7-6) | 3% |

-continued

| 5-HHBB(F,F)-F | (7-6) | 4% |
| 3-HH2BB(F,F)-F | (7-15) | 3% |
| 4-HH2BB(F,F)-F | (7-15) | 3% |

The following Compound (1-1-23) in a proportion of 0.5 weight % was added to the above composition.

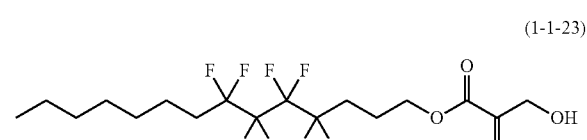

(1-1-23)

NI=118.8° C.; η=20.1 mPa·s; Δn=0.093; Δε=3.7.

Usage Example 5

| V-HBB-2 | (3-4) | 10% |
| 1O1-HBBH-4 | (4-1) | 4% |
| 1O1-HBBH-5 | (4-1) | 4% |
| 3-HHB(F,F)-F | (6-3) | 9% |
| 3-H2HB(F,F)-F | (6-15) | 9% |
| 4-H2HB(F,F)-F | (6-15) | 8% |
| 5-H2HB(F,F)-F | (6-15) | 8% |
| 3-HBB(F,F)-F | (6-24) | 9% |
| 5-HBB(F,F)-F | (6-24) | 20% |
| 3-H2BB(F,F)-F | (6-27) | 10% |
| 5-HHBB(F,F)-F | (7-6) | 3% |

| | | |
|---|---|---|
| 3-HH2BB(F,F)-F | (7-15) | 4% |
| 5-HHEBB-F | (7-17) | 2% |

The following Compound (1-1-12) in a proportion of 1 weight % was added to the above composition.

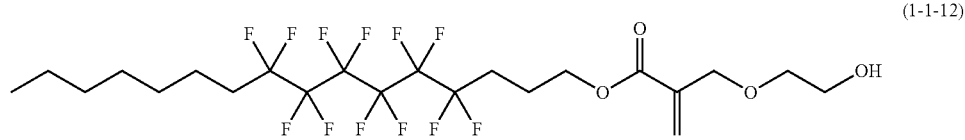 [SMILES: C=C(COCCO)C(=O)OCCCC(F)(F)C(F)(F)C(F)(F)C(F)(F)C(F)(F)C(F)(F)CCCCCCC]

(1-1-12)

NI=108.0° C.; η=32.8 mPa·s; Δn=0.122; Δε=8.2.

Usage Example 6

| | | |
|---|---|---|
| 5-HBBH-3 | (4-1) | 3% |
| 3-HB(F)BH-3 | (4-2) | 3% |
| 5-HB-F | (5-2) | 12% |
| 6-HB-F | (5-2) | 9% |
| 7-HB-F | (5-2) | 7% |
| 2-HHB-OCF3 | (6-1) | 8% |
| 3-HHB-OCF3 | (6-1) | 6% |
| 4-HHB-OCF3 | (6-1) | 7% |
| 5-HHB-OCF3 | (6-1) | 6% |
| 3-HHB(F,F)-OCF2H | (6-3) | 4% |
| 3-HHB(F,F)-OCF3 | (6-3) | 4% |
| 3-HH2B-OCF3 | (6-4) | 4% |

-continued

| | | |
|---|---|---|
| 5-HH2B-OCF3 | (6-4) | 4% |
| 3-HH2B(F)-F | (6-5) | 3% |
| 3-HBB(F)-F | (6-23) | 10% |
| 5-HBB(F)-F | (6-23) | 10% |

The following Compound (1-2-8) in a proportion of 0.1 weight % was added to the above composition.

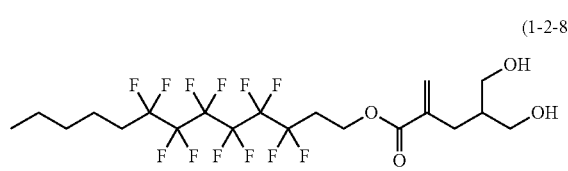

(1-2-8)

NI=85.5° C.; η=14.6 mPa·s; Δn=0.092; Δε=4.4.

Usage Example 7

| | | |
|---|---|---|
| 2-HH-5 | (2-1) | 4% |
| 3-HH-4 | (2-1) | 5% |

-continued

| | | |
|---|---|---|
| 5-B(F)BB-2 | (3-8) | 4% |
| 5-HB-CL | (5-2) | 10% |
| 3-HHB(F,F)-F | (6-3) | 11% |
| 3-HHEB(F,F)-F | (6-12) | 8% |
| 4-HHEB(F,F)-F | (6-12) | 3% |
| 5-HHEB(F,F)-F | (6-12) | 3% |
| 3-HBB(F,F)-F | (6-24) | 20% |
| 5-HBB(F,F)-F | (6-24) | 15% |
| 2-HBEB(F,F)-F | (6-39) | 5% |
| 3-HBEB(F,F)-F | (6-39) | 3% |
| 5-HBEB(F,F)-F | (6-39) | 4% |
| 3-HHBB(F,F)-F | (7-6) | 5% |

The following Compound (1-3-1) in a proportion of 7 weight % was added to the above composition.

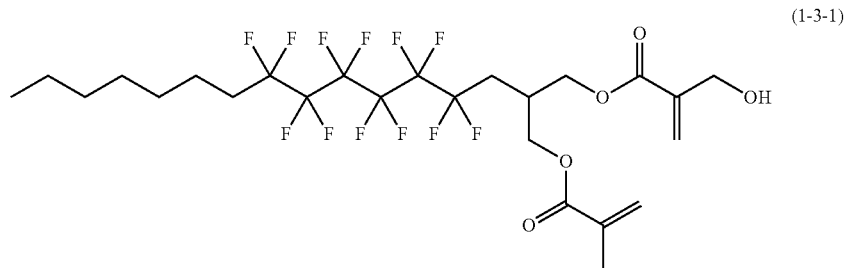 [SMILES: C=C(C)C(=O)OCC(COC(=O)C(=C)CO)CC(F)(F)C(F)(F)C(F)(F)C(F)(F)C(F)(F)C(F)(F)CCCCCCC]

(1-3-1)

NI=75.6° C.; η=22.6 mPa·s; Δn=0.108; Δε=8.8.

Usage Example 8

| | | |
|---|---|---|
| V2-HHB-1 | (3-1) | 6% |
| 3-HB-CL | (5-2) | 5% |
| 5-HB-CL | (5-2) | 5% |
| 3-HHB-OCF3 | (6-1) | 4% |
| 5-HHB(F)-F | (6-2) | 5% |
| V-HHB(F)-F | (6-2) | 6% |
| 3-H2HB-OCF3 | (6-13) | 5% |
| 5-H2HB(F,F)-F | (6-15) | 4% |
| 5-H4HB-OCF3 | (6-19) | 15% |
| 5-H4HB(F,F)-F | (6-21) | 7% |
| 3-H4HB(F,F)-CF3 | (6-21) | 8% |
| 5-H4HB(F,F)-CF3 | (6-21) | 10% |
| 2-H2BB(F)-F | (6-26) | 5% |
| 3-H2BB(F)-F | (6-26) | 10% |
| 3-HBEB(F,F)-F | (6-39) | 5% |

The following Compound (1-1-5) in a proportion of 2 weight % was added to the above composition.

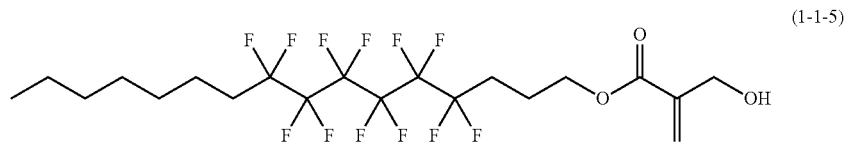 [SMILES: C=C(CO)C(=O)OCCCC(F)(F)C(F)(F)C(F)(F)C(F)(F)C(F)(F)C(F)(F)CCCCCCC]

(1-1-5)

NI=73.3° C.; η=24.7 mPa·s; Δn=0.099; Δε=8.1.

Usage Example 9

| | | |
|---|---|---|
| 3-HH-4 | (2-1) | 8% |
| 3-HH-5 | (2-1) | 7% |
| 3-HB-O2 | (2-5) | 13% |
| 3-HHB-1 | (3-1) | 8% |
| 3-HHB-O1 | (3-1) | 4% |
| 5-HB-CL | (5-2) | 15% |
| 7-HB(F,F)-F | (5-4) | 4% |
| 2-HHB(F)-F | (6-2) | 7% |
| 3-HHB(F)-F | (6-2) | 8% |
| 5-HHB(F)-F | (6-2) | 7% |
| 3-HHB(F,F)-F | (6-3) | 7% |
| 3-H2HB(F,F)-F | (6-15) | 6% |
| 4-H2HB(F,F)-F | (6-15) | 6% |

The following Compound (1-1-19) in a proportion of 1.5 weight % was added to the above composition.

(1-1-19)

NI=71.3° C.; η=14.9 mPa·s; Δn=0.073; Δε=3.1.

Usage Example 10

| | | |
|---|---|---|
| 3-HH-4 | (2-1) | 10% |
| 3-HH-5 | (2-1) | 9% |
| 3-HHB-1 | (3-1) | 12% |
| 5-HB-CL | (5-2) | 4% |
| 7-HB(F)-F | (5-3) | 6% |
| 2-HHB(F,F)-F | (6-3) | 5% |
| 3-HHB(F,F)-F | (6-3) | 4% |
| 3-HHEB-F | (6-10) | 9% |
| 5-HHEB-F | (6-10) | 8% |
| 3-HHEB(F,F)-F | (6-12) | 10% |
| 4-HHEB(F,F)-F | (6-12) | 6% |
| 3-GHB(F,F)-F | (6-109) | 7% |
| 4-GHB(F,F)-F | (6-109) | 5% |
| 5-GHB(F,F)-F | (6-109) | 5% |

The following Compound (1-1-7) in a proportion of 3 weight % was added to the above composition.

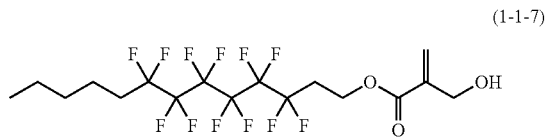 [SMILES: C=C(CO)C(=O)OCCC(F)(F)C(F)(F)C(F)(F)C(F)(F)C(F)(F)C(F)(F)CCCCC]

(1-1-7)

NI=87.5° C.; η=21.9 mPa·s; Δn=0.071; Δε=5.9.

Usage Example 11

| | | |
|---|---|---|
| 3-HH-VFF | (2-1) | 10% |
| 5-HH-VFF | (2-1) | 20% |
| 2-BTB-1 | (2-10) | 9% |
| 3-HHB-1 | (3-1) | 5% |
| VFF-HHB-1 | (3-1) | 9% |
| VFF2-HHB-1 | (3-1) | 10% |

-continued

| | | |
|---|---|---|
| 3-H2BTB-2 | (3-17) | 5% |
| 3-H2BTB-3 | (3-17) | 4% |
| 3-H2BTB-4 | (3-17) | 4% |
| 3-HB-C | (8-1) | 18% |
| 1V2-BEB(F,F)-C | (8-15) | 6% |

The following Compound (1-1-23) in a proportion of 4 weight % was added to the above composition.

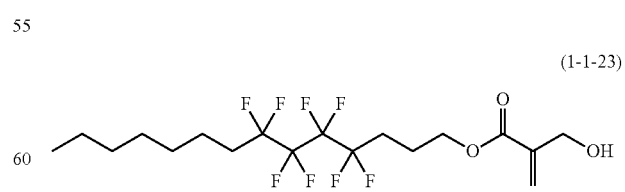

(1-1-23)

NI=82.0° C.; η=10.9 mPa·s; Δn=0.129; Δε=6.6.

A liquid crystal composition containing Compound (1) can be used for a display device such as a liquid crystal projector and a liquid crystal television.

What is claimed is:
1. A compound represented by Formula (1):

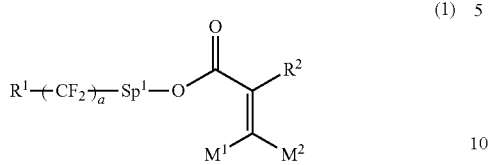
(1)

in Formula (1),
$R^1$ is an alkyl group having 1 to 15 carbon atoms, and in this alkyl group, at least one —$CH_2$— is optionally substituted with —O— or —S—, and at least one —$(CH_2)_2$— is optionally substituted with —CH=CH— or —C≡C—, and in these groups represented by $R^1$, at least one hydrogen atom is optionally substituted with a fluorine or chlorine atom;
$a$ is an integer of 2 to 12;
$M^1$ and $M^2$ are independently a hydrogen atom, a fluorine atom, a chlorine atom, an alkyl group having 1 to 5 carbon atoms, or an alkyl group having 1 to 5 carbon atoms in which at least one hydrogen atom is substituted with a fluorine atom or a chlorine atom; and
$R^2$ is a group selected from among groups represented by Formula (1-a), Formula (1-b), and Formula (1-c);

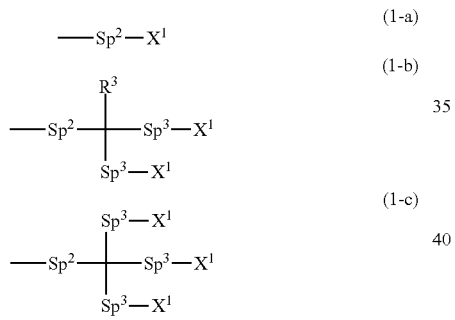
(1-a)
(1-b)
(1-c)

in Formula (1-a), Formula (1-b), and Formula (1-c),
$Sp^2$ and $Sp^3$ are independently a single bond or an alkylene group having 1 to 10 carbon atoms, and in this alkylene group, at least one —$CH_2$— is optionally substituted with —O—, —CO—, —COO—, —OCO—, or —OCOO—, and at least one —$(CH_2)_2$— is optionally substituted with —CH=CH— or —C≡C—, and in these groups represented by $Sp^2$ and $Sp^3$, at least one hydrogen atom is optionally substituted with a fluorine or chlorine atom;
$R^3$ is a hydrogen atom, an alkyl group having 1 to 10 carbon atoms, an alkoxy group having 1 to 9 carbon atoms, or an alkoxyalkyl group having 1 to 9 carbon atoms;
$X^1$ is independently —OH, —$NH_2$, —$N(R^4)_2$, —COOH, —SH, or —$Si(R^4)_3$;
in —$N(R^4)_2$, and —$Si(R^4)_3$,
$R^4$ is a hydrogen atom or an alkyl group having 1 to 10 carbon atoms, and in this alkyl group, at least one —$CH_2$— is optionally substituted with —O—, and at least one —$(CH_2)_2$— is optionally substituted with —CH=CH—, and in these groups represented by $R^4$, at least one hydrogen atom is optionally substituted with a fluorine or chlorine atom, in Formula (1),
$Sp^1$ is a single bond or an alkylene group having 1 to 15 carbon atoms, and in this alkylene group, at least one —$CH_2$— is optionally substituted with —O—, —CO—, —COO—, —OCO—, or —OCOO—, and at least one —$(CH_2)_2$— is optionally substituted with —CH=CH— or —C≡C—, and in these groups represented by $Sp^1$, at least one hydrogen atom is optionally substituted with a fluorine atom, a chlorine atom, or a group represented by Formula (1-d);

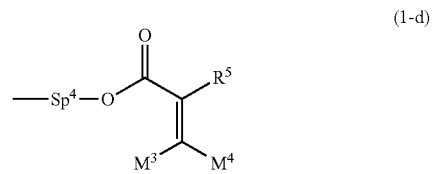
(1-d)

in Formula (1-d),
$Sp^4$ is a single bond or an alkylene group having 1 to 10 carbon atoms, and in this alkylene group, at least one —$CH_2$— is optionally substituted with —O—, —CO—, —COO—, —OCO—, or —OCOO—, and at least one —$(CH_2)_2$— is optionally substituted with —CH=CH— or —C≡C—, and in these groups represented by $Sp^4$, at least one hydrogen atom is optionally substituted with a fluorine or chlorine atom;
$M^3$ and $M^4$ are independently a hydrogen atom, a fluorine atom, a chlorine atom, an alkyl group having 1 to 5 carbon atoms, or an alkyl group having 1 to 5 carbon atoms in which at least one hydrogen atom is substituted with a fluorine atom or a chlorine atom; and
$R^5$ is a hydrogen atom or an alkyl group having 1 to 10 carbon atoms, and in this alkyl group, at least one —$CH_2$— is optionally substituted with —O—, at least one —$(CH_2)_2$— is optionally substituted with —CH=CH— or —C≡C—, and at least one hydrogen atom is optionally substituted with a fluorine atom or a chlorine atom.

2. The compound according to claim 1, wherein, in Formula (1), $R^2$ is a group represented by Formula (1-a) or Formula (1-b).

3. The compound according to claim 1, wherein, in Formula (1), $R^2$ is a group represented by Formula (1-a) or Formula (1-b), and in Formula (1-a) and Formula (1-b), $X^1$ is independently —OH, —$NH_2$, —COOH, or —SH.

4. The compound according to claim 1, which is represented by any one of Formula (1-1) to Formula (1-6):

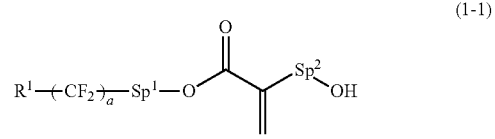
(1-1)

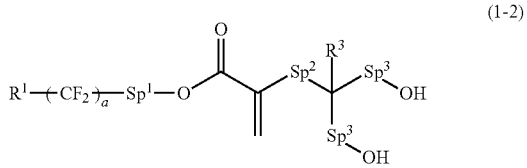
(1-2)

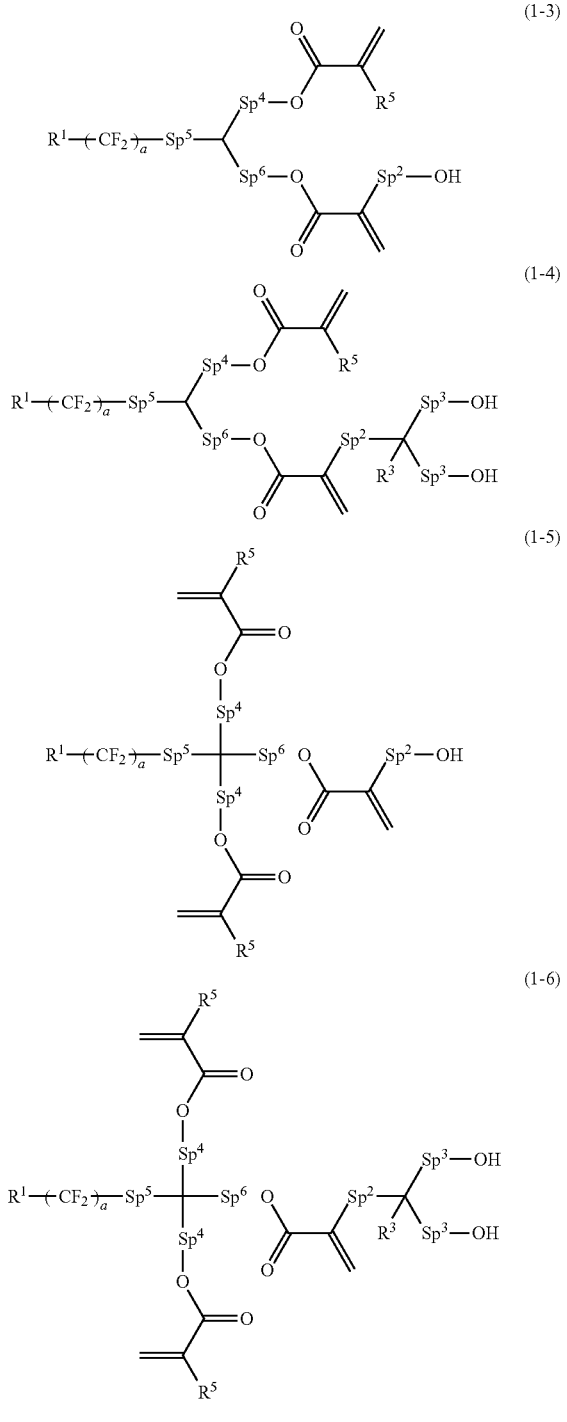

optionally substituted with —CH=CH—, and in these groups represented by Sp¹, Sp², Sp³, and Sp⁴, at least one hydrogen atom is optionally substituted with a fluorine atom;

Sp⁵ and Sp⁶ are independently a single bond or an alkylene group having 1 to 7 carbon atoms, and in this alkylene group, at least one —CH₂— is optionally substituted with —O—, and at least one —(CH₂)₂— is optionally substituted with —CH=CH—, and in these groups represented by Sp⁵ and Sp⁶, at least one hydrogen atom is optionally substituted with a fluorine atom;

R³ is a hydrogen, an alkyl group having 1 to 7 carbon atoms, an alkoxy group having 1 to 6 carbon atoms, or an alkoxyalkyl group having 1 to 6 carbon atoms;

R⁵ is a hydrogen atom or an alkyl group having 1 to 5 carbon atoms.

5. The compound according to claim 1, which is represented by any one of Formula (1-7) to Formula (1-24):

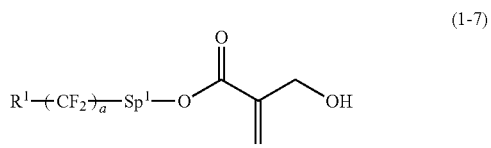
(1-7)

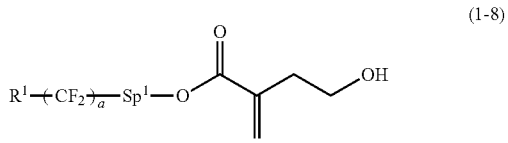
(1-8)

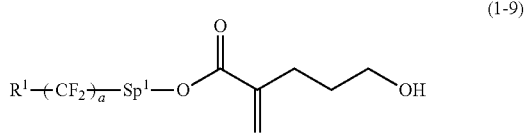
(1-9)

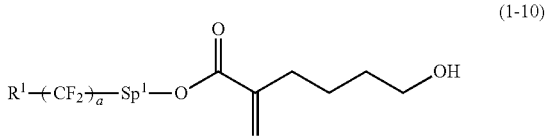
(1-10)

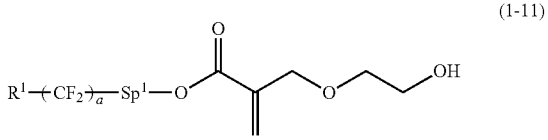
(1-11)

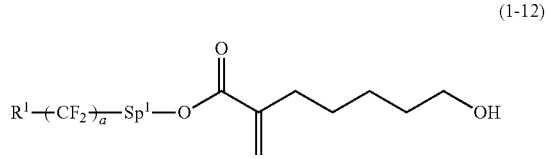
(1-12)

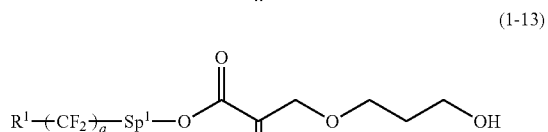
(1-13)

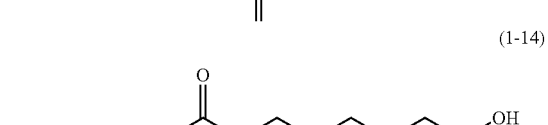
(1-14)

in Formula (1-1) to Formula (1-6),

R¹ is an alkyl group having 1 to 15 carbon atoms, and in this alkyl group, at least one —CH₂— is optionally substituted with —O—, and at least one —(CH₂)₂— is optionally substituted with —CH=CH—, and in these groups represented by R¹, at least one hydrogen atom is optionally substituted with a fluorine atom;

a is an integer of 2 to 8;

Sp¹, Sp², Sp³, and Sp⁴ are independently a single bond or an alkylene group having 1 to 10 carbon atoms, and in this alkylene group, at least one —CH₂— is optionally substituted with —O—, and at least one —(CH₂)₂— is -continued (1-15)
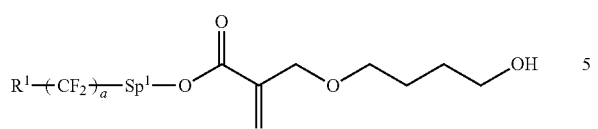

(1-16)
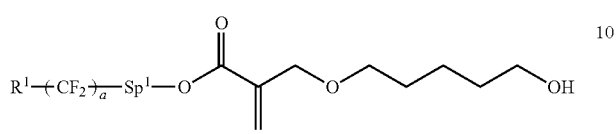

(1-17)
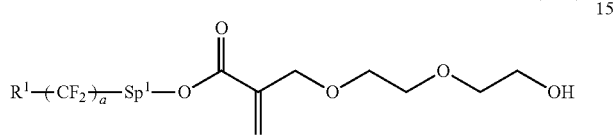

(1-18)
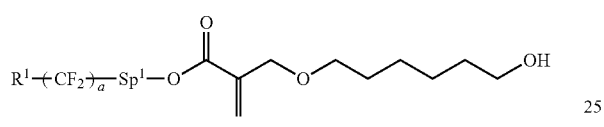

(1-19)
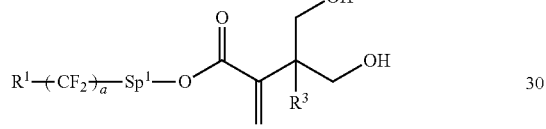

(1-20)
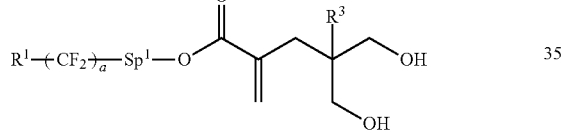

(1-21)
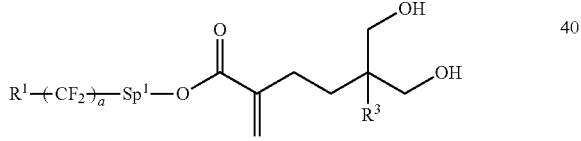

(1-22)
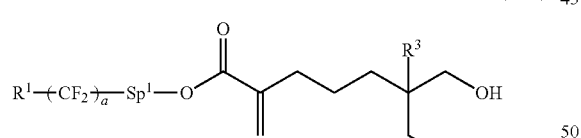

(1-23)
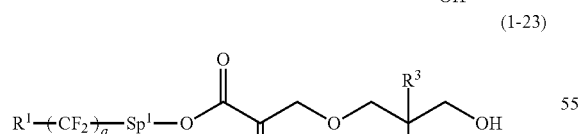

(1-24)

in Formula (1-7) to Formula (1-24), $R^1$ is an alkyl group having 1 to 15 carbon atoms, and in this alkyl group, at least one —CH$_2$— is optionally substituted with —O—, and at least one —(CH$_2$)$_2$— is optionally substituted with —CH=CH—;

a is an integer of 2 to 8;

$Sp^1$ is a single bond or an alkylene group having 1 to 7 carbon atoms, and in this alkylene group, at least one —CH$_2$— is optionally substituted with —O—; and $R^3$ is a hydrogen atom or an alkyl group having 1 to 5 carbon atoms.

6. The compound according to claim 1, which is represented by any one of Formula (1-25) to Formula (1-48):

(1-25)
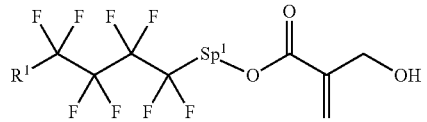

(1-26)
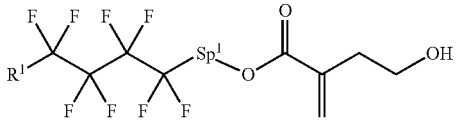

(1-27)
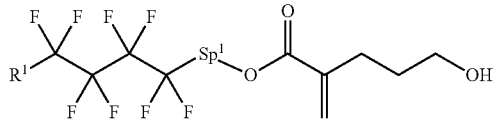

(1-28)
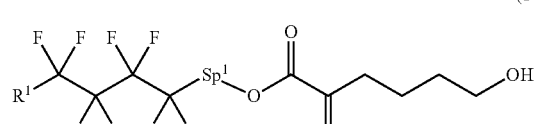

(1-29)
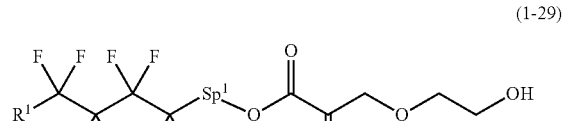

(1-30)
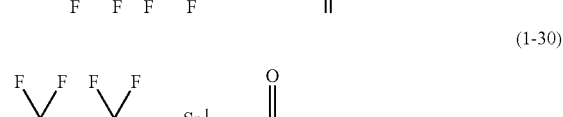

(1-31)
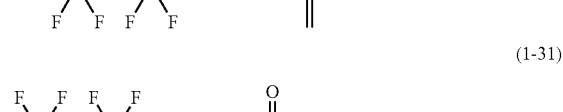

(1-32)
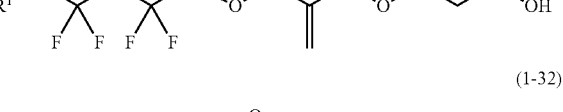

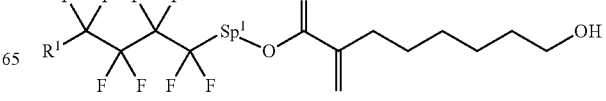

(1-33) 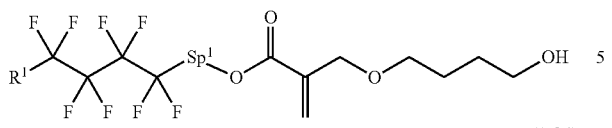

(1-34) 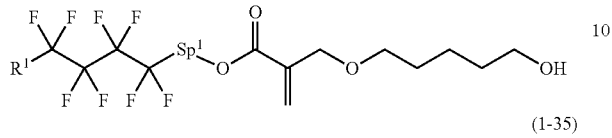

(1-35) 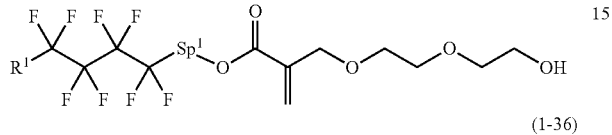

(1-36) 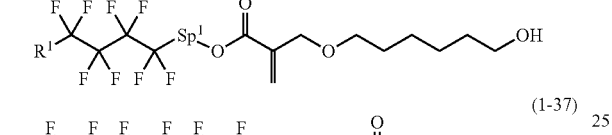

(1-37) 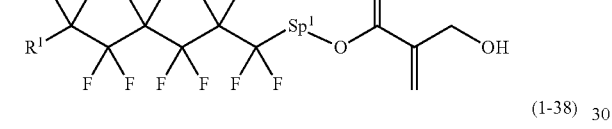

(1-38) 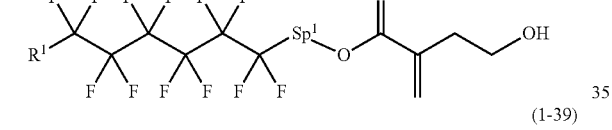

(1-39) 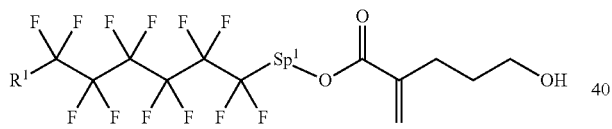

(1-40) 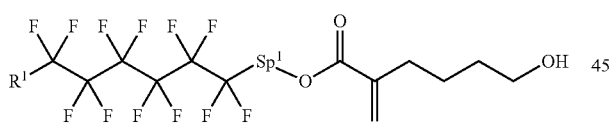

(1-41) 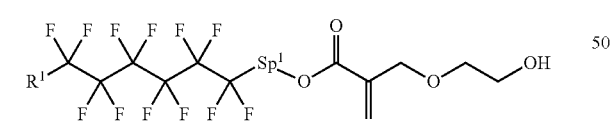

(1-42) 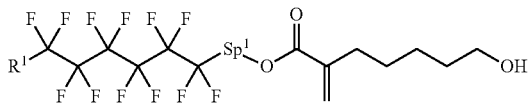

(1-43) 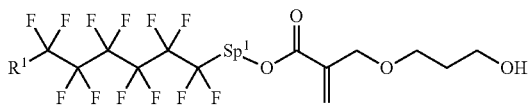

(1-44) 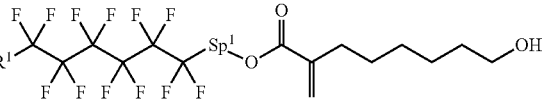

(1-45) 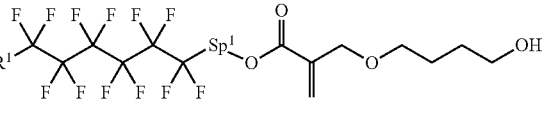

(1-46) 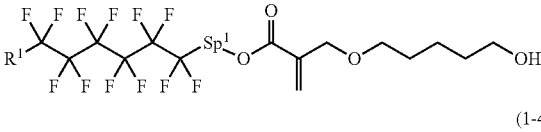

(1-47) 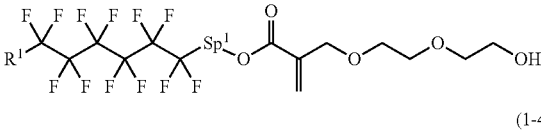

(1-48) 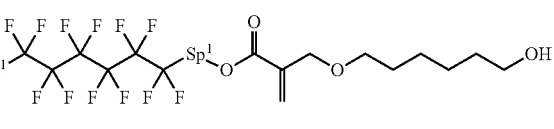

in Formula (1-25) to Formula (1-48), $R^1$ is an alkyl group having 1 to 15 carbon atoms, and in this alkyl group, at least one —$CH_2$— is optionally substituted with —O—;

$Sp^1$ is a single bond or an alkylene group having 1 to 7 carbon atoms, and in this alkylene group, at least one —$CH_2$— is optionally substituted with —O—.

7. The compound according to claim 1, which is represented by any one of Formula (1-49) to Formula (1-56):

(1-49) 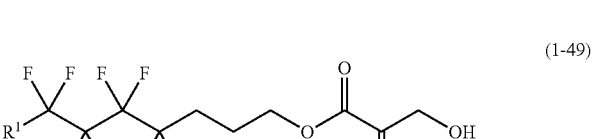

(1-50) 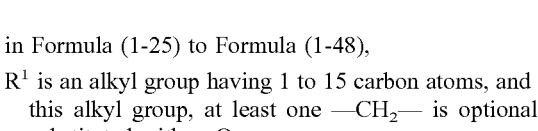

(1-51) 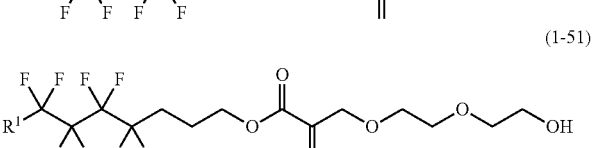

(1-52) 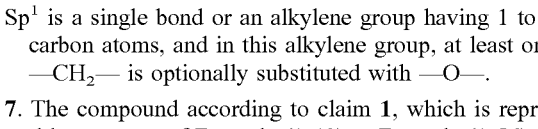

(1-49) 

(1-50) 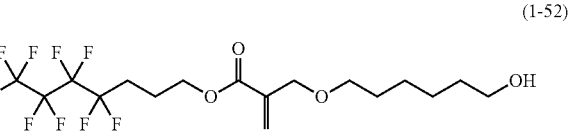

(1-51) 

-continued

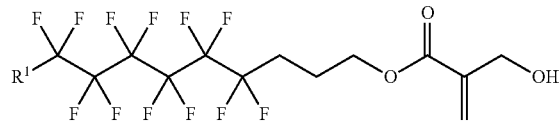 (1-53)

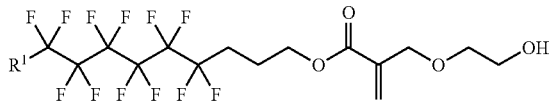 (1-54)

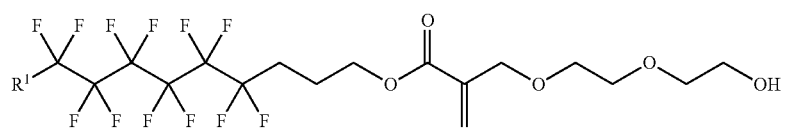 (1-55)

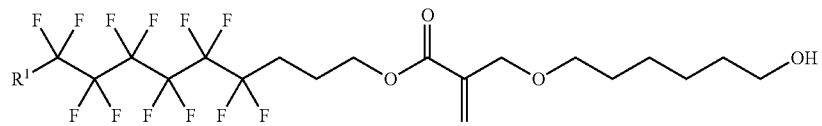 (1-56)

in Formula (1-49) to Formula (1-56), $R^1$ is an alkyl group having 1 to 10 carbon atoms.

8. A liquid crystal composition comprising at least one compound according to claim 1.

9. The liquid crystal composition according to claim 8, which comprises at least one compound selected from the group of compounds represented by Formulae (2) to (4):

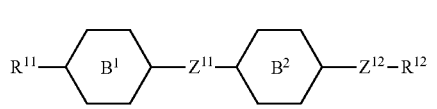 (2)

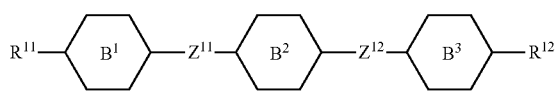 (3)

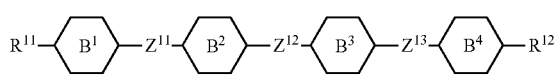 (4)

in Formulae (2) to (4), $R^{11}$ and $R^{12}$ are independently an alkyl group having 1 to 10 carbon atoms or an alkenyl group having 2 to 10 carbon atoms, and in these alkyl and alkenyl groups, at least one —CH$_2$— is optionally substituted with —O—, and in these groups represented by $R^{11}$ and $R^{12}$, at least one hydrogen atom is optionally substituted with a fluorine atom;

the ring $B^1$, the ring $B^2$, the ring $B^3$, and the ring $B^4$ are independently 1,4-cyclohexylene, 1,4-phenylene, 2-fluoro-1,4-phenylene, 2,5-difluoro-1,4-phenylene, or pyrimidine-2,5-diyl; and $Z^{11}$, $Z^{12}$, and $Z^{13}$ are independently a single bond, —COO—, —CH$_2$CH$_2$—, —CH=CH—, or —C≡C—.

10. The liquid crystal composition according to claim 8, which comprises at least one compound selected from the group of compounds represented by Formulae (5) to (7):

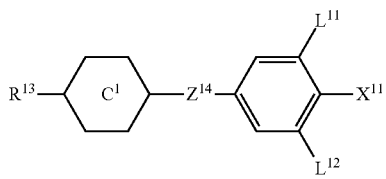 (5)

 (6)

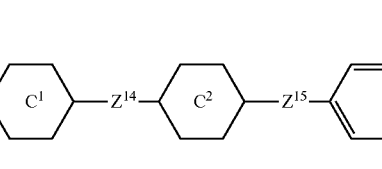 (7)

in Formulae (5) to (7), $R^{13}$ is an alkyl group having 1 to 10 carbon atoms or an alkenyl group having 2 to 10 carbon atoms, and in these alkyl and alkenyl groups, at least one —CH$_2$— is optionally substituted with —O—, and in these groups represented by $R^{13}$, at least one hydrogen atom is optionally substituted with a fluorine atom;

$X^{11}$ is a fluorine atom, a chlorine atom, —OCF$_3$, —OCHF$_2$, —CF$_3$, —CHF$_2$, —CH$_2$F, —OCF$_2$CHF$_2$, or —OCF$_2$CHFCF$_3$;

the ring $C^1$, the ring $C^2$, and the ring $C^3$ are independently 1,4-cyclohexylene, 1,4-phenylene, tetrahydropyran-2,5-diyl, pyrimidine-2,5-diyl, or 1,4-phenylene in which at least one hydrogen atom is substituted with a fluorine atom;

$Z^{14}$, $Z^{15}$, and $Z^{16}$ are independently a single bond, —COO—, —OCO—, —CH$_2$O—, —OCH$_2$—, —CF$_2$O—, —OCF$_2$—, —CH$_2$CH$_2$—, —CH=CH—, —C≡C—, or —(CH$_2$)$_4$—; and $L^{11}$ and $L^{12}$ are independently a hydrogen atom or a fluorine atom.

11. The liquid crystal composition according to claim 8, which comprises at least one compound selected from the group of compounds represented by Formula (8):

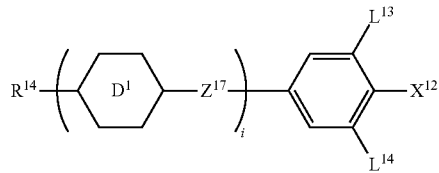
(8)

in Formula (8), $R^{14}$ is an alkyl group having 1 to 10 carbon atoms or an alkenyl group having 2 to 10 carbon atoms, and in these alkyl and alkenyl groups, at least one —$CH_2$— is optionally substituted with —O—, and in these groups represented by $R^{14}$, at least one hydrogen atom is optionally substituted with a fluorine atom;)

$X^{12}$ is —C≡N or —C≡C—C≡N;

the ring $D^1$ is 1,4-cyclohexylene, 1,4-phenylene, tetrahydropyran-2,5-diyl, 1,3-dioxane-2,5-diyl, pyrimidine-2,5-diyl, or 1,4-phenylene in which at least one hydrogen atom is substituted with a fluorine atom;

$Z^{17}$ is a single bond, —COO—, —OCO—, —$CH_2O$—, —$OCH_2$—, —$CF_2O$—, —$OCF_2$—, —$CH_2CH_2$—, or —C≡C—;

$L^{13}$ and $L^{14}$ are independently a hydrogen atom or a fluorine atom; and i is 1, 2, 3, or 4.

12. The liquid crystal composition according to claim 8, which comprises at least one compound selected from the group of compounds represented by Formulae (11) to (19):

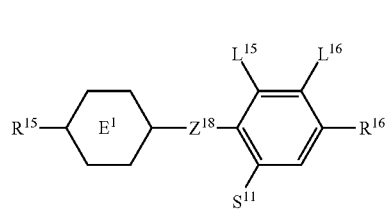
(11)

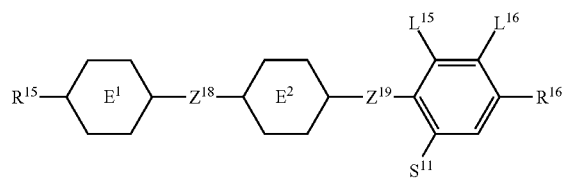
(12)

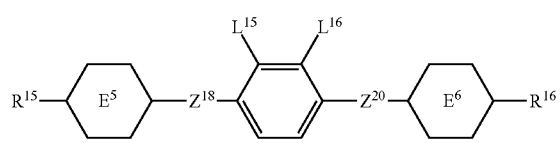
(13)

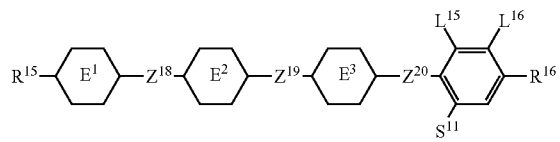
(14)

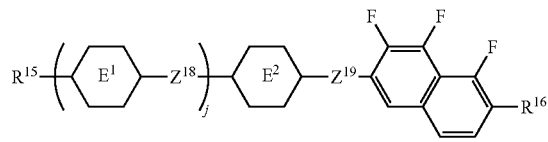
(15)

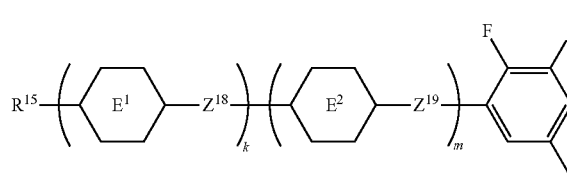
(16)

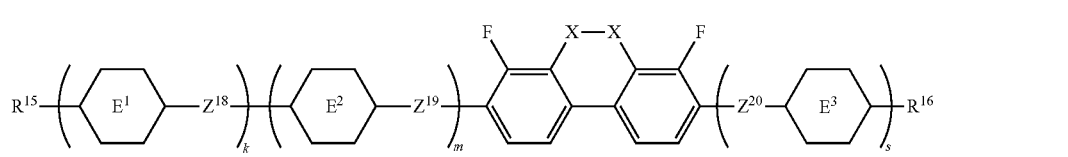
(17)

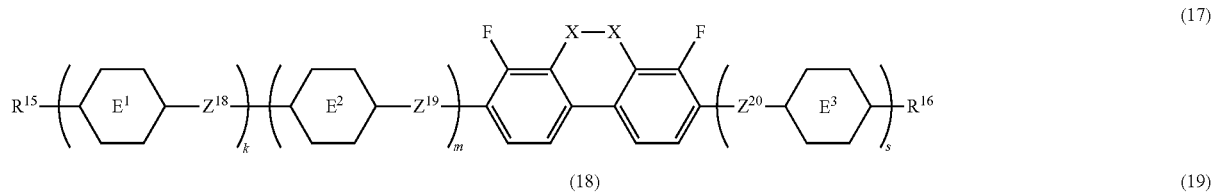
(18)

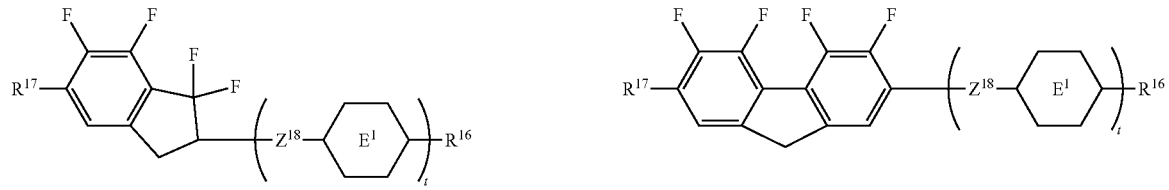
(19)

in Formulae (11) to (19), $R^{15}$, $R^{16}$, and $R^{17}$ are independently an alkyl group having 1 to 10 carbon atoms or an alkenyl group having 2 to 10 carbon atoms, and in these alkyl and alkenyl groups, at least one —$CH_2$— is optionally substituted with —O—, and in these groups represented by $R^{15}$, $R^{16}$, and $R^{17}$, at least one hydrogen atom is optionally substituted with a fluorine atom, and $R^{17}$ may be a hydrogen atom or a fluorine atom;

the ring $E^1$, the ring $E^2$, the ring $E^3$, and the ring $E^4$ are independently 1,4-cyclohexylene, 1,4-cyclohexenylene, 1,4-phenylene, tetrahydropyran-2,5-diyl, decahydronaphthalene-2,6-diyl, or 1,4-phenylene in which at least one hydrogen atom is substituted with a fluorine atom;

the ring $E^5$ and the ring $E^6$ are independently 1,4-cyclohexylene, 1,4-cyclohexenylene, 1,4-phenylene, tetrahydropyran-2,5-diyl, or decahydronaphthalene-2,6-diyl;

$Z^{18}$, $Z^{19}$, $Z^{20}$, and $Z^{21}$ are independently a single bond, —COO—, —OCO—, —$CH_2$O—, —O$CH_2$—, —$CF_2$O—, —O$CF_2$—, —$CH_2CH_2$—, —$CF_2OCH_2CH_2$—, or —O$CF_2CH_2CH_2$—;

$L^{15}$ and $L^{16}$ are independently a fluorine atom or a chlorine atom;

$S^{11}$ is a hydrogen atom or a methyl group;

X is —CHF— or —$CF_2$—;

j, k, m, n, p, q, r, and s are independently 0 or 1, a sum of k, m, n, and p is 1 or 2, and a sum of q, r, and s is 0, 1, 2, or 3, and t is 1, 2, or 3.

13. The liquid crystal composition according to claim 8, which comprises at least one polymerizable compound represented by Formula (20) other than the compound represented by Formula (1):

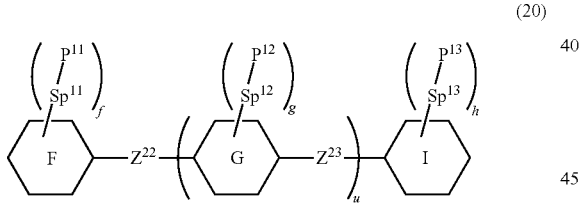

(20)

in Formula (20), the ring F and the ring I are independently cyclohexyl, cyclohexenyl, phenyl, 1-naphthyl, 2-naphthyl, tetrahydropyran-2-yl, 1,3-dioxan-2-yl, pyrimidin-2-yl, or pyridin-2-yl, and in these rings, at least one hydrogen atom is optionally substituted with a halogen atom, an alkyl group having 1 to 12 carbon atoms, an alkoxy group having 1 to 12 carbon atoms, or an alkyl group having 1 to 12 carbon atoms in which at least one hydrogen atom is substituted with a halogen atom;

the ring G is 1,4-cyclohexylene, 1,4-cyclohexenylene, 1,4-phenylene, naphthalene-1,2-diyl, naphthalene-1,3-diyl, naphthalene-1,4-diyl, naphthalene-1,5-diyl, naphthalene-1,6-diyl, naphthalene-1,7-diyl, naphthalene-1,8-diyl, naphthalene-2,3-diyl, naphthalene-2,6-diyl, naphthalene-2,7-diyl, phenanthrene-2,7-diyl, tetrahydropyran-2,5-diyl, 1,3-dioxane-2,5-diyl, pyrimidine-2,5-diyl, or pyridine-2,5-diyl, and in these rings, at least one hydrogen atom is optionally substituted with a halogen atom, an alkyl group having 1 to 12 carbon atoms, an alkoxy group having 1 to 12 carbon atoms, or an alkyl group having 1 to 12 carbon atoms in which at least one hydrogen atom is substituted with a halogen atom;

$Z^{22}$ and $Z^{23}$ are independently a single bond or an alkylene group having 1 to 10 carbon atoms, and in this alkylene group, at least one —$CH_2$— is optionally substituted with —O—, —CO—, —COO—, or —OCO—, and at least one —$CH_2CH_2$— is optionally substituted with —CH=CH—, —C($CH_3$)=CH—, —CH=C($CH_3$)—, or —C($CH_3$)=C($CH_3$)—, and in these groups represented by $Z^{22}$ and $Z^{23}$, at least one hydrogen atom is optionally substituted with a fluorine or chlorine atom;

$P^{11}$, $P^{12}$, and $P^{13}$ are independently a polymerizable group;

$Sp^{11}$, $Sp^{12}$, and $Sp^{13}$ are independently a single bond or an alkylene group having 1 to 10 carbon atoms, and in this alkylene group, at least one —$CH_2$— is optionally substituted with —O—, —COO—, —OCO—, or —OCOO—, and at least one —$CH_2CH_2$— is optionally substituted with —CH=CH— or —C≡C—, and in these groups represented by $Sp^{11}$, $Sp^{12}$, and $Sp^{13}$, at least one hydrogen atom is optionally substituted with a fluorine or chlorine atom;

u is 0, 1, or 2; and f, g, and h are independently 0, 1, 2, 3, or 4, and a sum of f, g, and h is 1 or more.

14. The liquid crystal composition according to claim 13, wherein, in Formula (20), $P^{11}$, $P^{12}$, and $P^{13}$ are independently a group selected from the group of polymerizable groups represented by Formula (P-1) to Formula (P-5):

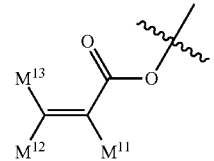

(P-1)

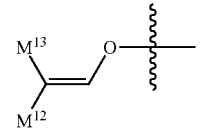

(P-2)

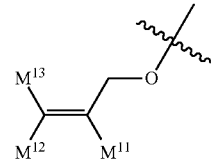

(P-3)

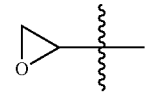

(P-4)

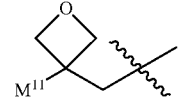

(P-5)

in Formula (P-1) to Formula (P-5), $M^{11}$, $M^{12}$, and $M^{13}$ are independently a hydrogen atom, a fluorine atom, an alkyl group having 1 to 5 carbon atoms, or an alkyl group having 1 to 5 carbon atoms in which at least one hydrogen atom is substituted with a halogen atom.

15. The liquid crystal composition according to claim 13, wherein the polymerizable compound represented by Formula (20) is at least one compound selected from the group of polymerizable compounds represented by Formula (20-1) to Formula (20-7):

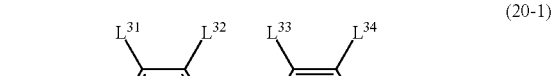
(20-1)

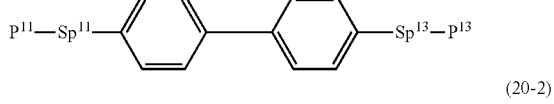
(20-2)

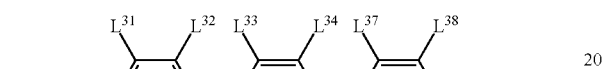
(20-3)

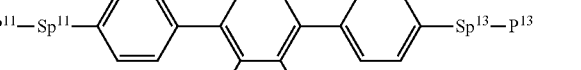
(20-4)

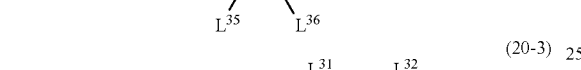
(20-5)

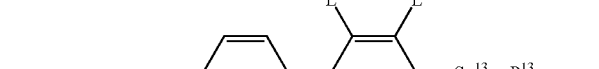
(20-6)

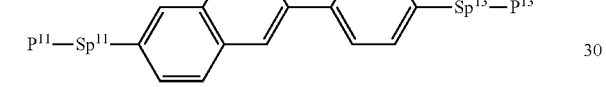

(20-7)

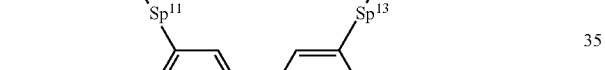

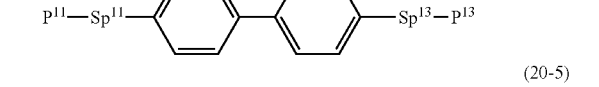

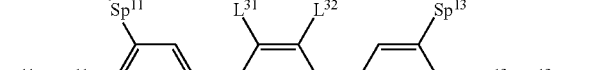

in Formula (20-1) to Formula (20-7), $L^{31}$, $L^{32}$, $L^{33}$, $L^{34}$, $L^{35}$, $L^{36}$, $L^{37}$, and $L^{38}$ are independently a hydrogen atom, a fluorine atom, or a methyl group;

$Sp^{11}$, $Sp^{12}$, and $Sp^{13}$ are independently a single bond or an alkylene group having 1 to 10 carbon atoms, and in this alkylene group, at least one —CH$_2$— is optionally substituted with —O—, —COO—, —OCO—, or —OCOO—, and at least one —CH$_2$CH$_2$— is optionally substituted with —CH=CH— or —C≡C—, and in these groups represented by $Sp^{11}$, $Sp^{12}$, and $Sp^{13}$, at least one hydrogen atom is optionally substituted with a fluorine atom or a chlorine atom;

$P^{11}$, $P^{12}$, and $P^{13}$ are independently a group selected from the group of polymerizable groups represented by Formula (P-1) to Formula (P-3),

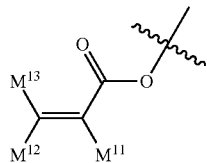
(P-1)

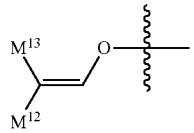
(P-2)

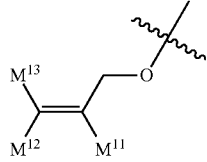
(P-3)

in Formula (P-1) to Formula (P-3), $M^{11}$, $M^{12}$, and $M^{13}$ are independently a hydrogen atom, a fluorine atom, an alkyl group having 1 to 5 carbon atoms, or an alkyl group having 1 to 5 carbon atoms in which at least one hydrogen atom is substituted with a halogen atom.

16. The liquid crystal composition according to claim 13, which comprises at least one selected from the group consisting of a polymerizable compound different from the compound represented by Formula (1) or Formula (20), a polymerization initiator, a polymerization inhibitor, an optically active compound, an antioxidant, a UV absorber, a light stabilizer, a heat stabilizer, a dye, and an antifoaming agent.

17. A liquid crystal display element including a product obtained by polymerizing the liquid crystal composition according to claim 8.

18. The compound according to claim 2, which is represented by any one of Formula (1-1) to Formula (1-6):

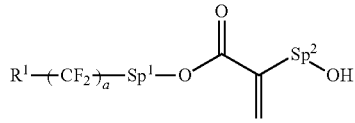
(1-1)

-continued

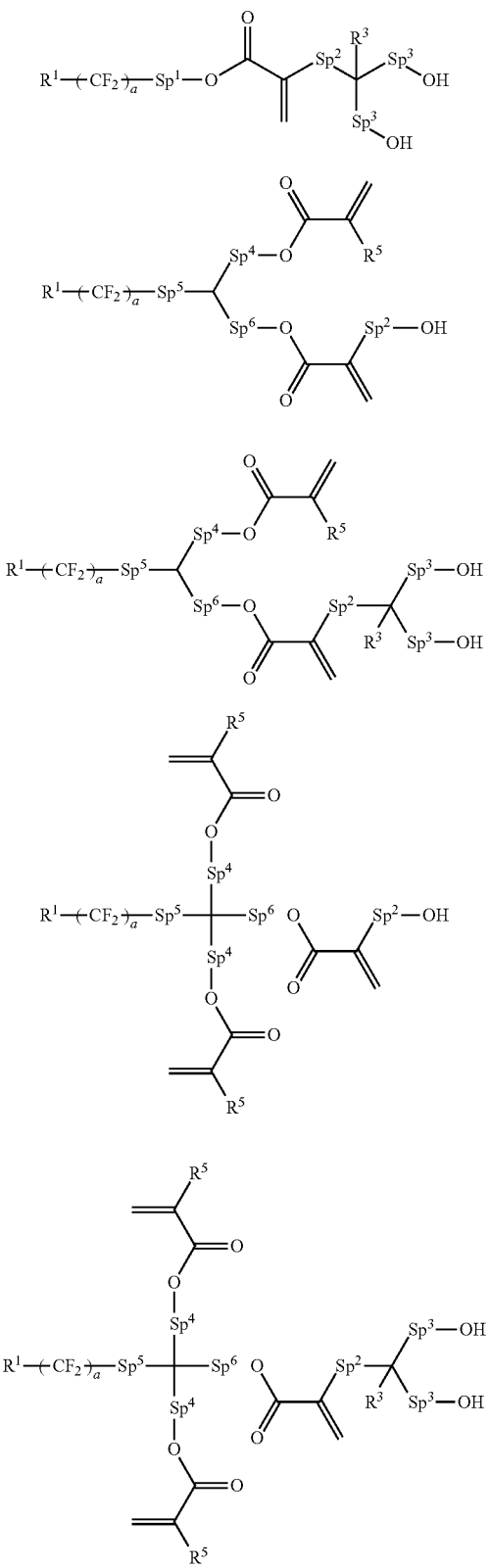

(1-2)
(1-3)
(1-4)
(1-5)
(1-6)

in Formula (1-1) to Formula (1-6),
R¹ is an alkyl group having 1 to 15 carbon atoms, and in this alkyl group, at least one —CH₂— is optionally substituted with —O—, and at least one —(CH₂)₂— is optionally substituted with —CH═CH—, and in these groups represented by R¹, at least one hydrogen atom is optionally substituted with a fluorine atom;

a is an integer of 2 to 8;

Sp¹, Sp², Sp³, and Sp⁴ are independently a single bond or an alkylene group having 1 to 10 carbon atoms, and in this alkylene group, at least one —CH₂- is optionally substituted with —O—, and at least one —(CH₂)₂— is optionally substituted with —CH═CH—, and in these groups represented by Sp¹, Sp², Sp³, and Sp⁴, at least one hydrogen atom is optionally substituted with a fluorine atom;

Sp⁵ and Sp⁶ are independently a single bond or an alkylene group having 1 to 7 carbon atoms, and in this alkylene group, at least one —CH₂— is optionally substituted with —O—, and at least one —(CH₂)₂— is optionally substituted with —CH═CH—, and in these groups represented by Sp⁵ and Sp⁶, at least one hydrogen atom is optionally substituted with a fluorine atom;

R³ is a hydrogen, an alkyl group having 1 to 7 carbon atoms, an alkoxy group having 1 to 6 carbon atoms, or an alkoxyalkyl group having 1 to 6 carbon atoms;

R⁵ is a hydrogen atom or an alkyl group having 1 to 5 carbon atoms.

19. The compound according to claim 3, which is represented by any one of Formula (1-1) to Formula (1-6):

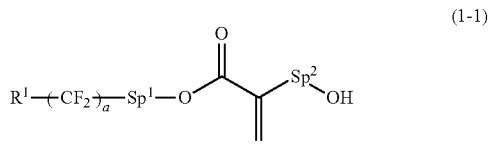

(1-1)

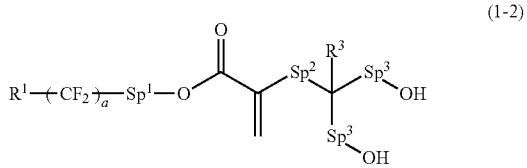

(1-2)

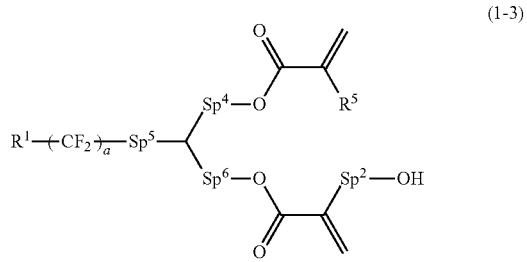

(1-3)

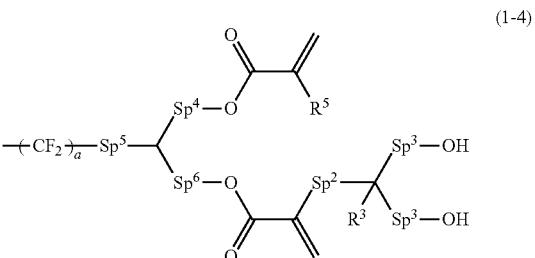

(1-4)

-continued

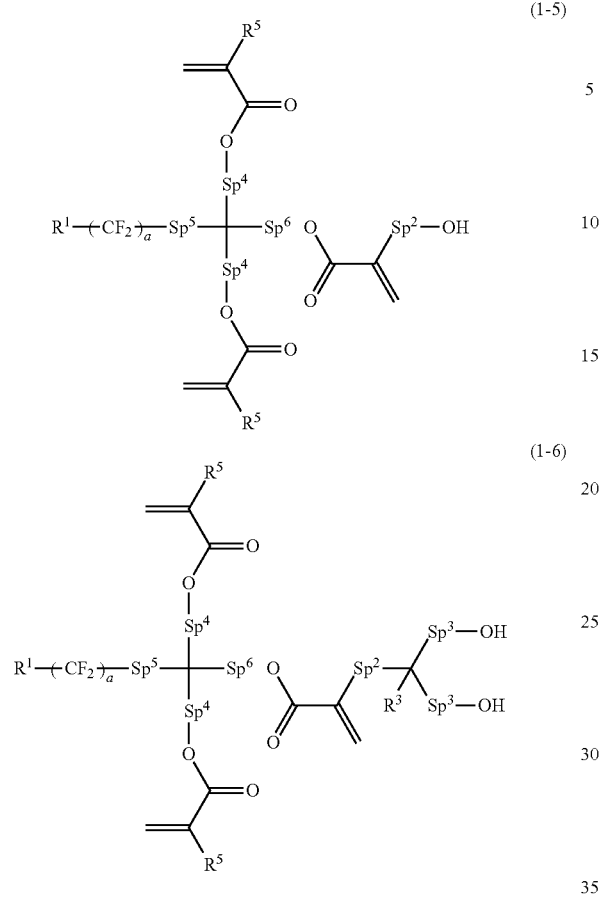

(1-5)

(1-6)

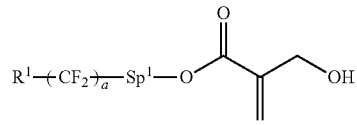

(1-7)

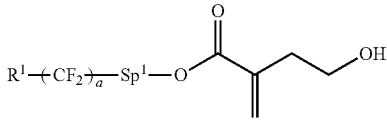

(1-8)

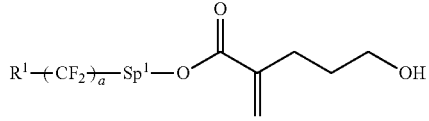

(1-9)

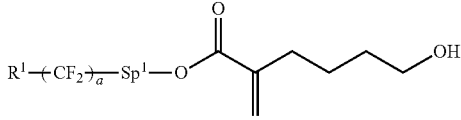

(1-10)

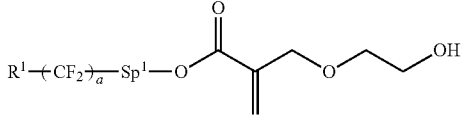

(1-11)

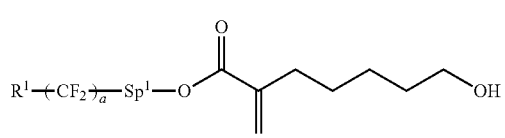

(1-12)

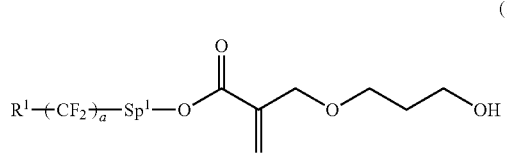

(1-13)

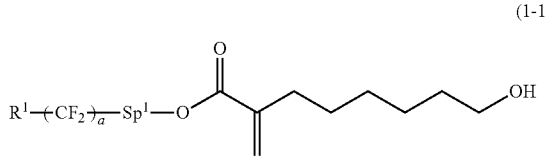

(1-14)

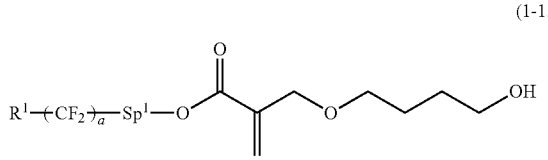

(1-15)

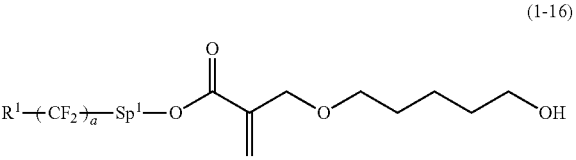

(1-16)

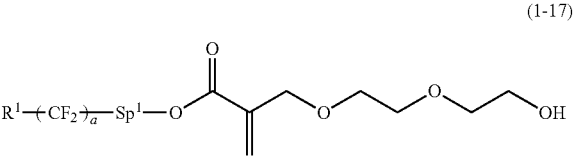

(1-17)

in Formula (1-1) to Formula (1-6), $R^1$ is an alkyl group having 1 to 15 carbon atoms, and in this alkyl group, at least one —$CH_2$— is optionally substituted with —O—, and at least one —$(CH_2)_2$— is optionally substituted with —CH=CH—, and in these groups represented by $R^1$, at least one hydrogen atom is optionally substituted with a fluorine atom;

a is an integer of 2 to 8;

$Sp^1$, $Sp^2$, $Sp^3$, and $Sp^4$ are independently a single bond or an alkylene group having 1 to 10 carbon atoms, and in this alkylene group, at least one —$CH_2$- is optionally substituted with —O—, and at least one —$(CH_2)_2$— is optionally substituted with —CH=CH—, and in these groups represented by $Sp^1$, $Sp^2$, $Sp^3$, and $Sp^4$, at least one hydrogen atom is optionally substituted with a fluorine atom;

$Sp^5$ and $Sp^6$ are independently a single bond or an alkylene group having 1 to 7 carbon atoms, and in this alkylene group, at least one —$CH_2$— is optionally substituted with —O—, and at least one —$(CH_2)_2$— is optionally substituted with —CH=CH—, and in these groups represented by $Sp^5$ and $Sp^6$, at least one hydrogen atom is optionally substituted with a fluorine atom;

$R^3$ is a hydrogen, an alkyl group having 1 to 7 carbon atoms, an alkoxy group having 1 to 6 carbon atoms, or an alkoxyalkyl group having 1 to 6 carbon atoms;

$R^5$ is a hydrogen atom or an alkyl group having 1 to 5 carbon atoms.

20. The compound according to claim 2, which is represented by any one of Formula (1-7) to Formula (1-24):

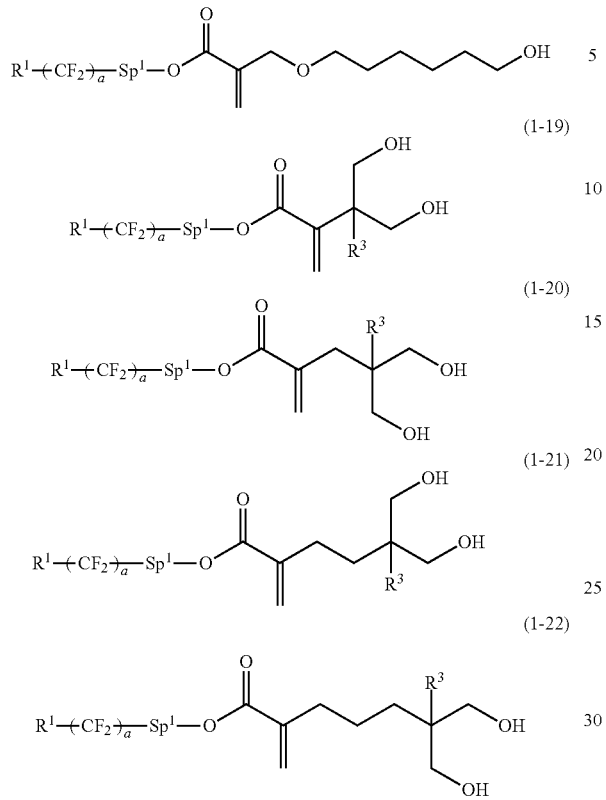

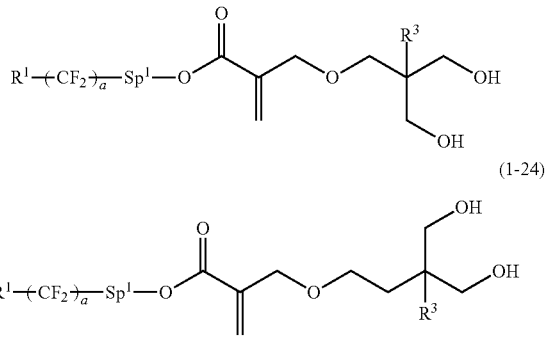

in Formula (1-7) to Formula (1-24),

R¹ is an alkyl group having 1 to 15 carbon atoms, and in this alkyl group, at least one —CH$_2$— is optionally substituted with —O—, and at least one —(CH$_2$)$_2$— is optionally substituted with —CH=CH—;

a is an integer of 2 to 8;

Sp¹ is a single bond or an alkylene group having 1 to 7 carbon atoms, and in this alkylene group, at least one —CH$_2$— is optionally substituted with —O—; and R³ is a hydrogen atom or an alkyl group having 1 to 5 carbon atoms.

* * * * *